US011952634B2

(12) United States Patent
Peterson et al.

(10) Patent No.: US 11,952,634 B2
(45) **Date of Patent: *Apr. 9, 2024**

(54) METHOD FOR PREDICTING RESPONSE TO BREAST CANCER THERAPEUTIC AGENTS AND METHOD OF TREATMENT OF BREAST CANCER

(71) Applicant: Medivation Prostate Therapeutics LLC, New York, NY (US)

(72) Inventors: Amy Christian Peterson, San Francisco, CA (US); Hirdesh Uppal, San Ramon, CA (US)

(73) Assignee: Medivation Prostate Therapeutics LLC, New York, NY (US)

( * ) Notice: Subject to any disclaimer, the term of this patent is extended or adjusted under 35 U.S.C. 154(b) by 123 days.

This patent is subject to a terminal disclaimer.

(21) Appl. No.: 17/523,235

(22) Filed: Nov. 10, 2021

(65) Prior Publication Data

US 2022/0056541 A1 Feb. 24, 2022

Related U.S. Application Data

(63) Continuation of application No. 16/215,340, filed on Dec. 10, 2018, now Pat. No. 11,186,876, which is a continuation of application No. 14/962,864, filed on Dec. 8, 2015, now Pat. No. 10,196,693.

(60) Provisional application No. 62/167,110, filed on May 27, 2015, provisional application No. 62/142,504, filed on Apr. 3, 2015, provisional application No. 62/091,195, filed on Dec. 12, 2014.

(51) Int. Cl.

| | |
|---|---|
| ***A61K 31/4164*** | (2006.01) |
| ***A61K 31/337*** | (2006.01) |
| ***A61K 31/4166*** | (2006.01) |
| ***A61K 45/06*** | (2006.01) |
| ***A61P 35/00*** | (2006.01) |
| ***C12Q 1/6886*** | (2018.01) |

(52) U.S. Cl.

CPC .......... *C12Q 1/6886* (2013.01); *A61K 31/337* (2013.01); *A61K 31/4166* (2013.01); *A61K 45/06* (2013.01); *C12Q 2600/106* (2013.01); *C12Q 2600/112* (2013.01); *C12Q 2600/158* (2013.01)

(58) Field of Classification Search

CPC ............................ A61K 31/4164; A61P 35/00

USPC .......................................................... 514/389

See application file for complete search history.

(56) References Cited

U.S. PATENT DOCUMENTS

| | | | | |
|---|---|---|---|---|
| 8,110,594 | B2 | 2/2012 | Jung et al. | |
| 8,183,274 | B2 | 5/2012 | Sawyers et al. | |
| 8,648,105 | B2 | 2/2014 | Jung et al. | |
| 9,126,941 | B2 | 9/2015 | Sawyers et al. | |
| 9,517,229 | B2 | 12/2016 | Protter et al. | |
| 10,111,861 | B2 | 10/2018 | Protter et al. | |
| 10,196,693 | B2 | 2/2019 | Peterson et al. | |
| 11,186,876 | B2 * | 11/2021 | Peterson | A61K 31/337 |
| 2003/0219767 | A1 | 11/2003 | Ayers et al. | |
| 2007/0004753 | A1 | 1/2007 | Sawyers et al. | |
| 2007/0059720 | A9 | 3/2007 | Fuqua et al. | |
| 2007/0192880 | A1 | 8/2007 | Muyan et al. | |
| 2008/0139634 | A2 | 6/2008 | Jung et al. | |
| 2009/0111864 | A1 | 4/2009 | Jung et al. | |
| 2009/0299640 | A1 | 12/2009 | Ellis et al. | |
| 2010/0172975 | A1 | 7/2010 | Sawyers et al. | |
| 2010/0210665 | A1 | 8/2010 | Sawyers et al. | |
| 2011/0003839 | A1 | 1/2011 | Jung et al. | |
| 2011/0130296 | A1 | 6/2011 | Benz et al. | |
| 2011/0145176 | A1 | 6/2011 | Perou et al. | |
| 2011/0152348 | A1 | 6/2011 | Worm et al. | |
| 2012/0214864 | A1 | 8/2012 | Richer et al. | |
| 2013/0004482 | A1 | 1/2013 | Perou et al. | |
| 2013/0345161 | A1 | 12/2013 | Perou et al. | |
| 2014/0107180 | A1 | 4/2014 | Macleod et al. | |
| 2014/0154681 | A1 | 6/2014 | Wallden | |
| 2015/0253329 | A1 | 9/2015 | Mouchantat | |
| 2016/0078167 | A1 | 3/2016 | Rosner et al. | |
| 2016/0168646 | A1 | 6/2016 | Peterson et al. | |
| 2017/0087132 | A1 | 3/2017 | Protter et al. | |
| 2019/0169697 | A1 | 6/2019 | Peterson et al. | |

FOREIGN PATENT DOCUMENTS

| | | | |
|---|---|---|---|
| WO | WO-2006124118 | A1 | 11/2006 |
| WO | WO-2007126765 | A2 | 11/2007 |
| WO | WO-2010099238 | A1 | 9/2010 |
| WO | WO-2010118354 | A1 | 10/2010 |
| WO | WO-2010125117 | A2 | 11/2010 |
| WO | WO-2011028905 | A1 | 3/2011 |
| WO | WO-2011044327 | A1 | 4/2011 |
| WO | WO-2012125828 | A2 | 9/2012 |
| WO | WO-2012125858 | A1 | 9/2012 |
| WO | WO-2013066440 | A1 | 5/2013 |
| WO | WO-2014031164 | A1 | 2/2014 |

(Continued)

OTHER PUBLICATIONS

Second Examiner's Report dated Aug. 10, 2022 in Canadian Patent Application No. 2,970,469.

U.S. Appl. No. 16/168,896, Peterson et al.

Perou, C., et al., "Molecular portraits of human breast tumours," *Nature*, 2000, 406:747-752.

Sorlie, T., et al., "Gene expression patterns of breast carcinomas distinguish tumor subclasses with clinical implications," *PNAS*, 2001, 98(19):10869-10874.

Bertucci, F., et al., "How basal are triple-negative breast cancers?," *Int. J. Cancer*, 2008, 123:236-240.

(Continued)

*Primary Examiner* — Raymond J Henley, III

(74) *Attorney, Agent, or Firm* — Banner & Witcoff, LTD.

(57) ABSTRACT

Methods for treating triple negative breast cancer with an androgen receptor inhibitor are provided, as well as methods for screening for the likelihood of the effectiveness of such treatment.

42 Claims, 29 Drawing Sheets

Specification includes a Sequence Listing.

(56) References Cited

FOREIGN PATENT DOCUMENTS

WO WO-2016094408 A1 6/2016

OTHER PUBLICATIONS

Ogawa, Y., et al., "Androgen receptor expression in breast cancer: relationship with clinicopathological factors and biomarkers," *Int. J. Clin. Oncol.*, 2008, 13:431-435.
Wang, X., et al., "Increased expression of osteopontin in patients with triple-negative breast cancer," *Eur. J. Clin. Invest.*, 2008, 38:438-446.
Parker, J., et al., "Supervised Risk Predictor of Breast Cancer Based on Intrinsic Subtypes," *J. Clin. Oncol.*, 2009, 27(8):1160-1167.
Choo, J., et al., "Biomarkers for Basal-like Breast Cancer," *Cancers*, 2010, 2:1040-1065.
Collins, L., et al., "Androgen receptor expression in breast cancer in relation to molecular phenotype: results from the Nurses' Health Study," *Mod. Pathol.*, 2011, 24(7):924-931.
Garay, J., et al., "Androgen receptor as a targeted therapy for breast cancer," *Am. J. Cancer Res.*, 2012, 2(4):434-445.
Kelly, C., et al., "Agreement in Risk Prediction Between the 21-Gene Recurrence Score Assay (Oncotype DX) and the PAM50 Breast Cancer Intrinsic Classifier™ in Early-Stage Estrogen Receptor-Positive Breast Cancer," *The Oncologist*, 2012, 17:492-498.
Gucalp, A., et al., "Phase II Trial of Bicalutamide in Patients with Androgen Receptor-Positive, Estrogen Receptor-Negative Metastatic Breast Cancer," *Clin. Cancer Res.*, 2013, 19(19):5505-5512.
Nielsen, T., et al., "Immunohistochemical and clinical characterization of the basal-like subtype of invasive breast carcinoma," *Clinical Cancer Research*, 2004, 10:5367-5374.
Prat, A., et al., "Predicting response and survival in chemotherapy-treated triple-negative breast cancer," *British Journal of Cancer*, 2014, 111:1532-1541.
Traina, T.A., et al., "A Phase 1 Open-Label Study Evaluating The Safety, Tolerability, and Pharmacokinetics of Enzalutamide Alone or Combined With an Aromatase Inhibitor in Women With Advanced Breast Cancer," *Ann. Oncol.*, 2014, 25:i4. doi: 10.1093/annonc/mdu064.1.
IMPAKT 2014 News: "Enzalutamide With or Without an Aromatase Inhibitor for Advanced Breast Cancer," 2014 Breast Cancer Conference (May 8-10, 2014, Brussels, Belgium), available at: https://www.esmo.org/Conferences/Past-Conferences/IMPAKT-2014-Breast-Cancer/News/Enzalutamide-With-or-Without-an-Aromatase-Inhibitor-for-Advanced-Breast-Cancer.
Notice of Allowance in U.S. Appl. No. 14/236,036, dated Mar. 24, 2016.
Office Action in U.S. Appl. No. 14/236,036, dated May 20, 2015.
International Search Report and Written Opinion for PCT/US2012/048471, dated Apr. 1, 2013.
International Preliminary Report on Patentability for PCT/US2012/048471, dated Feb. 4, 2014.
Supplemental Search Report and Search Opinion for EP 12 84 6720, dated Feb. 9, 2015.
De Amicis, F., et al., "Androgen Receptor Overexpression Induces Tamoxifen Resistance in Human Breast Cancer Cells," *Breast Cancer Res. Treat.*, 2010, 121:1-11.
"Tamoxifen" Dec. 2004 [online]: Wikipedia [retrieved on May 5, 2015], available at: http://en.wikipedia.org/wiki/Tamoxifen.
Cochrane, D., et al., "Role of the androgen receptor in breast cancer and preclinical analysis of enzalutamide," *Breast Cancer Research*, 2014, 16(1):R7.
Doane, A., et al., "An estrogen receptor-negative breast cancer subset characterized by a hormonally regulated transcriptional program and response to androgen," *Oncogene*, 2006, 25(28):3994-4008.
Graham, T., et al., "Reciprocal regulation of ZEB1 and AR in triple negative breast cancer cells," *Breast Cancer Research and Treatment*, 2009, 123(1):139-147.
Ni, M., et al., "Targeting Androgen Receptor in Estrogen Receptor-Negative Breast Cancer," *Cancer Cell*, 2011, 20(1):119-131.
Robinson, J., et al., "Androgen receptor driven transcription in molecular apocrine breast cancer is mediated by FoxA1," *The EMBO Journal*, 2011, 31(6):3019-3027.
Santana-Davila, R., et al., "Treatment options for patients with triple-negative breast cancer," *Journal of Hematology & Oncology*, 2010, 3(1):1-11.
Parker, J., et al., "A novel biomarker to predict sensitivity to enzalutamide (ENZA) in TNBC," *Journal of Clinical Oncology*, 2015, 33(15):1083.
Traina, T., et al., "Results from a phase 2 study of enzalutamide (ENZA), an androgen receptor (AR) inhibitor, in advanced AR+triple-negative breast cancer (TNBC)," *Journal of Clinical Oncology*, 2015, 33(15):1003.
Zhao, T., et al., "A Phase II Clinical Trial of Flutamide in the Treatment of Advanced Breast Cancer," *Tumori*, 1988, 74:53-56.
Perrault, D., et al. "Phase II study of flutamide in patients with metastatic breast cancer. A National Cancer Institute of Canada Clinical Trials Group Study," *Investigational New Drugs*, 1988, 6:207-210.
Barton, V., et al., "Multiple Molecular Subtypes of Triple-Negative Breast Cancer Critically Rely on Androgen Receptor and Respond to Enzalutamide In Vivo," *Mol. Cancer Ther.*, 2015, 14(3):769-778.
Cochrane, D., et al., "Abstract P2-14-02: Preclinical Evaluation of Enzalutamide in Breast Cancer Models," *Cancer Res.*, 2012, 72(24 Suppl):Abstract nr P2-14-02. doi: 10.1158/0008-5472.SABCS12-P2-14-02.
Hudis, C., et al., "Triple-Negative Breast Cancer: An Unmet Medical Need," *The Oncologist*, 2011, 16(1 Suppl): 1-11.
Gucalp, A., et al., "Triple-Negative Breast Cancer Role of the Androgen Receptor," *The Cancer Journal*, 2010, 16(1):62-65.
Park, S., et al., "Expression of androgen receptors in primary breast cancer," *Annals of Oncology*, 2010, 21(3):488-492. doi: 10.1093/annonc/mdp510.
Venkitaraman, R., "Triple-negative/basal-like breast cancer: clinical, pathologic and molecular features," *Expert Rev. Anticancer Ther.*, 2010, 10(2):199-207. doi: 10.1586/era.09.189.
Ogawa, Y., et al., "Androgen receptor expression in breast cancer: relationship with clinicopathological factors and biomarkers," *Int. J. Clin. Oncol.*, 2008, 13:431-435. doi: 10.1007/s10147-008-0770-6.
Tan, A., et al., "Therapeutic Strategies for Triple-Negative Breast Cancer," *The Cancer Journal*, 2008, 14(6):343-351.
Nahleh, Z., "Androgen receptor as a target for the treatment of hormone receptor-negative breast cancer: an unchartered territory," *Future Oncol.*, 2008, 4(1):15-21.
Loibl, S., et al., "Androgen-Receptor Expression in Triple Negative Breast Cancer: Results from the Neoadjuvant Gepartrio Trial," *Annals of Oncology*, 2009, 20(2 Suppl):ii45. doi: 10.1093/annonc/mdp103.
Cimino-Mathews, A., et al., "Androgen Receptor Expression Is Usually Maintained in Initial Surgically-Resected Breast Cancer Metastases, but Often Lost in Terminal Metastases Found at Autopsy," Annual Meeting Abstracts, 33A.
Cimino-Mathews, A., et al., "Androgen receptor expression is usually maintained in initial surgically resected breast cancer metastases but is often lost in end-stage metastases found at autopsy," *Human Pathology*, 2012, 43:1003-1011.
Minami, C., et al., "Management Options in Triple-Negative Breast Cancer," *Breast Cancer: Basic and Clinical Research*, 2011, 5:175-179. doi: 10.4137/BCBCR.S6562.
Chen, J., et al., "Expression of androgen receptor in breast carcinoma and its relationship with estrogen receptor, progesterone receptor and HER2 status," *Chin. J. Pathol.*, 2010, 39(11):743-746. doi: 10.3760/cma.j.issn.0529-5807.2010.11.007.
Richer, J.K., et al., "P2.22 MDV3100, An Androgen Receptor Signaling Inhibitor, Abrogates Breast Cancer Proliferation and Tumor Growth in Preclinical Models," *Annals of Oncology*, 2012, 23(1 Suppl):i31. doi: 10.1093/annonc/mds018.
Elias, A., et al., "MDV3100-08: A phase I open-label, dose-escalation study evaluating the safety, tolerability, and pharmacokinet-

(56) References Cited

OTHER PUBLICATIONS ics of MDV3100 in women with incurable breast cancer," *Journal of Clinical Oncology*, 2012, 30(15 Suppl): TPS668. doi: 10.1200/jco.2012.30.15_suppl.tps668.
D'Amato, N., et al., "Abstract 4756: Elucidating the role of AR in breast cancer," *Cancer Research*, 2013, 73(8 Suppl): Abstract nr 4756. doi: 10.1158/1538-7445.AM2013-4756.
Barton, V., et al., "Abstract A047: Targeting androgen receptor decreases proliferation of triple-negative breast cancer," *Molecular Cancer Research*, 2013, 11(10 Suppl):Abstract nr A047.
Barton, V., et al., "Abstract OR38-2: Targeting Androgen Receptor Decreases Proliferation and Invasion in Preclinical Models of Triple Negative Breast Cancer," Therapies for Cancer, Endocrine Society's 96th Annual Meeting and Expo, Jun. 21-24, 2014, Chicago.
Barton, V., et al., "Androgen Receptor Biology in Triple Negative Breast Cancer: a Case for Classification as AR+ or Quadruple Negative Disease," *Horm. Canc.*, 2015, 6:206-213. doi: 10.1007/s12672-015-0232-3.
Barton, V., et al., "Abstract P3-04-02: Multiple subtypes of triple negative breast cancer are dependent on androgen receptor," *Cancer Res.*, 2015, 75(9 Suppl): Abstract nr P3-04-02.
Gordon, M., et al., "Abstract P6-03-07: Targeting multiple pathways in breast cancer: Androgen receptor, HER2, and mTOR," *Cancer Research*, 2015, 75(9 Suppl): Abstract nr P6-03-07, available at: http://cancerres.aacrjournals.org/content/75/9_Supplement/P6-03-07.
Gordon, M., et al., "Abstract SAT-312: The Anti-Androgen Enzalutamide Synergizes with Trastuzumab and Everolimus to Inhibit Breast Cancer Growth Via Distinct Mechanisms," Biomarkers and Hormone-Dependent Cancers, Endocrine Society's 97th Annual Meeting and Expo, Mar. 5-8, 2015, San Diego, 2 pgs.
Barton, V., et al., "Anti-androgen therapy in triple-negative breast cancer," *Ther. Adv. Med. Oncol.*, 2016, 8(4):305-308. doi: 10.1177/1758834016646735.
Notice of Allowance and Notice of Allowability, including Reasons for Allowance, for U.S. Appl. No. 15/373,914, dated Aug. 16, 2017.
Original and Allowed Claims from U.S. Appl. No. 15/373,914, filed Dec. 9, 2016.
Tibshirani, R., et al., "Diagnosis of multiple cancer types by shrunken centroids of gene expression," *PNAS*, 2002, 99(10):6567-6572.
Amendment Accompanying Request for Continued Examination filed Jun. 24, 2016 in U.S. Appl. No. 14/236,036 now U.S. Pat. No. 9,517,229.
Notice of Allowance and Notice of Allowability, including Reasons for Allowance, for U.S. Appl. No. 14/236,036, now U.S. Pat. No. 9,517,229, dated Aug. 19, 2016.
Richer, J., et al., "The Role of Androgen Receptors in Postmenopausal Breast Cancer" [Abstract], presented at the Department of Defense Era of Hope Conference, Aug. 2-5, 2011, available online Jul. 26, 2011.
Preliminary Amendment filed Jan. 29, 2014 in U.S. Appl. No. 14/236,036, now U.S. Pat. No. 9,517,229.
Response to Office Action filed Nov. 20, 2015 in U.S. Appl. No. 14/236,036, now U.S. Pat. No. 9,517,229.
Chacón, R., et al., "Triple-negative breast cancer," *Breast Cancer Research*, 2010, 12(2 Suppl): S3.
The Cancer Genome Atlas Network, "Comprehensive molecular portraits of human breast tumours," *Nature*, 2012, 490:61-70.
Bullard, J., et al., "Evaluation of statistical methods for normalization and differential expression in mRNA-Seq experiments," *BMC Bioinformatics*, 2010, 11:94.
Wang, K., et al., "MapSplice: Accurate mapping of RNA-seq reads for splice junction discovery," *Nucleic Acids Research*, 2010, 38(18). doi: 10.1093/nar/gkq622.
Carey, L., et al., "TBCRC 001: Randomized Phase II Study of Cetuximab in Combination with Carboplatin in Stage IV Triple-Negative Breast Cancer," *Journal of Clinical Oncology*, 2012, 30(21):2615-2623.
Von Minckwitz, G., et al., "Bevacizumab plus chemotherapy versus chemotherapy alone as second-line treatment for patients with HER2-negative locally recurrent or metastatic breast cancer after first-line treatment with bevacizumab plus chemotherapy (TANIA): an open-label, randomised phase 3 trial," *Lancet Oncology*, 2014, 15:1269-1278.
Carey, L. A., et al., "TBCRC 001: EGFR inhibition with cetuximab added to carboplatin in metastatic triple-negative (basal-like) breast cancer," *Journal of Clinical Oncology*, 2008, 26(15 Suppl):1009.
Gerratana, L., et al., "Pattern of metastasis and outcome in patients with breast cancer," *Clin. Exp. Metastasis*, 2015, 32:125-133.
Hänzelmann, S., et al., "GSVA: gene set variation analysis for microarray and RNA-Seq data," *BMC Bioinformatics*, 2013, 14:7.
Hatzis, C., et al., "Effects of Tissue Handling on RNA Integrity and Microarray Measurements From Resected Breast Cancers," *J. Nat'l Cancer Inst.*, 2011, 103(24):1871-1883.
Hoadley, K., et al., "Multiplatform Analysis of 12 Cancer Types Reveals Molecular Classification within and across Tissues of Origin," *Cell*, 2014, 158:929-944.
Kassam, F., et al., "Survival Outcomes for Patients with Metastatic Triple-Negative Breast Cancer: Implications for Clinical Practice and Trial Design," *Clinical Breast Cancer*, 2009, 9(1):29-33.
Kast, K., et al., "Impact of breast cancer subtypes and patterns of metastasis on outcome," *Breast Cancer Res. Treat.*, 2015, 150:621-629.
Loibl, S., et al., "Androgen receptor expression in primary breast cancer and its predictive and prognostic value in patients treated with neoadjuvant chemotherapy," *Breast Cancer Res. Treat.*, 2011, 130:477-487.
Miller, K., et al., "Abstract P3-07-25: Improved clinical outcomes on enzalutamide observed in patients with PREDICT AR+ triple-negative breast cancer: prognosis or prediction?," *Cancer Research*, 2016, 76(4 Suppl):Abstract nr P3-07-25.
Twelves, C., et al., "Clinical Roundtable Monograph: Effective Management of Quality of Life in Metastatic Breast Cancer," *Clinical Advances in Hematology & Oncology*, 2014, 12(2 Suppl 4):1-16.
Prat, A., et al., "A PAM50-Based Chemoendocrine Score for Hormone Receptor-Positive Breast Cancer with an Intermediate Risk of Relapse," *Clin. Cancer Res.*, 2017, 23(12):3035-3045.
Schneider, B., et al., "Triple-Negative Breast Cancer: Risk Factors to Potential Targets," *Clin. Cancer Res.*, 2008, 14(24):8010-8018.
Nielsen, T., et al., "A Comparison of PAM50 Intrinsic Subtyping with Immunohistochemistry and Clinical Prognostic Factors in Tamoxifen-Treated Estrogen Receptor-Positive Breast Cancer," *Clin. Cancer Res.*, 2010, 16(21):5222-5232.
O'Shaughnessy, J., et al., "Iniparib plus Chemotherapy in Metastatic Triple-Negative Breast Cancer," *The New England Journal of Medicine*, 2011, 364(3):205-214.
Prat, A., et al., "Molecular Characterization of Basal-Like and Non-Basal-Like Triple-Negative Breast Cancer," *The Oncologist*, 2013, 18:123-133.
Rodriguez, A., et al., "A randomized, parallel-arm, phase II trial to assess the efficacy of preoperative ixabepilone with or without cetuximab in patients with triple-negative breast cancer (TNBC)," *Journal of Clinical Oncology*, 2014, 32(15 Suppl):1133.
Storey, J., et al., "Statistical significance for genomewide studies," *PNAS*, 2003, 100(16):9440-9445.
Thomas, E., et al., "Ixabepilone Plus Capecitabine for Metastatic Breast Cancer Progressing After Anthracycline and Taxane Treatment," *Journal of Clinical Oncology*, 2007, 25(33):5210-5217.
Traina, T., et al., "Enzalutamide for the Treatment of Androgen Receptor-Expressing Triple-Negative Breast Cancer," *Journal of Clinical Oncology*, 2018, 36:1-9.
U.S. Office Action that issued in U.S. Appl. No. 15/373,914, dated Feb. 16, 2018.
Zhang, J., et al., "Novel therapeutic strategies for patients with triple-negative breast cancer," *OncoTargets and Therapy*, 2016, 9:6519-6528.
Wu, Y., et al., "Androgen Receptor-mTor Crosstalk is Regulated by Testosterone Availability: Implication for Prostate Cancer Cell Survival," *Anticancer Res.*, 2010, 30(10):3895-3901.

(56) References Cited

OTHER PUBLICATIONS

Thakkar, A., et al., "Vitamin D and androgen receptor-targeted therapy for triple-negative breast cancer," *Breast Cancer Res. Treat.*, 2016, 157:77-90.
Tentler, J., et al., "Patient-derived tumour xenografts as models for oncology drug development," *Nat. Rev. Clin. Oncol.*, 2012, 9(6):338-350.
Takayama, K., et al., "TET2 repression by androgen hormone regulates global hydroxymethylation status and prostate cancer progression," *Nature Comm.*, 2015, 6(8219).
Lehmann, B., et al., "Identification of human triple-negative breast cancer subtypes and preclinical models for selection of targeted therapies," *Journal of Clinical Investigation*, 2011, 121(7):2750-2767.
Sun, T., et al., "The role of microRNA-221 and -222 in Androgen-independent Prostate Cancer Cell lines," *Cancer Res.*, 2009, 69(8):3356-3363.
Saha, P., et al., "Concepts and targets in triple-negative breast cancer: recent results and clinical implications," *Therapeutic Advances in Medical Oncology*, 2016, 8(5):351-359.
Ricciardi, G., et al., "Androgen Receptor (AR), E-Cadherin, and Ki-67 as Emerging Targets and Novel Prognostic Markers in Triple-Negative Breast Cancer (TNBC) Patients," *PLOS One*, 2015, 10(6).
Rampurwala, M., et al., "Role of the Androgen Receptor in Triple-Negative Breast Cancer," *Clinical Advances in Hematology and Oncology*, 2016, 14(3):186-193.
Phipps, A., et al., "Body size and risk of luminal, HER2-overexpressing, and triple-negative breast cancer in postmenopausal women," *Cancer Epidemiol. Biomarkers Prev.*, 2008, 17(8):2078-2086.
Palma, G., et al., "Triple negative breast cancer: looking for the missing link between biology and treatments," *Oncotarget*, 2015, 6(29):26560-26574.
Niemeier, L., et al., "Androgen receptor in breast cancer: expression in estrogen receptor-positive tumors and in estrogen receptor-negative tumors with apocrine differentiation," *Modern Pathology*, 2010, 23:205-212.
Narayanan, R., et al., "Androgen Receptor: A Complex Therapeutic Target for Breast Cancer," *Cancers*, 2016, 8(12):108.
Mizokami, A., et al., "Prostate cancer stromal cells and LNCaP cells coordinately activate the androgen receptor through synthesis of testosterone and dihydrotestosterone from dehydroepiandrosterone," *Endocrine-Related Cancer*, 2009, 16:1139-1155.
Masiello, D., et al., "Bicalutamide Functions as an Androgen Receptor Antagonist by Assembly of a Transcriptionally Inactive Receptor," *Journal of Biological Chemistry*, 2002, 277(29):26321-26326.
Mancini, P., et al., "Standard of Care and Promising New Agents for Triple Negative Metastatic Breast Cancer," *Cancers*, 2014, 6:2187-2223.
Levine, D., et al., "A phase II evaluation of goserelin and bicalutamide in patients with ovarian cancer in second or higher complete clinical disease remission," *Cancer*, 2007, 110(11):2448-2456. Abstract Only.
Jiang, H., et al., "Androgen receptor expression predicts different clinical outcomes for breast cancer patients stratified by hormone receptor status," *Oncotarget*, 2016, 7(27):41285-41293.
Isakoff, S., "Triple Negative Breast Cancer: Role of Specific Chemotherapy Agents," *Cancer J.*, 2010, 16(1):53-61.
Ieni, A., et al., "Prognostic value of androgen receptor expression in triple negative breast carcinomas: personal experience and comments on a review about 'Triple-negative breast cancer: treatment challenges and solutions' by Collignon et al," *Breast Cancer—Targets and Therapy*, 2016, 8:157-159.
Gonzalez-Angulo, A., et al., "Metformin: A Therapeutic Opportunity in Breast Cancer," *Clin. Cancer Res.*, 2010, 16(6):1695-1700.
Foulkes, W., et al., "Triple-Negative Breast Cancer," *The New England Journal of Medicine*, 2010, 363(20):1938-1948.
Farla, P., et al., "Antiandrogens prevent stable DNA-binding of the androgen receptor," *Journal of Cell Science*, 2005, 118:4187-4198.
De Ruijter, T., et al., "Characteristics of triple-negative breast cancer," *J. Cancer Res. Clin. Oncol.*, 2011, 137:183-192.
De Leon, J., et al., "Targeting the regulation of androgen receptor signaling by the heat shock protein 90 cochaperone FKBP52 in prostate cancer cells," *Proc. Nat'l Academy of Science*, 2011, 108(29):11878-11883.
Davis, S. L., et al., "Triple-negative breast cancer: bridging the gap from cancer genomics to predictive biomarkers," *Ther. Adv. Med. Oncol.*, 2014, 6(3):88-100.
Cummings, S., et al., "Serum Estradiol Level and Risk of Breast Cancer During Treatment with Raloxifene," *JAMA*, 2002, 287(2):216-220.
Collignon, J., et al., "Triple-negative breast cancer: treatment challenges and solutions," *Breast Cancer Targets and Therapy*, 2016, 8:93-107.
Choi, Y., et al., "Triple-negative, basal-like, and quintuple-negative breast cancers: better prediction model for survival," *BMC Cancer*, 2010, 10:507.
Carey, L., et al., "Triple-negative breast cancer: disease entity or title of convenience?," *Nat. Rev. Clin. Oncol.*, 2010, 7(12):683-692. Abstract only.
Asano, Y., et al., "Expression and Clinical Significance of Androgen Receptor in Triple-Negative Breast Cancer," *Cancers*, 2017, 9(1), 4.
"Different subtypes of triple-negative breast cancer respond to different therapies," *eScience News*, 2011, 2 pages.
Anders, C., et al., "Understanding and Treating Triple-Negative Breast Cancer," *Oncology* (Williston Park), 2008, 22(11):1233-1243.
Anders, C., et al., "Biology, Metastatic Patterns, and Treatment of Patients with Triple-Negative Breast Cancer," *Clin. Breast Cancer*, 2009, 9(2 Suppl):S73-S81.
Adam, R., et al., "Heparin-Binding Epidermal Growth Factor-Like Growth Factor Stimulates Androgen-Independent Prostate Tumor Growth and Antagonizes Androgen Receptor Function," *Endocrinology*, 2002, 143(12):4599-4608.
Abstracts, Royal College of Radiologists Breast Group Annual Scientific Meeting, Brighton, UK, Nov. 1-2, 2010, *Breast Cancer Research*, 2010, 12(3 Suppl):S1-S16.
Abramson, V., et al., "Subtyping of triple-negative breast cancer: implications for therapy," *Cancer*, 2015, 121(1):8-16.
Amiri-Kordestani, L., et al., "Association of clinical benefit rate (CBR) with survival: A pooled-analysis of metastatic breast cancer (MBC) trials submitted to the U.S. Food and Drug Administration (FDA)," *J. Clin. Oncol.*, 2016, 34(15 Suppl):Abstract.
Vera-Badillo, F., et al., "Androgen Receptor Expression and Outcomes in Early Breast Cancer: A Systematic Review and Meta-Analysis," *J. Nat'l Cancer Inst.*, 2014, 106(1):djt319.
Krop, I., et al., "Abstract GS4-07: Results from a randomized placebo-controlled phase 2 trial evaluating exemestane ± enzalutamide in patients with hormone receptor-positive breast cancer," Proceedings of the 2017 San Antonio Breast Cancer Symposium, Dec. 5-9, 2017, San Antonio, TX; Cancer Res., 2018, 78(4 Suppl):Abstract nr GS4-07.
Ramos, C., et al., "Androgen receptor (AR) activation in breast cancer (BC) liver metastases," *J. Clin. Oncol.*, 2017, 35(15 Suppl):11619.
Kumar, V., et al., "Androgen Receptor Immunohistochemistry as a Companion Diagnostic Approach to Predict Clinical Response to Enzalutamide in Triple-Negative Breast Cancer," *JCO Precision Oncology*, 2017, 1:1-19. doi: 10.1200/PO.17.00075.
Hammond, M. E., et al., "American Society of Clinical Oncology/College of American Pathologists Guideline Recommendations for Immunohistochemical Testing of Estrogen and Progesterone Receptors in Breast Cancer," *J. Clin. Oncol.*, 2010, 28(16):2784-2795.
Traina, T., et al., "Overall survival (OS) in patients (Pts) with diagnostic positive (Dx+) breast cancer: Subgroup analysis from a phase 2 study of enzalutamide (ENZA), an androgen receptor (AR) inhibitor, in AR+ triple-negative breast cancer (TNBC) treated with 0-1 prior lines of therapy," *J. Clin. Oncol.*, 2017, 35(15 Suppl):1089.
European Office Action for EP Patent Application No. 15 831 013.6-1111, dated Apr. 4, 2018.

(56) References Cited

OTHER PUBLICATIONS

Farmer, P., et al., "Identification of molecular apocrine breast tumours by microarray analysis," *Oncogene*, 2005, 24:4660-4671.
International Search Report and Written Opinion from the EPO in PCT/US2015/064500 dated Apr. 26, 2016, 13 pages.
Traina, T., et al., "Stage 1 results from MDV3100-11: A 2-stage study of enzalutamide (ENZA), an androgen receptor (AR) inhibitor, in advanced AR+ triple-negative breast cancer (TNBC)," SABCS 2014 San Antonio Breast Cancer Symposium, P5-19-09, p. 1130, retrieved from: https://www.sabcs.org/Portals/SABCS2016/Documents/2014SABCSCall4Abstracts.pdf.
Mrklic, I., et al., "Expression of androgen receptors in triple negative breast carcinomas," *ACTA Histochemica*, 2013, 115(4):344-348.
Fioretti, F., et al., "Revising the role of the androgen receptor in breast cancer," *Journal of Molecular Endocrinology*, 2014, 52(3):R257-R265.
Sundem, G., "Study Shows Anti-Androgen Receptor Therapy for Triple-Negative Breast Cancer May Benefit More Than Just High-Androgen Receptor Tumors," Colorado Cancer Blogs, Jun. 23, 2014, retrieved from: http://www.coloradocancerblogs.org/study-shows-anti-androgen-receptor-therapy-triple-negative-breast-cancer-may-benefit-just-high-androgen-receptor-tumors/ [retrieved on Mar. 24, 2016].
Thike, A., et al., "Loss of androgen receptor expression predicts early recurrence in triple-negative and basal-like breast cancer," *Modern Pathology*, 2014, 27(3):352-360.
Cheang, M., et al., "Basal-Like Breast Cancer Defined by Five Biomarkers Has Superior Prognostic Value than Triple-Negative Phenotype," *Clinical Cancer Research*, 2008, 14(5):1368-1376.
Notice of Opposition filed against European Patent No. 2739153, dated May 21, 2019.
Cochrane, D.R., et al., "The Role of Androgen Receptor in Postmenopausal Breast Cancer," *Endocrine Reviews*, 2011, 32(Suppl.): Abstract No. P1-47. doi: 10.1093/edrv/32.supp.1.
Higano, C., et al., "Antitumor Activity of MDV3100 in Pre- and Post-Docetaxel Advanced Prostate Cancer: Long-Term Follow-Up of the Phase 1-2 Study," American Society of Clinical Oncology Genitourinary Cancers Symposium, Feb. 17-19, 2011.
Jung, M., et al., "Structure-Activity Relationship for Thiohydantoin Androgen Receptor Antagonists for Castration-Resistant Prostate Cancer (CRPC)," *J. Med. Chem.*, 2010, 53(7):2779-2796.
Naderi, A., et al., "Synergy between inhibitors of androgen receptor and MEK has therapeutic implications in estrogen receptor-negative breast cancer," *Breast Cancer Research*, 2011, 13:R36.
Risbridger, G., et al., "Breast and prostate cancer: more similar than different," *Nature Reviews*, 2010, 10:205-212.
Tran, C., et al., "Development of a Second-Generation Antiandrogen for Treatment of Advanced Prostate Cancer," *Science*, 2009, 324(5928):787-790.
European Search Report for EP Patent Application No. 19192143.6, dated Dec. 18, 2019.
Japanese Office Action for JP Patent Application No. 2017-531209, dispatched Jan. 27, 2020.
Ahmad, N., et al., "Steroid hormone receptors in cancer development: A target for cancer therapeutics," *Cancer Letters*, 2011, 300: 1-9.
"Bicalutamide for the Treatment of Androgen Receptor Positive (AR(+)), Estrogen Receptor Negative, Progesterone Receptor Negative (ER(−)/PR(−)) Metastatic Breast Cancer Patients: A Phase II Feasibility Study," available at: http://abstract.asco.org/AbstView_114_94715.html, 11 pages, last full review May 25, 2012.
Badve, S., et al., "Basal-like and triple-negative breast cancers: a critical review with an emphasis on the implications for pathologists and oncologists," *Modern Pathology*, 2011, 24: 157-167.
Barton, V., et al., "Androgen Receptor Supports an Anchorage-Independent, Cancer Stem Cell-like Population in Triple-Negative Breast Cancer," *Cancer Res.*, 2017, 77(13): 3455-3466.
Belikov, S., et al., FoxA1 corrupts the antiandrogenic effect of bicalutamide but only weakly attenuates the effect of MDV3100 (Enzalutamide™M), *Mol. Cell. Endocrinol.*, 2013, 365: 95-107.
Bernales, S., et al., "Effect of MDV3100, a novel androgen receptor signaling inhibitor, on cell proliferation and tumor size in an apocrine breast cancer xenograft model," *J. Clin. Oncol.*, 2012, 30(15 Suppl): 3072. Abstract.
Berrada, N., et al., "Treatment of triple-negative metastatic breast cancer: toward individualized targeted treatments or chemosensitization," *Annals Oncol.*, 2010, 21(7 Suppl): vii30-vii35.
Bertucci, F., "Basal Breast Cancer," *Cancer & Chemotherapy Rev.*, 2010, 5: 3-10.
Bhattacharya, S., et al., "Development of enzalutamide for metastatic castration-resistant prostate cancer," *Ann. N.Y. Acad. Sci.*, 2015, 1358: 13-27.
Bosch, A., et al., "Triple-negative breast cancer: Molecular features, pathogenesis, treatment and current lines of research," *Cancer Treatment Reviews*, 2010, 36: 206-215.
Bouchalova, K., et al., "Triple Negative Breast Cancer—Current Status and Prospective Targeted Treatment Based on HER1 (EGFR), TOP2A and C-MYC Gene Assessment," *Biomed. Pap. Med. Fac. Univ. Palacky Olomouc Czech Repub.*, 2009, 153(1): 13-18.
Burness, M., et al., "Epidermal Growth Factor Receptor in Triple-Negative and Basal-Like Breast Cancer: Promising Clinical Target or Only a Marker?" *Cancer J.*, 2010, 16(1):23-32.
Cadoo, K., et al., "Advances in Molecular and Clinical Subtyping of Breast Cancer and Their Implications for Therapy," *Surg. Oncol. Clin. N. Am.*, 2013, 22: 823-840.
Carotenuto, P., et al., "Triple Negative Breast Cancer: From Molecular Portrait to Therapeutic Intervention," *Critical Reviews™ in Eukaryotic Gene Expression*, 2010, 20(1): 17-34.
Carvalho, F., et al., "Triple-negative breast carcinomas are a heterogeneous entity that differs between young and old patients," *Clinics*, 2010, 65(10): 1033-1036.
Castan, J. C., et al., "Stage 1 results from MDV3100-11: A 2-stage study of enzalutamide (ENZA), an androgen receptor (AR) inhibitor, in advanced AR+ triple-negative breast cancer (TNBC)," *Annals of Oncology*, 2015, 26(3 Suppl): iii6-iii9.
Chacón, R., et al., "Triple-negative breast cancer," *Breast Cancer Res.*, 2010, 12(2 Suppl): S3.
Chen, Y., et al., "Anti-androgens and androgen-deleting therapies in prostate cancer: new agents for an established target," *Lancet Oncol.*, 2009, 10: 981-991.
Chia, K., et al., "Non-canonical AR activity facilitates endocrine resistance in breast cancer," *Endocrine-Related Cancer*, 2019, 26(2): 251-264.
Christenson, J., et al., "MMTV-PyMT and Derived Met-1 Mouse Mammary Tumor Cells as Models for Studying the Role of the Androgen Receptor in Triple-Negative Breast Cancer Progression," *Horm. Canc.*, 2017, 8: 69-77.
Clarke, B., et al., "Modulators of Androgen and Estrogen Receptor Activity," *Crit. Rev. in Eukaryotic Gene Expression*, 2010, 20(4): 275-294.
Clarke, B., et al.,"New selective estrogen and androgen receptor modulators," *Curr. Opinion in Rheumatology*, 2009, 21: 374-379.
Cleere, D., "Triple-negative breast cancer: a clinical update," *Commun. Oncol.*, 2010, 7(5): 203-211.
Cochrane, D., et al., "Abstract LB-109: MDV3100, an androgen receptor signaling inhibitor, inhibits tumor growth in breast cancer preclinical models regardless of estrogen receptor status," Proceedings: AACR 103rd Annual Meeting, Mar. 31-Apr. 4, 2012, Chicago, IL; *Cancer Res.*, 2012, 72(8 Suppl): Abstract nr LB-109.
Constantinidou, A., et al., "Beyond triple-negative breast cancer: the need to define new subtypes," *Expert Rev. Anticancer Ther.*, 2010, 10(8): 1197-1213.
Conzen, S., "Nuclear Receptors and Breast Cancer," *Mol. Endocrinol.*, 2008, 22(10): 2215-2228.
Cortes, J., et al., "Overall survival (OS) from the phase 2 study of enzalutamide (ENZA), an androgen receptor (AR) signaling inhibitor, in AR+ advanced triple-negative breast cancer (aTNBC)," *Eur. J. Cancer*, 2015, 51(3 Suppl): S265.
D'Amato, N., et al., "Cooperative Dynamics of AR and ER Activity in Breast Cancer," *Mol. Cancer Res.*, 2016, 14(11): 1054-1067.

(56) References Cited

OTHER PUBLICATIONS

D'Amato, N., et al., "Targeting Androgen Receptor in Her2-Driven Breast Cancer," Presentation OR07-4, Jun. 15, 2013.
Dawood, S., "Triple-Negative Breast Cancer: Epidemiology and Management Options," *Drugs*, 2010, 70(17): 2247-2258.
Dawson, S.J., et al., "Triple negative breast cancers: Clinical and prognostic implications," *Eur. J. Cancer*, 2009, 45(1 Suppl): 27-40.
De Laurentiis, M., et al., "Treatment of triple negative breast cancer (TNBC): current options and future perspectives," *Cancer Treatment Reviews*, 2010, 36S3: S80-S86.
Dimitrakakis, C., "Androgens and Breast Cancer in Men and Women," *Endocrinol. Metab. Clin. N. Am.*, 2011, 40: 533-547.
Dizdar, O., et al., "Current and emerging treatment options in triple-negative breast cancer," *Oncol. Rev.*, 2010, 4: 5-13.
Elias, A., et al., "Effect of MDV3100, an androgen receptor signaling inhibitor, on tumor growth of estrogen and androgen receptor-positive (ER+/AR+) breast cancer xenografts," *J. Clin. Oncol.*, 2012, 30(15 Suppl): 564-564.
Elias, A.D., et al., "Abstract P1-16-05: MDV3100-08: A phase 1 study evaluating the safety and pharmacokinetics of enzalutamide plus fulvestrant in women with advanced hormone receptor-positive breast cancer," Proceedings of the Thirty-Eighth Annual CTRC-AACR San Antonio Breast Cancer Symposium, Dec. 8-12, 2015, San Antonio, TX; *Cancer Res.*, 2016, 76(4 Suppl): Abstract nr P1-16-05.
Elias, A., "Triple-Negative Breast Cancer: A Short Review," *Am. J. Clin. Oncol.*, 2010, 33(6): 637-645.
Ellis, P., "Recent advances in systemic therapy for breast cancer: new technologies for a new era," *Breast Cancer Res.*, 2009, 11(4): 107.
Elsawaf, Z., et al., "Triple-Negative Breast Cancer: Clinical and Histological Correlations," *Breast Care*, 2011, 6: 273-278.
Feng, J., et al., "Androgen and AR contribute to breast cancer development and metastasis: an insight of mechanisms," *Oncogene*, 2017, 36: 2775-2790.
Folkerd, E., et al., "Influence of Sex Hormones on Cancer Progression," *J. Clin. Oncol.*, 2010, 28: 4038-4044.
Further Submissions, Opposition to EP 2739153, dated Dec. 16, 2019, 10 pages.
Garay, J., et al., "The growth response to androgen receptor signaling in Erα-negative human breast cells is dependent on p21 and mediated by MAPK activation," *Breast Cancer Research*, 2012, 14: R27.
Gluz, O., et al., "Triple-negative breast cancer—current status and future directions," *Annals of Oncol.*, 2009, 20(12): 1913-1927.
Goetz, M., et al., "Gene-Expression-Based Predictors for Breast Cancer," *N. Engl. J. Med.*, 2007, 356: 752-753.
Gordon, M., et al., "Synergy between Androgen Receptor Antagonism and Inhibition of mTOR and HER2 in Breast Cancer," *Mol. Cancer Ther.*, 2017, 16(7): 1389-1400.
Greenberg, S., et al., "Triple-Negative Breast Cancer: Role of Antiangiogenic Agents," *Cancer J.*, 2010, 16(1): 33-38.
Gucalp, A., et al., "Androgen Receptor-Positive, Triple-Negative Breast Cancer," *Cancer*, 2017, 123(10): 1686-1688.
Gucalp, A., et al., "Targeting the androgen receptor in triple-negative breast cancer," *Curr. Probl. Cancer*, 2016, 40: 141-50.
Gucalp, A., et al., "The Androgen Receptor in Breast Cancer: Biology and Treatment Considerations," *Curr. Breast Cancer Rep.*, 2012, 4: 56-65.
History of Changes for Study NCT00468715, "Bicalutamide in Treating Patients with Metastatic Breast Cancer," ClinicalTrials.gov archive, Apr. 3, 2019, 1-10.
Honma, N., et al., "Clinical importance of androgen receptor in breast cancer patients treated with adjuvant tamoxifen monotherapy," *Breast Cancer*, 2013, 20: 323-330.
Hurvitz, S., et al., "What's positive about 'triple-negative' breast cancer?" *Future Oncol.*, 2009, 5(7): 1015-1025.
Irshad, S., et al., "Molecular heterogeneity of triple-negative breast cancer and its clinical implications," *Curr. Op. Oncol.*, 2011, 23: 566-577.
Ismail-Khan, R., et al., "A Review of Triple-Negative Breast Cancer," *Cancer Control*, 2010, 17(3): 173-176.
Jordan, V.C., "A Century of Deciphering the Control Mechanisms of Sex Steroid Action in Breast and Prostate Cancer: The Origins of Targeted Therapy and Chemoprevention," *Cancer Res.*, 2009, 69: 1243-1254.
Kemppainen, J., et al., "Agonist and Antagonist Activities of Hydroxyflutamide and Casodex Relate to Androgen Receptor Stabilization," *Urology*, 1996, 48(1): 157-163.
Lee, S., et al., "Male Breast Cancer During Finasteride Therapy," *J. Natl. Cancer Inst.*, 2004, 96(4): 338-339.
Lehmann, B., et al., "PIK3CA mutations in androgen receptor-positive triple negative breast cancer confer sensitivity to the combination of PI3K and androgen receptor inhibitors," *Breast Cancer Res.*, 2014, 16: 406, 14 pages.
Lerma, E., et al., "Triple Negative Breast Carcinomas: Similarities and Differences With Basal Like Carcinomas," *Appl. Immunohistochem. Mol. Morphol.*, 2009, 17(6): 483-494.
Leung, J., et al., "Non-Genomic Actions of the Androgen Receptor in Prostate Cancer," *Frontiers in Endocrinology*, 2017, vol. 8, Article 2, 8 pages.
Liedtke, C., et al., "Current Issues of Targeted Therapy in Metastatic Triple-Negative Breast Cancer," *Breast Care*, 2011, 6: 234-239.
Ligresti, G., et al., "Breast cancer: Molecular basis and therapeutic strategies (Review)," *Mol. Med. Reports*, 2008, 1: 451-458.
Lu, H., et al., "Research progress in triple-negative breast cancer," *Chinese-German J. Clin. Oncol.*, 2010, 9(4): 239-242.
Lundin, K.B., et al., "Androgen receptor genotypes predict response to endocrine treatment in breast cancer patients," *Br. J. Cancer*, 2011, 105(11): 1676-1683 [Abstract only].
Lyons, T., et al., "Androgen Receptor-Targeted Therapy for Breast Cancer," *Curr. Breast Cancer Rep.*, 2017, 9: 242-250.
Ma, X., et al., "A two-gene expression ratio predicts clinical outcome in breast cancer patients treated with tamoxifen," *Cancer Cell*, 2004, 5: 607-616.
Maegawa, R., et al., "Triple-Negative Breast Cancer: Unique Biology and Its Management," *Cancer Investigation*, 2010, 28: 878-883.
Mina, A., et al., "Targeting the androgen receptor in triple-negative breast cancer: current perspectives," *OncoTargets and Therapy*, 2017, 10: 4675-4685.
O'Shaughnessy, J., "Improving Quality of Life in Patients With Metastatic Breast Cancer," *Clin. Adv. Hematol. Oncol.*, 2014, 12(2)(4 Suppl): 10-12.
Pal, S.K., et al., "Triple-negative breast cancer: Novel therapies and new directions," *Maturitas*, 2009, 63: 269-274.
Pal, S.K., et al., "Triple negative breast cancer: unmet medical needs," *Breast Cancer Res. Treat.*, 2011, 125: 627-636.
Park, S., et al., "Androgen receptor expression is significantly associated with better outcomes in estrogen receptor-positive breast cancers," *Annals of Oncol.*, 2011, 22(8): 1755-1762.
Response to Office Action filed Dec. 19, 2017, in U.S. Appl. No. 14/962,864, now U.S. Pat. No. 10,196,693.
Allowed Claims filed Dec. 8, 2015, in U.S. Appl. No. 14/962,864, now U.S. Pat. No. 10,196,693.
Non-Final Office Action dated Oct. 13, 2017, in U.S. Appl. No. 14/962,864, now U.S. Pat. No. 10,196,693.
Notice of Allowance dated Feb. 5, 2018, in U.S. Appl. No. 14/962,864, now U.S. Pat. No. 10,196,693.
Notice of Allowance dated Mar. 30, 2018, in U.S. Appl. No. 14/962,864, now U.S. Pat. No. 10,196,693.
Phan, V.T., et al., "Abstract P2-07-04: A novel diagnostic androgen receptor gene signature links clinical outcomes and preclinical response to enzalutamide, paclitaxel or the combination in triple-negative breast cancer," Proceedings of the Thirty-Eighth Annual CTRC-AACR San Antonio Breast Cancer Symposium, Dec. 8-12, 2015, San Antonio, TX; *Cancer Res.*, 2016, 76(4 Suppl): Abstract nr P2-07-04.
Proverbs-Singh, T., et al., "Targeting the androgen receptor in prostate and breast cancer: several new agents in development," *Endocrine-Related Cancer*, 2015, 22: R87-R106.
Response to Opposition filed Oct. 14, 2019, in EP 2739153.

(56) References Cited

OTHER PUBLICATIONS

Cochrane, D., et al., "The Role of Androgen Receptors in Post-menopausal Breast Cancer," poster presented at the Department of Defense Era of Hope Conference, Aug. 2-5, 2011.
Schwartzberg, L., et al., "A Phase I/Ib Study of Enzalutamide Alone and in Combination with Endocrine Therapies in Women with Advanced Breast Cancer," *Clin. Cancer Res.*, 2017, 23(15): 4046-4054.
Schwartzberg, L., et al., "Enzalutamide plus exemestane: A pilot study to assess safety, pharmacokinetics, and effects on circulating estrogens in women with advanced hormone-positive breast cancer," *J. Clin. Oncol.*, 2014, 32(15 Suppl): 545-545.
Schwartzberg, L., et al., "Enzalutamide plus exemestane: A pilot study to assess safety, pharmacokinetics, and effects on circulating estrogens in women with advanced hormone-positive breast cancer," poster presented May 30-Jun. 3, 2014.
Sgroi, D., et al., "RE: A two-gene expression ratio predicts clinical outcome in breast cancer patients treated with tamoxifen," *Cancer Cell*, 2004, 6: 445.
Shah, P., et al., "The role of the androgen receptor in triple-negative breast cancer," *Women's Health*, 2013, 9(4): 351-360.
Summons to Attend Oral Proceedings and Preliminary Opinion in Opposition to EP 2739153, dated Jan. 13, 2020.
Traina, T.A., et al., "Abstract OT3-2-08: A phase 2 single-arm study of the clinical activity and safety of enzalutamide in patients with advanced androgen receptor-positive triple-negative breast cancer," Proceedings of the Thirty-Sixth Annual CTRC-AACR San Antonio Breast Cancer Symposium, Dec. 10-14, 2013, San Antonio, TX; *Cancer Res.*, 2013, 73(24 Suppl): Abstract nr OT3-2-08.
Traina, T.A., et al., "Androgen Receptor Inhibition Can Stabilize Disease in Patients with Ar(+), ER(−)/PR(−) Metastatic Breast Cancer," *Annals of Oncol.*, 2009, 20(2 Suppl): ii63-ii64.
Trudeau, M., et al., "A phase 2 single-arm study to assess clinical activity, efficacy and safety of enzalutamide (ENZA) with trastuzumab in HER2+ AR+ metastatic or locally advanced breast cancer," *J. Clin. Oncol.*, 2017, 33(15 Suppl). doi: 10.1200/jco.2015.33.15_suppl.tps640.
Wellberg, E., et al., "The Androgen Receptor Supports Tumor Progression After the Loss of Ovarian Function in a Preclinical Model of Obesity and Breast Cancer," *Horm. Canc.*, 2017, 8(5-6): 269-285. doi: 10.1007/s12672-017-0302-9.
Yanagita, Y., et al., "Astellas' Drug Discovery Strategy: Focus on Oncology," *Jpn. J. Clin. Oncol.*, 2012, 42(4): 241-246.
Yardley, D.A., et al., "Abstract OT3-2-01: A phase 2 randomized, double-blind, placebo-controlled multicenter trial evaluating the efficacy and safety of enzalutamide in combination with exemestane in estrogen or progesterone receptor-positive and HER2 non-amplified advanced breast cancer," Proceedings of the Thirty-Sixth Annual CTRC-AACR San Antonio Breast Cancer Symposium Dec. 10-14, 2013, San Antonio, TX; *Cancer Res.*, 2013, 73(24 Suppl): Abstract nr OT3-2-01.
Zarif, J., et al., "The Importance of Non-Nuclear AR Signaling in Prostate Cancer Progression and Therapeutic Resistance," *Cell Signal*, 2016, 28(5): 348-356.
Extended European Search Report for EP 18190012.7, dated Dec. 20, 2018.
Extended European Search Report for EP 19187649.9, dated Jan. 16, 2020.
Bianchini, G., et al., "Triple-negative breast cancer: challenges and opportunities of a heterogeneous disease," *Nature Reviews Clinical Oncology*, 2016, 13: 674-690.
Caiazza, F., et al., "Preclinical evaluation of the AR inhibitor enzalutamide in triple-negative breast cancer cells," *Endocrine-Related Cancer*, 2016, 23: 323-334.
Giovannelli, P., et al., "The Androgen Receptor in Breast Cancer," *Frontiers in Endocrinology*, 2018, 9, Article 492.
Huang, R., et al., "Androgen Receptor Expression and Bicalutamide Antagonize Androgen Receptor Inhibit β-Catenin Transcription Complex in Estrogen Receptor-Negative Breast Cancer," *Cellular Physiol. Biochem.*, 2017, 43: 2212-2225.
Lehmann, B., et al., "Identification of human triple-negative breast cancer subtypes and preclinical models for selection of targeted therapies," *Journal of Clinical Investigation*, 2011, 121(7): 2750-2767 [Data Included].
European Office Action for EP Patent Application No. 19192143.6, dated Apr. 26, 2021.
Canadian Office Action for CA Patent Application No. 2,970,469, dated Jan. 5, 2022.
Notice of Allowance dated Jul. 26, 2023, in Canadian Patent Application No. 2,970,469.

* cited by examiner

METHOD FOR PREDICTING RESPONSE TO BREAST CANCER THERAPEUTIC AGENTS AND METHOD OF TREATMENT OF BREAST CANCER

CROSS-REFERENCE TO RELATED APPLICATIONS

This application is a continuation of U.S. patent application Ser. No. 16/215,340, filed Dec. 10, 2018, which is a continuation of co-pending U.S. patent application Ser. No. 14/962,864, filed Dec. 8, 2015, now U.S. Pat. No. 10,196,693, which claims the benefit of the following U.S. Provisional Applications, the entire disclosures of which are incorporated herein by reference: No. 62/091,195, filed Dec. 12, 2014; No. 62/142,504, filed Apr. 3, 2015; and No. 62/167,110, filed May 27, 2015.

SEQUENCE LISTING

The instant application contains a Sequence Listing which has been submitted in ASCII format via EFS-Web and is hereby incorporated by reference in its entirety. Said ASCII copy, created on Nov. 9, 2021, is named 212181-0001-02-US-000001-SL.txt and is 262,558 bytes in size.

FIELD OF THE INVENTION

The field relates to breast cancer therapy.

BACKGROUND OF THE INVENTION

Breast cancer is considered a genetically heterogeneous and biologically diverse disease. The long-recognized clinical and phenotypic differences have been shown to correlate with differences in gene expression. Previous studies of breast tumors have identified five distinct subtypes of breast carcinomas that are associated with different clinical outcomes: luminal A (estrogen receptor (ER)+); luminal B (ER+); HER2 overexpressing; normal breast-like; and basal-like. See, Perou et al. *Nature,* 406(6797):747-52 (2000); Sorlie et al. *PNAS,* 98(19):10869-74 (2001).

Analysis of breast cancer biopsy and surgical specimens typically includes an assessment of nuclear and cell surface receptors (ER, PgR, and HER2), gene amplification of HER2 (if HER2 analysis by immunohistochemistry (IHC) is not definitive), and other prognostic tests such as microvessel invasion and proliferation markers. Endocrine therapies that target ER signaling pathways for ER+ disease and HER2-targeted therapies for HER2+ disease play a critical role in the treatment of most patients with breast cancer. However, little progress has been made in identifying effective targeted therapies for patients whose disease lacks these receptors, i.e., the so-called "triple negative" breast cancers or "TNBC", and nonselective cytotoxic chemotherapy remains the primary therapeutic option.

The androgen receptor (AR) is the most commonly expressed nuclear hormone receptor in breast cancer, though its functional role in initiating or driving malignancy is not yet well understood. In a study of 3093 breast cancers, AR expression (10% or more nuclear staining by IHC) was observed in 77% of invasive breast tumors and across all molecular phenotypes (Collins et al., *Mod Pathol* 2011; 24(7):924-931). However, androgen receptor levels are not routinely assessed, since they have not been shown to predict responses to currently used therapies.

The use of AR inhibitors has been proposed as part of a therapeutic regimen for the treatment of breast cancer. See, e.g., Garay and Park, *Am. J. Cancer Res.* 2012; 2(4):434-445. Interest has been generated recently in the treatment of TNBC. Lack of expression of all three of estrogen receptor, progesterone receptor and HER2 predicts non-response to available endocrine (tamoxifen, aromatase inhibitors) and anti-HER2 (trastuzumab) targeted therapies. From 10 to 35% of such TNBC tumors express androgen receptor (Ogawa et al., *Int J. Oncol.* 2008; 13:431435), AR-targeted therapies may prove to be a valuable treatment for a large proportion of breast cancers, including triple negative cancers.

Despite the interest in androgen receptor signaling inhibition as a modality for the treatment of breast cancer, and in the treatment of TNBC in particular, there remains a need for predicting whether the individual patient will be responsive in advance of therapy. A test to predict the likelihood of whether or not a particular patient will respond to a therapy that inhibits androgen receptor signaling, and TNBC patients in particular, would be a valuable tool in planning patient treatment.

SUMMARY OF THE INVENTION

In one embodiment, provided is a method of screening a treatment for triple negative breast cancer comprising the use of an androgen receptor inhibitor, the method comprising assaying a biological sample obtained from a subject to determine whether the biological sample obtained from the subject is classified as basal-like subtype or another subtype. If the biological sample is classified as other than a basal-like subtype, the breast cancer treatment comprising an androgen receptor inhibitor is more likely to be effective than if the sample were classified as basal-like subtype.

Also provided is a method of screening for the likelihood of the effectiveness of a treatment for triple negative breast cancer comprising an androgen receptor inhibitor, in a subject in need of such treatment. The method comprises:

assaying a biological sample obtained from the subject to determine whether the biological sample is classified as a basal-like subtype or another subtype; and wherein if the biological sample is classified as other than a basal-like subtype, the breast cancer treatment comprising an androgen receptor inhibitor is more likely to be effective than if the sample were classified as basal-like subtype.

Also provided is a method of classifying a biological sample from a subject as an indicator of the likelihood of the effectiveness of a treatment of the patient for triple negative breast cancer, said treatment comprising an androgen receptor inhibitor, the method comprising:

assaying a biological sample obtained from the subject to determine whether the biological sample is classified as a basal-like subtype or another subtype; and wherein the biological sample classified as other than basal-like subtype indicates that the breast cancer treatment comprising an androgen receptor inhibitor is more likely to be effective than if the sample were classified as basal-like subtype.

In certain embodiments of the screening and classifying methods (collectively "the aforementioned methods"), assaying the biological sample to determine whether the biological sample is classified as a basal-like subtype or another subtype is performed by detecting the expression of the set of intrinsic genes listed in Table 1.

In certain embodiments of the aforementioned methods, the Basal Centroid classifier score of the sample is determined from the expression of the set of intrinsic genes listed in Table 1.

In one embodiment of the aforementioned methods, if the Basal Centroid classifier score is less than or equal to 0.9, the breast cancer treatment comprising an androgen receptor inhibitor is determined to be likely more effective in treating the subject than if the Basal Centroid classifier score is greater than 0.9. In another embodiment, if the Basal Centroid classifier score is less than or equal to 0.6, the breast cancer treatment comprising an androgen receptor inhibitor is determined to be likely more effective in treating the subject than if the Basal Centroid classifier score is greater than 0.6. In another embodiment, if the Basal Centroid classifier score is in the range from 0.2 to 0.8, the breast cancer treatment comprising an androgen receptor inhibitor is likely to be effective in treating the subject. In another embodiment, if the Basal Centroid classifier score is in the range from 0.4 to 0.7, the breast cancer treatment comprising an androgen receptor inhibitor is likely to be effective in treating the subject.

In certain embodiments of the aforementioned methods, the Basal Centroid classifier score and the Luminal A Centroid classifier score of the sample are determined from the expression of the set of intrinsic genes listed in Table 1. The methods further comprises calculating a Weighted Basal and Luminal A classifier score from the Basal Centroid classifier score and the Luminal A Centroid classifier score according to the following equation:

Weighted Basal and Luminal *A* classifier score=−0.25(Basal Centroid classifier score)+0.27(Luminal *A* Centroid classifier score)

wherein if the Weighted Basal and Luminal A classifier score is greater than −0.3, the breast cancer treatment comprising an androgen receptor inhibitor is more likely to be effective in the subject than if the Weighted Basal and Luminal A classifier score is less than or equal to −0,3. In another embodiment, if the Weighted Basal and Luminal A classifier score is greater than −0.2, the breast cancer treatment comprising an androgen receptor inhibitor is more likely to be effective in the subject than if the Weighted Basal and Luminal A classifier score is less than or equal to −0.2. In another embodiment, if the Weighted Basal and Luminal A classifier score is greater than −0.25, the breast cancer treatment comprising an androgen receptor inhibitor is more likely to be effective in the subject than if the Weighted Basal and Luminal A classifier score is less than or equal to −0.25.

In some embodiments, the equation for determining the Weighted Basal and Luminal A classifier score takes the form:

Weighted Basal and Luminal *A* classifier score=−0.2468275(Basal Centroid classifier score)+0.2667110(Luminal *A* Centroid classifier score)

In certain embodiments of the aforementioned methods, the breast cancer is characterized by the presence of androgen receptor-positive tumor cells.

In certain embodiments of the aforementioned methods, the biological sample is selected from the group consisting of a cell, tissue and bodily fluid. In certain embodiments, the body fluid is selected from the group consisting of blood, lymph, urine, saliva, fluid from ductal lavage and nipple aspirate. In some embodiments, the tissue is obtained from a biopsy.

In any of the aforementioned methods, an assay to determine the androgen receptor status of the cells of the sample, i.e. AR-positive vs. AR-negative, may be carried out.

Also provided is a method of treating triple negative breast cancer in a subject, said subject having a breast cancer comprising breast cancer cells that have been classified as other than basal-like subtype, said method comprising administering a breast cancer treatment to the subject comprising an androgen receptor inhibitor, thereby treating the triple negative breast cancer in the subject.

In one embodiment of the treatment method, the breast cancer cells of the subject are characterized by a Basal Centroid classifier score of less than or equal to 0.9, determined from the expression by said cells of the set of intrinsic genes listed in Table 1. In another embodiment of the treatment method, the breast cancer cells of the subject are characterized by a Basal Centroid classifier score of less than or equal to 0.6. In another embodiment of the treatment method, the breast cancer cells of the subject are characterized by a Basal Centroid classifier score in the range from 0.2 to 0.8. In another embodiment of the treatment method, the breast cancer cells of the subject are characterized by a Basal Centroid classifier score in the range from 0.4 to 0.7.

In another embodiment of the treatment method, the breast cancer cells of the subject are characterized by Weighted Basal and Luminal A classifier score greater than −0,3. In another embodiment of the treatment method, the breast cancer cells of the subject are characterized by a Weighted Basal and Luminal A classifier score greater than −0.2. In another embodiment of the treatment method, the breast cancer cells of the subject are characterized by a Weighted Basal and Luminal A classifier score greater than −0.25.

Also provided is a triple negative breast cancer treatment comprising an androgen receptor inhibitor for use in the treatment of a triple negative breast cancer in a subject in need thereof, wherein said method of treatment comprises: (a) assaying a biological sample from the subject to determine whether the biological sample is classified as basal-like subtype or another subtype; and (b) administering said triple negative breast cancer treatment to the subject if the biological sample is classified as other than basal-like subtype.

Also provided is a therapeutic agent for triple negative breast cancer therapy or treatment for use in a subject in need thereof, wherein said agent is an androgen receptor inhibitor, comprising: (a) assaying a biological sample from the subject to determine whether the biological sample is classified as basal-like subtype or another subtype; and (b) administering said agent to the subject if the biological sample is classified as other than basal-like subtype.

Also provided is an androgen receptor inhibitor for use in the treatment of a triple negative breast cancer in a subject wherein a biological sample from the subject has been assayed to determine whether sample is classified as basal-like subtype or another subtype.

Also provided is a method of treating triple negative breast cancer in a subject in need of such treatment comprising: (a) assaying the biological sample to determine whether the biological sample is classified as a basal-like subtype or another subtype; and (b) if the biological sample is classified as other than a basal-like subtype, administering a breast cancer treatment to the subject comprising an androgen receptor inhibitor, thereby treating the breast cancer in the subject.

In certain embodiments of the aforementioned methods of treatment, treatments and androgen receptor inhibitors for use in treatment, assaying the biological sample to determine whether the biological sample is classified as a basal-like subtype or another subtype is performed by detecting the expression of the intrinsic genes listed in Table 1.

In certain embodiments of the aforementioned methods of treatment, treatments and androgen receptor inhibitors for use in treatment, assaying the biological sample comprises determining the Basal Centroid classifier score of the sample from the expression of the set of intrinsic genes listed in Table 1, wherein the breast cancer treatment is administered if the Basal Centroid classifier score is less than or equal to 0.9. In one embodiment, the breast cancer treatment is administered if the Basal Centroid classifier score is less than or equal to 0.6. In one embodiment, the breast cancer treatment is administered if the Basal Centroid classifier score is in the range from 0.2 to 0.8. In another embodiment, the breast cancer treatment is administered if the Basal Centroid classifier score is in the range from 0.4 to 0.7.

In certain embodiments of the aforementioned methods of treatment, treatments and androgen receptor inhibitors for use in treatment, assaying the biological sample comprises determining the Basal Centroid classifier score and the Luminal A Centroid classifier score of the sample from the expression of the set of intrinsic genes listed in Table 1, and calculating a Weighted Basal and Luminal A classifier score, wherein the breast cancer treatment is administered to the subject if the Weighted Basal and Luminal A classifier score greater than −0.3. In one embodiment, the breast cancer treatment is administered if the Weighted Basal and Luminal A classifier score is greater than −0.2. In another embodiment, the breast cancer treatment is administered if the Weighted Basal and Luminal A classifier score is greater than −0.25.

In certain embodiments of the aforementioned methods of treatment, treatments and androgen receptor inhibitors for use in treatment, the breast cancer of the subject is further characterized by the presence of androgen receptor-positive tumor cells.

In embodiments of the aforementioned methods of treatment, treatments and androgen receptor inhibitors for use in treatment, the androgen receptor inhibitor is selected from the group consisting of enzalutamide, bicalutamide; flutamide; nilutamide, ARN509, ketoconazole, abiraterone acetate, VN/124-1 (TOK-001), orteronel (TAK-700), finasteride, galeterone, cyproterone acetate; andarine and combinations thereof. The list of androgen receptor inhibitor is exemplary and not meant to be limiting.

In certain embodiments, the androgen receptor inhibitor is enzalutamide. In once such embodiment, enzalutamide is orally administered once daily at a dose of 160 mg. In some embodiments, enzalutamide is administered as a single capsule comprising 160 mg enzalutamide. In other embodiments, enzalutamide is administered as four capsules, each capsule comprising 40 mg enzalutamide.

In embodiments of the aforementioned methods of treatment, treatments and androgen receptor inhibitors for use in treatment, the breast cancer treatment comprising an androgen receptor inhibitor further comprises one or more other anti-cancer agents that is not an androgen receptor inhibitor. Such other anti-cancer agents that are not androgen receptor inhibitors may be selected from the group consisting of cyclophosphamide, fluorouracil, 5-fluorouracil, methotrexate, thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, capecitabine, anastrozole, exemestane, letrozole, leuprolide, abareiix, buserlin, goserelin, megestroi acetate, risedronate, pamidronate, ibandronate, alendronate, denosumab, zoledronate, trastuzumab, tykerb or bevacizumab, and combinations thereof. The list of other anti-cancer agents is exemplary and not meant to be limiting.

In one embodiment, the non-AR inhibitor anticancer agent is paclitaxel. In another embodiment, the AR inhibitor is enzalutamide and the non-AR inhibitor anticancer agent is paclitaxel.

In certain embodiments, the treatment method comprises a step of testing the subject to determine whether the subject has a breast cancer comprising breast cancer cells that are other than basal-like subtype.

In certain embodiments, the treatment method comprises a step of testing the subject to determine the Basal Centroid classifier score of breast cancer cells of the subject.

In certain embodiments, the treatment method comprises a step of testing the subject to determine the Weighted Basal and Luminal A classifier score of breast cancer cells of the subject.

In some embodiments of the aforementioned methods of treatment, treatments and androgen receptor inhibitors for use in treatment, the subject has received zero or one rounds of prior treatment with an anti-cancer agent, other than an androgen receptor inhibitor, for treatment of triple negative breast cancer.

In embodiments of the aforementioned screening methods, classifying methods, treatment methods, treatments, and androgen receptor inhibitors for use in treatment, the biological sample may be selected from the group consisting of a cell, tissue and bodily fluid In certain embodiments, the body fluid is selected from the group consisting of blood, lymph, urine, saliva, fluid from ductal lavage and nipple aspirate. In some embodiments, the tissue is obtained from a biopsy.

In any of the aforementioned screening methods, classifying methods, treatment methods, treatments, and androgen receptor inhibitors for use in treatment, an assay to determine the androgen receptor status of the cells of the sample, i.e. AR-positive vs. AR-negative, may be carried out.

As envisioned in the present invention with respect to the disclosed compositions of matter and methods, in one aspect the embodiments of the invention comprise the components and/or steps disclosed herein. In another aspect, the embodiments of the invention consist essentially of the components and/or steps disclosed herein. In yet another aspect, the embodiments of the invention consist of the components and/or steps disclosed herein.

Definitions

The articles "a" and "an" are used herein to refer to one or to more than one i.e. to at least one) of the grammatical object of the article. By way of example, "an element" means one element or more than one elements.

"About" will be understood by persons of ordinary skill in the art and will vary to some extent depending on the context in which it is used. As used herein, "about" is meant to encompass variations of ±20% or ±10%, more preferably ±5%, even more preferably ±1%, and still more preferably ±0.1%.

"Androgen receptor inhibitor" means a compound or molecule that directly or indirectly inhibits the androgen receptor (AR) signaling pathway. In one embodiment, direct inhibitors of the AR receptor include enzalutamide, bicalutamide (Casodex), flutamide, nilutamide, ARN509 and the like. In another embodiment, indirect inhibitors of AR include Cyp 17 inhibitors such as ketoconazole, abiraterone acetate, VN/124-1 (TOK-001), orteronel (TAK-700) and the like. In another embodiment, AR inhibitors include finasteride, galeterone, cyproterone acetate, and andarine, and the like.

By "detecting expression" is intended determining the quantity or presence of an RNA transcript or its expression product of an intrinsic gene.

By "inhibit" or other forms of inhibit means to hinder or restrain a particular characteristic. It is understood that this is typically in relation to some standard or expected value, in other words it is relative, but that it is not always necessary for the standard or relative value.

As used throughout, by a "subject" is meant an individual, typically a mammal or fowl. Mammals can include, for example, domesticated animals (e.g., cat or dog), livestock (e.g., cattle, horses, pigs, sheep, goats, etc.), laboratory animals (e.g., mouse, rabbit, rat, guinea pig, etc.) and primates. Preferably, the mammal is a human being.

"Triple negative breast cancer" or "TNBC" refers to any breast cancer that does not express the genes for estrogen receptor (ER), progesterone receptor (PR) and Her2/neu. The term includes primary epithelial TNBCs, as well as TNBC that involved with other tumors. The cancer can include a triple negative carcinoma of the breast, ductal carcinoma of the breast, lobular carcinoma of the breast, undifferentiated carcinoma of the breast, cystosarcoma phyllodes of the breast, angiosarcoma of the breast, and primary lymphoma of the breast. TNBC can also include any stage of triple negative breast cancer, and can include breast neoplasms having histologic and ultrastructural heterogeneity (e.g., mixed cell types).

"A TNBC treatment comprising androgen receptor inhibitor" is a TNBC treatment that includes administration of an androgen receptor inhibitor. The treatment may include other anti-cancer or chemotherapeutic agents.

A subject "in need of" treatment for TNBC is a subject having TNBC or presenting with one or more symptoms of TNBC, or a subject having an increased risk of developing TNBC relative to the population at large. Preferably, a subject "in need" of treatment for TNBC is a subject who is afflicted with TNBC.

As used herein, "therapeutically effective amount" or "therapeutically effective dose" refers to an agent, compound, material, or composition containing a compound that is at least sufficient to produce a therapeutic effect. An effective amount is the quantity of a therapeutic agent necessary for preventing, curing, ameliorating, arresting or partially, arresting a symptom of a disease or disorder.

"Treating" or "treatment" does not mean a complete cure. It means that the symptoms of the underlying disease are reduced, and/or that one or more of the underlying cellular, physiological, or biochemical causes or mechanisms causing the symptoms are reduced. It is understood that reduced, as used in this context, means relative to the state of the disease, including the molecular state of the disease, not just the physiological state of the disease.

$$\text{Weighted Basal and Luminal } A \text{ classifier score}=-0.2468275(\text{Basal Centroid classifier score})+0.2667110(\text{Luminal } A \text{ Centroid classifier score}).$$

Figure 14A:
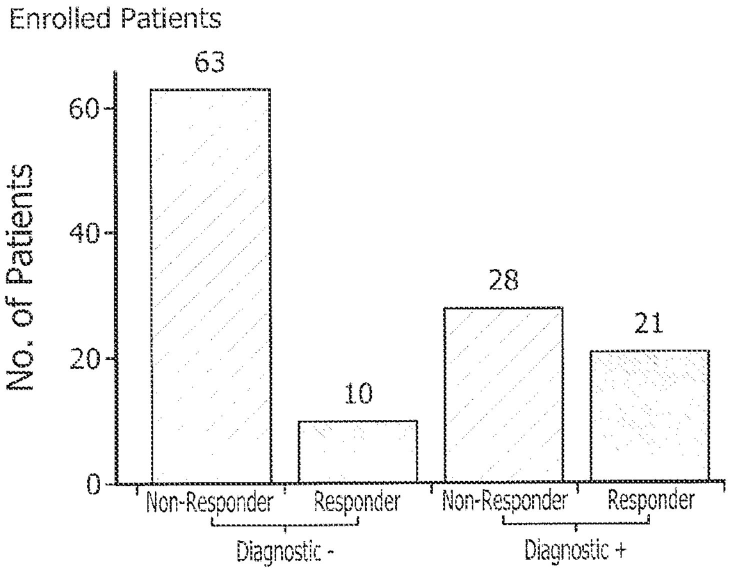
FIGS. 14A-14D comprise the results of patient responses in the clinical trial of the drug enzalutamide for the treatment of TNBC. Gene expression analysis was carried out on patient breast tumor samples using PAM50 intrinsic gene set of Table 1. The Spearman rank correlation to the Basal-like gene expression centroid was evaluated for each sample and assigned as the "Basal Centroid classifier score". The Spearman rank correlation to the Luminal A gene expression centroid was evaluated for each sample and assigned as the "Luminal A classifier score", A Weighted Basal and Luminal A classifier score of the patient samples was determined from the following formula.
Figure 14B:
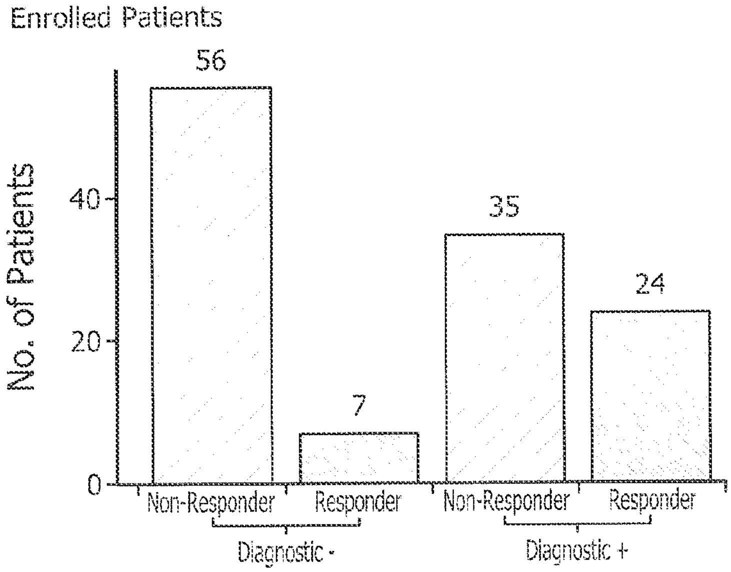
Figure 14C:
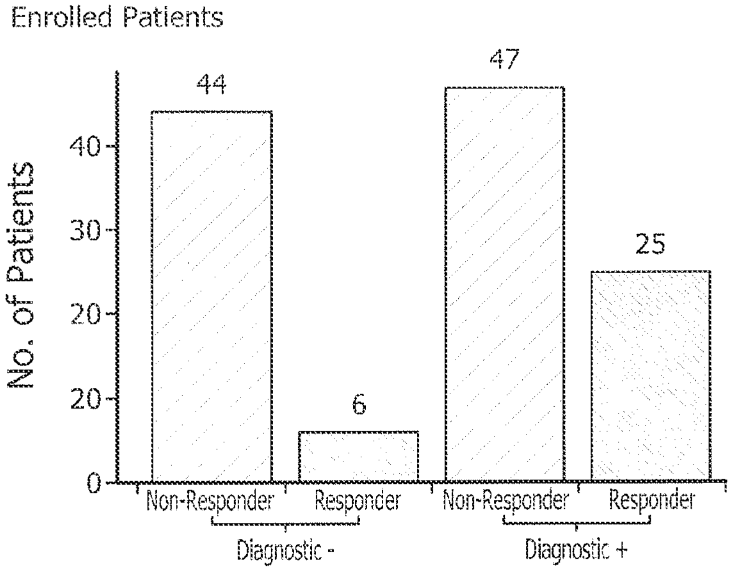
Figure 14D:
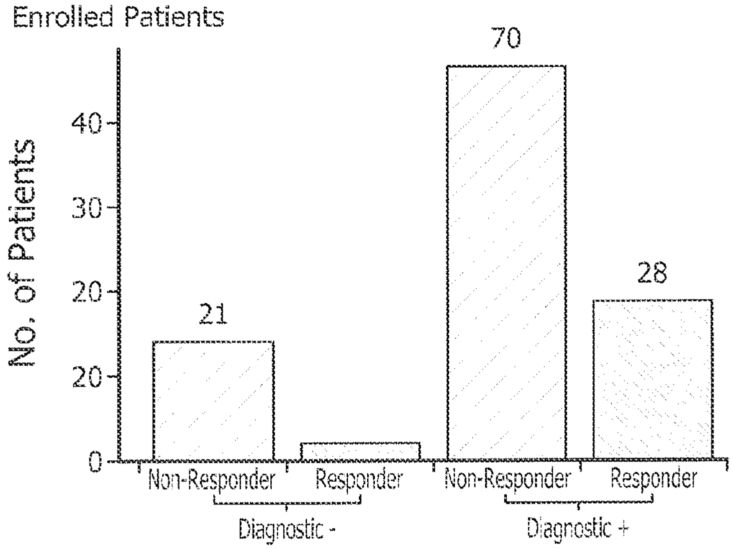

The enzalutamide response/non-response data was analyzed using Weighted Basal and Luminal A classifier score cut-offs of >–0.2 (FIG. 14A), >–0.25 (FIG. 14B), >–0.3 (FIG. 14C) and >–0.35 (FIG. 14D). The data is set forth in FIG. 14A-14D. In each figure, "Diagnostic +" represents patients whose samples met the indicated prognostic signature comprising the indicted threshold cut-off. "Diagnostic –" represents patients whose samples did not meet the indicated threshold cut-off. Patients were scored as "Responder" or "Non-Responder" to the enzalutamide therapy according to the criteria set forth in Example 1.

Figure 15:
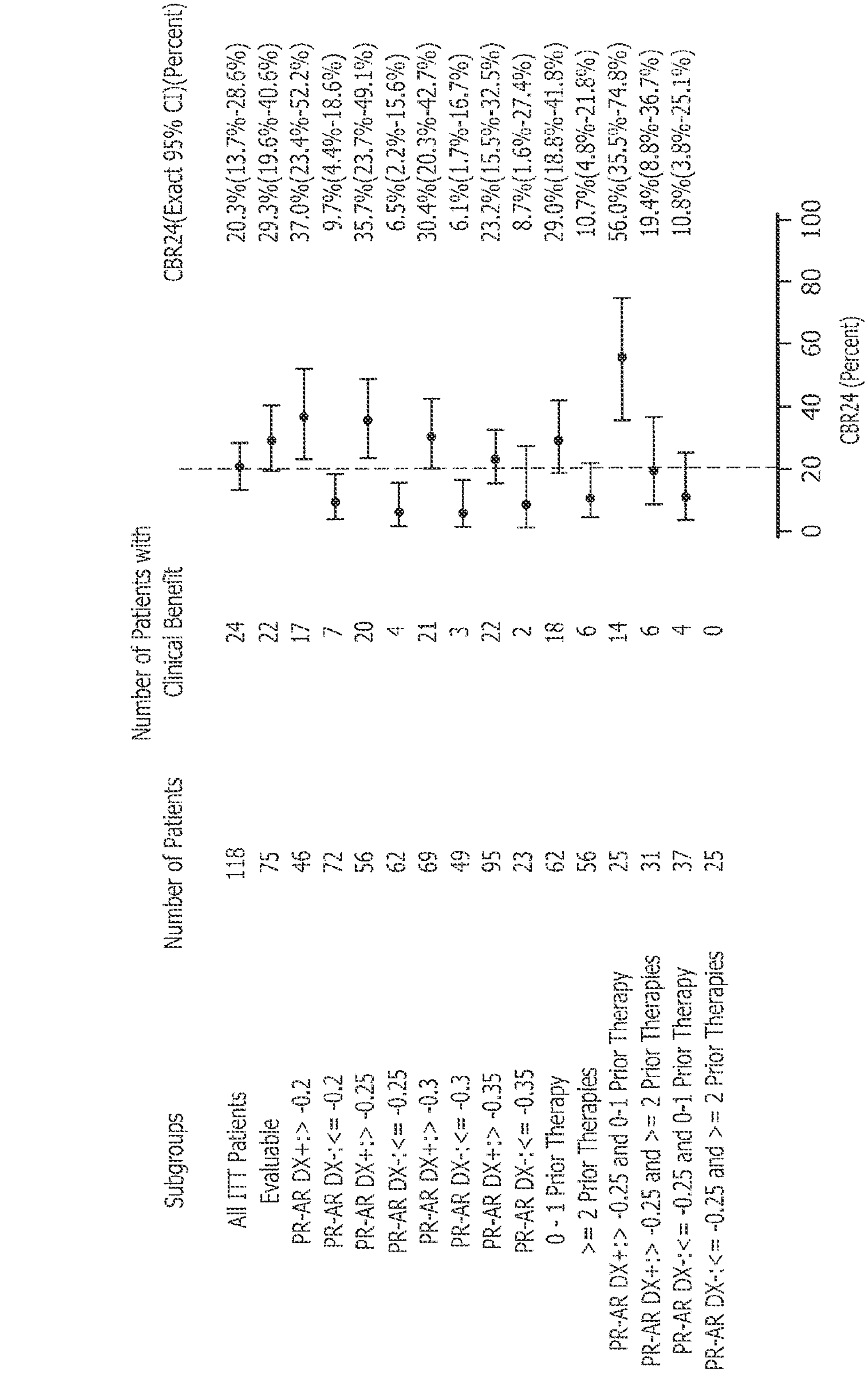

FIG. 15 comprises a representation of the response to enzalutamide of various patient subgroups treated with enzalutamide in the clinical trial. Response is shown in terms of Clinical Benefit Rate at ≥24 weeks (CBR24). The subgroups include Intent-To-Treat (ITT) patients; Evaluable Patients; patients whose breast tumor tissue was classified as a non-Basal like subtype by the PAM50 subtype classifier (PAM50 non-basal); patients whose tumors were classified as Basal-like subtype (PAM50 basal); and patients whose breast tumor tissue samples were analyzed to by applying the indicated cut-offs of >–0.2, >–0.25, >–0.3, and >–0.35 to the Weighted Basal and Luminal A classifier score. "PR-AR DX –" signifies patients whose samples did not meet the indicated threshold cut-off "PR-AR DX +" signifies patients whose samples did meet the indicated threshold cut-off. Also shown are response data (applying a Weighted Basal and Luminal A classifier score cut-off of >–0.25) for samples from patients in the study receiving enzalutamide therapy after having received from zero to one prior therapies for treatment of TNBC with a drug other than an androgen receptor inhibitor ("and 0-1 prior therapy") or after having received two or more prior therapies for treatment of TNBC with a drug other than an androgen receptor inhibitor ("and >=2 prior therapies").

Figure 16:
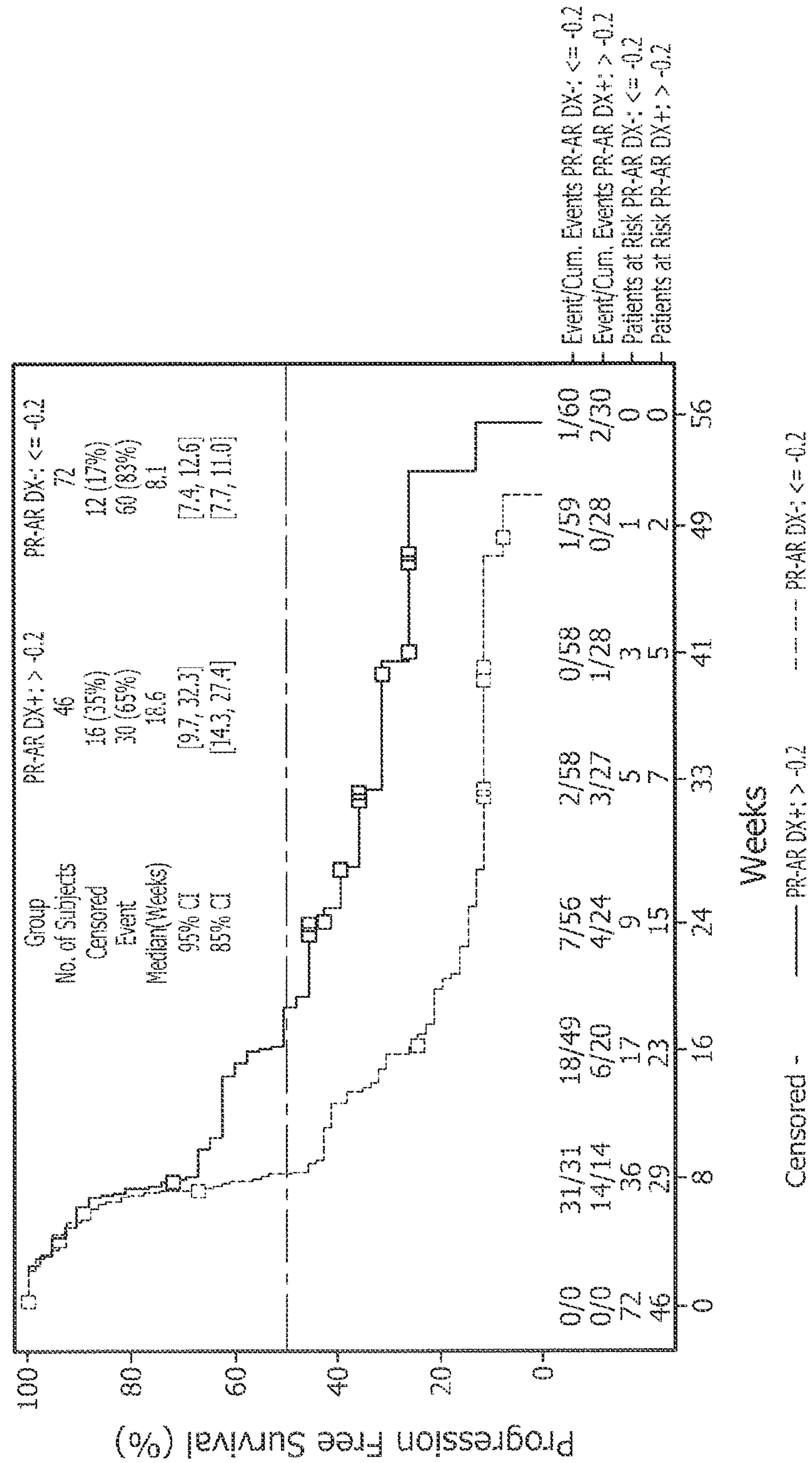

FIG. 16 is a Kaplan-Meier plot showing progression-free survival of patients treated with enzalutamide as a function of time to 56 weeks. The curves correspond to patients that were identified as meeting the signature condition of a Weighted Basal and Luminal A classifier score of greater than –0.2 ("PR-AR DX+: >–0.2", top curve) versus a classifier score of less than or equal to –0.2 ("PR-AR DX–: <=–0.2", bottom curve).

Figure 17:
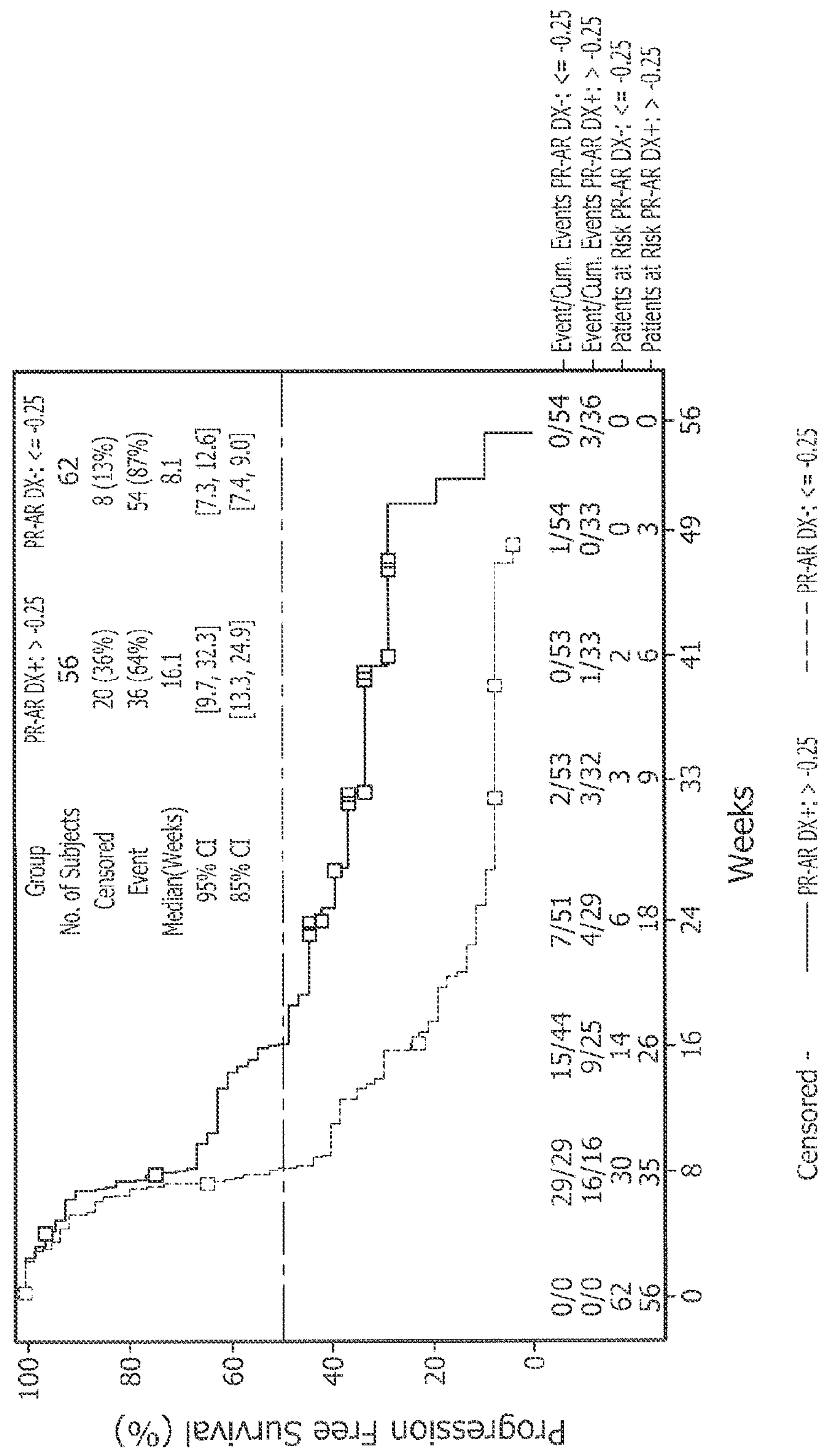

FIG. 17 is a Kaplan-Meier plot showing progression-free survival of patients treated with enzalutamide as a function of time to 56 weeks. The curves correspond to patients that were identified as meeting the signature condition of a Weighted Basal and Luminal A classifier score of greater than −0.25 ("PR-AR DX+: >−0.25", top curve) versus a classifier score of less than or equal to −0.25 ("PR-AR DX−: <=−0.25", bottom curve).

Figure 18:
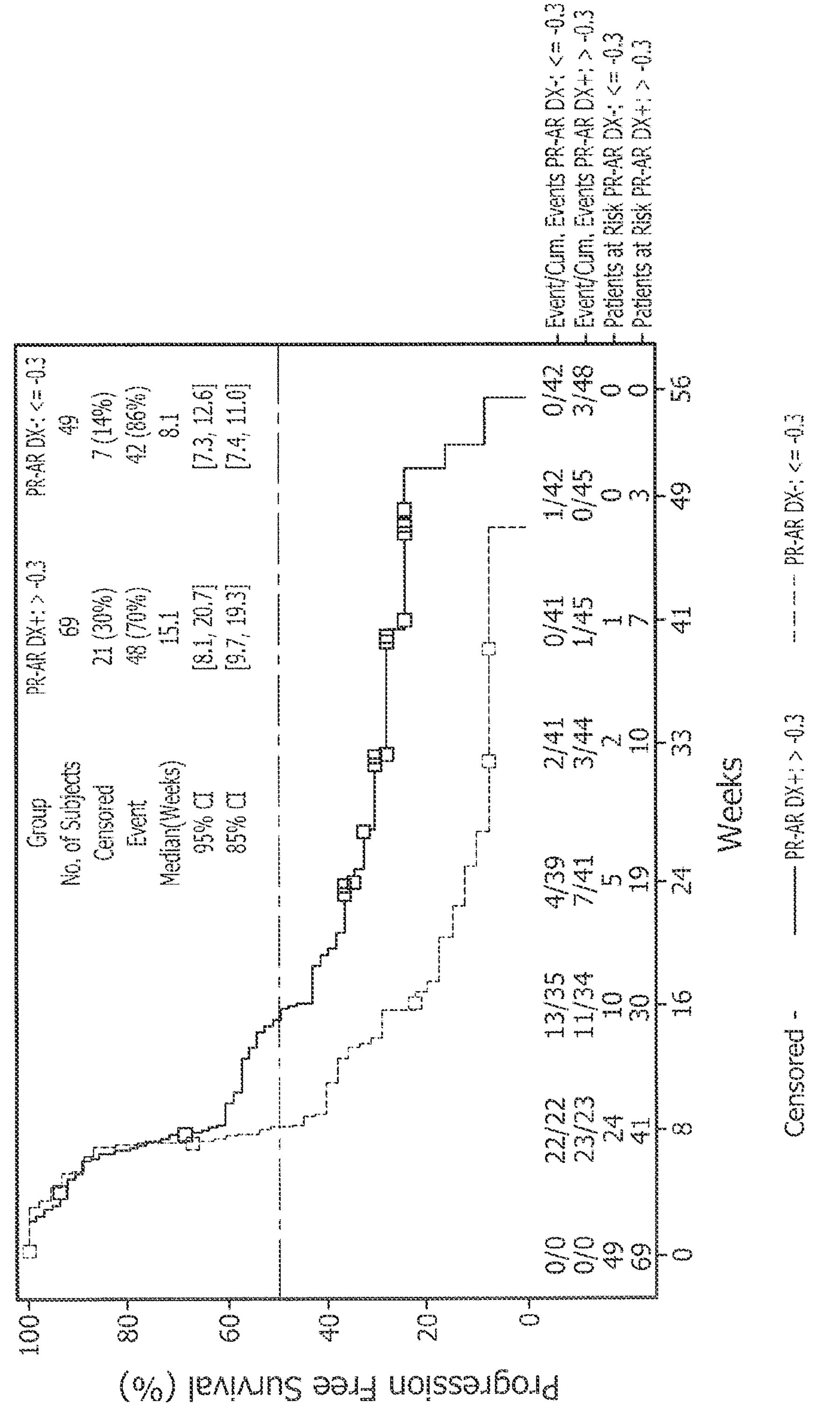

FIG. 18 is a Kaplan-Meier plot showing progression-free survival of patients treated with enzalutamide as a function of time to 56 weeks. The curves correspond to patients that were identified as meeting the signature condition of a Weighted Basal and Luminal A classifier score of greater than −0.3 ("PR-AR DX+: >−0.3", top curve) versus a classifier score of less than or equal to −0.30 ("PR-AR DX−: <=−0.3", bottom curve).

Figure 19:
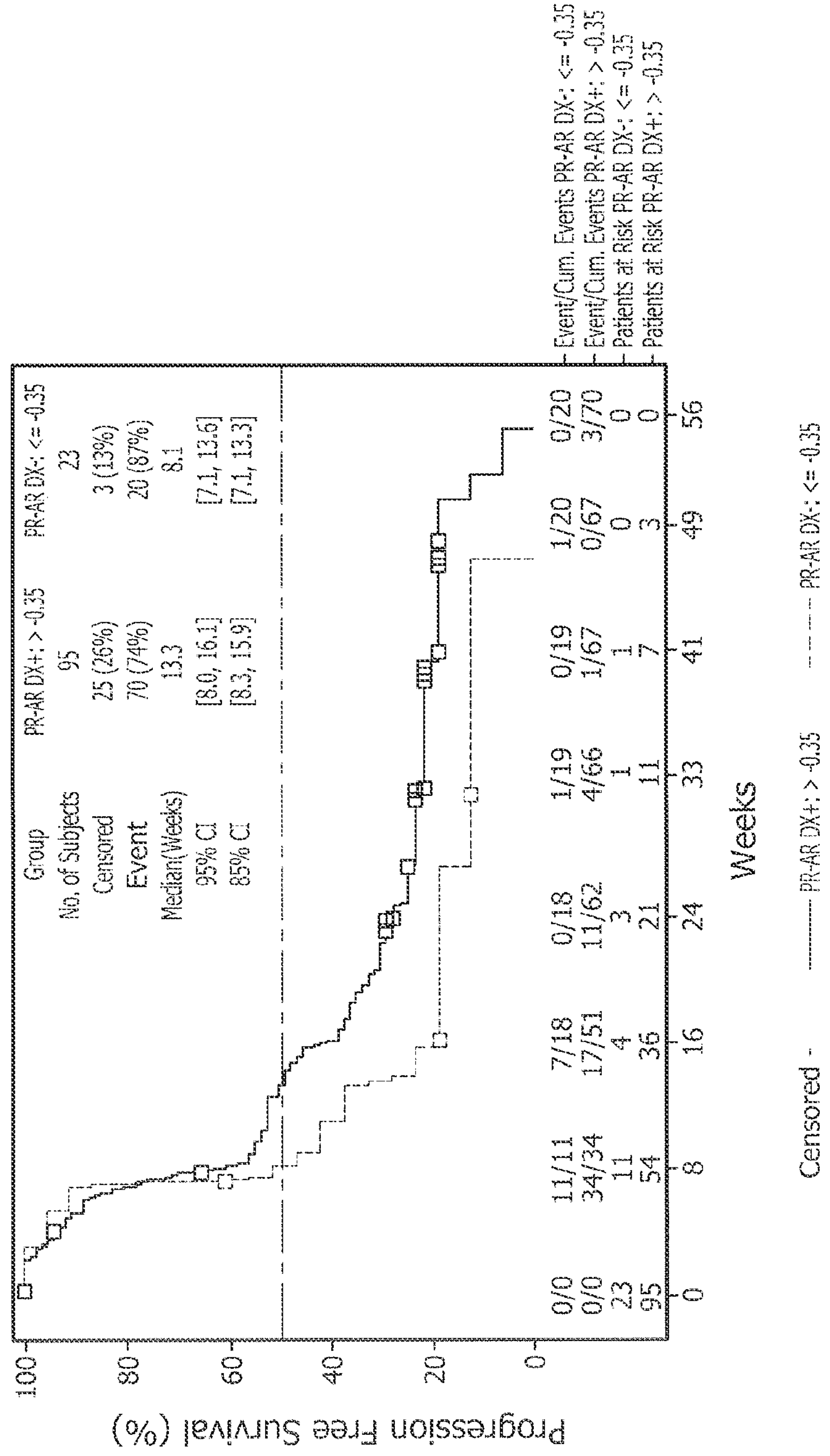

FIG. 19 is a Kaplan-Meier plot showing progression-free survival of patients treated with enzalutamide as a function of time to 56 weeks. The curves correspond to patients that were identified as meeting the signature condition of a Weighted Basal and Luminal A classifier score of greater than −0.35 ("PR-AR DX+: >−0.35", top curve) versus a classifier score of less than or equal to −0.35 ("PR-AR DX−: <=−0.35", bottom curve).

Figure 20:
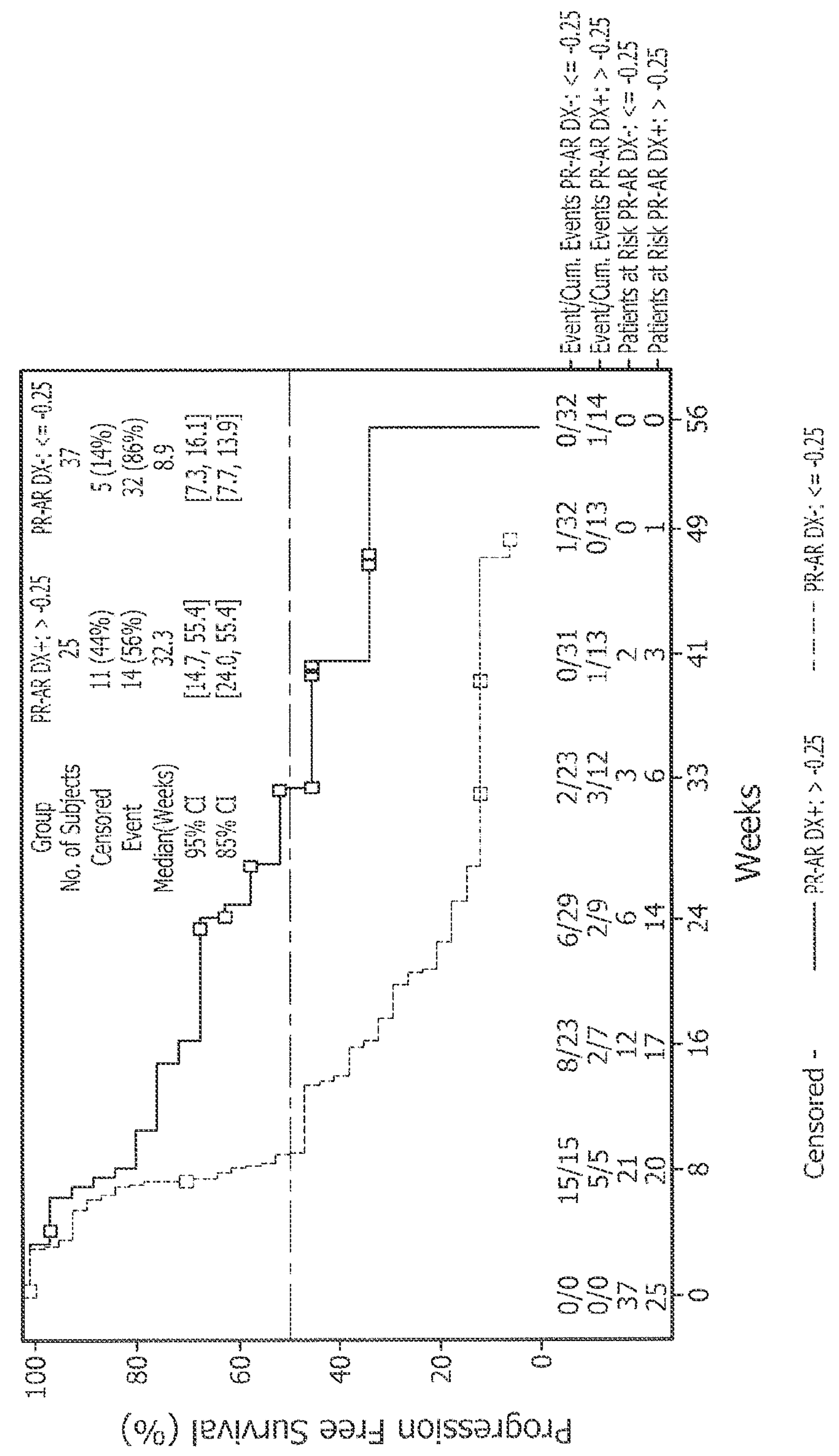

FIG. 20 is a Kaplan-Meier plot showing progression-free survival of patients treated with enzalutamide after receiving from zero to one prior therapies for treatment of TNBC with a drug other than an androgen receptor inhibitor. The curves correspond to patients that were identified as meeting the signature condition of a Weighted Basal and Luminal A classifier score of greater than −0.25 ("PR-AR DX+: >−0.25", top curve) versus a classifier score of less than or equal to −0.25 ("PR-AR DX−: <=−0.25", bottom curve).

Figure 21A:
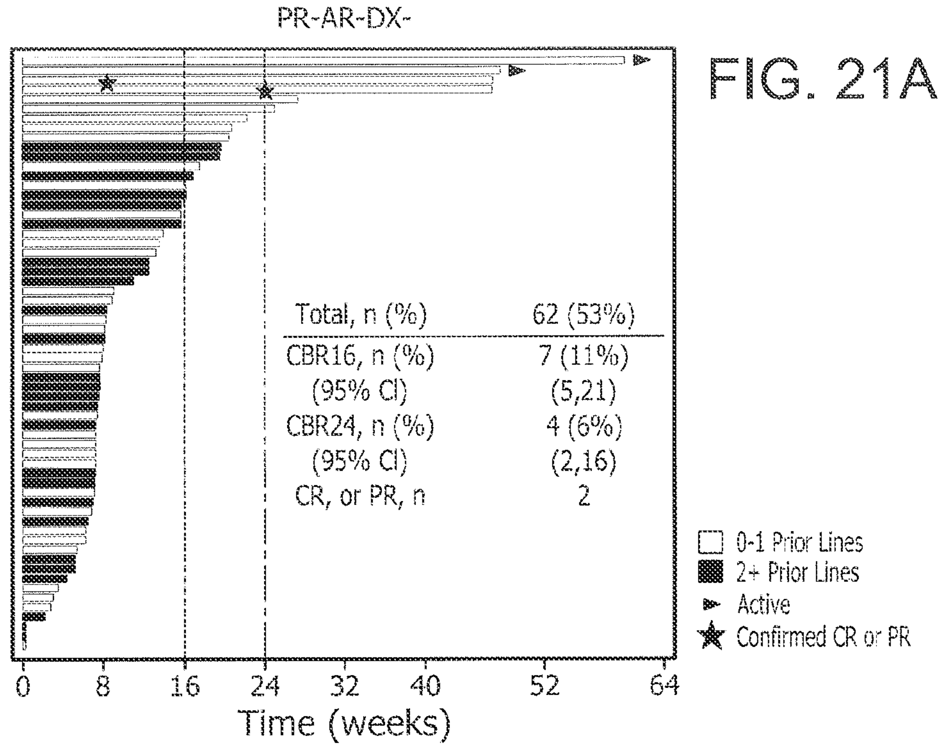
Figure 21B:
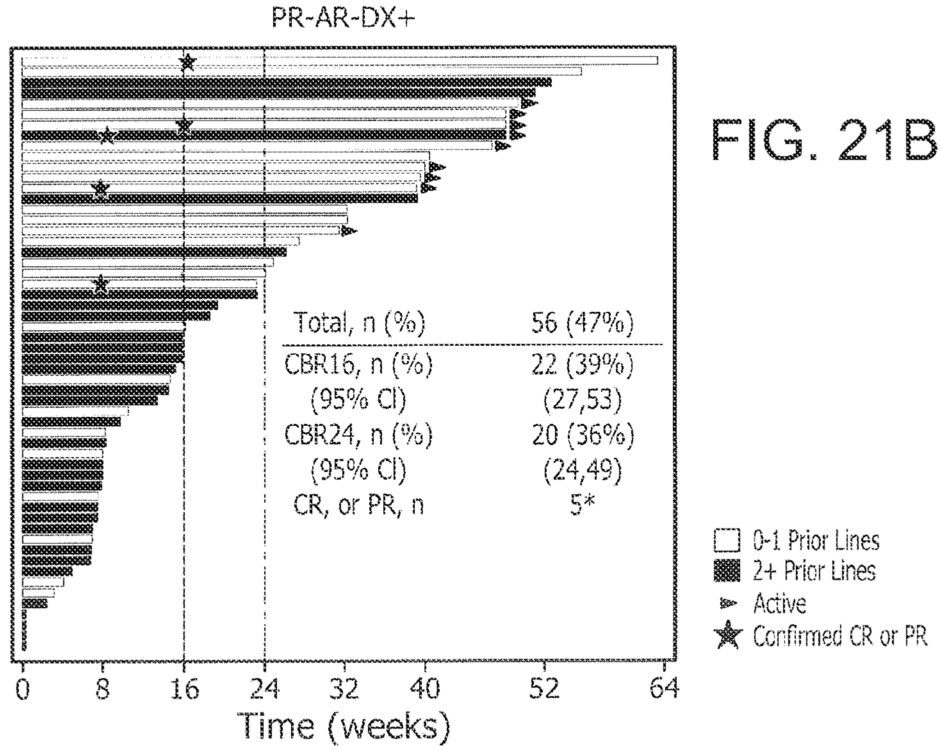

FIGS. 21A and 21B comprise graphs of the effect of the novel prognostic signature utilizing a Weighted Basal and Luminal A classifier score cut-off of >−0.25 as a predictor of response to AR inhibitor therapy in patients receiving zero or one (0-1 Prior Lines) or two or more (2+ Prior Lines) prior therapies for treatment of TNBC with a drug other than an androgen receptor inhibitor. The 56 patients of FIG. 21B were identified as meeting the signature condition of a Weighted Basal and Luminal A classifier score of greater than −0.25 The 62 study patients identified by a classifier score of less than or equal to −0.25 are identified in FIG. 21A. Each bar in the figures represents a single patient. Patient bars marked with a triangle ("Active") are active in the study. Patient bars marked with a star signify complete response (CR) or partial response (PR).

Figure 22A:
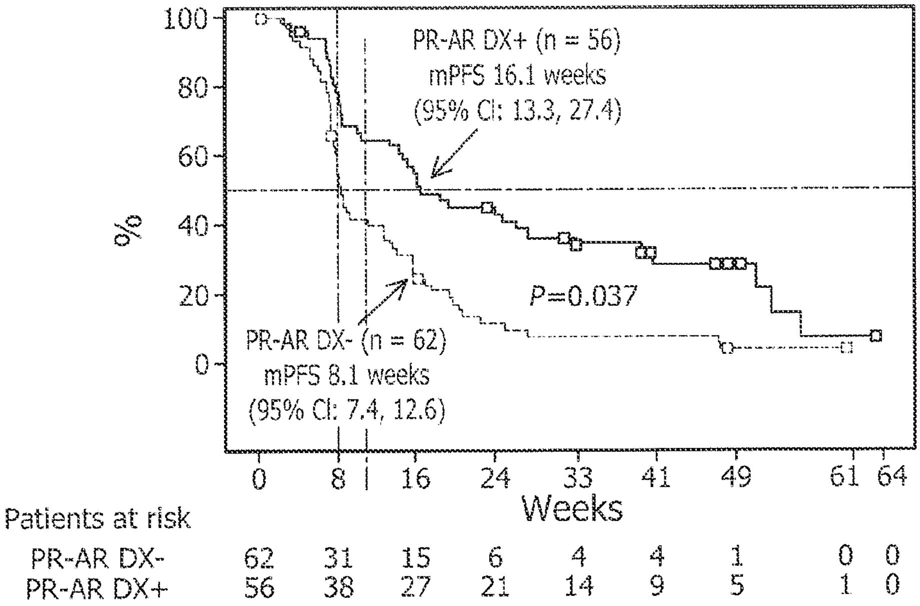
Figure 22B:
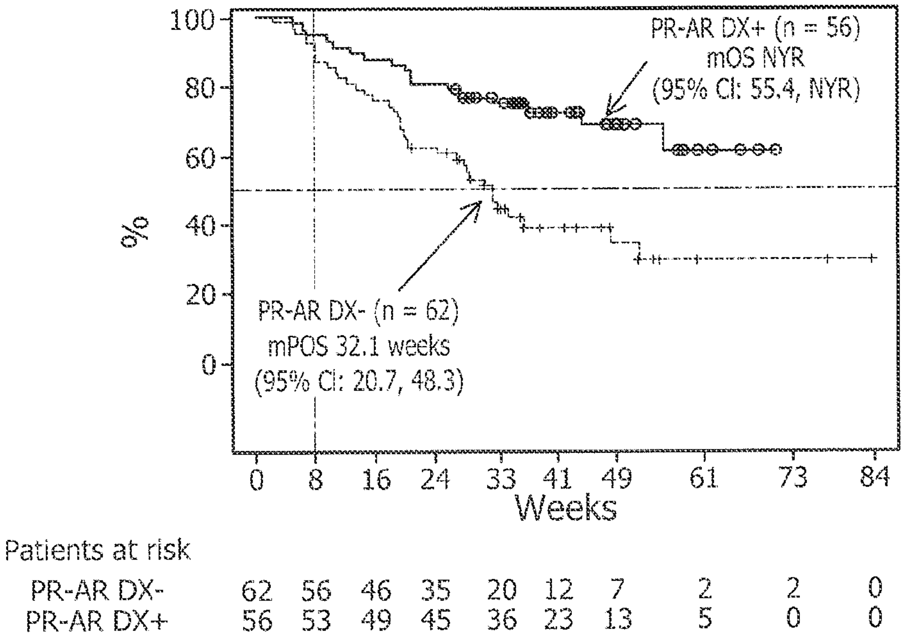

FIGS. 22A and 22B comprise Kaplan-Meier plots respectively showing median progression-free survival (FIG. 22A) (mPFS) and overall survival (mOS) of patients treated with enzalutamide as a function of time. The curves correspond to patients that were identified as meeting the signature condition of a Weighted Basal and Luminal A classifier score of greater than −0.25 ("PR-AR DX+", top curves) versus a classifier score of less than or equal to −0.25 ("PR-AR DX−", bottom curves). FIG. 22A: mPFS=16.1 weeks for patients meeting signature condition; mPFS=8.1 weeks for patients not meeting signature condition. FIG. 22B: mOS=NYR (not yet reached) at 84 weeks for patients meeting signature condition; mOS=32.1 weeks for patients not meeting signature condition.

Figure 23:
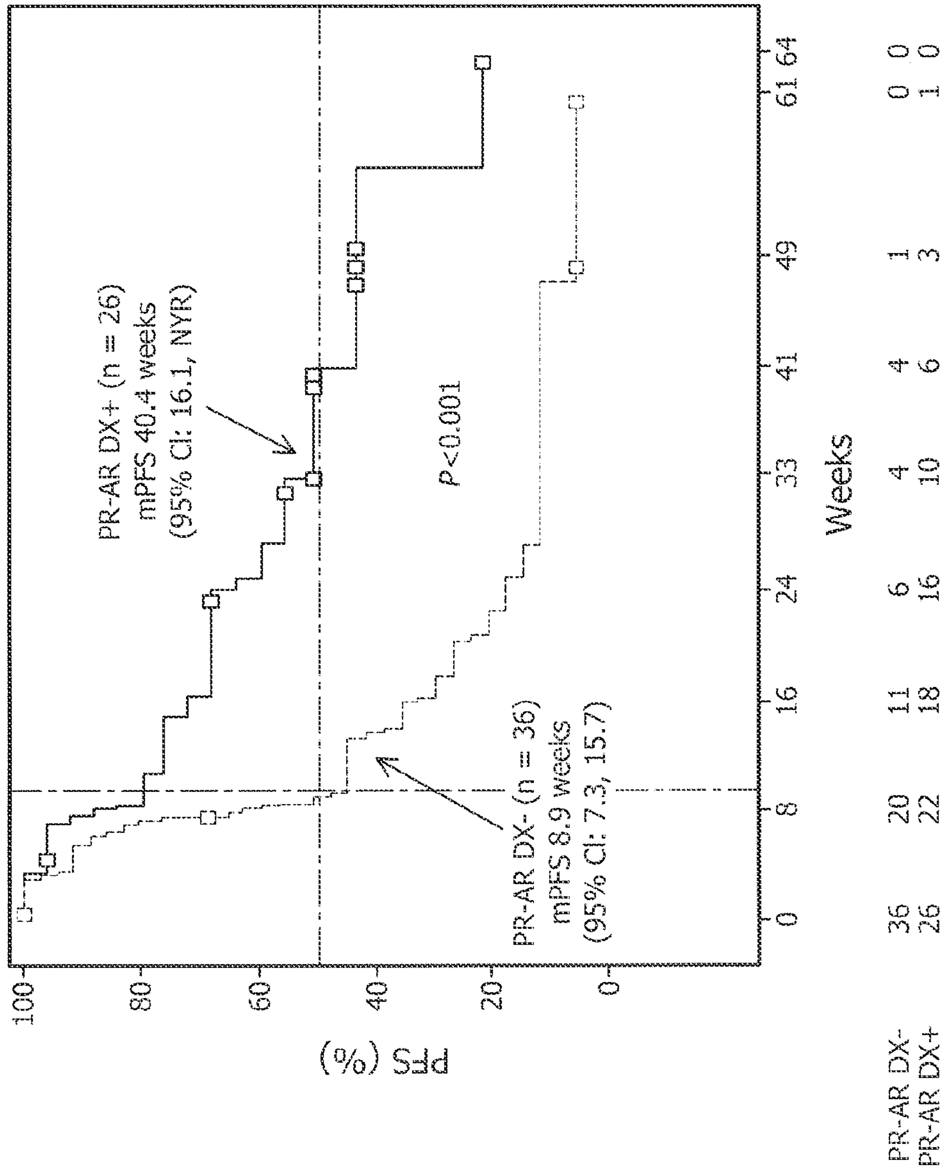

FIG. 23 is a Kaplan-Meier plot showing progression-free survival of patients treated with enzalutamide after receiving from zero to one prior therapies for treatment of TNBC with a drug other than an androgen receptor inhibitor. The curves correspond to patients that were identified as meeting the signature condition of a Weighted Basal and Luminal A classifier score of greater than −0.25 ("PR-AR DX+: >−0.25", top curve) versus a classifier score of less than or equal to −0.25 ("PR-AR DX−: <=−0.25", bottom curve). The data represents a continuation of the study of FIG. 20, taken beyond the 56 week interval of FIG. 20 to 64 weeks in FIG. 23. In FIG. 23, mPFS=40.4 weeks for patients meeting signature condition; mPFS=8.9 weeks for patients not meeting signature condition. "NYR" means "not yet reached" in the statement of the 95% confidence interval (CI) for the data represented by patients meeting the signature condition in FIG. 23.

Figure 24A:
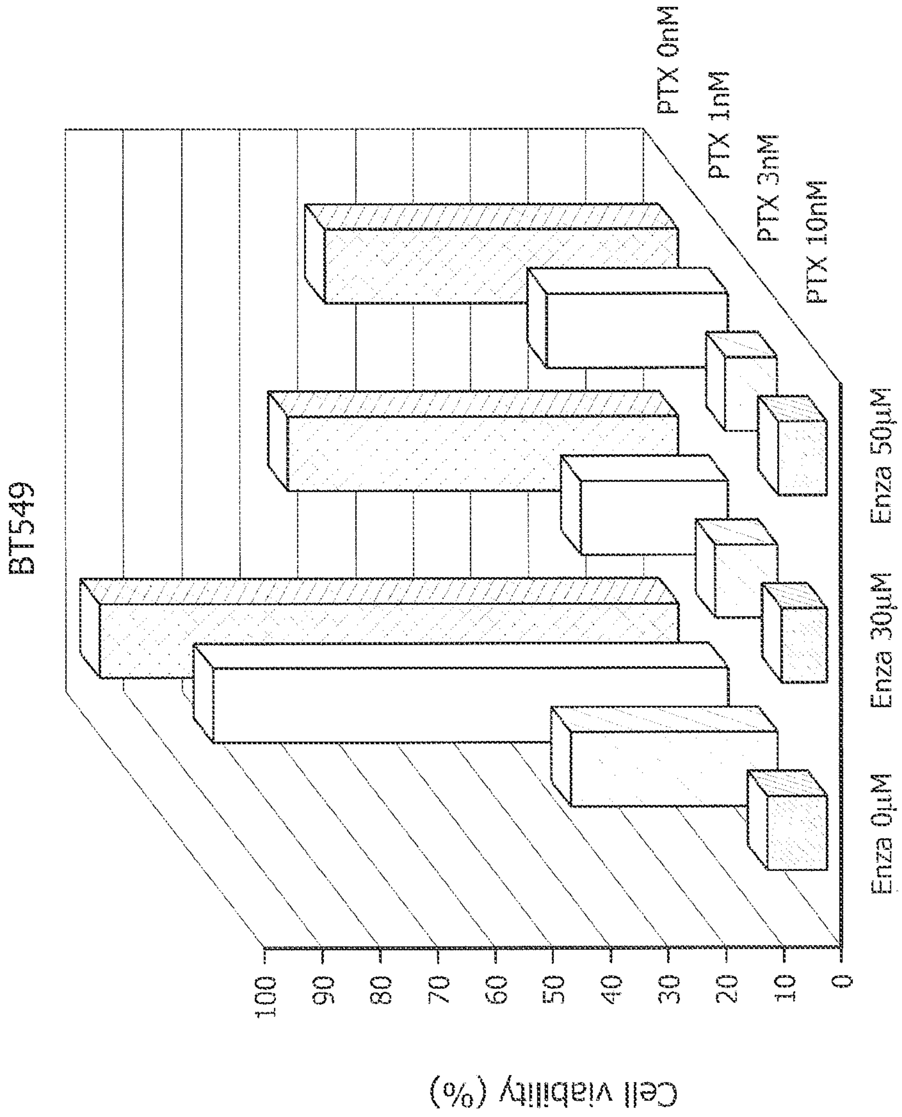
Figure 24B:
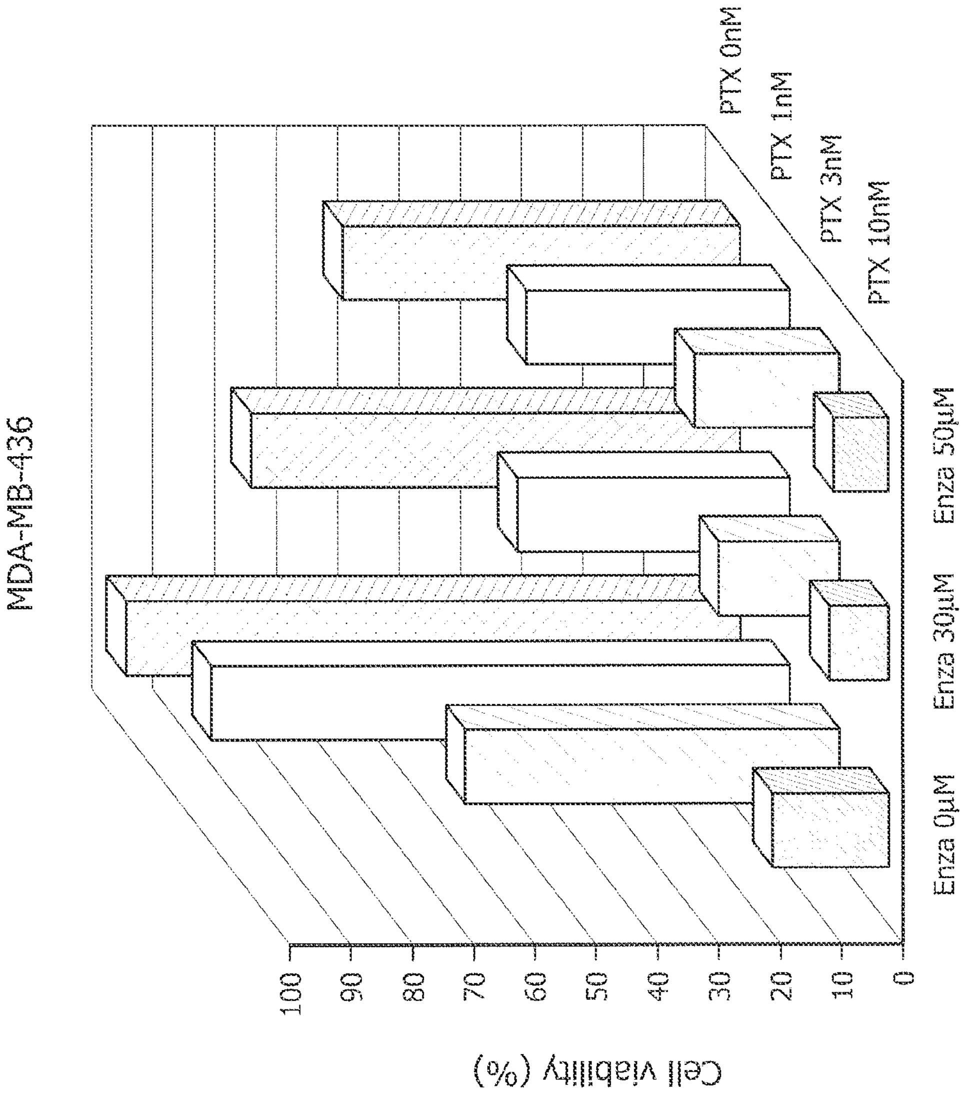
Figure 24C:
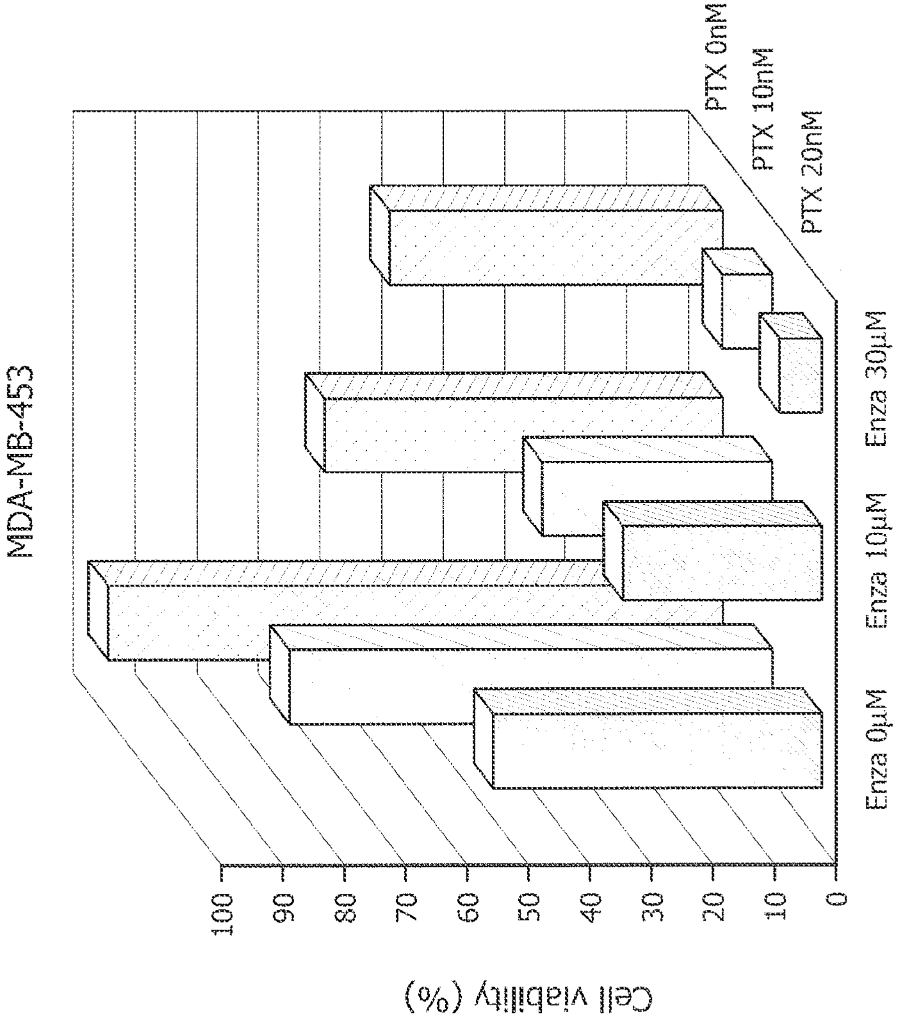

FIGS. 24A, 24B and 24C show the viability of TNBC cell lines BT549, MDA-MB-436 and MDA-MB-453, respectively, when treated with the indicated concentrations of enzalutamide (Enza), paclitaxel (PTX) or combinations thereof. Mean values are presented for each cell line (n=5).

Figure 25A:
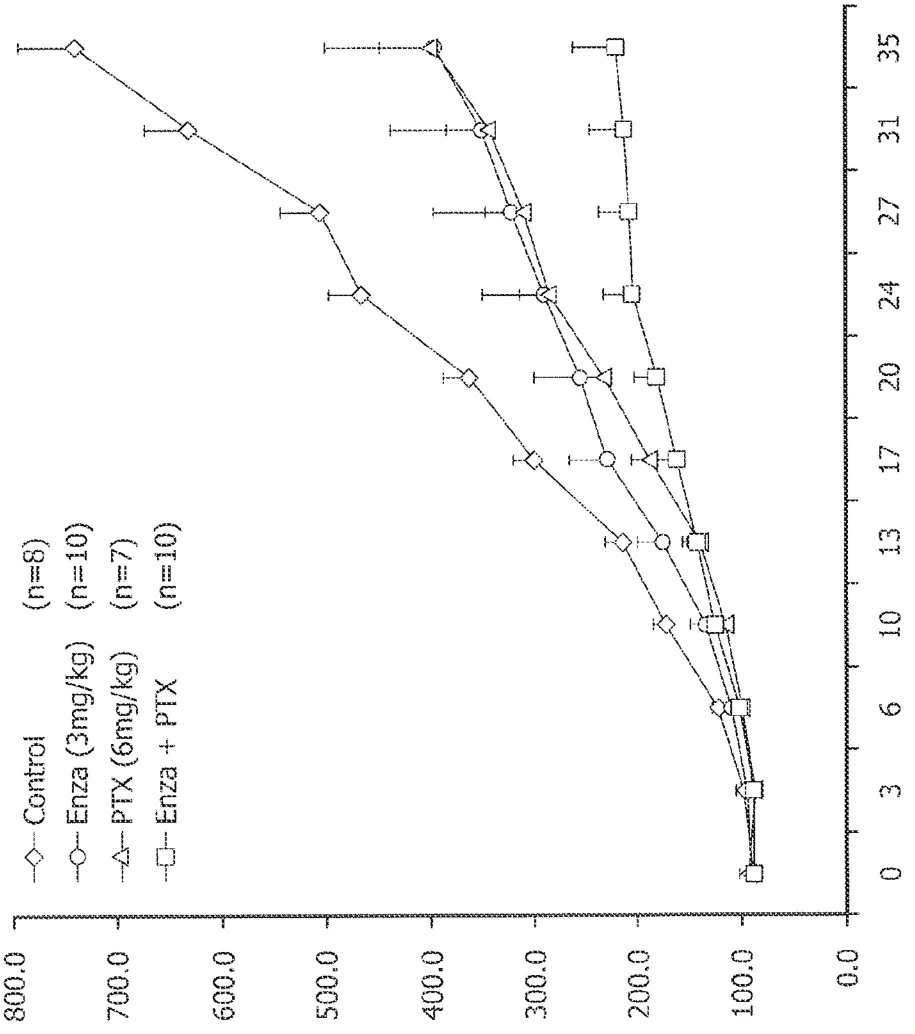
Figure 25B:
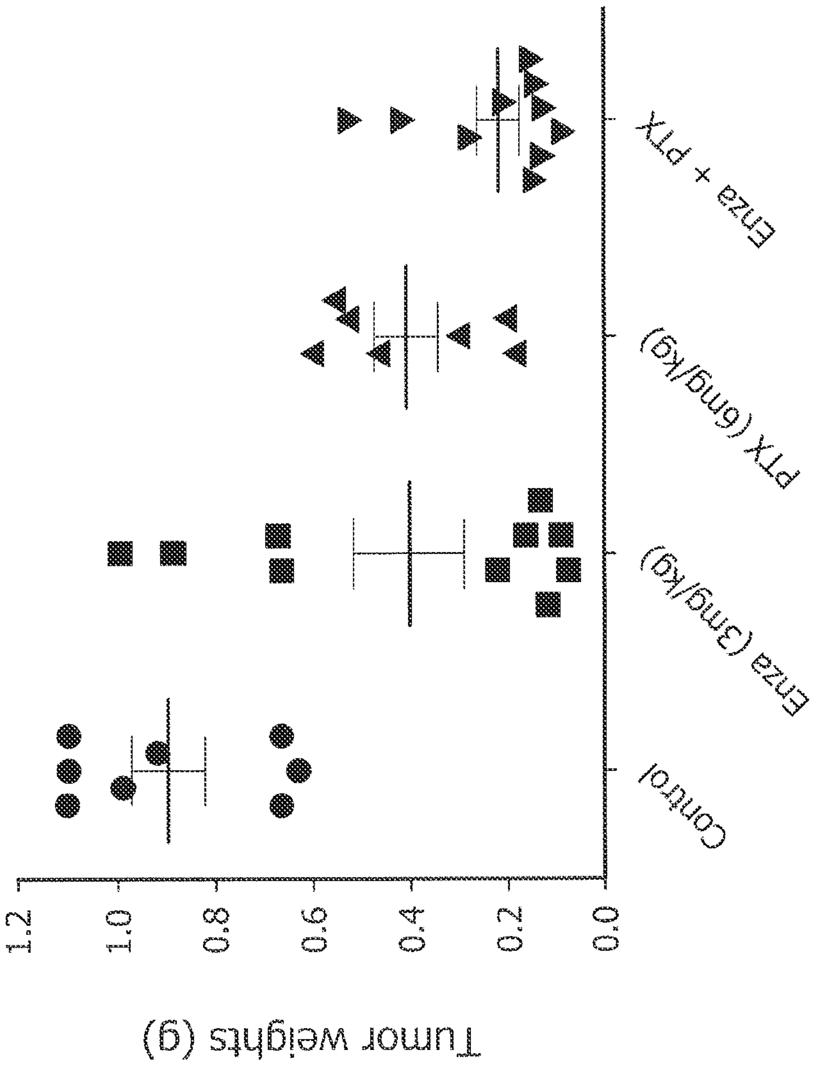

FIGS. 25A and 25B show the growth of tumors induced in NOD-SCID mice transplanted with cells of the TNBC cell line MDA-MB-453 following (i) oral gavage (PO) with enzalutamide (Enza) at 3 mg/kg/day (n=10), (ii) paclitaxel (PTX) at 6 mg/kg QMWF (IP) (n=7), or (iii) the combination of (i) and (ii) (n=10). Tumor volume was measured on the days indicated in FIG. 25A. Data points in FIG. 25A represent the average tumor volume for each group, and error bars reflect the SEM of the data. Tumor weights in FIG. 25B were determined at day 35.

DETAILED DESCRIPTION OF THE INVENTION

The present invention provides a method of treating TNBC in subjects afflicted with TNBC in which breast cancer cells of the TNBC-afflicted subject are characterized by a score derived from the expression by those cells of a certain set of intrinsic genes described more particularly below. The present invention also provides a method of assessing whether a TNBC treatment comprising an AR inhibitor is recommended (will likely be effective) for administration as a course of therapy for a patient afflicted with TNBC. Thus, the present invention provides in one embodiment a method of evaluating a treatment for triple negative breast cancer comprising the use of an androgen receptor inhibitor, the method comprising assaying a biological sample obtained from a subject to determine whether the biological sample obtained from the subject is classified as basal-like subtype or another subtype. If the biological sample is classified as other than a basal-like subtype, the breast cancer treatment comprising an androgen receptor inhibitor is more likely to be effective than if the sample were classified as basal-like subtype. Thus, the present invention provides in one embodiment a method of treating triple negative breast cancer in a subject having a cancer comprising breast cancer cells that have been previously classified as other than basal-like subtype. The method comprises administering a breast cancer treatment to the subject comprising an androgen receptor inhibitor, thereby treating the triple negative breast cancer in the subject.

The present invention further provides a method of treating TNBC by determining whether a TNBC patient should receive a treatment including AR inhibitor therapy, and then administering the optimal AR inhibitor treatment to the patient based on that determination. While the studies referenced herein were conducted on patient samples comprising tumor tissue staining positive by immunohistochemistry (IHC) for the AR receptor, the scope of the present invention is not so limited to the treatment and prognosis of AR(+) TNBC.

Studies of breast tumors based upon intrinsic gene analysis have identified five distinct subtypes of breast carcinomas: Luminal A (LumA), Luminal B (LumB), HER2-enriched (Her-2-E), Basal-like, and Normal-like (Perou et al. *Nature,* 406(6797):747-52 (2000); Sorlie et al. *PNAS,* 98(19):10869-74 (2001)). The HER2-enriched subtype may be referred to herein by "HER2", it being understood that the latter also means the HER2-enriched subtype. The Basal-like subtype may be referred to herein as "Basal", it being understood that the latter also means the Basal-like subtype. A breast cancer sample or cell is thus "classified" by assigning the cell or sample to an aforementioned subtype. A breast cancer sample or cell can also be considered "classified" in negative terms, i.e., a cell or sample may be classified as "non-Basal" or "other than Basal" upon determination that the cell or sample is of the LumA, LumB, HER2, or Normal-like sub-type.

We have unexpectedly found that the presence of the basal-like subtype is indicative of a likelihood of clinical non-response in TNBC to treatment with an AR inhibitor. We have found that a Basal Centroid classifier score of less than or equal to 0.9 is indicative of a likelihood of clinical response to an AR inhibitor. We have also unexpectedly found that an empirically determined weighted score based upon Basal-like and Luminal A subtype analysis conducted on biological samples from TNBC patients is indicative of a likelihood of clinical response to treatment with an AR inhibitor. Thus, in one embodiment, an assay is thus performed on a biological sample from a patient suffering from TNBC to determine the breast cancer subtype. In another embodiment, an assay is performed on a biological sample from a patient suffering from TNBC to determine the Basal Centroid classifier score, or both the Basal Centroid classifier score and the Luminal A classifier score.

The assay for determining whether the biological sample is classified as a subtype other than a basal-like subtype can comprise an assay for determining the presence of a basal-like subtype; a negative result indicates a non-basal subtype. Any assay capable of identifying the presence of a basal-like subtype may be utilized for this purpose. With approximately 70-90% of triple-negative carcinomas revealed to be basal-like breast carcinomas (Bertucci et al., *Int. J. Cancer* 2008, 123, 236-240; Wang et al., *Eur. J. Clin. Invest.* 2008, 38, 438-446), the tripe negative phenotype has been used as a surrogate for the basal-like subtype. However, studies have shown that triple-negative and basal-like breast tumors are not synonymous. See, e.g., Choo and Nielsen, *Cancers* 2010, 2, 1040-1065. Thus, care must be exercised in selecting an assay for identifying the basal-like subtype.

Recently, an assay for basal-like subtype has been announced that relies on the following profile which has been found to be characteristic of the basal-like subtype: ER negative, HER2 negative, and cytokeratin 5/6 and/or HER1 positive. A panel of four antibodies (ER, HER1, HER2, and cytokeratin 5/6) has thus been proposed as an immunohistochemical profile for identifying breast basal-like tumors (Nielsen et al., *Clinical Cancer Research* 2014; 10:5367-5374).

The Basal-like and Luminal A subtype analysis is performed by means of a gene expression assay which utilizes expression of intrinsic genes as classifier genes for breast cancer classification. Intrinsic genes, as described in Perou et al. (2000) *Nature* 406:747-752, are statistically selected to have low variation in expression between biological sample replicates from the same individual and high variation in expression across samples from different individuals. The present invention utilizes the PAM50 gene expression assay (Parker et al. *J Clin Oncol.,* 27(8):1160-7 (2009) and U.S. Patent Application Publication No. 2011/0145176, both incorporated herein, by reference, in their entireties). The PAM50 gene expression assay can be used to identify intrinsic subtypes of breast cancer (Luminal A, Luminal B, HER2-enriched, Basal-like, and Normal-like) from standard biological samples, such as formalin fixed paraffin embedded tumor tissue. The PAM50 gene expression classifier is a supervised, centroid-based prediction method to classify breast cancers into one of the five aforesaid molecular subtypes using a 50-gene intrinsic gene signature.

As described in Parker et al. and in U.S. Patent Application Publication No. 2011/0145176, as well as in U.S. Patent application Publication No. 2013/0004482, the PAM50 gene expression assay method utilizes a supervised algorithm to classify subject samples according to breast cancer intrinsic subtype. This algorithm, referred to herein as the "PAM50 classification model" or "PAM50 classifier" is based on the gene expression profile of a defined subset of 50 intrinsic genes that has been identified for classifying breast cancer intrinsic subtypes. The subset of genes, along with primers specific for their detection, is provided in Table 1 of U.S. Patent Application Publication No. 2013/0004482 and reproduced below as Table 1 of this disclosure. Select sequences of the same 50 intrinsic genes are set forth in Table 2 below. The entire disclosure of Publication No. 2013/0004482, is incorporated herein by reference.

The detection and estimation of the expression of the set of 50 subtype predictor genes of Table 1 is performed by any suitable means.

The PAM50 gene expression classifier operates by using a supervised prediction algorithm developed based on the profiles of objectively-selected prototype samples for "training" the algorithm. The samples are selected and subtyped using an expanded intrinsic gene set according to the methods disclosed in U.S. Patent Publication No. 2009/0299640, the entire disclosure of which is incorporated herein by reference. After stratifying the training samples according to subtype, a centroid-based prediction algorithm is used to construct centroids for each molecular subtype based on the expression profile of the intrinsic gene set described in Table 1. The centroid is the average gene expression for each gene in each subtype (or "class") divided by the within-class standard deviation for that gene. Nearest centroid classification takes the gene expression profile of a new sample, and compares it to each of these class centroids. Subtype prediction is done by calculating the Spearman's rank correlation of each test case to the five centroids of the PAM50 subtypes, and assigning a sample to a subtype based on the nearest centroid.

According to one embodiment, which does not necessarily involve assigning the patient sample to a PAM50 subtype, the Spearman rank correlation to the basal-like gene expression centroid is determined. The Spearman rank correlation between the sample and the basal-like centroid is assigned as the "Basal Centroid classifier score". The Spearman rank correlation to the Luminal A gene expression centroid is determined. The Spearman rank correlation between the sample and the Luminal A centroid is assigned as the "Luminal A Centroid classifier score". Methods for utilizing the PAM50-based signature to provide a Basal Centroid classifier score and a Luminal A Centroid classifier score are known to those skilled in the art. See, for example, U.S. Patent Application Publication No. 2009/0299640;

Parker et al., J Clin. Oncol., 27(8):1160-7 (2009); U.S. Patent Application Publication No. 2011/0145176. Also see, for example, Prat et al., *British Journal of Cancer*, (2014) 111, 1532-1541, incorporated herein by reference.

We have found, as demonstrated by the clinical trial of TNBC patients treated with the AR inhibitor enzalutamide, that a Basal Centroid classifier score of less than or equal to 0.9 is indicative of a likelihood of clinical response to an AR inhibitor. In some embodiments, a Basal Centroid classifier scores of less than or equal to 0.9, from 0.2 to 0.8, from 0.4 to 0.7 are used to predict the likelihood of clinical response to an AR inhibitor. In one embodiment, a Basal Centroid classifier score of less than or equal to 0.6 is used to predict the likelihood of clinical response to an AR inhibitor.

We have further found that the Basal Centroid classifier score and Luminal A Centroid classifier score, when combined subject to certain empirically defined weighting factors, provides a score ("Weighted Basal and Luminal A classifier score") that can be used to further predict responsiveness to androgen receptor inhibitor therapy in an individual TNBC patient. The Weighted Basal and Luminal A classifier score is determined from the following equation:

Weighted Basal and Luminal *A* classifier score=−0.25(Basal Centroid classifier score)+0.27(Luminal *A* Centroid classifier score).

In some embodiments, the equation for determining the Weighted Basal and Luminal A classifier score takes the form:

Weighted Basal and Luminal *A* classifier score=−0.2468275(Basal Centroid classifier score)+0.2667110(Luminal *A* Centroid classifier score).

As demonstrated by the clinical trial of TNBC patients treated with the AR inhibitor enzalutamide, if the Weighted Basal and Luminal A classifier score is greater than −0.3, the patient is identified as one likely responsive to AR inhibitor therapy. Alternatively, if the Weighted Basal and Luminal A classifier score is greater than −0.2, the patient may also be identified as one likely responsive to AR inhibitor therapy. Increased accuracy is obtained by selecting −0.25 as the cut-off for predicting responsiveness to AR inhibitor therapy. Thus, in a preferred embodiment, if the Weighted Basal and Luminal A classifier score is greater than −0.25, the patient is identified as one likely responsive to AR inhibitor therapy. If the TNBC patient is identified through determination of the Weighted Basal and Luminal A classifier score as one who is likely responsive to AR inhibitor therapy for TNBC, an appropriate AR inhibitor therapy may then be administered to treat the TNBC condition in the patient.

The utility of the Weighted Basal and Luminal A classifier score for predicting patient response to AR inhibitor therapy is illustrated in FIGS. 14A-14D and FIG. 15. The figures comprise a representation of the response to enzalutamide of various TNBC patient subgroups treated with enzalutamide in the clinical trial. Patient responsiveness to enzalutamide therapy was correlated with Weighted Basal and Luminal A classifier score, applying a series of cut-offs of >−0.2 (FIG. 14A), >−0.25 (FIG. 14B), >−0.3 (FIG. 14C), and >−0.35 (FIG. 14D) to the Weighted Basal and Luminal A classifier score. "Diagnostic −" in FIGS. 14A-D and "PR-AR DX −" in FIG. 15 signify patients whose samples did not meet the indicated Weighted Basal and Luminal A classifier score threshold cut-off. "Diagnostic+" in FIGS. 14A-14D and "PR-AR DX+" in FIG. 15 signify patients whose samples did meet the indicated threshold cut-off. As is apparent from a consideration of the data, a Weighted Basal and Luminal A classifier score of greater than −0.25 provided the highest level of accuracy in predicting TNBC patient responsiveness to enzalutamide therapy, with the criteria of greater than −0.2, or greater than −0.3, also providing acceptable results.

The correlation between patient response and Weighted Basal and Luminal A classifier score is further illustrated in the Kaplan-Meier plot of FIGS. 16-19, showing progression-free survival of TNBC patients treated with enzalutamide, as a function of time to 56 weeks. The curves in FIG. 16 correspond to patients that were identified as meeting the signature condition of a Weighted Basal and Luminal A classifier score of greater than −0.2 ("PR-AR DX+: >−0.2", top curve) versus a classifier score of less than or equal to −0.2 ("PR-AR DX−: <=−0.2", bottom curve). FIGS. 17, 18 and 19 are similar to FIG. 16, where the signature conditions of greater than −0.25 (FIG. 17), greater than −0.3 (FIG. 18) and greater than −0.35 (FIG. 19) were imposed. It may be appreciated that the magnitude of the vertical separation between the respective curves on each individual plot is a measure of the accuracy of correlation between patient Weighted Basal and Luminal A classifier score and progression-free survival. On this basis, it may be further appreciated from a comparison of FIGS. 16-19 that applying the criterion of a Weighted Basal and Luminal A classifier score greater than −0.25 (FIG. 17) provides the most accuracy in correlating Weighted Basal and Luminal A classifier score to TNBC patient responsiveness to enzalutamide therapy, with the criteria of greater than −0.2 (FIG. 16) or greater than −0.3 (FIG. 18) also provided acceptable results.

It was also found that the novel Weighted Basal and Luminal A classifier score as a predictor of responsiveness to AR inhibitor therapy for TNBC achieves even greater accuracy in patients who have either received no prior TNBC therapy, or have received no more than one round of prior TNBC therapy. As may be appreciated from a comparison of FIG. 20 and FIG. 17, imposing the criterion of a Weighted Basal and Luminal A classifier score of greater than −0.25 in the zero to 1 prior therapy patient group (FIG. 20), versus the larger group of all trial patients (FIG. 17), resulted in increased accuracy in identifying patients responsive to enzalutamide therapy, as evidenced by the greater vertical separation between the curves in FIG. 20, versus the vertical separation of the curves in FIG. 17. The trend is further observed in FIG. 23, in which the progression-free survival time in the study subjects of FIG. 20 is shown beyond the 56 weeks in FIG. 20, to 64 weeks in FIG. 23.

This result is also illustrated in FIGS. 21A and 21B, showing the extent of time on treatment without progression of disease (progression-free survival) for 56 patients that were identified as meeting the signature condition of a Weighted Basal and Luminal A classifier score of greater than −0.25 (FIG. 21B) versus 62 patients identified by a classifier score of less than or equal to −0.25 (FIG. 21A). Each bar represents a patient. Patients received either zero or one prior TNBC therapy before enzalutamide treatment (0-1 Prior Lines) with a drug other than an androgen receptor inhibitor, or two or more prior therapies (2+ Prior Lines) with a drug other than an androgen receptor inhibitor. Patient bars marked with a triangle ("Active") are active in the study. Patient bars marked with a star signify complete response (CR) or partial response (PR). The best time on treatment without disease progression is apparent in responder patients who received one or no prior lines of therapy (FIG. 21B).

The correlation between patient response and Weighted Basal and Luminal A classifier score is further illustrated in the Kaplan-Meier plots of FIGS. 22A and 22B, comparing the endpoints of median progression-free survival (mPFS) (FIG. 22A) and median overall survival (mOS) (FIG. 22B) of study patients. The curves in FIGS. 22A and 22B correspond to patients that were identified as meeting the signature condition of a Weighted Basal and Luminal A classifier score of greater than −0.25 ("PR-AR DX+", top curves) versus a classifier score of less than or equal to −0.25 ("PR-AR DX−", bottom curves). The results thus show that the Weighted Basal and Luminal A classifier of greater than −0.25 score correlates with overall survival, in addition to progression-free survival. The patients not meeting the prognostic signature condition were characterized by a median progression-free survival of 8.1 weeks and median overall survival of 32.1 weeks. In contrast, patients meeting the prognostic signature condition were characterized by a median progression-free survival of 16.1 weeks and median overall survival not yet reached (mOS NYR) at 84 weeks.

Gene Expression Detection

As the first step in determining the Basal Centroid Classifier Score or Weighted Basal and Luminal A classifier score of a TNBC patient, gene expression detection of the genes of the intrinsic gene set of Table 1 is carried out on patient samples by any method for determining the quantity or presence of an RNA transcript or its expression product of an intrinsic gene. Such methods are described in U.S. Patent Application Publication Nos. 2009/0299640 and 2013/0004482, incorporated herein by reference. They include, for example means, methods based on hybridization analysis of polynucleotides, methods based on sequencing of polynucleotides, immunohistochemistry methods, and proteomics-based methods. The methods generally detect expression products (e.g., mRNA) of the intrinsic genes listed in Table 1.

RNA sequencing as a method for assaying gene expression may be utilized in one embodiment. The assay for gene expression of the intrinsic gene set can also be performed by other technologies used to evaluate gene expression/quantification, including but not limited to real-time PCR, microarrays, microfluidic gene expression, and targeted gene sequencing. Such methods include, for example, hybridization analysis of polynucleotides, methods based on sequencing of polynucleotides, immunohistochemistry methods, and proteomics-based methods. PCR-based methods, such as reverse transcription PCR (RT-PCR) (Weis et al., *TIG* 8:263-64, 1992), and array-based methods such as microarray (Schena et al., *Science* 270:467-70, 1995) may be used.

General methods for RNA extraction are well known in the art and are disclosed in standard textbooks of molecular biology, including Ausubel et al., ed., *Current Protocols in Molecular Biology*, John Wiley & Sons, New York 1987-1999. Methods for RNA extraction from paraffin embedded tissues are disclosed, for example, in Rupp and Locker, *Lab Invest.* 56:A67, (1987): and De Andres et al., Biotechniques 18:42-44, (1995). Isolated RNA can be used in hybridization or amplification assays that include, but are not limited to, PCR analyses and probe arrays. Intrinsic gene expression product level determination in a sample may also involve nucleic acid amplification, for example, by RT-PCR (U.S. Pat. No. 4,683,202), ligase chain reaction, self-sustained sequence replication, transcriptional amplification, rolling circle replication, and other methods utilizing nucleic acid amplification method, followed by the detection of the amplified molecules using techniques well known to those of skill in the art.

Microarrays may be used for expression profiling. Each array includes a reproducible pattern of capture probes attached to a solid support. Labeled RNA or DNA is hybridized to complementary probes on the array and then detected by laser scanning Hybridization intensities for each probe on the array are determined and converted to a quantitative value representing relative gene expression levels. See, for example, U.S. Pat. Nos. 6,040,138, 5,800,992 and 6,020,135, 6,033,860, and 6,344,316. High-density oligonucleotide arrays are particularly useful for determining the gene expression profile for a large number of RNAs in a sample.

Total RNA for analysis of the intrinsic gene set may be isolated from a biological sample, such as a tumor. If the source of RNA is a primary tumor, RNA (e.g., mRNA) can be extracted, for example, from frozen or archived paraffin-embedded and fixed (e.g., formalin-fixed) tissue samples (e.g., pathologist-guided tissue core samples).

Gene Analysis and Data Processing

Patient sample gene expression data from the intrinsic gene set may be pre-processed by known techniques to achieve sequence data alignment, data normalization and mean centering of data, for example. Methods of normalization include, for example, (i) global normalization that uses all genes on the array; (ii) housekeeping genes normalization that uses constantly expressed housekeeping/invariant genes; and (iii) internal controls normalization that uses known amount of exogenous control genes added during hybridization (Quackenbush *Nat. Genet.* 32 (Suppl.), 496-501 (2002)). Gene count estimates can also be normalized to a fixed quartile, such as a fixed upper quartile. The resulting normalized gene expression estimates may then be adjusted such that the median expression value of each gene is equivalent to the median of a known subset, such as a gene subset from TNBC patients.

According to one embodiment, patient sample expression data for processing by the PAM50 classifier is first pre-processed by alignment and data centering techniques. RNA-sequence data is first aligned to Human (*Homo sapiens*) genome sequence hg19 (https://genome.ucsc.edu/cgi-bin/hgGateway?db=hg19) (http://www.ncbi.nlm.nih.gov/assembly/GCF_000001405.25/) using, for example, MapSplice (Nucleic Acids Res. 2010 October; 38(18):e178. doi: 10.1093/nar/gkg622). Gene and isoform level counts may be estimated, for example, using RNA-Seq by Expectation-Maximization (RSEM) (deweylab.biostat.wisc.edu/rsem/). Gene count estimates are normalized to a fixed upper quartile. The resulting normalized gene expression estimates may then be adjusted such that the median expression value of each gene is equivalent to the median of the triple negative subset of the TCGA RNA-seq data reported in "Comprehensive Molecular Portraits of Human Breast Tumors", The Cancer Genome Atlas Network, Nature 490, 61-70 (Oct. 4, 2012) (www.nature.com/nature/journal/v490/n7418/full/naturel 1412.html.

Following pre-processing, the patient sample expression data from the PAM50 gene array is processed according to the known techniques for processing intrinsic gene set data.

Complete instructions for processing of patient sample gene expression data from the PAM50 intrinsic gene set is described in detail in at least the following, and will not be detailed herein except by way of summary: Parker et al. J Clin Oncol., 27(8):1160-7 (2009); U.S. Patent Application Publication No. 2011/0145176; and U.S. Patent Application Publication No. 2013/0004482. (U.S. Patent Application Publication No. 2013/0004482 describes the application of the PAM50 classifier for screening breast cancer subjects' possible responsiveness to anthracycline therapy relying on, inter alia, classification of the patient tumor into the HER2 subtype by the PAM50 classifier.) The Spearman rank correlation to the basal-like gene expression centroid is determined. The Spearman rank correlation between the sample and the basal-like centroid is assigned as the Basal Centroid classifier score. The Spearman rank correlation to the Luminal A gene expression centroid is determined. The Spearman rank correlation between the sample and the Luminal A centroid is assigned as the Luminal A Centroid classifier score. The Basal Centroid classifier score and Luminal A Centroid classifier score so determined are then inserted into the equation, $$\text{Weighted Basal and Luminal } A \text{ classifier score} = -0.25(\text{Basal Centroid classifier score}) + 0.27(\text{Luminal } A \text{ Centroid classifier score})$$

to provide the Weighted Basal and Luminal A classifier score for the patient sample.

Samples

Samples for analysis of intrinsic subtype classification may comprise a biological sample comprising a cancer cell or tissue, such as a breast tissue sample or a primary breast tumor tissue sample. In some embodiments, the biological sample comprises breast tissue or cells. By "biological sample" is intended any sampling of cells, tissues, or bodily fluids in which expression of an intrinsic gene can be detected. Examples of such biological samples include, but are not limited to, biopsies and smears. Bodily fluids useful in the present disclosure include blood, lymph, urine, saliva, nipple aspirates, fluid from ductal lavage, gynecological fluids, or any other bodily secretion or derivative thereof. Blood can include whole blood, plasma, serum, or any derivative of blood. In some embodiments, the biological sample includes breast cells, and may particularly comprise breast tissue from a biopsy, such as a breast tumor tissue sample. Biological samples may be obtained from a subject by a variety of techniques including, for example, by scraping or swabbing an area, by using a needle to aspirate cells or bodily fluids, or by removing a tissue sample (i.e., biopsy). Methods for collecting various biological samples are well known in the art. In some embodiments, a breast tissue sample is obtained by, for example, fine needle aspiration biopsy, core needle biopsy, or excisional biopsy. In another embodiment, fluid is obtained by ductal lavage. A thin catheter is inserted into the natural opening of the milk duct. A saline solution is then infused through the catheter to rinse the duct, which loosens cells from the duct lining. The solution containing the loosened cells is withdrawn through the catheter and biopsied. Fixative and staining solutions may be applied to the cells or tissues for preserving the specimen and for facilitating examination. In one embodiment, the biological sample is a formalin-fixed, paraffin-embedded breast tissue sample, particularly a primary breast tumor sample. In various embodiments, the tissue sample is obtained from a pathologist-guided tissue core sample.

Therapeutic Agents

Androgen receptor inhibitors directly or indirectly inhibit the androgen receptor (AR) signaling pathway. In one embodiment, direct inhibitors of the AR receptor include enzalutamide, bicalutamide (Casodex), flutamide, nilutamide, ARN509, and the like. In another embodiment, indirect inhibitors of AR include Cyp 17 inhibitors such as ketoconazole, abiraterone acetate, VN/124-1 (TOK-001), orteronel (TAK-700) and the like. In another embodiment, AR inhibitors include finasteride, galeterone, cyproterone acetate, and andarine, and the like. The antigen receptor inhibitor may result in complete or partial inhibition of the biological activity of the androgen receptor.

In a preferred embodiment, the AR inhibitor is enzalutamide (Xtandi®), which has the systematic (IUPAC) name 4-(3-(4-cyano-3-(trifluoromethyl)phenyl)-5,5-dimethyl-4-oxo-2-thioxoimidazolidin-1-yl)-2-fluoro-N-methylbenzamide, directly binds the androgen receptor (AR) and has three sites of activity. It inhibits binding of androgens to AR, inhibits nuclear translocation of AR, and inhibits AR-mediated DNA binding.

In certain embodiments, the breast cancer treatment comprising an androgen receptor inhibitor further comprises one or more other anti-cancer agents that is not an androgen receptor inhibitor. Such non-AR inhibitor anticancer agents that may also be administered to patients in conjunction with AR inhibitor therapy include, for example, cyclophosphamide, fluorouracil (or 5-fluorouracil or 5-FU), methotrexate, thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb or bevacizumab, or combinations thereof.

In one embodiment, the non-AR inhibitor anticancer agent is paclitaxel. In one embodiment, the AR inhibitor is enzalutamide and the non-AR inhibitor anticancer agent is paclitaxel. As described hereinafter, it has been found that the combination of enzalutamide and paclitaxel results in enhanced cytotoxicity in tumor cells that are positive for the prognostic marker consisting of a Weighted Basal and Luminal A classifier score of greater than −0.25.

A therapeutically effective amount of one or more AR inhibitors is administered to the subject according to the present invention, to treat TNBC utilizing dosing and treatment regimens that are typically employed when administering AR inhibitors in the treatment of cancer. The AR inhibitor can be administered in the breast cancer treatments described herein, by the routes by which such agents are typically administered. A representative regimen for one such AR inhibitor, enzalutamide, is 160 mg/day orally, once daily. The dosage form may comprise, for example, a capsule. The daily dose may be administered, for example, in the form of a capsule comprising 160 mg enzalutamide. In another embodiment, four capsules, each comprising 40 mg enzalutamide, are administered. Lower or higher doses may be utilized. The non-AR inhibitor agents are administered according to well-known dosages and treatment regimens for such agents as used in the treatment of breast cancer.

TABLE 1

PAM50 Intrinsic Gene List

| Gene | Genbank Accession No. | Forward Primer | SEQ ID NO: | Reverse Primer | SEQ ID NO: |
|---|---|---|---|---|---|
| ACTR3B | NM_020445 NM_001040135 | AAAGATTCCTG GGACCTGA | 1 | TGGGGCAGTTCT GTATTACTTC | 51 |
| ANLN | NM_018685 | ACAGCCACTTTC AGAAGCAAG | 2 | CGATGGTTTTGT ACAAGATTTCTC | 52 |
| BAGI | NM_004323 | CTGGAAGAGTT GAATAAAGAGC | 3 | GCAAATCCTTGG GCAGA | 53 |
| BCL2 | NM_000633 | TACCTGAACCG GCACCTG | 4 | GCCGTACAGTTC CACAAAGG | 54 |
| BIRC5 | NM_001012271 | GCACAAAGCCA TTCTAAGTC | 5 | GACGCTTCCTAT CACTCTATTC | 55 |
| BKVRA | BX647539 | GCTGGCTGAGC AGAAAG | 6 | TTCCTCCATCAA GAGTTCAACA | 56 |
| CCNB1 | NM_031966 | CTTTCGCCTGAG CCTATTT | 7 | GGGCACATCCAG ATGTTT | 57 |
| CCNE1 | BC035498 | GGCCAAAATCG ACAGGAC | 8 | GGGTCTGCACAG ACTGCAT | 58 |
| CDC20 | BG256659 | CTGTCTGAGTGC CGTGGAT | 9 | TCCTTGTAATGG GGAGACCA | 59 |
| CDC6 | NM_001254 | GTAAATCACCTT CTGAGCCT | 10 | ACTTGGGATATG TGAATAAGACC | 60 |
| CDCA1 | NM_031423 | GGAGGCGGAAG AAACCAG | 11 | GGGGAAAGACA AAGTTTCCA | 61 |
| CDH3 | BC041846 | GACAAGGAGAA TCAAAAGATCA GC | 12 | ACTGTCTGGGTC CATGGCTA | 62 |
| CENPF | NM_016343 | GTGGCAGCAGA TCACAA | 13 | GGATTTCGTGGT GGGTTC | 63 |
| CEP55 | AB091343 | CCTCACGAATT GCTGAACTT | 14 | CCACAGTCTGTG ATAAACGG | 64 |
| CXXC5 | BC006428 | CATGAAATAGT GCATAGTTTGCC | 15 | CCATCAACATTC TCTTTATGAACG | 65 |
| EGFR | NM_005228 | ACACAGAATCT ATACCCACCAG AGT | 16 | ATCAACTCCCAA ACGGTCAC | 66 |
| ERBB2 | NM_001005862 | GCTGGCTCTCAC ACTGATAG | 17 | GCCCTTACACAT CGGAGAAC | 67 |
| ESR1 | NM_001122742 | GCAGGGAGAGG AGTTTGT | 18 | GACTTCAGGGTG CTGGAC | 68 |
| EXO1 | NM_130398 | CCCATCCATGTG AGGAAGTATAA | 19 | TGTGAAGCCAGC AATATGTATC | 69 |
| FGFR4 | AB209631 | CTTCTTGGACCT TGGCG | 20 | TATTGGGAGGCA GGAGGTTTA | 70 |
| FOXA1 | NM_004496 | GCTACTACGCA GACACG | 21 | CTGAGTTCATGT TGCTGACC | 71 |
| FOXC1 | NM_001453 | GATGTTCGAGT CACAGAGG | 22 | GACAGCTACTAT TCCCGTT | 72 |
| GPR160 | AJ249248 | TTCGGCTGGAA GGAACC | 23 | TATGTGAGTAAG CTCGGAGAC | 73 |
| GRB7 | NM_005310 | CGTGGCAGATG TGAACGA | 24 | AGTGGGCATCCC GTAGA | 74 |

TABLE 1-continued

PAM50 Intrinsic Gene List

| Gene | Genbank Accession No. | Forward Primer | SEQ ID NO: | Reverse Primer | SEQ ID NO: |
|---|---|---|---|---|---|
| HSPCISO (UBE2T) | NM_014176 | GGAGATCCGTC AACTCCAAA | 25 | AGTGGACATGCG AGTGGAG | 75 |
| KIF2C | NM_006845 | TGGGTCGTGTC AGGAAAC | 26 | CACCGCTGGAAA CTGAAC | 76 |
| KNTC2 | NM_006101 | CGCAGTCATCC AGAGATGTG | 27 | CGTGCACATCCA TGACCTT | 77 |
| KRT14 | BC042437 | ACTCAGTACAA GAAAGAACCG | 28 | GAGGAGATGACC TTGCC | 78 |
| KRT17 | AK095281 | GTTGGACCAGT CAACATCTCTG | 29 | GCCATAGCCACT GCCACT | 79 |
| KRT5 | M21389 | TGTGGCTCATTA GGCAAC | 30 | CTTCGACTGGAC TCTGT | 80 |
| MAPT | NM_001123066 | GACTCCAAGCG CGAAAAC | 31 | CAGACATGTTGG TATTGCACATT | 81 |
| MDM2 | M92424 | CCAACAAAATA TTCATGGTTCTT G | 32 | AGGCGATCCTGG GAAATTAT | 82 |
| MELK | NM_014791 | CCAGTAGCATT GTCCGAG | 33 | CCCATTTGTCTG TCTTCAC | 83 |
| MIA | BG765502 | GTCTCTGGTAAT GCACACT | 34 | CTGATGGTTGAG GCTGTT | 84 |
| MK167 | NM_002417 | GTGGAATGCCT GCTGACC | 35 | CGCACTCCAGCA CCTAGAC | 85 |
| MLPH | NM_024101 | AGGGGTGCCCT CTGAGAT | 36 | TCACAGGGTCAA ACTTCCAGT | 86 |
| MMP11 | NM_005940 | CGAGATCGCCA AGATGTT | 37 | GATGGTAGAGTT CCAGTGATT | 87 |
| MYBL2 | BX647151 | AGGCGAACACA CAACGTC | 38 | TCTGGTCACGCA GGGCAA | 88 |
| MYC | NM_002467 | AGCCTCGAACA ATTGAAGA | 39 | ACACAGATGATG GAGATGTC | 89 |
| NATI | BC013732 | ATCGACTGTGT AAACAACTAGA GAAGA | 40 | AGTAGCTACATC TCCAGGTTCTCT G | 90 |
| ORC6L | NM_014321 | TTTAAGAGGGC AATGGAAGG | 41 | CGGATTTTATCA ACGATGCAG | 91 |
| PGR | NM_000926 | TGCCGCAGAAC TCACTTG | 42 | CATTTGCCGTCC TTCATCG | 92 |
| PHGDH | AK093306 | CCTCAGATGAT GCCTATCCA | 43 | GCAGGTCAAAAC TCTCAAAG | 93 |
| PTTG1 | BE904476 | CAGCAAGCGAT GGCATAGT | 44 | AGCGGGCTTCTG TAATCTGA | 94 |
| RRM2 | AK123010 | AATGCCACCGA AGCCTC | 45 | GCCTCAGATTTC AACTCGT | 95 |
| SFRP1 | BC036503 | TCGAACTGAAG GCTATTTACGA G | 46 | CTGCTGAGAATC AAAGTGGGA | 96 |
| SLC39A6 | NM_012319 | GTCGAAGCCGC AATTAGG | 47 | GGAACAAACTGC TCTGCCA | 97 |
| TMEM45B | AK098106 | CAAACGTGTGT TCTGGAAGG | 48 | ACAGCTCTTTAG CATTTGTGGA | 98 |

TABLE 1-continued

| PAM50 Intrinsic Gene List | | | | | |
|---|---|---|---|---|---|
| Gene | Genbank Accession No. | Forward Primer | SEQ ID NO: | Reverse Primer | SEQ ID NO: |
| TYMS | BQ056428 | TGCCCTGTATGA TGTCAGGA | 49 | GGGACTATCAAT GTTGGGTTCTC | 99 |
| UBE2C | BC032677 | GTGAGGGGTGT CAGCTCAGT | 50 | CACACAGTTCAC TGCTCCACA | 100 |

TABLE 2

| PAM50 Intrinsic Gene Sequences | | |
|---|---|---|
| Gene | Genbank Accession No. | SEQ ID NO: |
| ACTR3B | NM_020445 | 101 |
| | NM_001040135 | 102 |
| ANLN | NM_018685 | 103 |
| BAG1 | NM_004323 | 104 |
| BCL2 | NM_000633 | 105 |
| BIRC5 | NM_001012271 | 106 |
| BKVRA | BX647539 | 107 |
| CCNB1 | NM_031966 | 108 |
| CCNE1 | BC035498 | 109 |
| CDC20 | BG256659 | 110 |
| CDC6 | NM_001254 | 111 |
| CDCA1 | NM_031423 | 112 |
| CDH3 | BC041846 | 113 |
| CENPF | NM_016343 | 114 |
| CEP55 | AB091343 | 115 |
| CXXC5 | BC006428 | 116 |
| EGFR | NM_005228 | 117 |
| ERBB2 | NM_001005862 | 118 |
| ESR1 | NM_001122742 | 119 |
| EXO1 | NM_130398 | 120 |
| FGFR4 | AB209631 | 121 |
| FOXA1 | NM_004496 | 122 |
| FOXC1 | NM_001453 | 123 |
| GPR160 | AJ249248 | 124 |
| GRB7 | NM_005310 | 125 |
| HSPC150 (UBE2T) | NM_014176 | 126 |
| KIF2C | NM_006845 | 127 |
| KNTC2 | NM_006101 | 128 |
| KRT14 | BC042437 | 129 |
| KRT17 | AK095281 | 130 |
| KRT5 | M21389 | 131 |
| MAPT | NM_001123066 | 132 |
| MDM2 | M92424 | 133 |
| MELK | NM_014791 | 134 |
| MIA | BG765502 | 135 |
| MK167 | NM_002417 | 136 |
| MLPH | NM_024101 | 137 |
| MMP11 | NM_005940 | 138 |
| MYBL2 | BX647151 | 139 |
| MYC | NM_002467 | 140 |
| NATI | BC013732 | 141 |
| ORC6L | NM_014321 | 142 |
| PGR | NM_000926 | 143 |
| PHGDH | AK093306 | 144 |
| PTTG1 | BE904476 | 145 |
| RRM2 | AK123010 | 146 |
| SFRP1 | BC036503 | 147 |
| SLC39A6 | NM_012319 | 148 |
| TMEM45B | AK098106 | 149 |
| TYMS | BQ056428 | 150 |
| UBE2C | BC032677 | 151 |

The practice of the invention is illustrated by the following non-limiting examples.

EXAMPLES

Example 1

Clinical Study Protocol

A clinical trial was conducted to determine clinical benefit of enzalutamide treatment in patients whose tumors are androgen receptor-positive (AR+) and triple-negative. In this study, AR+ is defined as any nuclear AR staining by immunohistochemistry (IHC) and TNBC is defined as <1% staining by IHC for estrogen receptor (ER) and progesterone receptor (PgR), 0 or 1+ by IHC for human epidermal growth factor receptor 2 (HER2), or negative for HER2 amplification by in situ hybridization (ISH) for 2+ IHC disease. AR staining was carried out by IHC with two different antibodies each of which were individually optimized on breast cancer tissue. Enzalutamide (160 mg/day) was administered as four 40 mg soft gelatin capsules orally once daily with or without food. Patients received enzalutamide until disease progression per Response Evaluation Criteria in Solid Tumors version 1.1 (RECIST 1.1) was documented unless treatment was discontinued due to other reasons specified in the trial protocol. The study periods included prescreening (patients could sign consent to submit to tissue for testing for AR expression at any time in their disease course); screening (28 days before first dose of study drug); treatment (day 1 through discontinuation); safety follow-up (approximately 30 days after the last dose of study drug or before initiation of a new antitumor treatment, whichever occurs first); and long-term follow-up (assessment of subsequent breast cancer therapies and survival status every 3 to 6 months after treatment discontinuation). Objective response—complete response (CR) or partial response (PR)—was determined by investigators according to the RECIST 1.1.

The trial was a Simon 2-stage study where a minimum benefit was required in a pre-defined patient population prior to expanding the study to a larger size. In Stage 1, 42 patients enrolled into the study to obtain the pre-defined 26 Evaluable patients. The requisite clinical benefit to proceed to Stage 2 was observed in Stage 1 and an additional 76 patients were enrolled for a total of 118 patients overall. Patients who received prior treatment with an androgen receptor signaling inhibitor, who had central nervous system (CNS) metastases were excluded; there was no limit to number of prior therapies, and patients with patients measurable disease or bone-only nonmeasurable disease were eligible. Clinical Benefit Rate at 16 weeks (CBR16) was defined as the proportion of Evaluable Patients with a best response of complete remission (CR), partial response (PR)

or stable disease (SD) ≥16 weeks (CBR16). The Clinical Benefit Rate at ≥24 weeks (CBR16) was also assessed.

In Stage 1, 42 patients were enrolled to get 26 Evaluable Patients (n=26). Evaluable patients were those who had both AR staining in >10% of tumor and at least 1 post-baseline tumor assessment. The Intent-To-Treat (ITT) population (n=42 in Stage 1) was defined as all enrolled patients who had centrally assessed AR+ TNBC and received at least 1 dose of study drug. Twenty-six (62%) of 42 ITT patients were Evaluable, while 16 of 42 were not Evaluable. Of the 16 not meeting the criteria for Evaluable, 10 had AR expression below 10%; 6 had AR expression ≥10% but did not have a post-baseline assessment (2 were discovered to have CNS metastases shortly after study entry and were withdrawn from treatment prior to having a post-baseline tumor assessment). More than 50% of the patients received enzalutamide as their first or second line of therapy, while >30% had ≥3 prior regimens before receiving enzalutamide.

Intrinsic Gene Expression Analysis

Human breast tumors from TNBC patients were obtained from the aforementioned clinical study of enzalutamide, an AR antagonist. The patient breast cancer tissue was stained for AR expression. The patient staining was graded by a pathologist on both the staining intensity (3+, 2+ and 1+) as well as the percentage of tumor cells stained as given in the standard operating procedure. AR staining was evaluated both in the nucleus and cytoplasm.

RNA-seq data utilized in this study were pre-processed as follows. The RNA-seq data was aligned to Human (*Homo sapiens*) genome sequence hg19 from the Human Genome Browser—hg19 Assembly created by the Genome Bioinformatics Group of UC Santa Cruz (genome.ucsc.edu/cgi-bin/hgGateway?db=hg19) (www.ncbi.nlm.nih.gov/assembly/GCF_000001405.25/) using MapSplice (Nucleic Acids Res. 2010 October; 38(18):e178. doi: 10.1093/nar/gkq622). Gene and isoform level counts were estimated using RNA-Seq by Expectation-Maximization (RSEM) (deweylab.biostat.wisc.edu/rsem/). Gene count estimates were normalized to a fixed upper quartile. The resulting normalized gene expression estimates were adjusted such that the median expression value of each gene was equivalent to the median of the triple negative subset of the TCGA RNA-seq data reported in "Comprehensive Molecular Portraits of Human Breast Tumors", The Cancer Genome Atlas Network, Nature 490, 61-70 (Oct. 4, 2012) (www.nature.com/nature/journal/v490/n7418/full/nature11412.html).

Intrinsic subtype classification was performed into the LumA, LumB, Basal, HER2 and Normal groups using the PAM50 classification model as described in Parker et al. J Clin Oncol., 27(8):1160-7 (2009). The intrinsic subtype classification was carried out on genomic data obtained from RNA sequencing of RNA obtained from formalin fixed, paraffin embedded tissue collected from subjects' breast tumors. The data was pre-processed as indicated above. Subtype classification was performed on a "Training and Test" set and a further "Validation" set. The Training and Test set consisted of 122 patient samples out of which 42 patients were from the pre-screened population but not enrolled in the study and 80 patients samples were from the enrolled population in the clinical study. The Validation set consisted of 55 patient samples which had 15 patients from the pre-screened population not enrolled on the study and 40 samples from the enrolled population.

The data was analyzed according to the known methods for analyzing PAM50 intrinsic gene set data, as described by Parker et al. et al., supra. Essentially, the detection and estimation of the expression of the set of 50 subtype predictor genes of Table 1 from patient tumor samples was carried out. The expression profile of the set of 50 subtype predictor genes by the described method that provides Basal-like, HER2, LumA, LumB and Normal subtype classifications was analyzed. The Spearman correlation was calculated for each sample and PAM50 centroid. These values were used as continuous estimates of distance or similarity of a sample to each centroid. The subtype of each sample was assigned as the closest (largest positive correlation) centroid. The underlying measures of correlation to each subtype were used to classify a sample as one of 4 tumor subtypes (Basal-like, HER2, LumA and LumB) or Normal-like.

Further, the Spearman rank correlation to the Basal-like gene expression centroid was evaluated. The Spearman rank correlation between the sample and the Basal-like centroid was assigned as the "Basal Centroid classifier score". The Spearman rank correlation to the Luminal A gene expression centroid was evaluated. The Spearman rank correlation between the sample and the Luminal A centroid was assigned as the "Luminal A classifier score".

Figure 1:
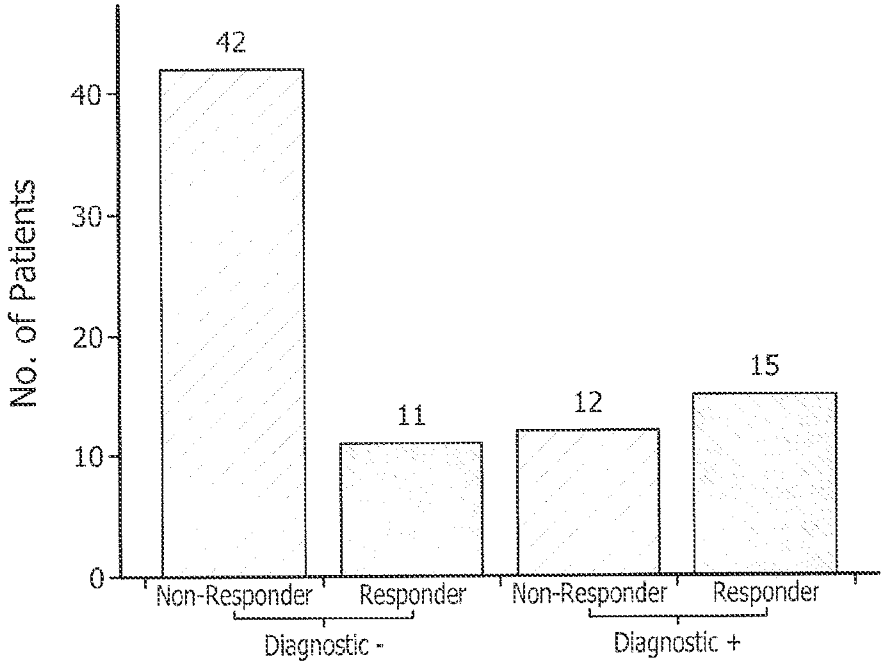
FIG. 1 is a graph of the results from some of the patients enrolled into either the prescreening or screening period of a clinical trial evaluating enzalutamide in patients whose TNBC also expressed AR. "Diagnostic −" represents patients having the Basal-like subtype, as determined by PAM50 gene breast cancer subtype classification. "Diagnostic +" represents the patients with Her2, LumA, LumB or Normal subtypes. Patients were scored as "Responder" or "Non-Responder" to the enzalutamide therapy according to the criteria set forth in Example 1.

In the enrolled patients (Intent-To-Treat (ITT) population, Basal-like subtype generally correlated with non-response to enzalutamide therapy, while existence of one of the other subtypes generally correlated with response to enzalutamide therapy. See FIG. 1, wherein "Diagnostic −" represents the Basal-like subtype patients and "Diagnostic+" represents the patients with Her2, LumA, LumB or Normal subtypes. Thus, a PAM50 gene expression classifier result indicating a non-Basal-like tumor type is a marker for predicting responsiveness to enzalutamide therapy in TNBC.

Example 2

The results of the clinical study of Example 1 were further analyzed utilizing the patient Basal Centroid classifier scores. The therapeutic response data was evaluated imposing a series of threshold cut-offs on the Basal Centroid classifier score. The enzalutamide response/non-response data was analyzed using Basal Centroid classifier score cut-offs of 0.2, 0.3, 0.4, 0.5, 0.6, 0.65, 0.7, 0.8 and 0.9. The data is set forth in FIGS. 2A/B through 10A/B. In each figure, "Diagnostic+" represents patients whose samples met the indicated prognostic signature comprising the indicted threshold cut-off. "Diagnostic −" represents patients whose samples did not meet the indicated threshold cut-off.

| | FIG. | | | | | | | | |
|---|---|---|---|---|---|---|---|---|---|
| | 2A/B | 3A/B | 4A/B | 5A/B | 6A/B | 7A/B | 8A/B | 9A/B | 10A/B |
| Basal Centroid classifier score | 0.2 | 0.3 | 0.4 | 0.5 | 0.6 | 0.65 | 0.7 | 0.8 | 0.9 |

Figure 2A:
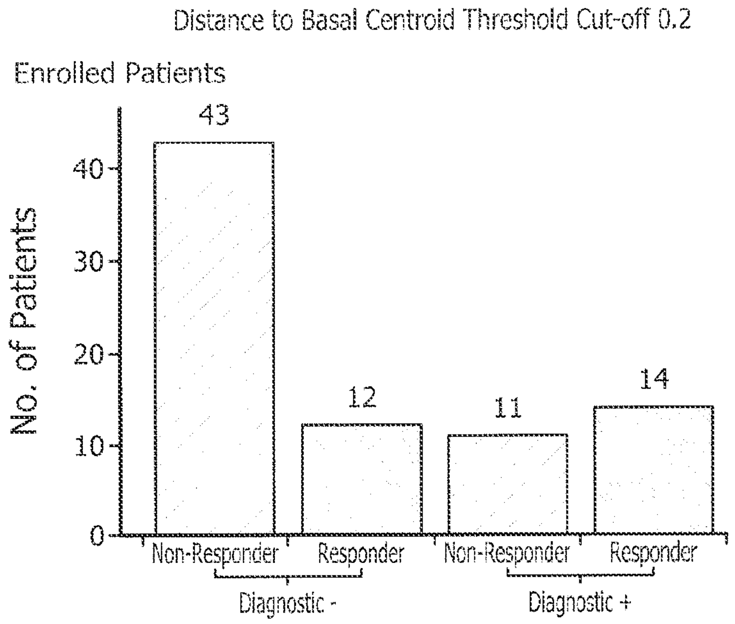
FIGS. 2A and 2B are graphs of results of the same TNBC clinical trial in which patient gene expression classifier scores for the Basal-like subtype were correlated with patient response. A threshold cut-off of 0.2 for the patient Basal Centroid classifier score was applied. "Diagnostic+" represents patients whose samples met the indicated prognostic signature comprising the indicted threshold cut-off "Diagnostic −" represents patients whose samples did not meet the indicated threshold cut-off. Patients were scored as "Responder" or "Non-Responder" to the enzalutamide therapy according to the criteria set forth in Example 1.
Figure 2B:
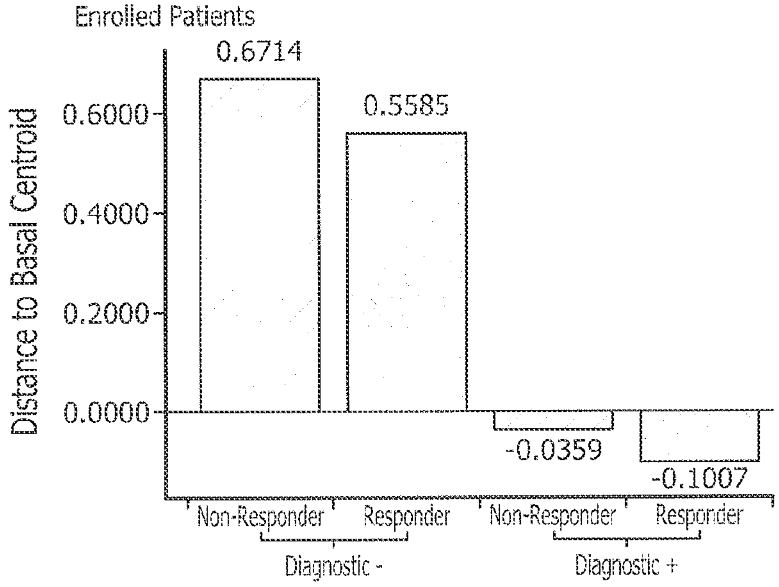
Figure 3A:
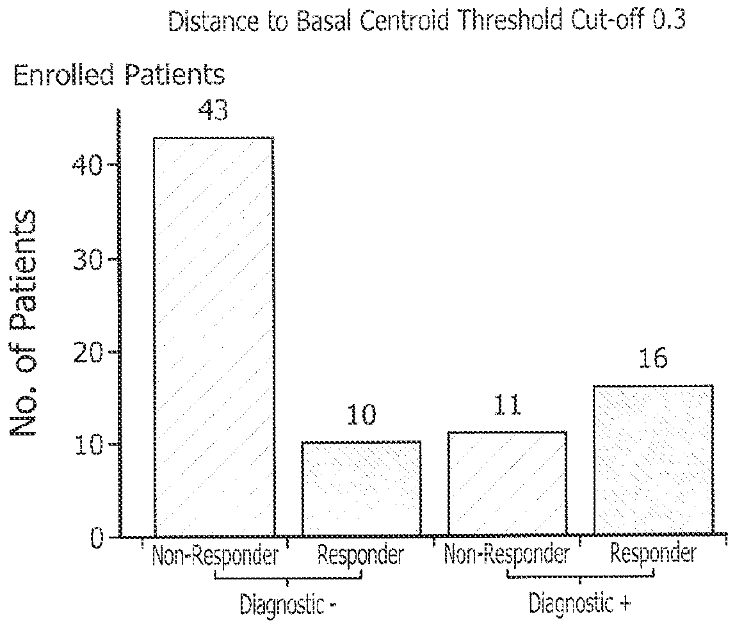
FIGS. 3A and 3B are graphs of results of the same TNBC clinical trial in which patient gene expression classifier scores for the Basal-like subtype were correlated with patient response. A threshold cut-off of 0.3 for the patient Basal Centroid classifier score was applied, "Diagnostic +" represents patients whose samples met the indicated prognostic signature comprising the indicted threshold cut-off. "Diagnostic −" represents patients whose samples did not meet the indicated threshold cut-off. Patients were scored as "Responder" or "Non-Responder" to the enzalutamide therapy according to the criteria set forth in Example 1.
Figure 3B:
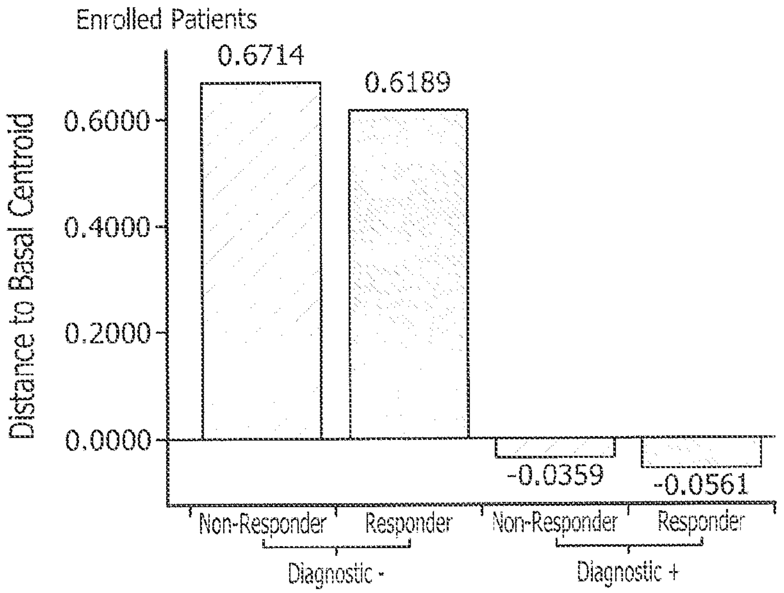
Figure 4A:
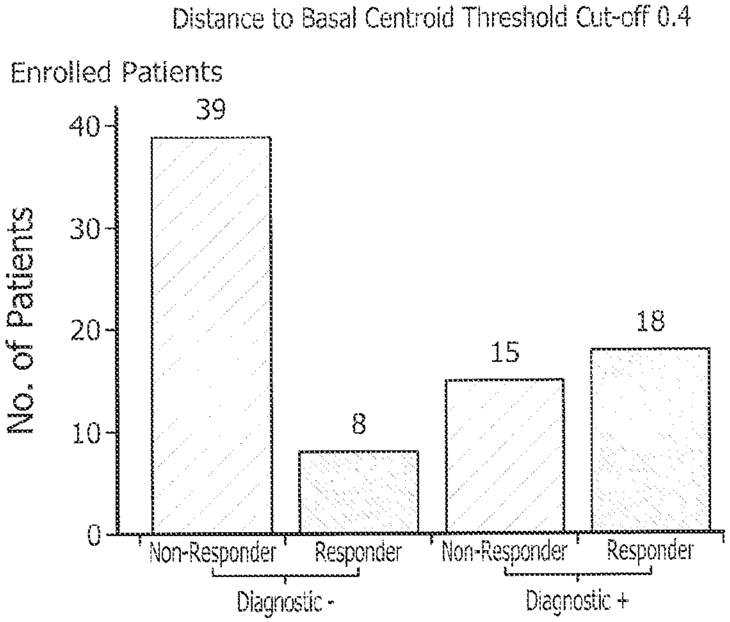
FIGS. 4A and 4B are graphs of results of the same TNBC clinical trial in which patient gene expression classifier scores for the Basal-like subtype were correlated with patient response. A threshold cut-off of 0.4 for the patient Basal Centroid classifier score was applied. "Diagnostic+" represents patients whose samples met the indicated prognostic signature comprising the indicted threshold cut-off. "Diagnostic −" represents patients whose samples did not meet the indicated threshold cut-off. Patients were scored as "Responder" or "Non-Responder" to the enzalutamide therapy according to the criteria set forth in Example 1.
Figure 4B:
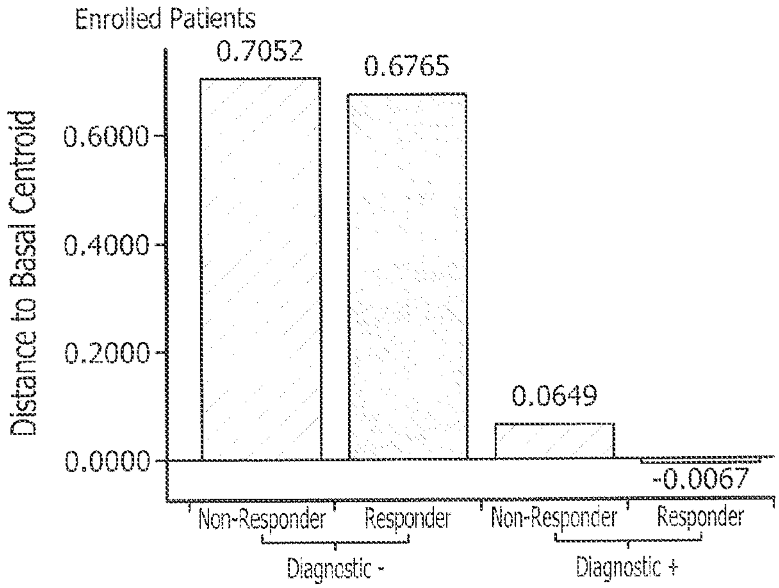
Figure 5A:
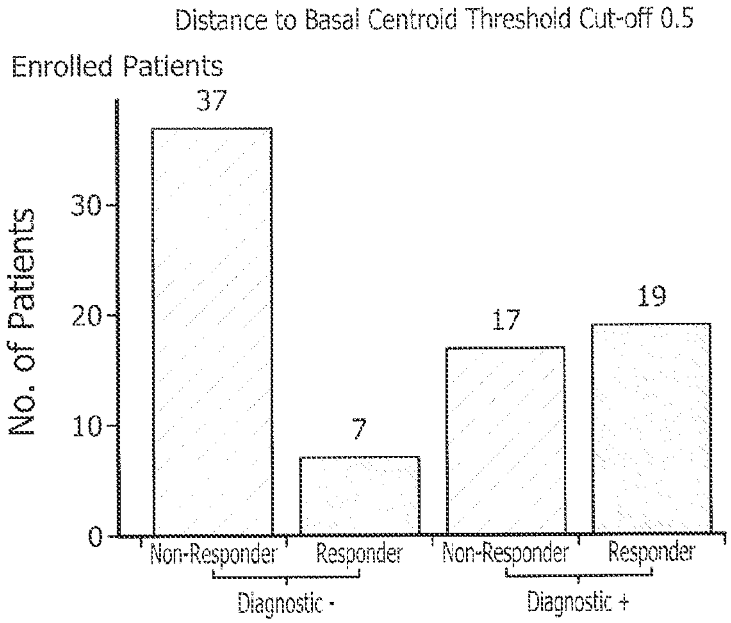
FIGS. 5A and 5B are graphs of results of the same TNBC trial in which patient gene expression classifier scores for the Basal-like subtype were correlated with patient response. A threshold cut-off of 0.5 for the patient Basal Centroid classifier score was applied. "Diagnostic+" represents patients whose samples met the indicated prognostic signature comprising the indicted threshold cut-off "Diagnostic −" represents patients whose samples did not meet the indicated threshold cut-off. Patients were scored as "Responder" or "Non-Responder" to the enzalutamide therapy according to the criteria set forth in Example 7.
Figure 5B:
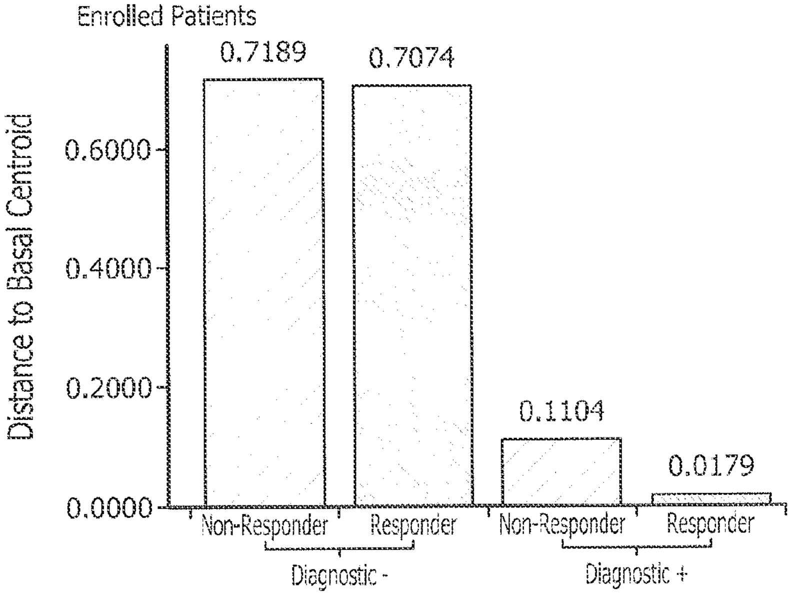
Figure 6A:
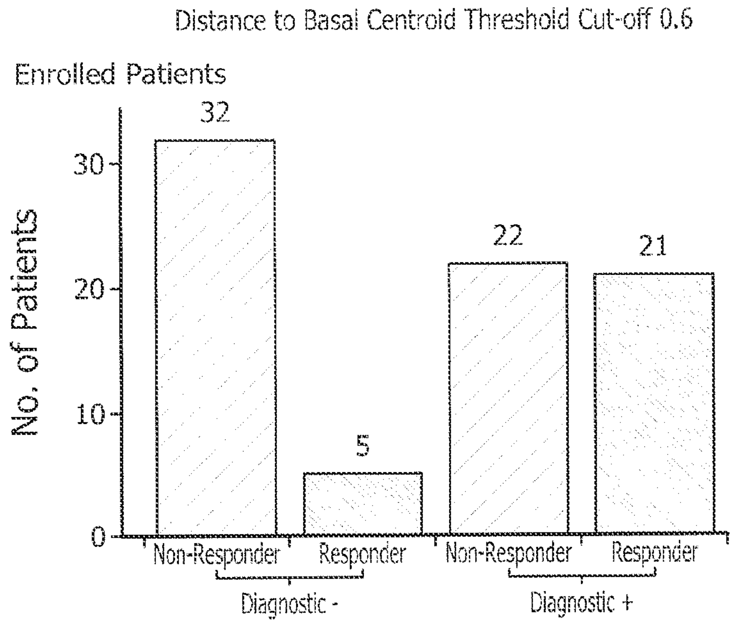
FIGS. 6A and 6B are graphs of results of the same TNBC clinical trial in which patient gene expression classifier scores for the Basal-like subtype were correlated with patient response. A threshold cut-off of 0.6 for the patient Basal Centroid classifier score was applied. "Diagnostic+" represents patients whose samples met the indicated prognostic signature comprising the indicted threshold cut-off "Diagnostic −" represents patients whose samples did not meet the indicated threshold cut-off. Patients were scored as "Responder" or "Non-Responder" to the enzalutamide therapy according to the criteria set forth in Example 1.
Figure 6B:
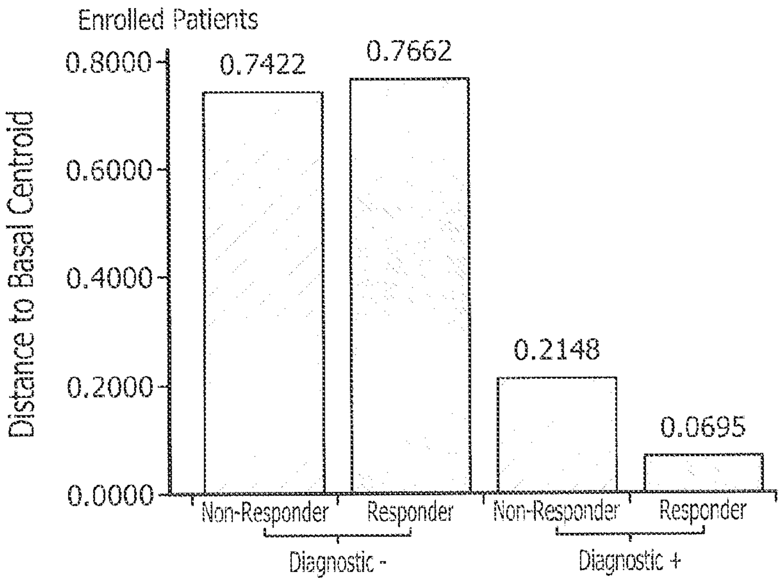
Figure 7A:
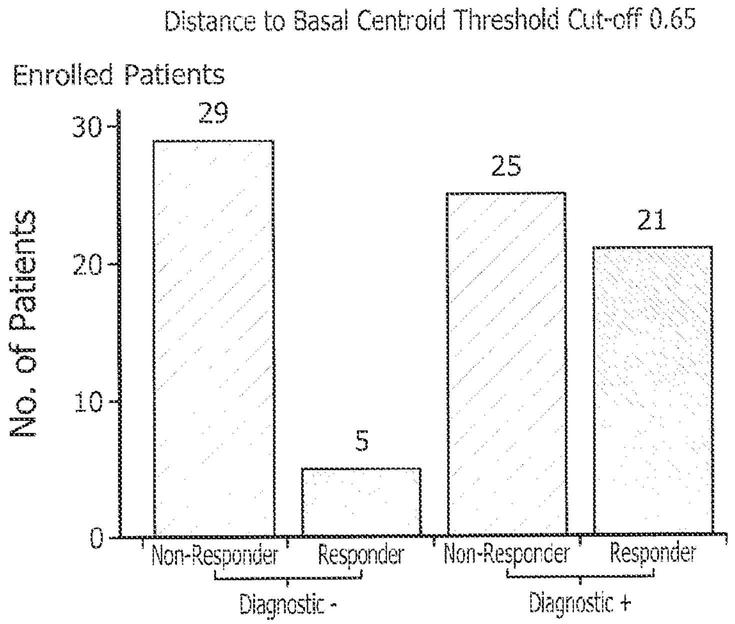
FIGS. 7A and 7B are graphs of results of the same TNBC clinical trial in which patient gene expression classifier scores for the Basal-like subtype were correlated with patient response. A threshold cut-off of 0.65 for the patient Basal Centroid classifier score was applied. "Diagnostic+" represents patients whose samples met the indicated prognostic signature comprising the indicted threshold cut-off. "Diagnostic −" represents patients whose samples did not meet the indicated threshold cut-off. Patients were scored as "Responder" or "Non-Responder" to the enzalutamide therapy according to the criteria set forth in Example 1.
Figure 7B:
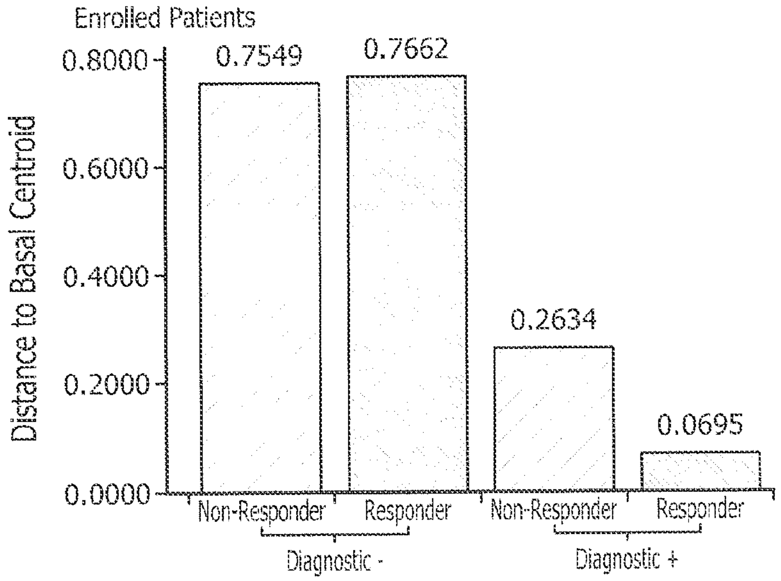
Figure 8A:
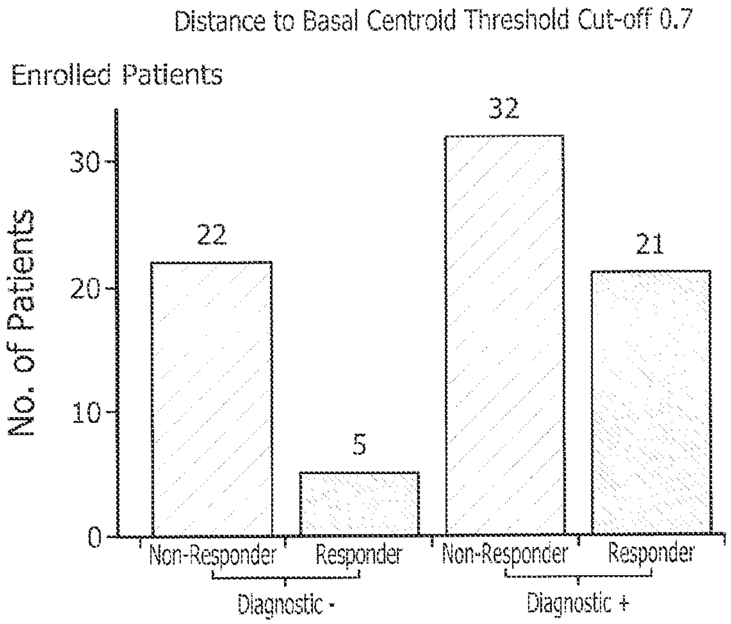
FIGS. 8A and SB are graphs of results of the same TNBC clinical trial in which patient gene expression classifier scores for the Basal-like subtype were correlated with patient response. A threshold cut-off of 0.7 for the patient Basal Centroid classifier score was applied. "Diagnostic+" represents patients whose samples met the indicated prognostic signature comprising the indicted threshold cut-off "Diagnostic –" represents patients whose samples did not meet the indicated threshold cut-off. Patients were scored as "Responder" or "Non-Responder" to the enzalutamide therapy according to the criteria set forth in Example 1.
Figure 8B:
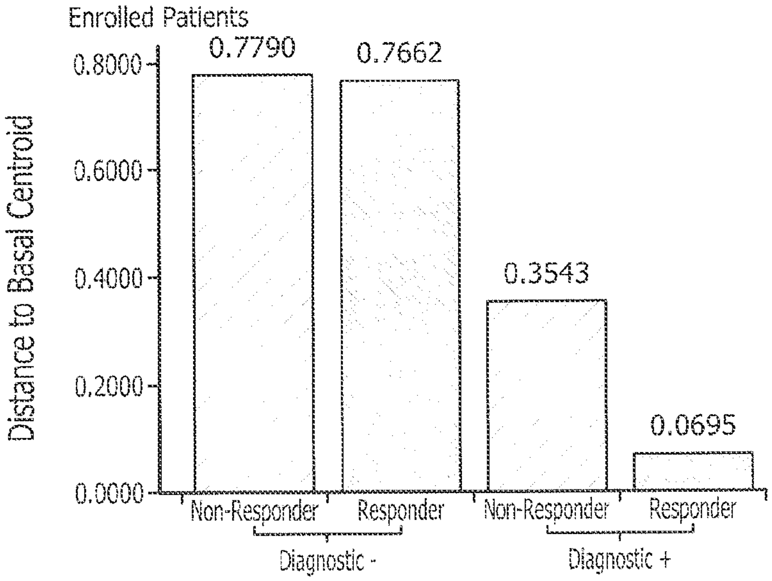
Figure 9A:
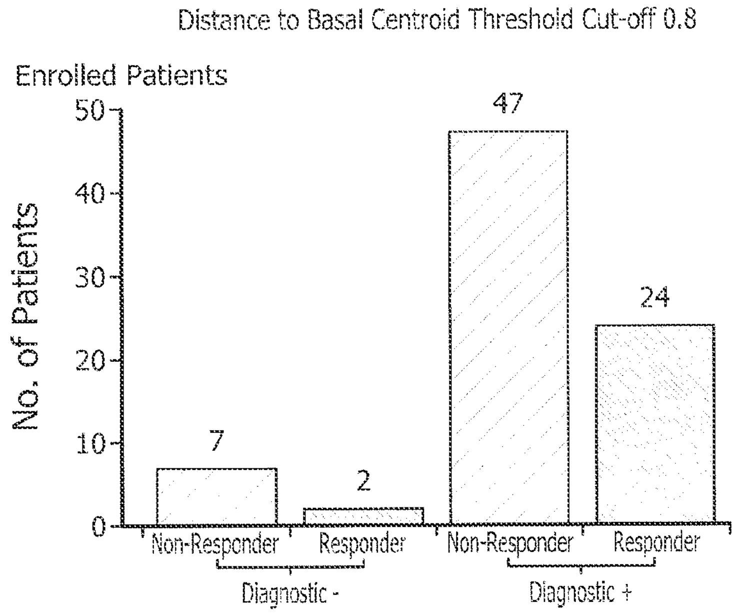
FIGS. 9A and 9B are graphs of results of the same TNBC clinical trial in which patient gene expression classifier scores for the Basal-like subtype were correlated with patient response. A threshold cut-off of 0.8 for the patient Basal Centroid classifier score was applied. "Diagnostic+" represents patients whose samples met the indicated prognostic signature comprising the indicted threshold cut-off. "Diagnostic –" represents patients whose samples did not meet the indicated threshold cut-off. Patients were scored as "Responder" or "Non-Responder" to the enzalutamide therapy according to the criteria set forth in Example 1.
Figure 9B:
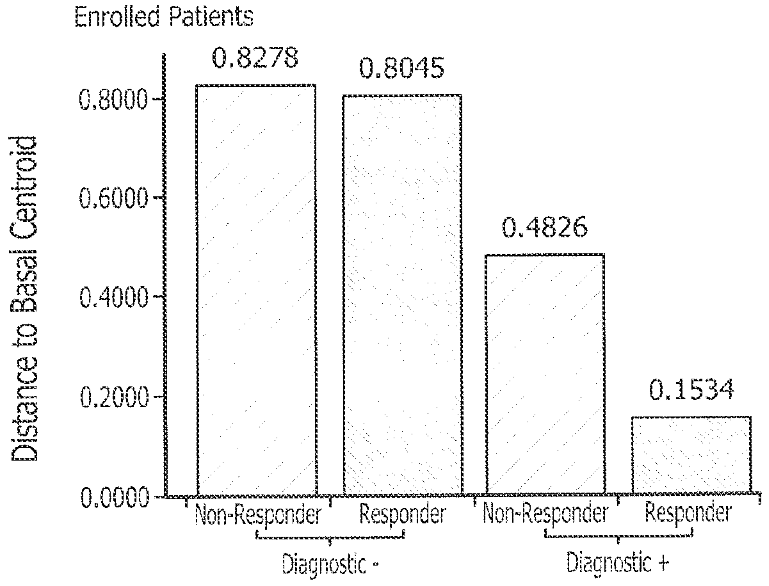
Figure 10A:
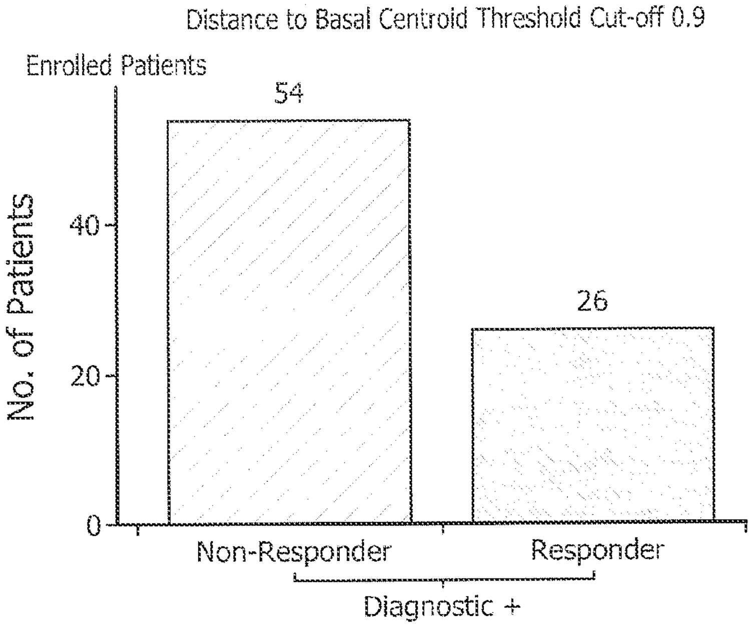
FIGS. 10A and 10B are graphs of results of the same TNBC clinical trial in which patient gene expression classifier scores for the Basal-like subtype were correlated with patient response. A threshold cut-off of 0.9 for the patient Basal Centroid classifier score was applied. "Diagnostic+" represents patients whose samples met the indicated prognostic signature comprising the indicted threshold cut-off. "Diagnostic –" represents patients whose samples did not meet the indicated threshold cut-off. Patients were scored as "Responder" or "Non-Responder" to the enzalutamide therapy according to the criteria set forth in Example 1.
Figure 10B:
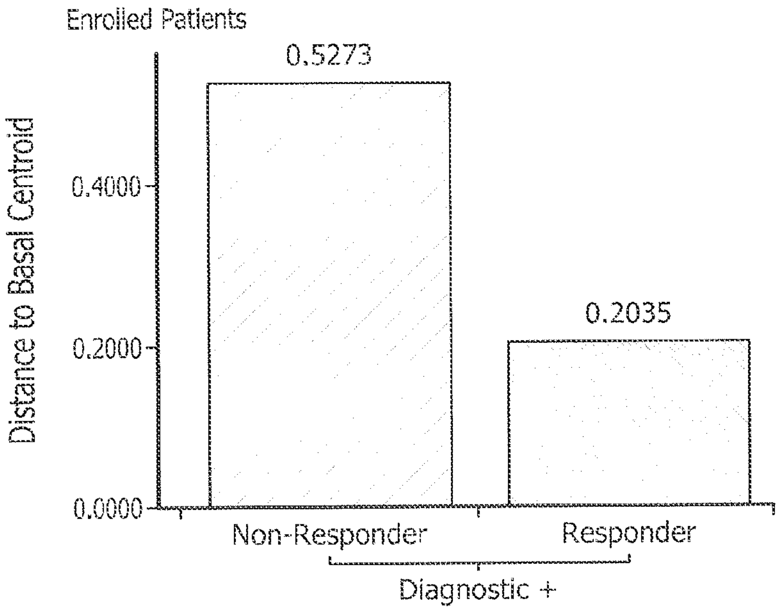

As shown in FIGS. 2A/B-10A/B, a target Basal Centroid classifier score of 0.6 or less for defining Dx+ and Dx− patients best correlated with response to enzalutamide therapy, while defining the Dx+ and Dx− based upon scores from 0.2 to 0.9 enriched the predictive value somewhat less. Thus, defining the population of responders and non-responders upon a Basal Centroid classifier cutoff score that is in the range of 0.2-0.9 is a further basis for predicting responsiveness to enzalutamide therapy in TNBC, with a sample's Basal Centroid classifier score of 0.6 or less being a preferred embodiment for a marker to predict responsiveness. As shown in FIG. 6A, defining Dx+ and Dx− pursuant to a relative Basal Centroid classifier score of 0.6 resulted in a prediction that yielded a large Diagnostic+ population with most responders in the Diagnostic+ population and high non-responders in the Diagnostic − population.

Example 3

Figure 11:
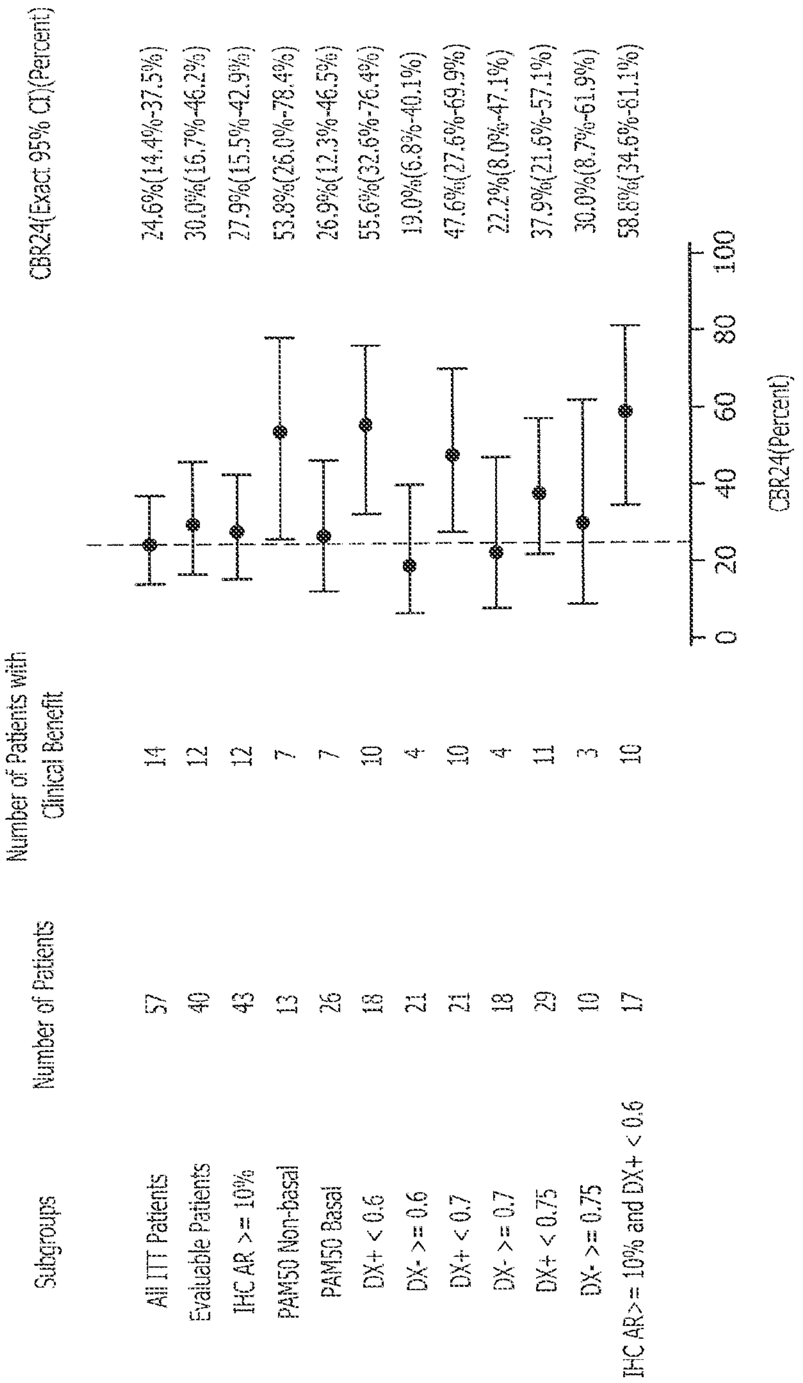
FIG. 11 comprises a representation of the response to enzalutamide of various patient subgroups treated with enzalutamide in the clinical trial. Response is shown in terms of Clinical Benefit Rate at ≥24 weeks (CBR24). The subgroups include Intent-To-Treat (ITT) patients; Evaluable Patients; patients with breast tumor tissue which was AR staining 10% (IHC AR >=10%); patients whose breast tumor tissue was classified as a non-Basal like subtype by the PAM50 subtype classifier (PAM50 non-basal); patients whose tumors were classified as Basal-like subtype (PAM50 basal); and patient samples analyzed by applying the indicated cut-offs of <0.6, ≥0.6, <0.7, ≥0.7, <0.75 and ≥0.75, from patient Basal Centroid classifier scores. "DX –" signifies patients whose samples did not meet the indicated threshold cut-off "DX +" signifies patients whose samples did meet the indicated threshold cut-off. Also shown in in FIG. 11 are data for the combined criteria IHC AR >=10% and DX+<0.6.

The results of the clinical study of Example 1 are further analyzed and summarized in FIG. 11, showing the response of various patient subgroups to enzalutamide therapy in terms of Clinical Benefit Rate at ≥24 weeks (CBR24). The subgroups include all Intent-To-Treat (ITT) patients; Evaluable Patients; patients with breast tumor tissue which was AR staining ≥10% (IHC AR >=10%); patients whose breast tumor tissue was classified as a non-Basal like subtype by the PAM50 subtype classifier (PAM50 non-basal); patients whose tumors were classified as Basal like subtype (PAM50 basal); and patient samples analyzed by applying the indicated cut-offs of <0.6, ≥0.6, <0.7, ≥0.7, <0.75 ≥0.75 to the Basal Centroid classifier score. "DX −" signifies patients whose samples did not meet the indicated threshold cut-off. "DX+" signifies patients whose samples did meet the indicated threshold cut-off. Also shown in in FIG. 11 are data for the samples satisfying the combined criteria IHC AR >=10% and DX+<0.6, that is the sample met the criteria of (i) staining for AR of more than 10% and (ii) a PAM50 gene expression Basal Centroid classifier score of 0.6 or less.

Example 4

Figure 12:
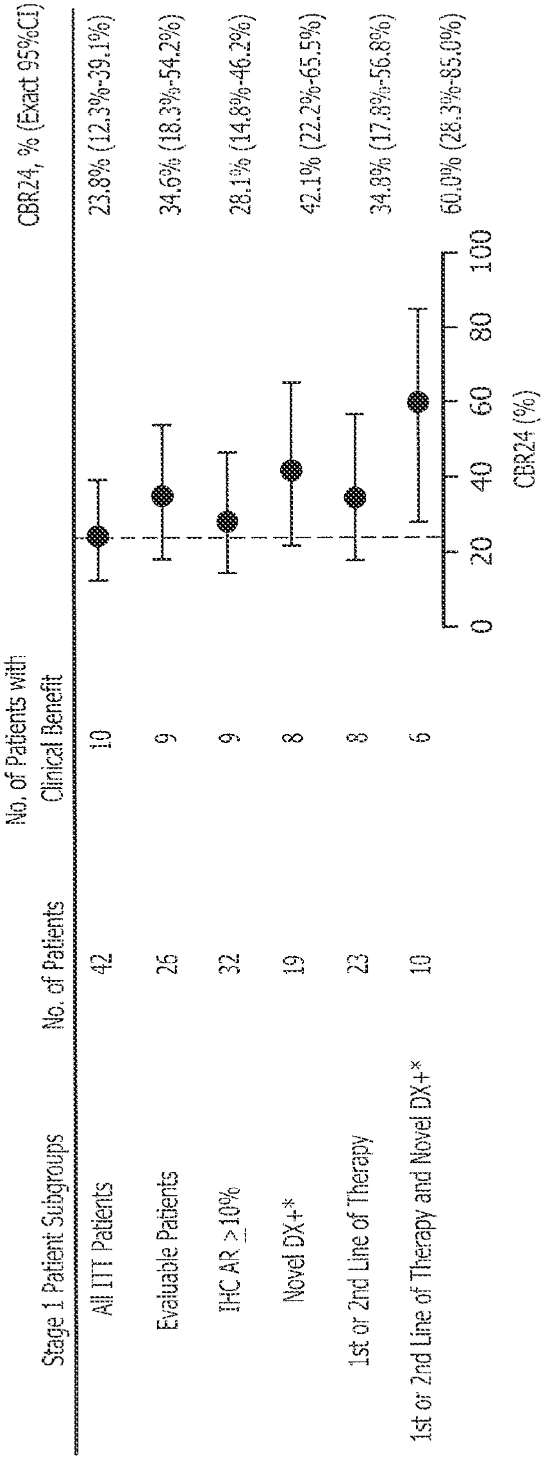
FIG. 12 is a further representation of the response to enzalutamide of various patient subgroups treated with enzalutamide in the clinical trial. Response is shown in terms of Clinical Benefit Rate at ≥24 weeks (CBR24). The subgroups include Intent-To-Treat (ITT) patients; Evaluable Patients; patients with breast tumor tissue which was AR staining 10% (IHC AR >=10%); and patients in which the enzalutamide therapy is administered as the first (1st line) or second (2nd line) of therapy. The subgroups further include a subgroup of patient samples analyzed by applying a <0.6 cut-off to Basal Centroid classifier scores ("Novel DX+"), and a subgroup comprising samples from 1st and 2nd line therapy, applying the <0.6 cut-off to Basal Centroid classifier scores.

The results of the clinical study of Example 1 are further analyzed and summarized in FIG. 12, showing the response of various patient subgroups to enzalutamide therapy in terms of Clinical Benefit Rate at ≥24 weeks (CBR24). The subgroups include all Intent-To-Treat (ITT) patients; Evaluable Patients; patients with breast tumor tissue which was AR staining ≥10% (IHC AR >=10%); and patients in which the enzalutamide therapy is the sole (1st line) or second (2nd line) of therapy. The subgroups further include subgroup of patient samples analyzed by applying a <0.6 Basal Centroid classifier score cut-off ("Novel DX+,"), and a subgroup comprising samples from 1st and 2nd line therapy, applying the <0.6 cut-off. A CBR of 42% using the prognostic Basal Centroid classifier score of <0.6 (and 60% when used in a group comprising both 1st line and 2nd line patients) exceeds typical benchmarks for predicting responsiveness to therapy in TNBC and is on a par with the predictive ability of models used to predict response to hormonal agent therapy in ER+/PgR+ breast cancer.

Example 5

Figure 13:
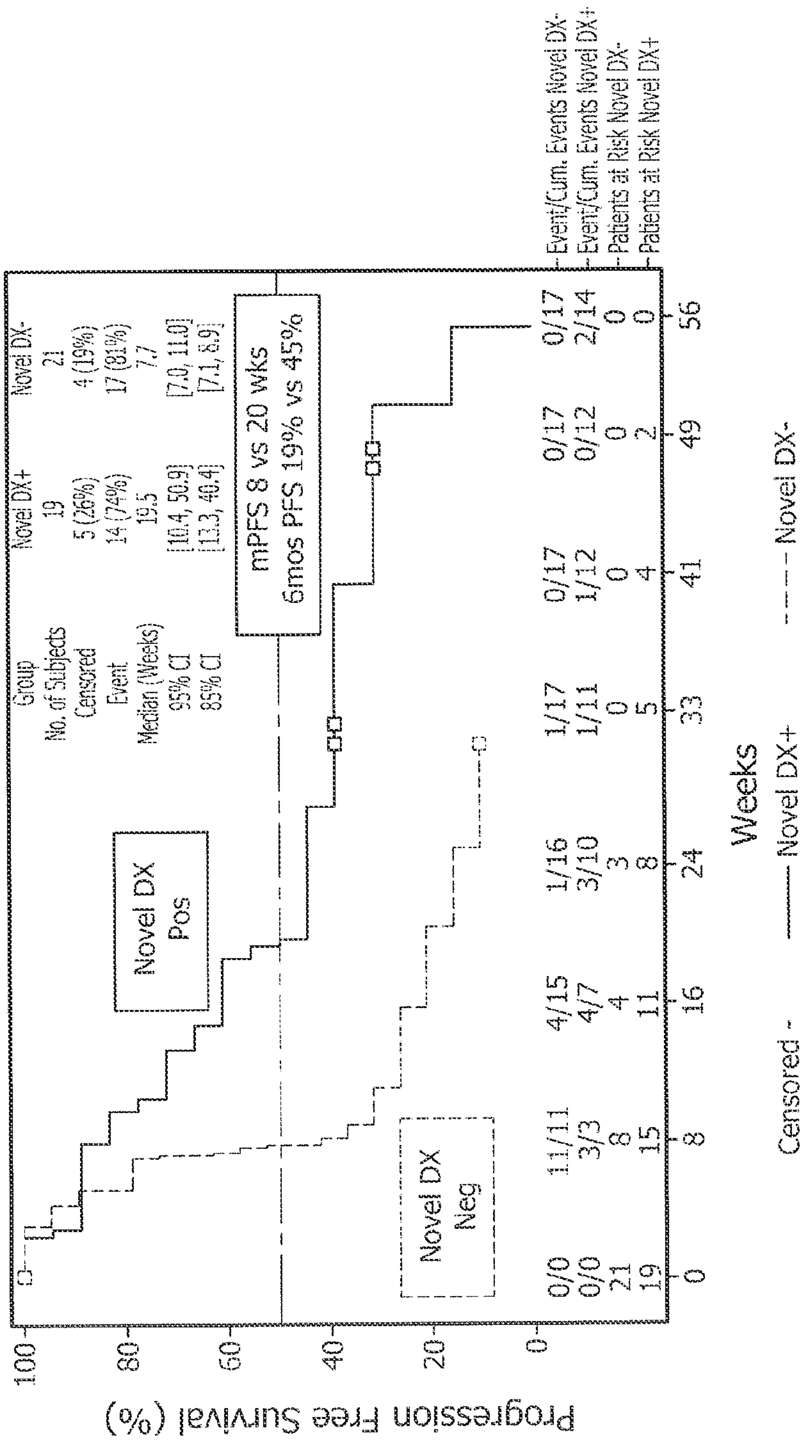
FIG. 13 is a Kaplan-Meier plot showing median progression-free survival (MPS) of patients treated with enzalutamide as a function of time. The curves correspond to patients that were identified as meeting the novel prognostic signature condition of a Basal Centroid classifier score of <0.6 ("Novel DX Pos") versus patients who did not meet the definition ("Novel DX Neg").

The effect of the novel prognostic signature utilizing a Basal Centroid classifier score of <0.6 as a predictor of response to AR inhibitor therapy is further illustrated in FIG. 13 with respect to patient progression-free survival time to 56 weeks. The results demonstrate a prolonged progression-free survival in patients that were identified as meeting the novel prognostic signature condition of a Basal Centroid classifier score of <0.6 ("Novel DX Pos") versus patients having a ≥0.6 distance score ("Novel DX Neg").

Example 6

The results of the clinical study of Example 1 were further analyzed utilizing the patient Basal Centroid classifier and Luminal A classifier scores. The classifier scores and response data were analyzed. As a result of analysis, a Weighted Basal and Luminal A classifier score was empirically devised that predicted responsiveness to androgen receptor inhibitor therapy in the clinical trial. The Weighted Basal and Luminal A classifier score of patient samples was determined from the following formula:

$$\text{Weighted Basal and Luminal } A \text{ classifier score} = -0.2468275(\text{Basal Centroid classifier score}) + 0.2667110(\text{Luminal } A \text{ Centroid classifier score}).$$

The therapeutic response data was then evaluated imposing a series of threshold cut-offs on the Weighted Basal and Luminal A classifier score. Specifically, the enzalutamide response/non-response data was analyzed using Weighted Basal and Luminal A classifier score cut-offs of greater than −0.2, greater than −0.25, greater than −0.3 and greater than −0.35. The data is set forth in FIGS. 14A (>−0.2), 14B (>−0.25), 14C (>−0.3), and 14D (>−0.35). In each figure, "Diagnostic+" represents patients whose samples met the indicated prognostic signature comprising the indicted threshold cut-off "Diagnostic −" represents patients whose samples did not meet the indicated threshold cut-off.

As shown in FIGS. 14A-14D, selecting a criterion of a Weighted Basal and Luminal A classifier of greater than x, with r in the range of −0.2 to −0.3, best correlated with response to enzalutamide therapy, with the criterion of a score of greater than −0.25 being optimal. Thus, defining the population of responders and non-responders based upon a Weighted Basal and Luminal A classifier score that is greater than −0.2, or greater than −0.3 is a basis for predicting responsiveness to enzalutamide therapy in TNBC, with a Weighted Basal and Luminal A classifier score of greater than −0.25 being a preferred embodiment of a criterion for predicting responsiveness.

Example 7

The results of the clinical study of Example 1 are further analyzed and summarized in FIG. 15, showing the response of various patient subgroups to enzalutamide therapy in terms of Clinical Benefit Rate at ≥24 weeks (CBR24). The subgroups include all Intent-To-Treat (ITT) patients; Evaluable Patients; patients whose breast tumor tissue samples were analyzed by applying the indicated cut-offs of >−0.2, >−0.25, >−0.3, and >−0.35, to the Weighted Basal and Luminal A classifier score. "PR-AR DX −" signifies patients whose samples did not meet the indicated threshold cut-off. "PR-AR DX+" signifies patients whose samples did meet the indicated threshold cut-off. Thus, for example, "PR-AR DX+>−0.25" indicates the patients whose samples met the criterion of a Weighted Basal and Luminal A classifier score greater than −0.25.

Also shown in in FIG. 15 are data for samples from patients in the study receiving enzalutamide therapy (i) after having received from zero to one prior therapies for treatment of TNBC with a drug other than an androgen receptor inhibitor ("and 0-1 prior therapy") or (ii) after having received two or more prior therapies for treatment of TNBC with a drug other than an androgen receptor inhibitor ("and >=2 prior therapies"). A Weighted Basal and Luminal A classifier score cut-off of >−0.25 was applied to these patient samples.

Example 8

The effect of the novel prognostic signature utilizing a Weighted Basal and Luminal A classifier score cut-off of >−0.2 as a predictor of response to AR inhibitor therapy is further illustrated in FIG. 16 with respect to patient progression-free survival time to 56 weeks. The results demonstrate a prolonged progression-free survival in patients that were identified as meeting the prognostic signature condition of a Weighted Basal and Luminal A classifier score of greater than −0.2 ("PR-AR DX+: >−0.2", top curve) versus a classifier score of less than or equal to −0.2 ("PR-AR DX−: <=−0.2", bottom curve).

Example 9

The effect of the novel prognostic signature utilizing a Weighted Basal and Luminal A classifier score cut-off of >−0.25 as a predictor of response to AR inhibitor therapy is further illustrated in FIG. 17 with respect to patient progression-free survival time to 56 weeks. The results demonstrate a prolonged progression-free survival in patients that were identified as meeting the prognostic signature condition of a Weighted Basal and Luminal A classifier score of greater than −0.25 ("PR-AR DX+: >−0.25", top curve) versus less than or equal to −0.25 ("PR-AR DX−: <=−0.25", bottom curve).

Example 10

The effect of the novel prognostic signature utilizing a Weighted Basal and Luminal A classifier score cut-off of >−0.3 as a predictor of response to AR inhibitor therapy is further illustrated in FIG. 18 with respect to patient progression-free survival time to 56 weeks. The results demonstrate a prolonged progression-free survival in patients that were identified as meeting the prognostic signature condition of a Weighted Basal and Luminal A classifier score of greater than −0.3 ("PR-AR DX+: >−0.3", top curve) versus a classifier score of less than or equal to −0.3 ("PR-AR DX−: <=−0.3", bottom curve).

Example 11

The effect of the novel prognostic signature utilizing a Weighted Basal and Luminal A classifier score cut-off of >−0.35 as a predictor of response to AR inhibitor therapy is further illustrated in FIG. 19 with respect to patient progression-free survival time to 56 weeks. The results demonstrate a prolonged progression-free survival in patients that were identified as meeting the prognostic signature condition of a Weighted Basal and Luminal A classifier score of greater than −0.35 ("PR-AR DX+: >−0.35", top curve) versus less than or equal to −0.35 ("PR-AR DX−: <=−0.35", bottom curve).

Example 12

The effect of the novel prognostic signature utilizing a Weighted Basal and Luminal A classifier score cut-off of >−0.25 as a predictor of response to AR inhibitor therapy is further illustrated in FIG. 20 with respect to patient progression-free survival time to 56 weeks, in patients receiving from zero to one prior therapies for treatment of TNBC with a drug other than an androgen receptor inhibitor. The results demonstrate a prolonged progression-free survival in patients that were identified as meeting the prognostic signature condition of a Weighted Basal and Luminal A classifier score of greater than −0.25 ("PR-AR DX+: >−0.25", top curve) versus less than or equal to −0.25 ("PR-AR DX−: <=−0.25", bottom curve). It may be appreciated from a comparison of FIGS. 17 and 20, that the −0.25 cut-off was able to identify a longer duration of progression-free survival that characterized the zero to 1 prior therapy group (FIG. 20) versus the shorter duration of progression-free survival that characterized the population of all study patients (FIG. 17).

The effect of the novel prognostic signature utilizing a Weighted Basal and Luminal A classifier score cut-off of >−0.25 as a predictor of response to AR inhibitor therapy in patients receiving from zero to one prior therapies for treatment of TNBC with a drug other than an androgen receptor inhibitor is further shown in FIG. 23. FIG. 23 is similar to FIG. 20, except that the progression-free survival time in the study is determined beyond the 56 weeks in FIG. 20 to 64 weeks in FIG. 23.

Example 13

The effect of the novel prognostic signature utilizing a Weighted Basal and Luminal A classifier score cut-off of >−0.25 as a predictor of response to AR inhibitor therapy is further illustrated in FIGS. 21A and 21B, with respect to time on treatment without progression of patients receiving zero or one (0-1 Prior Lines), or two or more (2+ Prior Lines), prior therapies for treatment of TNBC with a drug other than an androgen receptor inhibitor. The 56 patients that were identified as meeting the signature condition of a Weighted Basal and Luminal A classifier score of greater than −0.25 are represented in FIG. 21B. The 62 study patients identified by a classifier score of less than or equal to −0.25 are identified in FIG. 21A. Each bar in the figures represents a single patient. The best time on treatment without disease progression is apparent in responder patients who received one or no prior lines of therapy (FIG. 21B). Patient bars marked with a triangle ("Active") are active on study. Patient bars marked with a star signify complete response (CR) or partial response (PR).

Example 14

The effect of the novel prognostic signature utilizing a Weighted Basal and Luminal A classifier score cut-off of >−0.25 as a predictor of response to AR inhibitor therapy is further illustrated in FIGS. 22A and 22B with respect to patient progression-free survival time to 64 weeks (FIG. 22A) and overall survival to 84 weeks (FIG. 22B). The results of FIG. 22A demonstrate a prolonged progression-free survival in patients that were identified as meeting the prognostic signature condition of a Weighted Basal and Luminal A classifier score of greater than −0.25 ("PR-AR DX+: >−0.25", top curve) versus less than or equal to −0.25 ("PR-AR DX−: <=−0.25", bottom curve). The results of FIG. 22B demonstrate a prolonged overall survival in patients that were identified as meeting the prognostic signature condition of a Weighted Basal and Luminal A classifier score of greater than −0.25 ("PR-AR DX+: >−0.25", top curve) versus less than or equal to −0.25 ("PR-AR DX−: <=−0.25", bottom curve). The patients not meeting the prognostic signature condition were characterized by a median progression-free survival of 8.1 weeks and median overall survival of 32.1 weeks. In contrast, patients meeting the prognostic signature condition were characterized by a median progression-free survival of 16.1 weeks and median overall survival not yet reached at 84 weeks.

Example 15

A Phase II clinical trial of the androgen receptor antagonist bicalutamide has been reported. Ayca et al., "Phase II Trial of Bicalutamide in Patients with Androgen Receptor Positive, Hormone Receptor Negative Metastatic Breast Cancer", *Clin Cancer Res* 19: 5505-5512 (Oct. 1, 2013). The trial was designed to study the effect of bicalutamide in treating metastatic breast cancer that is AR-positive, estrogen receptor (ER)-negative, and progesterone receptor (PgR)-negative.

Briefly, as described by Ayca et al., tumors from 452 patients with ER-negative/PgR-negative advanced breast cancer were tested centrally for AR by immunohistochemistry (IHC) (>10% nuclear staining considered positive). See Ayca et al., p. 5506 for additional eligibility criteria. If either the primary or a metastatic site was positive, patients were eligible to receive the AR antagonist bicalutamide at a dose of 150 mg daily. Twenty-eight patients were treated on study. Bicalutamide 150 mg was administered orally on a continuous daily schedule. Patients were treated until disease progression or unacceptable adverse events. A maximum of 2 dose reductions for grade >3 toxicity were allowed (100 and 50 mg). A maximum of 2 weeks was permitted for treatment delays due to toxicity. Two patients who initiated bicalutamide were removed from study, leaving 26 study participants with AR(+) ER/PgR(−) metastatic breast cancer. Five patients had stable disease >6 months (number of cycles completed: 6, 8, 10+, 13, 57+) as their best response on treatment. There were no confirmed complete or partial responses yielding a clinical benefit rate of 19% (95% CI, 7%-39%) in the target population (n=26). In an intention-to-treat analysis, a CBR of 18% (95% CI, 6%-37%) was observed. See Ayca et al., p. 5507.

Twenty-one of the 26 bicalutamide-treated study patients were determined to also be HER-2 negative, i.e., twenty-one patients had breast cancers that were triple negative (Her-2 (−), ER (−) and PgR(−)). Following the study, patient tumor samples from the twenty-one TNBC patients that received bicalutamide therapy were subjected to intrinsic subtype classification into the Luminal A, Luminal B, Basal-like, HER2-enriched and Normal-like groups using the PAM50 classification model. Each subtype score for each sample is listed in Table 3. Also set forth in Table 3 is the Weighted Basal and Luminal A classifier score of each sample. Based on the results obtained in Example 6 from the clinical trial of the AR-receptor antagonist enzalutamide, a greater than −0.25 Weighted Basal and Luminal A classifier score ("PR-AR DX+>−0.25") indicates that such patients are more likely to respond to the bicalutamide treatment than patients with a Weighted Basal and Luminal A classifier score of less than or equal to −0.25. Eight patients satisfied this criterion, and are designated in Table 3 as having a likely positive ("POS") prognosis on bicalutamide treatment. Each of the 21 patient samples displayed a confidence level of 1, except for sample No. 16, which had a confidence level of 0.99.

TABLE 3

| No. | Basal Score | Her2 Score | LumA Score | LumB Score | Normal Score | Weighted Basal/LumA Score | Prognosis |
|---|---|---|---|---|---|---|---|
| 1 | 0.542569 | −0.02857 | −0.59846 | 0.242161 | −0.25186 | −0.29354 | NEG |
| 2 | 0.405618 | −0.17714 | −0.11635 | −0.30343 | 0.296423 | −0.13115 | POS |
| 3 | 0.509628 | 0.038367 | −0.3915 | −0.20711 | 0.059208 | −0.23021 | POS |
| 4 | 0.753469 | 0.003025 | −0.59088 | −0.28912 | 0.055078 | −0.34357 | NEG |
| 5 | 0.766146 | −0.00543 | −0.69729 | −0.08581 | −0.07851 | −0.37508 | NEG |
| 6 | 0.638896 | −0.34665 | −0.22439 | −0.54103 | 0.447779 | −0.21755 | POS |
| 7 | 0.75078 | 0.112509 | −0.7188 | −0.01945 | −0.11001 | −0.37702 | NEG |
| 8 | 0.795342 | 0.039808 | −0.66511 | −0.22968 | 0.052293 | −0.37371 | NEG |
| 9 | 0.793421 | −0.06708 | −0.59818 | −0.372 | 0.158127 | −0.35538 | NEG |
| 10 | 0.699496 | −0.23275 | −0.43616 | −0.26617 | 0.192221 | −0.28898 | NEG |
| 11 | 0.634478 | −0.15333 | −0.33906 | −0.49273 | 0.304298 | −0.24704 | POS |
| 12 | 0.729556 | −0.15188 | −0.48984 | −0.35529 | 0.206531 | −0.31072 | NEG |
| 13 | 0.721104 | 0.015222 | −0.66387 | −0.074 | −0.03558 | −0.35505 | NEG |
| 14 | 0.747419 | −0.26098 | −0.42406 | −0.40687 | 0.255414 | −0.29758 | NEG |
| 15 | 0.702089 | −0.04 | −0.53719 | −0.25522 | 0.095414 | −0.31657 | NEG |
| 16 | 0.161104 | −0.10146 | −0.01647 | −0.29834 | 0.383721 | −0.04416 | POS |
| 17 | 0.571477 | −0.12826 | −0.27549 | −0.34146 | 0.260024 | −0.21453 | POS |
| 18 | 0.399184 | −0.03741 | −0.21268 | −0.22113 | 0.090708 | −0.15525 | POS |
| 19 | 0.622089 | −0.18588 | −0.31313 | −0.58329 | 0.431741 | −0.23706 | POS |
| 20 | 0.752797 | −0.13546 | −0.55064 | −0.40072 | 0.161008 | −0.33267 | NEG |
| 21 | 0.736567 | −0.1346 | −0.58339 | −0.24216 | 0.082737 | −0.3374 | NEG |

Example 16

The following study demonstrates the enhanced antitumor effect of the combination of enzalutamide plus paclitaxel in cells positive for the prognostic marker of a Weighted Basal and Luminal A classifier score greater than −0.25.

Triple negative breast cancer cell lines BT549, MDA-MB-436, MDA-MB-453 were selected for study. Messenger RNA datasets for the cell lines were down-loaded from the Cancer Cell Line Encyclopedia (CCLE) database. The Weighted Basal and Luminal A classifier score for each cell line was determined from the downloaded datasets. Applying a Weighted Basal and Luminal A classifier score of >−0.25 as a prognostic marker for responsiveness to AR inhibitor therapy, it was determined that MDA-MB453, but not BT549 and MDA-MB-436, satisfied this criterion.

Cells were maintained in 10% FBS supplemented growth media. Viability assays were performed in 10% FBS, and measured by CellTiter-Glo reagent according to the manufacturer's protocol (Promega). To determine molecular effects of enzalutamide alone or in combination with paclitaxel on androgen receptor signaling, cells (BT549, MDA-MB-436 or MDA-MB-453) were seeded on day one in 10% FBS. The cells were treated with enzalutamide or paclitaxel or the combination in 2% charcoal-stripped serum and were stimulated with 10 nM DHT for 4 hours. Cell fractionation was isolated for cytosolic and nuclear fractions. Protein expression levels were determined using a Western blotting method. The $IC_{50}$ for enzalutamide or paclitaxel for each cell line is shown in Table 4. Mean values are presented for each cell line (n=3). The prognostic marker-positive MDA-MB-453 cells exhibited greater sensitivity to enzalutamide compared to the prognostic marker-negative BT549 and MDA-MB-463 cells.

TABLE 4

| Cell Line | Enzalutamide $IC_{50}$ (μM) | Paclitaxel $IC_{50}$ (nM) |
|---|---|---|
| BT549 | 57.0 | 2.8 |
| MDA-MB-436 | 73.0 | 6.7 |
| MDA-MB-453 | 22.7 | 20.7 |

Viability of the cells was measured in the presence of the concentrations of enzalutamide (Enza) and paclitaxel (PTX) in FIGS. 24A-C. Mean values are presented for each cell line (n=5). In the prognostic marker-positive MDA-MB-453 cell line, the combination of enzalutamide plus paclitaxel resulted in enhanced cytotoxicity. See FIG. 24C.

Example 17

To generate a mouse xenograft model, 5- to 6-week-old female NOD-SCID mice were injected orthotopically into the mammary gland with $6.0\times10^6$ MDA-MB-453 cells. DHT (10.5 mg in a 60-day release pellet) or control pellets were implanted into animals. When tumor size reached ~100 $mm^3$, mice were treated by (i) oral gavage (PO) with enzalutamide ("Enza") at 3 mg/kg/day (n=10), (ii) paclitaxel ("PTX") at 6 mg/kg QMWF (IP) (n=7), or (iii) the combination of (i) and (ii) (n=10). A control group of mice (n=8) was treated with vehicle (0.5% Methocel solution). Tumor size was measured by caliper. Tumor weights were determined at day 35. The results are shown in FIG. 25A (tumor volume vs. time) and FIG. 25B (tumor weight). Data points in FIG. 25A represent the average tumor volume for each group, and error bars reflect the SEM of the data. The student T-Test was used to calculate p values: FIG. 25A: control v. enzalutamide, 0.007; control v. paclitaxel, 0.0007; enzalutamide vs. enzalutamide plus paclitaxel, 0.074; paclitaxel vs. enzalutamide plus paclitaxel, 0.013. FIG. 25B: control v. enzalutamide, 0.001; control v. paclitaxel, 0.0001; enzalutamide vs. enzalutamide plus paclitaxel, 0.08; paclitaxel vs. enzalutamide plus paclitaxel, 0.017. The data demonstrates that the combination of enzalutamide plus paclitaxel results in enhanced antitumor effect compared to either drug alone.

Representative tumors from each treated group were selected to perform immunohistochemistry against AR, Ki67 or p-AKT. Immunohistochemistry staining for Ki67 or AKT phosphorylation was significantly reduced in the enzalutamide plus paclitaxel tumors compared to the enzalutamide or paclitaxel single treated group (data not shown).

The disclosures of each and every patent, patent application, and publication cited herein are hereby incorporated herein by reference in their entirety. One skilled in the art will readily appreciate that the present invention is well adapted to carry out the objects and obtain the ends and advantages mentioned, as well as those inherent therein. While the invention has been disclosed with reference to specific embodiments, it is apparent that other embodiments and variations of this invention may be devised by others skilled in the art without departing from the true spirit and scope used in the practice of the invention. The appended claims are intended to be construed to include all such embodiments and equivalent variations.

The invention claimed is:

1. A method of treating triple negative breast cancer (TNBC) in a subject, said subject having a breast cancer comprising breast cancer cells that have been classified as other than basal-like subtype, said method comprising:

testing the subject to determine a Weighted Basal and Luminal A classifier score of breast cancer cells of the subject; and administering a breast cancer treatment to the subject comprising an androgen receptor inhibitor, thereby treating the triple negative breast cancer in the subject;

wherein the triple negative breast cancer cells of the subject are characterized by a Weighted Basal and Luminal A classifier score greater than −0.3 according to the formula:

$$\text{Weighted Basal and Luminal } A \text{ classifier score} = -0.25(\text{Basal Centroid classifier score}) + 0.27(\text{Luminal } A \text{ Centroid classifier score})$$

wherein said Basal Centroid classifier score and said Luminal A Centroid classifier score are determined for the triple negative breast cancer cells of the subject from the expression by said cells of the set of intrinsic genes listed in Table 1 using a PAM50 classifier and detecting the set of intrinsic genes by RNA sequencing.

2. The method according to claim 1, wherein the breast cancer cells of the subject are characterized by a Weighted Basal and Luminal A classifier score greater than −0.2.

3. The method according to claim 1, wherein the breast cancer cells of the subject are characterized by a Weighted Basal and Luminal A classifier score greater than −0.25.

4. The method according to claim 1, wherein the breast cancer of the subject is characterized by the presence of androgen receptor-positive tumor cells.

5. The method according to claim 1, wherein the androgen receptor inhibitor is selected from the group consisting of enzalutamide, bicalutamide, flutamide, nilutamide, ARN509, ketoconazole, abiraterone acetate, VN/124-1 (TOK-001), orteronel (TAK-700), finasteride, galeterone, cyproterone acetate, andarine, and combinations thereof.

6. The method according to claim 5, wherein the androgen receptor inhibitor is enzalutamide.

7. The method according to claim 1, wherein the androgen receptor inhibitor is enzalutamide.

8. The method according to claim 2, wherein the androgen receptor inhibitor is enzalutamide.

9. The method according to claim 3, wherein the androgen receptor inhibitor is enzalutamide.

10. The method according to claim 6, wherein the enzalutamide is orally administered once daily at a dose of 160 mg.

11. The method according to claim 10, wherein the enzalutamide is administered as a single capsule comprising 160 mg enzalutamide.

12. The method according to claim 10, wherein the enzalutamide is administered as four capsules, each capsule comprising 40 mg enzalutamide.

13. The method according to claim 1, wherein the breast cancer treatment comprising an androgen receptor inhibitor further comprises one or more other anti-cancer agents that is not an androgen receptor inhibitor.

14. The method according to claim 13, wherein the other anti-cancer agent that is not an androgen receptor inhibitor is selected from the group consisting of cyclophosphamide, fluorouracil, 5-fluorouracil, methotrexate, thiotepa, carboplatin, cisplatin, a taxane, paclitaxel, protein-bound paclitaxel, docetaxel, vinorelbine, tamoxifen, raloxifene, toremifene, fulvestrant, gemcitabine, irinotecan, ixabepilone, temozolomide, topotecan, vincristine, vinblastine, eribulin, mutamycin, capecitabine, anastrozole, exemestane, letrozole, leuprolide, abarelix, buserelin, goserelin, megestrol acetate, risedronate, pamidronate, ibandronate, alendronate, denosumab, zoledronate, trastuzumab, tykerb, bevacizumab, and combinations thereof.

15. The method according to claim 14, wherein the other anti-cancer agent that is not an androgen receptor inhibitor is paclitaxel.

16. The method according to claim 1, further comprising a step of testing the subject to determine whether the subject has a breast cancer comprising breast cancer cells that are other than basal-like subtype.

17. The method according to claim 3, wherein the subject has received zero or one round of prior treatment with an anti-cancer agent, other than an androgen receptor inhibitor, for treatment of triple negative breast cancer.

18. A method of treating triple negative breast cancer in a subject in need of such treatment comprising:

(a) providing a biological sample from the subject;

(b) assaying the biological sample to determine whether the biological sample is classified as a basal-like subtype or another subtype from the expression of the set of intrinsic genes listed in Table 1 using a PAM50 classifier and detecting the set of intrinsic genes by RNA sequencing; and (c) if the biological sample is classified as other than a basal-like subtype, administering a breast cancer treatment to the subject comprising an androgen receptor inhibitor, thereby treating the breast cancer in the subject.

19. The method according to claim 18, comprising:

(a) determining the Basal Centroid classifier score and the Luminal A Centroid classifier score of the sample from the expression of the set of intrinsic genes listed in Table 1 using the PAM 50 classifier; and (b) calculating a Weighted Basal and Luminal A classifier score from the Basal Centroid classifier score and the Luminal A Centroid classifier score according to the following equation:

Weighted Basal and Luminal *A* classifier score=−0.25(Basal Centroid classifier score)+0.27(Luminal *A* Centroid classifier score); and wherein the breast cancer treatment is administered to the subject if the Weighted Basal and Luminal A classifier score is greater than −0.3.

20. The method according to claim 19, wherein the breast cancer treatment is administered if the Weighted Basal and Luminal A classifier score is greater than −0.2.

21. The method according to claim 19, wherein the breast cancer treatment is administered if the Weighted Basal and Luminal A classifier score is greater than −0.25.

22. The method according to claim 18, wherein the breast cancer of the subject is characterized by the presence of androgen receptor-positive tumor cells.

23. The method according to claim 18, wherein the androgen receptor inhibitor is selected from the group consisting of enzalutamide, bicalutamide, flutamide, nilutamide, ARN509, ketoconazole, abiraterone acetate, VN/124-1 (TOK-001), orteronel (TAK-700), finasteride, galeterone, cyproterone acetate, andarine, and combinations thereof.

24. The method according to claim 23, wherein the androgen receptor inhibitor is enzalutamide.

25. The method according to claim 19, wherein the androgen receptor inhibitor is enzalutamide.

26. The method according to claim 20, wherein the androgen receptor inhibitor is enzalutamide.

27. The method according to claim 21, wherein the androgen receptor inhibitor is enzalutamide.

28. The method according to claim 24, wherein the enzalutamide is orally administered once daily at a dose of 160 mg.

29. The method according to claim 28, wherein the enzalutamide is administered as a single capsule comprising 160 mg enzalutamide.

30. The method according to claim 28, wherein the enzalutamide is administered as four capsules, each capsule comprising 40 mg enzalutamide.

31. The method according to claim 18, wherein the breast cancer treatment comprising an androgen receptor inhibitor further comprises one or more other anti-cancer agents that is not an androgen receptor inhibitor.

32. The method according to claim 31, wherein the other anti-cancer agent that is not an androgen receptor inhibitor is selected from the group consisting of cyclophosphamide, fluorouracil, 5-fluorouracil, methotrexate, thiotepa, carboplatin, cisplatin, a taxane, paclitaxel, protein-bound paclitaxel, docetaxel, vinorelbine, tamoxifen, raloxifene, toremifene, fulvestrant, gemcitabine, irinotecan, ixabepilone, temozolomide, topotecan, vincristine, vinblastine, eribulin, mutamycin, capecitabine, anastrozole, exemestane, letrozole, leuprolide, abarelix, buserelin, goserelin, megestrol acetate, risedronate, pamidronate, ibandronate, alendronate, denosumab, zoledronate, trastuzumab, tykerb, bevacizumab, and combinations thereof.

33. The method according to claim 32, wherein the other anti-cancer agent that is not an androgen receptor inhibitor is paclitaxel.

34. The method according to claim 18, wherein the biological sample is selected from the group consisting of a cell, tissue, and bodily fluid.

35. The method according to claim 34, wherein the biological sample comprises breast tissue or cells.

36. The method of claim 35, wherein the tissue is obtained from a biopsy.

37. The method of claim 35, wherein the bodily fluid is selected from the group consisting of blood, lymph, urine, saliva, fluid from ductal lavage, and nipple aspirate.

38. The method according to claim 21, wherein the subject has received zero or one round of prior treatment with an anti-cancer agent, other than an androgen receptor inhibitor, for treatment of triple negative breast cancer.

39. The method according to claim 1, wherein prior to determining the Basal centroid classifier score, the sample expression data is normalized and adjusted such that the median expression value of each gene in Table 1 is equivalent to the median of a known subset from a subject with triple negative breast cancer.

40. The method according to claim 18, wherein prior to determining the Basal centroid classifier score, the sample expression data is normalized and adjusted such that the median expression value of each gene in Table 1 is equivalent to the median of a known subset from a subject with triple negative breast cancer.

41. The method according to claim 1, wherein (i) the sample expression data is aligned to human genome sequence hg19; (ii) gene and isoform level counts are estimated using RNA sequencing by expectations maximization; (iii) the gene level counts estimates are normalized to a fixed upper quartile; and (iv) the resulting normalized gene expression estimates are then adjusted such that the median expression value of each gene is equivalent to the median of the triple negative subset of TCGA RNA sequence data.

42. The method according to claim 18, wherein (i) the sample expression data is aligned to human genome sequence hg19; (ii) gene and isoform level counts are estimated using RNA sequencing by expectations maximization; (iii) the gene level counts estimates are normalized to a fixed upper quartile; and (iv) the resulting normalized gene expression estimates are then adjusted such that the median expression value of each gene is equivalent to the median of the triple negative subset of TCGA RNA sequence data.

* * * * *

SEQUENCE LISTING

```
<160> NUMBER OF SEQ ID NOS: 151

<210> SEQ ID NO 1
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 1

aaagattcct gggacctga                                                  19


<210> SEQ ID NO 2
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 2

acagccactt tcagaagcaa g                                               21


<210> SEQ ID NO 3
<211> LENGTH: 22
<212> TYPE: DNA
```

-continued

<213> ORGANISM: Artificial Sequence
<220> FEATURE:
<223> OTHER INFORMATION: Chemically synthesized primer

<400> SEQUENCE: 3
ctggaagagt tgaataaaga gc 22

<210> SEQ ID NO 4
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 4
tacctgaacc ggcacctg 18

<210> SEQ ID NO 5
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 5
gcacaaagcc attctaagtc 20

<210> SEQ ID NO 6
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 6
gctggctgag cagaaag 17

<210> SEQ ID NO 7
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 7
ctttcgcctg agcctattt 19

<210> SEQ ID NO 8
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 8
ggccaaaatc gacaggac 18

<210> SEQ ID NO 9
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 9
ctgtctgagt gccgtggat 19

-continued

<210> SEQ ID NO 10
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 10
gtaaatcacc ttctgagcct 20

<210> SEQ ID NO 11
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 11
ggaggcggaa gaaaccag 18

<210> SEQ ID NO 12
<211> LENGTH: 24
<212> TYPE: DNA
<213> ORGANISM: Artificial Sequence
<220> FEATURE:
<223> OTHER INFORMATION: Chemically synthesized primer

<400> SEQUENCE: 12
gacaaggaga atcaaaagat cagc 24

<210> SEQ ID NO 13
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 13
gtggcagcag atcacaa 17

<210> SEQ ID NO 14
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 14
cctcacgaat tgctgaactt 20

<210> SEQ ID NO 15
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 15
catgaaatag tgcatagttt gcc 23

<210> SEQ ID NO 16
<211> LENGTH: 25
<212> TYPE: DNA
<213> ORGANISM: Artificial Sequence
<220> FEATURE:

<223> OTHER INFORMATION: Chemically synthesized primer

<400> SEQUENCE: 16
acacagaatc tatacccacc agagt 25

<210> SEQ ID NO 17
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 17
gctggctctc acactgatag 20

<210> SEQ ID NO 18
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 18
gcagggagag gagtttgt 18

<210> SEQ ID NO 19
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 19
cccatccatg tgaggaagta taa 23

<210> SEQ ID NO 20
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 20
cttcttggac cttggcg 17

<210> SEQ ID NO 21
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 21
gctactacgc agacacg 17

<210> SEQ ID NO 22
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 22
gatgttcgag tcacagagg 19

<210> SEQ ID NO 23
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 23
ttcggctgga aggaacc 17

<210> SEQ ID NO 24
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 24
cgtggcagat gtgaacga 18

<210> SEQ ID NO 25
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 25
ggagatccgt caactccaaa 20

<210> SEQ ID NO 26
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 26
tgggtcgtgt caggaaac 18

<210> SEQ ID NO 27
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 27
cgcagtcatc cagagatgtg 20

<210> SEQ ID NO 28
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 28
actcagtaca agaaagaacc g 21

<210> SEQ ID NO 29
<211> LENGTH: 22
<212> TYPE: DNA
<213> ORGANISM: Artificial Sequence
<220> FEATURE:
<223> OTHER INFORMATION: Chemically synthesized primer

<400> SEQUENCE: 29
gttggaccag tcaacatctc tg 22

<210> SEQ ID NO 30
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 30
tgtggctcat taggcaac 18

<210> SEQ ID NO 31
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 31
gactccaagc gcgaaaac 18

<210> SEQ ID NO 32
<211> LENGTH: 24
<212> TYPE: DNA
<213> ORGANISM: Artificial Sequence
<220> FEATURE:
<223> OTHER INFORMATION: Chemically synthesized primer

<400> SEQUENCE: 32
ccaacaaaat attcatggtt cttg 24

<210> SEQ ID NO 33
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 33
ccagtagcat tgtccgag 18

<210> SEQ ID NO 34
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 34
gtctctggta atgcacact 19

<210> SEQ ID NO 35
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 35
gtggaatgcc tgctgacc 18

<210> SEQ ID NO 36
<211> LENGTH: 18

-continued

<212> TYPE: DNA
<213> ORGANISM: Artificial Sequence
<220> FEATURE:
<223> OTHER INFORMATION: Chemically synthesized primer

<400> SEQUENCE: 36
aggggtgccc tctgagat 18

<210> SEQ ID NO 37
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 37
cgagatcgcc aagatgtt 18

<210> SEQ ID NO 38
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 38
aggcgaacac acaacgtc 18

<210> SEQ ID NO 39
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 39
agcctcgaac aattgaaga 19

<210> SEQ ID NO 40
<211> LENGTH: 27
<212> TYPE: DNA
<213> ORGANISM: Artificial Sequence
<220> FEATURE:
<223> OTHER INFORMATION: Chemically synthesized primer

<400> SEQUENCE: 40
atcgactgtg taaacaacta gagaaga 27

<210> SEQ ID NO 41
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 41
tttaagaggg caatggaagg 20

<210> SEQ ID NO 42
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 42

-continued tgccgcagaa ctcacttg 18

<210> SEQ ID NO 43
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 43
cctcagatga tgcctatcca 20

<210> SEQ ID NO 44
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 44
cagcaagcga tggcatagt 19

<210> SEQ ID NO 45
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 45
aatgccaccg aagcctc 17

<210> SEQ ID NO 46
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 46
tcgaactgaa ggctatttac gag 23

<210> SEQ ID NO 47
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 47
gtcgaagccg caattagg 18

<210> SEQ ID NO 48
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 48
caaacgtgtg ttctggaagg 20

<210> SEQ ID NO 49
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 49
tgccctgtat gatgtcagga 20

<210> SEQ ID NO 50
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 50
gtgaggggtg tcagctcagt 20

<210> SEQ ID NO 51
<211> LENGTH: 22
<212> TYPE: DNA
<213> ORGANISM: Artificial Sequence
<220> FEATURE:
<223> OTHER INFORMATION: Chemically synthesized primer

<400> SEQUENCE: 51
tggggcagtt ctgtattact tc 22

<210> SEQ ID NO 52
<211> LENGTH: 24
<212> TYPE: DNA
<213> ORGANISM: Artificial Sequence
<220> FEATURE:
<223> OTHER INFORMATION: Chemically synthesized primer

<400> SEQUENCE: 52
cgatggtttt gtacaagatt tctc 24

<210> SEQ ID NO 53
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 53
gcaaatcctt gggcaga 17

<210> SEQ ID NO 54
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 54
gccgtacagt tccacaaagg 20

<210> SEQ ID NO 55
<211> LENGTH: 22
<212> TYPE: DNA
<213> ORGANISM: Artificial Sequence
<220> FEATURE:
<223> OTHER INFORMATION: Chemically synthesized primer

<400> SEQUENCE: 55
gacgcttcct atcactctat tc 22

<210> SEQ ID NO 56
<211> LENGTH: 22
<212> TYPE: DNA
<213> ORGANISM: Artificial Sequence
<220> FEATURE:
<223> OTHER INFORMATION: Chemically synthesized primer

<400> SEQUENCE: 56
ttcctccatc aagagttcaa ca 22

<210> SEQ ID NO 57
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 57
gggcacatcc agatgttt 18

<210> SEQ ID NO 58
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 58
gggtctgcac agactgcat 19

<210> SEQ ID NO 59
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 59
tccttgtaat ggggagacca 20

<210> SEQ ID NO 60
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 60
acttgggata tgtgaataag acc 23

<210> SEQ ID NO 61
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 61
ggggaaagac aaagtttcca 20

<210> SEQ ID NO 62
<211> LENGTH: 20
<212> TYPE: DNA
<213> ORGANISM: Artificial Sequence
<220> FEATURE:
<223> OTHER INFORMATION: Chemically synthesized primer -continued

<400> SEQUENCE: 62
actgtctggg tccatggcta 20

<210> SEQ ID NO 63
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 63
ggatttcgtg gtgggttc 18

<210> SEQ ID NO 64
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 64
ccacagtctg tgataaacgg 20

<210> SEQ ID NO 65
<211> LENGTH: 24
<212> TYPE: DNA
<213> ORGANISM: Artificial Sequence
<220> FEATURE:
<223> OTHER INFORMATION: Chemically synthesized primer

<400> SEQUENCE: 65
ccatcaacat tctctttatg aacg 24

<210> SEQ ID NO 66
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 66
atcaactccc aaacggtcac 20

<210> SEQ ID NO 67
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 67
gcccttacac atcggagaac 20

<210> SEQ ID NO 68
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 68
gacttcaggg tgctggac 18

<210> SEQ ID NO 69

<211> LENGTH: 22
<212> TYPE: DNA
<213> ORGANISM: Artificial Sequence
<220> FEATURE:
<223> OTHER INFORMATION: Chemically synthesized primer

<400> SEQUENCE: 69
tgtgaagcca gcaatatgta tc 22

<210> SEQ ID NO 70
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 70
tattgggagg caggaggttt a 21

<210> SEQ ID NO 71
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 71
ctgagttcat gttgctgacc 20

<210> SEQ ID NO 72
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 72
gacagctact attcccgtt 19

<210> SEQ ID NO 73
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 73
tatgtgagta agctcggaga c 21

<210> SEQ ID NO 74
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 74
agtgggcatc ccgtaga 17

<210> SEQ ID NO 75
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 75
agtggacatg cgagtggag 19

<210> SEQ ID NO 76
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 76
caccgctgga aactgaac 18

<210> SEQ ID NO 77
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 77
cgtgcacatc catgacctt 19

<210> SEQ ID NO 78
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 78
gaggagatga ccttgcc 17

<210> SEQ ID NO 79
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 79
gccatagcca ctgccact 18

<210> SEQ ID NO 80
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 80
cttcgactgg actctgt 17

<210> SEQ ID NO 81
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 81
cagacatgtt ggtattgcac att 23

<210> SEQ ID NO 82
<211> LENGTH: 20
<212> TYPE: DNA

-continued

<213> ORGANISM: Artificial Sequence
<220> FEATURE:
<223> OTHER INFORMATION: Chemically synthesized primer

<400> SEQUENCE: 82
aggcgatcct gggaaattat 20

<210> SEQ ID NO 83
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 83
cccatttgtc tgtcttcac 19

<210> SEQ ID NO 84
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 84
ctgatggttg aggctgtt 18

<210> SEQ ID NO 85
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 85
cgcactccag cacctagac 19

<210> SEQ ID NO 86
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 86
tcacagggtc aaacttccag t 21

<210> SEQ ID NO 87
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 87
gatggtagag ttccagtgat t 21

<210> SEQ ID NO 88
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 88
tctggtcacg cagggcaa 18

-continued

<210> SEQ ID NO 89
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 89
acacagatga tggagatgtc 20

<210> SEQ ID NO 90
<211> LENGTH: 25
<212> TYPE: DNA
<213> ORGANISM: Artificial Sequence
<220> FEATURE:
<223> OTHER INFORMATION: Chemically synthesized primer

<400> SEQUENCE: 90
agtagctaca tctccaggtt ctctg 25

<210> SEQ ID NO 91
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 91
cggattttat caacgatgca g 21

<210> SEQ ID NO 92
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 92
catttgccgt ccttcatcg 19

<210> SEQ ID NO 93
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 93
gcaggtcaaa actctcaaag 20

<210> SEQ ID NO 94
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 94
agcgggcttc tgtaatctga 20

<210> SEQ ID NO 95
<211> LENGTH: 19
<212> TYPE: DNA
<213> ORGANISM: Artificial Sequence
<220> FEATURE:

<223> OTHER INFORMATION: Chemically synthesized primer

<400> SEQUENCE: 95
gcctcagatt tcaactcgt 19

<210> SEQ ID NO 96
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 96
ctgctgagaa tcaaagtggg a 21

<210> SEQ ID NO 97
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 97
ggaacaaact gctctgcca 19

<210> SEQ ID NO 98
<211> LENGTH: 22
<212> TYPE: DNA
<213> ORGANISM: Artificial Sequence
<220> FEATURE:
<223> OTHER INFORMATION: Chemically synthesized primer

<400> SEQUENCE: 98
acagctcttt agcatttgtg ga 22

<210> SEQ ID NO 99
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 99
gggactatca atgttgggtt ctc 23

<210> SEQ ID NO 100
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 100
cacacagttc actgctccac a 21

<210> SEQ ID NO 101
<211> LENGTH: 2199
<212> TYPE: DNA
<213> ORGANISM: Homo sapiens

<400> SEQUENCE: 101
cagcggcgct gcggcggctc gcgggagacg ctgcgcgcgg ggctagcggg cggcggagcg 60
gacggcgacg gggcgctctc gggctgccgg cggggccgag cgccgcgcgt cccgagcatg 120
gcaggctccc tgcctccctg cgtggtggac tgtggcaccg ggtataccaa gcttggctac 180

```
gcaggcaaca ctgagcccca gttcattatt ccttcatgta ttgccatcag agagtcagca    240
aaggtagttg accaagctca aaggagagtg ttgaggggag ttgatgacct tgactttttc    300
ataggagatg aagccatcga taaacctaca tatgctacaa agtggccgat acgacatgga    360
atcattgaag actgggatct tatggaaagg ttcatggagc aagtggtttt taaatatctt    420
cgagctgaac ctgaggacca ttattttta atgacagaac ctccactcaa tacaccagaa    480
aacagagagt atcttgcaga aattatgttt gaatcattta acgtaccagg actctacatt    540
gcagttcagg cagtgctggc cttggcggca tcttggacat ctcgacaagt gggtgaacgt    600
acgttaacgg ggatagtcat tgacagcgga gatggagtca cccatgttat cccagtggca    660
gaaggttatg taattggaag ctgcatcaaa cacatcccga ttgcaggtag agatattacg    720
tatttcattc aacagctgct aagggagagg gaggtgggaa tccctcctga gcagtcactg    780
gagaccgcaa aagccattaa ggagaaatac tgttacattt gccccgatat agtcaaggaa    840
tttgccaagt atgatgtgga tccccggaag tggatcaaac agtacacggg tatcaatgcg    900
atcaaccaga agaagtttgt tatagacgtt ggttacgaaa gattcctggg acctgaaata    960
ttctttcacc cggagtttgc caacccagac tttatggagt ccatctcaga tgttgttgat   1020
gaagtaatac agaactgccc catcgatgtg cggcgcccgc tgtataagaa tgtcgtactc   1080
tcaggaggct ccaccatgtt cagggatttc ggacgccgac tgcagaggga tttgaagaga   1140
gtggtggatg ctaggctgag gctcagcgag gagctcagcg gcgggaggat caagccgaag   1200
cctgtggagg tccaggtggt cacgcatcac atgcagcgct acgccgtgtg gttcggaggc   1260
tccatgctgg cctcgactcc cgagttcttt caggtctgcc acaccaagaa ggactatgaa   1320
gagtacgggc ccagcatctg ccgccacaac cccgtctttg gagtcatgtc ctagtgtctg   1380
cctgaacgcg tcgttcgatg gtgtcacgtt ggggaacaag tgtccttcag aacccagaga   1440
aggccgccgt tctgtaaata gcgacgtcgg tgttgctgcc cagcagcgtg cttgcattgc   1500
cggtgcatga ggcgcggcgc gggcccttca gtaaaagcca tttatccgtg tgccgaccgc   1560
tgtctgccag cctcctcctt ctcccgccct cctcaccctc gctctccctc ctcctcctcc   1620
tccgagctgc tagctgacaa atacaattct gaaggaatcc aaatgtgact ttgaaaattg   1680
ttagagaaaa caacattaga aaatggcgca aaatcgttag gtcccaggag agaatgtggg   1740
ggcgcaaacc cttttcctcc cagcctattt ttgtaaataa aatgtttaaa cttgaaatac   1800
aaatcgatgt ttatatttcc tatcattttg tattttatgg tatttggtac aactggctga   1860
tactaagcac gaatagatat tgatgttatg gagtgctgta atccaaagtt tttaattgtg   1920
aggcatgttc tgatatgttt ataggcaaac aaataaaaca gcaaactttt ttgccacatg   1980
tttgctagaa aatgattata ctttattgga gtgacatgaa gtttgaacac taaacagtaa   2040
tgtatgagaa ttactacaga tacatgtatc ttttagtttt ttttgtttga actttctgga   2100
gctgttttat agaagatgat ggtttgttgt cggtgagtgt tggatgaaat acttccttgc   2160
accattgtaa taaaagctgt tagaatattt gtaaatatc                          2199
```

<210> SEQ ID NO 102
<211> LENGTH: 1989
<212> TYPE: DNA
<213> ORGANISM: Homo sapiens

<400> SEQUENCE: 102

```
cagcggcgct gcggcggctc gcgggagacg ctgcgcgcgg ggctagcggg cggcggagcg     60
```

-continued

```
gacggcgacg gggcgctctc gggctgccgg cggggccgag cgccgcgcgt cccgagcatg    120

gcaggctccc tgcctccctg cgtggtggac tgtggcaccg ggtataccaa gcttggctac    180

gcaggcaaca ctgagcccca gttcattatt ccttcatgta ttgccatcag agagtcagca    240

aaggtagttg accaagctca aaggagagtg ttgaggggag ttgatgacct tgactttttc    300

ataggagatg aagccatcga taaacctaca tatgctacaa agtggccgat acgacatgga    360

atcattgaag actgggatct tatggaaagg ttcatggagc aagtggtttt taaatatctt    420

cgagctgaac ctgaggacca ttattttta atgacagaac ctccactcaa tacaccagaa    480

aacagagagt atcttgcaga aattatgttt gaatcattta acgtaccagg actctacatt    540

gcagttcagg cagtgctggc cttggcggca tcttggacat ctcgacaagt gggtgaacgt    600

acgttaacgg ggatagtcat tgacagcgga gatggagtca cccatgttat cccagtggca    660

gaaggttatg taattggaag ctgcatcaaa cacatcccga ttgcaggtag agatattacg    720

tatttcattc aacagctgct aagggagagg gaggtgggaa tccctcctga gcagtcactg    780

gagaccgcaa aagccattaa ggagaaatac tgttacattt gccccgatat agtcaaggaa    840

tttgccaagt atgatgtgga tccccggaag tggatcaaac agtacacggg tatcaatgcg    900

atcaaccaga agaagtttgt tatagacgtt ggttacgaaa gattcctggg acctgaaata    960

ttctttcacc cggagtttgc caacccagac tttatggagt ccatctcaga tgttgttgat   1020

gaagtaatac agaactgccc catcgatgtg cggcgcccgc tgtataagcc cgagttcttt   1080

caggtctgcc acaccaagaa ggactatgaa gagtacgggc ccagcatctg ccgccacaac   1140

cccgtctttg gagtcatgtc ctagtgtctg cctgaacgcg tcgttcgatg gtgtcacgtt   1200

ggggaacaag tgtccttcag aacccagaga aggccgccgt tctgtaaata gcgacgtcgg   1260

tgttgctgcc cagcagcgtg cttgcattgc cggtgcatga ggcgcggcgc gggcccttca   1320

gtaaaagcca tttatccgtg tgccgaccgc tgtctgccag cctcctcctt ctcccgccct   1380

cctcaccctc gctctccctc ctcctcctcc tccgagctgc tagctgacaa atacaattct   1440

gaaggaatcc aaatgtgact ttgaaaattg ttagagaaaa caacattaga aaatggcgca   1500

aaatcgttag gtcccaggag agaatgtggg ggcgcaaacc cttttcctcc cagcctattt   1560

ttgtaaataa aatgtttaaa cttgaaatac aaatcgatgt ttatatttcc tatcattttg   1620

tattttatgg tatttggtac aactggctga tactaagcac gaatagatat tgatgttatg   1680

gagtgctgta atccaaagtt tttaattgtg aggcatgttc tgatatgttt ataggcaaac   1740

aaataaaaca gcaaactttt ttgccacatg tttgctagaa aatgattata ctttattgga   1800

gtgacatgaa gtttgaacac taaacagtaa tgtatgagaa ttactacaga tacatgtatc   1860

ttttagtttt ttttgtttga actttctgga gctgttttat agaagatgat ggtttgttgt   1920

cggtgagtgt tggatgaaat acttccttgc accattgtaa taaaagctgt tagaatattt   1980

gtaaatatc                                                           1989
```

<210> SEQ ID NO 103
<211> LENGTH: 4786
<212> TYPE: DNA
<213> ORGANISM: Homo sapiens

<400> SEQUENCE: 103

```
ctcggcgctg aaattcaaat ttgaacggct gcagaggccg agtccgtcac tggaagccga     60

gaggagagga cagctggttg tgggagagtt cccccgcctc agactcctgg ttttttccag    120

gagacacact gagctgagac tcacttttct cttcctgaat ttgaaccacc gtttccatcg    180
```

-continued

```
tctcgtagtc cgacgcctgg ggcgatggat ccgtttacgg agaaactgct ggagcgaacc    240
cgtgccaggc gagagaatct tcagagaaaa atggctgaga ggcccacagc agctccaagg    300
tctatgactc atgctaagcg agctagacag ccactttcag aagcaagtaa ccagcagccc    360
ctctctggtg gtgaagagaa atcttgtaca aaaccatcgc catcaaaaaa acgctgttct    420
gacaacactg aagtagaagt ttctaacttg gaaaataaac aaccagttga gtcgacatct    480
gcaaaatctt gttctccaag tcctgtgtct cctcaggtgc agccacaagc agcagatacc    540
atcagtgatt ctgttgctgt cccggcatca ctgctgggca tgaggagagg gctgaactca    600
agattggaag caactgcagc ctcctcagtt aaaacacgta tgcaaaaact tgcagagcaa    660
cggcgccgtt gggataatga tgatatgaca gatgacattc ctgaaagctc actcttctca    720
ccaatgccat cagaggaaaa ggctgcttcc cctcccagac ctctgctttc aaatgcctcg    780
gcaactccag ttggcagaag ggccgtctg gccaatcttg ctgcaactat ttgctcctgg    840
gaagatgatg taaatcactc atttgcaaaa caaaacagtg tacaagaaca gcctggtacc    900
gcttgtttat ccaaatttc ctctgcaagt ggagcatctg ctaggatcaa tagcagcagt    960
gttaagcagg aagctacatt ctgttcccaa agggatggcg atgcctcttt gaataaagcc   1020
ctatcctcaa gtgctgatga tgcgtctttg gttaatgcct caatttccag ctctgtgaaa   1080
gctacttctc cagtgaaatc tactacatct atcactgatg ctaaaagttg tgagggacaa   1140
aatcctgagc tacttccaaa aactcctatt agtcctctga aaacgggggt atcgaaacca   1200
attgtgaagt caactttatc ccagacagtt ccatccaagg gagaattaag tagagaaatt   1260
tgtctgcaat ctcaatctaa agacaaatct acgacaccag gaggaacagg aattaagcct   1320
ttcctggaac gctttggaga gcgttgtcaa gaacatagca aagaaagtcc agctcgtagc   1380
acaccccaca gaacccccat tattactcca aatacaaagg ccatccaaga aagattattc   1440
aagcaagaca catcttcatc tactacccat ttagcacaac agctcaagca ggaacgtcaa   1500
aaagaactag catgtcttcg tggccgattt gacaagggca atatatggag tgcagaaaaa   1560
ggcggaaact caaaaagcaa acaactagaa accaaacagg aaactcactg tcagagcact   1620
cccctcaaaa aacaccaagg tgtttcaaaa actcagtcac ttccagtaac agaaaaggtg   1680
accgaaaacc agataccagc caaaaattct agtacagaac ctaaaggttt cactgaatgc   1740
gaaatgacga aatctagccc tttgaaaata acattgtttt tagaagagga caaatcctta   1800
aaagtaacat cagacccaaa ggttgagcag aaaattgaag tgatacgtga aattgagatg   1860
agtgtggatg atgatgatat caatagttcg aaagtaatta atgacctctt cagtgatgtc   1920
ctagaggaag gtgaactaga tatggagaag agccaagagg agatggatca agcattagca   1980
gaaagcagcg aagaacagga agatgcactg aatatctcct caatgtcttt acttgcacca   2040
ttggcacaaa cagttggtgt ggtaagtcca gagagtttag tgtccacacc tagactggaa   2100
ttgaaagaca ccagcagaag tgatgaaagt ccaaaaccag gaaaattcca aagaactcgt   2160
gtccctcgag ctgaatctgg tgatagcctt ggttctgaag atcgtgatct tctttacagc   2220
attgatgcat atagatctca aagattcaaa gaaacagaac gtccatcaat aaagcaggtg   2280
attgttcgga aggaagatgt tacttcaaaa ctggatgaaa aaaataatgc ctttccttgt   2340
caagttaata tcaaacagaa aatgcaggaa ctcaataacg aaataaatat gcaacagaca   2400
gtgatctatc aagctagcca ggctcttaac tgctgtgttg atgaagaaca tggaaaaggg   2460
tccctagaag aagctgaagc agaaagactt cttctaattg caactgggaa gagaacactt   2520
```

-continued

```
ttgattgatg aattgaataa attgaagaac gaaggacctc agaggaagaa taaggctagt   2580
ccccaaagtg aatttatgcc atccaaagga tcagttactt tgtcagaaat ccgcttgcct   2640
ctaaaagcag attttgtctg cagtacggtt cagaaaccag atgcagcaaa ttactattac   2700
ttaattatac taaaagcagg agctgaaaat atggtagcca caccattagc aagtacttca   2760
aactctctta acggtgatgc tctgacattc actactacat ttactctgca agatgtatcc   2820
aatgactttg aaataaatat tgaagtttac agcttggtgc aaaagaaaga tccctcaggc   2880
cttgataaga agaaaaaaac atccaagtcc aaggctatta ctccaaagcg actcctcaca   2940
tctataacca caaaaagcaa cattcattct tcagtcatgg ccagtccagg aggtcttagt   3000
gctgtgcgaa ccagcaactt cgcccttgtt ggatcttaca cattatcatt gtcttcagta   3060
ggaaatacta agtttgttct ggacaaggtc ccctttttat cttctttgga aggtcatatt   3120
tatttaaaaa taaaatgtca agtgaattcc agtgttgaag aaagaggttt tctaaccata   3180
tttgaagatg ttagtggttt tggtgcctgg catcgaagat ggtgtgttct ttctggaaac   3240
tgtatatctt attggactta tccagatgat gagaaacgca agaatcccat aggaaggata   3300
aatctggcta attgtaccag tcgtcagata gaaccagcca acagagaatt ttgtgcaaga   3360
cgcaacactt ttgaattaat tactgtccga ccacaaagag aagatgaccg agagactctt   3420
gtcagccaat gcagggacac actctgtgtt accaagaact ggctgtctgc agatactaaa   3480
gaagagcggg atctctggat gcaaaaactc aatcaagttc ttgttgatat tcgcctctgg   3540
caacctgatg cttgctacaa acctattgga aagccttaaa ccgggaaatt tccatgctat   3600
ctagaggttt ttgatgtcat cttaagaaac acacttaaga gcatcagatt tactgattgc   3660
attttatgct ttaagtacga aagggtttgt gccaatattc actacgtatt atgcagtatt   3720
tatatctttt gtatgtaaaa ctttaactga tttctgtcat tcatcaatga gtagaagtaa   3780
atacattata gttgattttg ctaaatctta atttaaaagc ctcattttcc tagaaatcta   3840
attattcagt tattcatgac aatatttttt taaaagtaag aaattctgag ttgtcttctt   3900
ggagctgtag gtcttgaagc agcaacgtct ttcaggggtt ggagacagaa acccattctc   3960
caatctcagt agtttttcg aaaggctgtg atcatttatt gatcgtgata tgacttgtta   4020
ctagggtact gaaaaaaatg tctaaggcct ttacagaaac atttttagta atgaggatga   4080
gaactttttc aaatagcaaa tatatattgg cttaaagcat gaggctgtct tcagaaaagt   4140
gatgtggaca taggaggcaa tgtgtgagac ttgggggttc aatattttat atagaagagt   4200
taataagcac atggtttaca tttactcagc tactatatat gcagtgtggt gcacattttc   4260
acagaattct ggcttcatta agatcattat ttttgctgcg tagcttacag acttagcata   4320
ttagtttttt ctactcctac aagtgtaaat tgaaaaatct ttatattaaa aaagtaaact   4380
gttatgaagc tgctatgtac taataatact ttgcttgcca aagtgtttgg gttttgttgt   4440
tgtttgtttg tttgtttgtt tttggttcat gaacaacagt gtctagaaac ccattttgaa   4500
agtggaaaat tattaagtca cctatcacct ttaaacgcct ttttttaaaa ttataaaata   4560
ttgtaaagca gggtctcaac ttttaaatac actttgaact tcttctctga attattaaag   4620
ttctttatga cctcatttat aaacactaaa ttctgtcacc tcctgtcatt ttattttta   4680
ttcattcaaa tgtatttttt cttgtgcata ttataaaaat atattttatg agctcttact   4740
caaataaata cctgtaaatg tctaaaggaa aaaaaaaaaa aaaaaa                  4786
```

<210> SEQ ID NO 104
<211> LENGTH: 3885

-continued

<212> TYPE: DNA
<213> ORGANISM: Homo sapiens

<400> SEQUENCE: 104

```
aggccggggc ggggctggga agtagtcggg cggggttgtg agacgccgcg ctcagcttcc     60
atcgctgggc ggtcaacaag tgcgggcctg gctcagcgcg ggggggcgcg gagaccgcga    120
ggcgaccggg agcggctggg ttcccggctg cgcgcccttc ggccaggccg ggagccgcgc    180
cagtcggagc cccggcccca gcgtggtccg cctccctctc ggcgtccacc tgcccggagt    240
actgccagcg ggcatgaccg acccaccagg ggcgccgccg ccggcgctcg caggccgcgg    300
atgaagaaga aaacccggcg ccgctcgacc cggagcgagg agttgacccg gagcgaggag    360
ttgaccctga gtgaggaagc gacctggagt gaagaggcga cccagagtga ggaggcgacc    420
cagggcgaag agatgaatcg gagccaggag gtgacccggg acgaggagtc gacccggagc    480
gaggaggtga ccagggagga aatggcggca gctgggctca ccgtgactgt cacccacagc    540
aatgagaagc acgaccttca tgttacctcc cagcagggca gcagtgaacc agttgtccaa    600
gacctggccc aggttgttga agaggtcata ggggttccac agtcttttca gaaactcata    660
tttaagggaa aatctctgaa ggaaatggaa acaccgttgt cagcacttgg aatacaagat    720
ggttgccggg tcatgttaat tgggaaaaag aacagtccac aggaagaggt tgaactaaag    780
aagttgaaac atttggagaa gtctgtggag aagatagctg accagctgga agagttgaat    840
aaagagctta ctggaatcca gcagggtttt ctgcccaagg atttgcaagc tgaagctctc    900
tgcaaacttg ataggagagt aaaagccaca atagagcagt ttatgaagat cttggaggag    960
attgacacac tgatcctgcc agaaaatttc aaagacagta gattgaaaag gaaaggcttg   1020
gtaaaaaagg ttcaggcatt cctagccgag tgtgacacag tggagcagaa catctgccag   1080
gagactgagc ggctgcagtc tacaaacttt gccctggccg agtgaggtgt agcagaaaaa   1140
ggctgtgctg ccctgaagaa tggcgccacc agctctgccg tctctggagc ggaatttacc   1200
tgatttcttc agggctgctg ggggcaactg gccatttgcc aattttccta ctctcacact   1260
ggttctcaat gaaaaatagt gtctttgtga ttttgagtaa agctcctatc tgttttctcc   1320
ttctgtctct gtggttgtac tgtccagcaa tccacctttt ctggagaggg ccacctctgc   1380
ccaaatttc ccagctgttt ggacctctgg gtgctttctt tgggctggtg agagctctaa   1440
tttgccttgg gccagtttca ggtttatagg ccccctcagt cttcagatac atgagggctt   1500
ctttgctctt gtgatcgtgt agtcccatag ctgtaaaacc agaatcacca ggaggttgca   1560
cctagtcagg aatattggga atggcctaga acaaggtgtt tggcacataa gtagaccact   1620
tatccctcat tgtgacctaa ttccagagca tctggctggg ttgttgggtt ctagactttg   1680
tcctcacctc ccagtgaccc tgactagcca caggccatga gataccaggg ggccgttcct   1740
tggatggagc ctgtggttga tgcaaggctt ccttgtcccc aagcaagtct tcagaaggtt   1800
agaacccagt gttgactgag tctgtgcttg aaaccaggcc agagccatgg attaggaagg   1860
gcaaagagaa ggcaccagaa tgagtaaagc aggcaggtgg tgaagccaac cataaacttc   1920
tcaggagtga catgtgcttc cttcaaaggc atttttgtta accatatcct tctgagttct   1980
atgtttcctt cacagctgtt ctatccattt tgtggactgt cccccacccc caccccatca   2040
ttgtttttaa aaaattaagg cctggcgcag cagctcatgc ctataatccc agcactttgg   2100
gaggctgagg cgggcggatc acttgaggcc aggagtttga gaccagccca ggcaacatag   2160
caaaacccca ttctgcttta aaaaaaaaaa aaaaaaaaat tagcttggcg tagtggcatg   2220
```

```
tgcctataat cccagctact ggggaggctg aggcacaaga atcatttgaa cctgggaggt   2280
agaggttgct gtgagccgag attacgcccc tgcactccag cctgggtcac agagtgagac   2340
tccatctcag aaaaaaaaaa aattgagtca ggtgcagtag ctccttcctg tagtcccagc   2400
tacttgggag gctgaggcta gaggatcact tgagcccagg agtttgagtc tagtctgggc   2460
aacatagcaa gaccccatct ctaaaattta agtaagtaaa agtagataaa taaaaagaaa   2520
aaaaaactgt ttatgtgctc atcataaagt agaagagtgg tttgcttttt tttttttttt   2580
tggattaatg aggaaatcat tctgtggctc tagtcataat ttatgcttaa taacattgat   2640
agtagccctt tgcgctataa ctctacctaa agactcacat catttggcag agagagagtc   2700
gttgaagtcc caggaattca ggactgggca ggttaagacc tcagacaagg tagtagaggt   2760
agacttgtgg acaaggctcg ggtcccagcc caccgcaccc caactttaat cagagtggtt   2820
cactattgat ctatttttgt gtgatagctg tgtggcgtgg gccacaacat ttaatgagaa   2880
gttactgtgc accaaactgc cgaacaccat tctaaactat tcatatatat tagtcattta   2940
attcttacat aacttgagag gtagacagat atccttattt tagagatgag gaaaccaaga   3000
gaacttaggt cattagcgca aggttgtaga gtaagcggca aagccaagac acaaagctgg   3060
gtggtttggt ttcagagcca gtgcttttcc cctctactgt actgcctctc aaccaacaca   3120
gggttgcaca ggcccattct ctgatttttt tcctcttgtc ctctgcctct ccctctagct   3180
cccacttcct ctctgctcta gttcattttc tttagagcag cccgagtgat catgaagtgc   3240
aaatcttgcc atgtcagtcc cctgcttaga accctccaat ggctcacttt ctctttaggc   3300
aaaagtcttt accccatgcc ttctcccatc tcatctcaac cccctcattt gttggctgtc   3360
tgctgtcagc cactcttctt tcaggtcctc agatgcactg caccctctcc tgcctggggg   3420
tctttgctcc tgctactacc tctgcttgaa cagctcctca ccttccttcc tccaacccta   3480
cccttgtata ggtgactttt gttcatcctt cagaattcaa ctcacatgtc tcttgcatgg   3540
agaaccctca cctactgtgt tgagaccctg tccagccccc aggtgggatc ctctctcgac   3600
ttcccataca tttctttcac agcatttaca tagtccatga tagtttactt gtgggattat   3660
ttggttaatc tttgccttta acaccagggt tccttgggtg aaggagcttc tttatcttgg   3720
taacagcatt atttcaagca taacttgtaa tatagttata ttacatatat aacatatata   3780
tatataacat aacatatata acatatataa caagcataac ttgttatata gtcttgtata   3840
tagtaagacc tcaataaata tttggagaac aaaaaaaaaa aaaaa                   3885
```

<210> SEQ ID NO 105
<211> LENGTH: 6492
<212> TYPE: DNA
<213> ORGANISM: Homo sapiens

<400> SEQUENCE: 105

```
tttctgtgaa gcagaagtct gggaatcgat ctggaaatcc tcctaatttt tactccctct     60
ccccgcgact cctgattcat tgggaagttt caaatcagct ataactggag agtgctgaag    120
attgatggga tcgttgcctt atgcatttgt tttggtttta caaaaaggaa acttgacaga    180
ggatcatgct gtacttaaaa aatacaacat cacagaggaa gtagactgat attaacaata    240
cttactaata ataacgtgcc tcatgaaata aagatccgaa aggaattgga ataaaaattt    300
cctgcatctc atgccaaggg ggaaacacca gaatcaagtg ttccgcgtga ttgaagacac    360
cccctcgtcc aagaatgcaa agcacatcca ataaaatagc tggattataa ctcctcttct    420
ttctctgggg gccgtggggt gggagctggg gcgagaggtg ccgttggccc ccgttgcttt    480
```

-continued

```
tcctctggga aggatggcgc acgctgggag aacagggtac gataaccggg agatagtgat    540
gaagtacatc cattataagc tgtcgcagag ggctacgag tgggatgcgg gagatgtggg    600
cgccgcgccc ccgggggccg cccccgcacc gggcatcttc tcctcccagc ccgggcacac    660
gccccatcca gccgcatccc gggacccggt cgccaggacc tcgccgctgc agaccccggc    720
tgcccccggc gccgccgcgg ggcctgcgct cagcccggtg ccacctgtgg tccacctgac    780
cctccgccag gccggcgacg acttctcccg ccgctaccgc cgcgacttcg ccgagatgtc    840
cagccagctg cacctgacgc ccttcaccgc gcggggacgc tttgccacgg tggtggagga    900
gctcttcagg gacggggtga actgggggag gattgtggcc ttctttgagt tcggtggggt    960
catgtgtgtg gagagcgtca accgggagat gtcgcccctg gtggacaaca tcgccctgtg   1020
gatgactgag tacctgaacc ggcacctgca cacctggatc caggataacg gaggctggga   1080
tgcctttgtg gaactgtacg gccccagcat gcggcctctg tttgatttct cctggctgtc   1140
tctgaagact ctgctcagtt tggccctggt gggagcttgc atcaccctgg gtgcctatct   1200
gggccacaag tgaagtcaac atgcctgccc caaacaaata tgcaaaaggt tcactaaagc   1260
agtagaaata atatgcattg tcagtgatgt accatgaaac aaagctgcag gctgtttaag   1320
aaaaaataac acacatataa acatcacaca cacagacaga cacacacaca cacaacaatt   1380
aacagtcttc aggcaaaacg tcgaatcagc tatttactgc caaagggaaa tatcatttat   1440
tttttacatt attaagaaaa aaagatttat ttatttaaga cagtcccatc aaaactcctg   1500
tctttggaaa tccgaccact aattgccaag caccgcttcg tgtggctcca cctggatgtt   1560
ctgtgcctgt aaacatagat tcgctttcca tgttgttggc cggatcacca tctgaagagc   1620
agacggatgg aaaaaggacc tgatcattgg ggaagctggc tttctggctg ctggaggctg   1680
gggagaaggt gttcattcac ttgcatttct ttgccctggg ggctgtgata ttaacagagg   1740
gagggttcct gtgggggga gtccatgcct ccctggcctg aagaagagac tctttgcata   1800
tgactcacat gatgcatacc tggtgggagg aaaagagttg ggaacttcag atggacctag   1860
tacccactga gatttccacg ccgaaggaca gcgatgggaa aaatgccctt aaatcatagg   1920
aaagtatttt tttaagctac caattgtgcc gagaaaagca ttttagcaat ttatacaata   1980
tcatccagta ccttaagccc tgattgtgta tattcatata ttttggatac gcaccccccca   2040
actcccaata ctggctctgt ctgagtaaga aacagaatcc tctggaactt gaggaagtga   2100
acatttcggt gacttccgca tcaggaaggc tagagttacc cagagcatca ggccgccaca   2160
agtgcctgct tttaggagac cgaagtccgc agaacctgcc tgtgtcccag cttggaggcc   2220
tggtcctgga actgagccgg ggccctcact ggcctcctcc agggatgatc aacagggcag   2280
tgtggtctcc gaatgtctgg aagctgatgg agctcagaat tccactgtca agaaagagca   2340
gtagaggggt gtggctgggc ctgtcaccct ggggccctcc aggtaggccc gttttcacgt   2400
ggagcatggg agccacgacc cttcttaaga catgtatcac tgtagaggga aggaacagag   2460
gccctgggcc cttcctatca gaaggacatg gtgaaggctg ggaacgtgag gagaggcaat   2520
ggccacggcc cattttggct gtagcacatg gcacgttggc tgtgtggcct tggcccacct   2580
gtgagtttaa agcaaggctt taaatgactt tggagagggt cacaaatcct aaaagaagca   2640
ttgaagtgag gtgtcatgga ttaattgacc cctgtctatg gaattacatg taaaacatta   2700
tcttgtcact gtagtttggt tttatttgaa aacctgacaa aaaaaaagtt ccaggtgtgg   2760
aatatggggg ttatctgtac atcctggggc attaaaaaaa aaatcaatgg tggggaacta   2820
```

-continued taaagaagta acaaaagaag tgacatcttc agcaaataaa ctaggaaatt ttttttctt 2880 ccagtttaga atcagccttg aaacattgat ggaataactc tgtggcatta ttgcattata 2940
taccatttat ctgtattaac tttggaatgt actctgttca atgtttaatg ctgtggttga 3000
tatttcgaaa gctgctttaa aaaaatacat gcatctcagc gttttttgt ttttaattgt 3060 atttagttat ggcctataca ctatttgtga gcaaaggtga tcgttttctg tttgagattt 3120
ttatctcttg attcttcaaa agcattctga gaaggtgaga taagccctga gtctcagcta 3180
cctaagaaaa acctggatgt cactggccac tgaggagctt tgtttcaacc aagtcatgtg 3240
catttccacg tcaacagaat tgtttattgt gacagttata tctgttgtcc ctttgacctt 3300
gtttcttgaa ggtttcctcg tccctgggca attccgcatt taattcatgg tattcaggat 3360
tacatgcatg tttggttaaa cccatgagat tcattcagtt aaaaatccag atggcaaatg 3420
accagcagat tcaaatctat ggtggtttga cctttagaga gttgctttac gtggcctgtt 3480
tcaacacaga cccacccaga gccctcctgc cctccttccg cgggggcttt ctcatggctg 3540
tccttcaggg tcttcctgaa atgcagtggt gcttacgctc caccaagaaa gcaggaaacc 3600
tgtggtatga agccagacct ccccggcggg cctcagggaa cagaatgatc agacctttga 3660
atgattctaa tttttaagca aaatattatt ttatgaaagg tttacattgt caaagtgatg 3720
aatatggaat atccaatcct gtgctgctat cctgccaaaa tcattttaat ggagtcagtt 3780
tgcagtatgc tccacgtggt aagatcctcc aagctgcttt agaagtaaca atgaagaacg 3840
tggacgtttt taatataaag cctgttttgt cttttgttgt tgttcaaacg ggattcacag 3900
agtatttgaa aaatgtatat atattaagag gtcacggggg ctaattgctg gctggctgcc 3960
ttttgctgtg gggttttgtt acctggtttt aataacagta aatgtgccca gcctcttggc 4020
cccagaactg tacagtattg tggctgcact tgctctaaga gtagttgatg ttgcattttc 4080
cttattgtta aaaacatgtt agaagcaatg aatgtatata aaagcctcaa ctagtcattt 4140
ttttctcctc ttcttttttt tcattatatc taattatttt gcagttgggc aacagagaac 4200
catccctatt ttgtattgaa gagggattca catctgcatc ttaactgctc tttatgaatg 4260
aaaaaacagt cctctgtatg tactcctctt tacactggcc agggtcagag ttaaatagag 4320
tatatgcact ttccaaattg gggacaaggg ctctaaaaaa agccccaaaa ggagaagaac 4380
atctgagaac ctcctcggcc ctcccagtcc ctcgctgcac aaatactccg caagagaggc 4440
cagaatgaca gctgacaggg tctatggcca tcgggtcgtc tccgaagatt tggcaggggc 4500
agaaaactct ggcaggctta agatttggaa taaagtcaca gaattaagga agcacctcaa 4560
tttagttcaa acaagacgcc aacattctct ccacagctca cttacctctc tgtgttcaga 4620
tgtggccttc catttatatg tgatctttgt tttattagta aatgcttatc atctaaagat 4680
gtagctctgg cccagtggga aaaattagga agtgattata aatcgagagg agttataata 4740
atcaagatta aatgtaaata atcagggcaa tcccaacaca tgtctagctt tcacctccag 4800
gatctattga gtgaacagaa ttgcaaatag tctctatttg taattgaact tatcctaaaa 4860
caaatagttt ataaatgtga acttaaactc taattaattc caactgtact tttaaggcag 4920
tggctgtttt tagactttct tatcacttat agttagtaat gtacacctac tctatcagag 4980
aaaaacagga aaggctcgaa atacaagcca ttctaaggaa attagggagt cagttgaaat 5040
tctattctga tcttattctg tggtgtcttt tgcagcccag acaaatgtgg ttacacactt 5100
tttaagaaat acaattctac attgtcaagc ttatgaaggt tccaatcaga tctttattgt 5160
tattcaattt ggatctttca gggatttttt ttttaaatta ttatgggaca aaggacattt 5220
gttggagggg tgggagggag gaagaatttt taaatgtaaa acattcccaa gtttggatca 5280
gggagttgga agttttcaga ataaccagaa ctaagggtat gaaggacctg tattggggtc 5340
gatgtgatgc ctctgcgaag aaccttgtgt gacaaatgag aaacattttg aagtttgtgg 5400
tacgaccttt agattccaga gacatcagca tggctcaaag tgcagctccg tttggcagtg 5460
caatggtata aatttcaagc tggatatgtc taatgggtat ttaaacaata aatgtgcagt 5520
tttaactaac aggatattta atgacaacct tctggttggt agggacatct gtttctaaat 5580
gtttattatg tacaatacag aaaaaaattt tataaaatta agcaatgtga aactgaattg 5640
gagagtgata atacaagtcc tttagtctta cccagtgaat cattctgttc catgtctttg 5700
gacaaccatg accttggaca atcatgaaat atgcatctca ctggatgcaa agaaaatcag 5760
atggagcatg aatggtactg taccggttca tctggactgc cccagaaaaa taacttcaag 5820
caaacatcct atcaacaaca aggttgttct gcataccaag ctgagcacag aagatgggaa 5880
cactggtgga ggatggaaag gctcgctcaa tcaagaaaat tctgagacta ttaataaata 5940
agactgtagt gtagatactg agtaaatcca tgcacctaaa ccttttggaa aatctgccgt 6000
gggccctcca gatagctcat ttcattaagt ttttccctcc aaggtagaat ttgcaagagt 6060
gacagtggat tgcatttctt ttggggaagc tttcttttgg tggttttgtt tattatacct 6120
tcttaagttt tcaaccaagg tttgcttttg ttttgagtta ctggggttat ttttgtttta 6180
aataaaaata agtgtacaat aagtgttttt gtattgaaag cttttgttat caagattttc 6240
atacttttac cttccatggc tctttttaag attgatactt ttaagaggtg gctgatattc 6300
tgcaacactg tacacataaa aaatacggta aggatacttt acatggttaa ggtaaagtaa 6360
gtctccagtt ggccaccatt agctataatg gcactttgtt tgtgttgttg gaaaaagtca 6420
cattgccatt aaactttcct tgtctgtcta gttaatattg tgaagaaaaa taaagtacag 6480
tgtgagatac tg 6492

<210> SEQ ID NO 106
<211> LENGTH: 2724
<212> TYPE: DNA
<213> ORGANISM: Homo sapiens

<400> SEQUENCE: 106
cccagaaggc cgcggggggt ggaccgccta agagggcgtg cgctcccgac atgccccgcg 60
gcgcgccatt aaccgccaga tttgaatcgc gggacccgtt ggcagaggtg gcggcggcgg 120
catgggtgcc ccgacgttgc cccctgcctg gcagcccttt ctcaaggacc accgcatctc 180
tacattcaag aactggccct tcttggaggg ctgcgcctgc accccggagc ggatggccga 240
ggctggcttc atccactgcc ccactgagaa cgagccagac ttggcccagt gtttcttctg 300
cttcaaggag ctggaaggct gggagccaga tgacgacccc attgggccgg gcacggtggc 360
ttacgcctgt aataccagca ctttgggagg ccgaggcggg cggatcacga gagaggaaca 420
taaaaagcat tcgtccggtt gcgctttcct ttctgtcaag aagcagtttg aagaattaac 480
ccttggtgaa tttttgaaac tggacagaga aagagccaag aacaaaattg caaaggaaac 540
caacaataag aagaaagaat ttgaggaaac tgcggagaaa gtgcgccgtg ccatcgagca 600
gctggctgcc atggattgag gcctctggcc ggagctgcct ggtcccagag tggctgcacc 660
acttccaggg tttattccct ggtgccacca gccttcctgt gggcccctta gcaatgtctt 720
aggaaaggag atcaacattt tcaaattaga tgtttcaact gtgctcttgt tttgtcttga 780

-continued

```
aagtggcacc agaggtgctt ctgcctgtgc agcgggtgct gctggtaaca gtggctgctt    840

ctctctctct ctctcttttt tgggggctca tttttgctgt tttgattccc gggcttacca    900

ggtgagaagt gagggaggaa gaaggcagtg tcccttttgc tagagctgac agctttgttc    960

gcgtgggcag agccttccac agtgaatgtg tctggacctc atgttgttga ggctgtcaca   1020

gtcctgagtg tggacttggc aggtgcctgt tgaatctgag ctgcaggttc cttatctgtc   1080

acacctgtgc ctcctcagag gacagttttt ttgttgttgt gttttttttgt tttttttttt   1140

ttggtagatg catgacttgt gtgtgatgag agaatggaga cagagtccct ggctcctcta   1200

ctgtttaaca acatggcttt cttattttgt ttgaattgtt aattcacaga atagcacaaa   1260

ctacaattaa aactaagcac aaagccattc taagtcattg gggaaacggg gtgaacttca   1320

ggtggatgag gagacagaat agagtgatag gaagcgtctg gcagatactc cttttgccac   1380

tgctgtgtga ttagacaggc ccagtgagcc gcggggcaca tgctggccgc tcctccctca   1440

gaaaaaggca gtggcctaaa tcctttttaa atgacttggc tcgatgctgt gggggactgg   1500

ctgggctgct gcaggccgtg tgtctgtcag cccaaccttc acatctgtca cgttctccac   1560

acgggggaga gacgcagtcc gcccaggtcc ccgctttctt tggaggcagc agctcccgca   1620

gggctgaagt ctggcgtaag atgatggatt tgattcgccc tcctccctgt catagagctg   1680

cagggtggat tgttacagct tcgctggaaa cctctggagg tcatctcggc tgttcctgag   1740

aaataaaaag cctgtcattt caaacactgc tgtggaccct actgggtttt taaaatattg   1800

tcagtttttc atcgtcgtcc ctagcctgcc aacagccatc tgcccagaca gccgcagtga   1860

ggatgagcgt cctggcagag acgcagttgt ctctgggcgc ttgccagagc cacgaacccc   1920

agacctgttt gtatcatccg ggctccttcc gggcagaaac aactgaaaat gcacttcaga   1980

cccacttatt tctgccacat ctgagtcggc ctgagataga cttttccctc taaactggga   2040

gaatatcaca gtggtttttg ttagcagaaa atgcactcca gcctctgtac tcatctaagc   2100

tgcttatttt tgatatttgt gtcagtctgt aaatggatac ttcactttaa taactgttgc   2160

ttagtaattg gctttgtaga gaagctggaa aaaaatggtt ttgtcttcaa ctcctttgca   2220

tgccaggcgg tgatgtggat ctcggcttct gtgagcctgt gctgtgggca gggctgagct   2280

ggagccgccc ctctcagccc gcctgccacg gcctttcctt aaaggccatc cttaaaacca   2340

gaccctcatg gctaccagca cctgaaagct tcctcgacat ctgttaataa agccgtaggc   2400

ccttgtctaa gtgcaaccgc ctagactttc tttcagatac atgtccacat gtccattttt   2460

caggttctct aagttggagt ggagtctggg aagggttgtg aatgaggctt ctgggctatg   2520

ggtgaggttc caatggcagg ttagagcccc tcgggccaac tgccatcctg gaaagtagag   2580

acagcagtgc ccgctgccca gaagagacca gcaagccaaa ctggagcccc cattgcaggc   2640

tgtcgccatg tggaaagagt aactcacaat tgccaataaa gtctcatgtg gttttatcta   2700

aaaaaaaaaa aaaaaaaaaa aaaa                                          2724
```

<210> SEQ ID NO 107
<211> LENGTH: 4934
<212> TYPE: DNA
<213> ORGANISM: Homo sapiens

<400> SEQUENCE: 107

```
aatgagggta tttataaact acttaaatta taaaaagaat gagacatcag acttacagtt     60

ttggatacta attttttca cttaacgttc attatgtgat aggagttttc catcctatta    120

taccgctgtg cgatctgatc ttgggcacgt taaccaacct cttgttgcct cgattttctc    180
```

-continued

```
acctgtaaaa gtgggggtaa tcataatgct tacttagtag gatagccctg aagaataagt    240
gacttagcga acataaatag cttacaatag ggttttcagc atgggaagga ttcagtaaat    300
gttagctgtc atcatcacca cctacaaagg aagcaatact gtgctgaaag tttttccatc    360
attaatgtaa tttctatagt acgattccca agaagatatt aaaattatgg aaataaaggt    420
attggtatat tcctaattat ttcctaaaag attgtattga taaatatgct catccttccc    480
ttaacgggat gcattccaga aaaacaagtc aaatgttaga caaagtatca gaagggaaat    540
tctgtagcca gagagctaaa aattacaata gggtctctaa ttatacttca actttttag    600
gaataattct cagtgtgttt tcccacattt catatgtaat ttttttttt ttttttttt    660
gagacagagc ctcgccctgt caccaggctg gagtacagtg gcgcgatctc ggctcactgc    720
aacttccacc tgctgggttc aagcaattct tctgacctca ggtgatccac ccgcctcggc    780
ctcccaaagt gctgggatta taacaggcgt ggcatgagtc accgcgcccg gccgatcttt    840
actttttat tctttgtacc ccctgcctat ccagttagca tgtgattaaa gtcaaagatt    900
tgccactttg ggccacatct attaattttc atctttgtta taattgtatt tagtttttga    960
tctacactgc ttattactcc cagtcatttt ttatagaact gaaaatctgg taaaatactc   1020
aaaattgcac tgacttctat gtagaggcga cactccatca gaaccgtggg ctgacaggga   1080
atcccactgt gcaggagctg cgcgcatttt catttctgat tctctttggc gtatccagga   1140
ctctgatgac atgatcatat atttatcagt agtaacaggt tgggccattt gtttttgtg   1200
gtaaatcata tatttaagat tttagaaata agttgatagc catgtatttt ggaatttgaa   1260
aaagacattg cattactcag cttcaaatta agctttaatc aaatagtgaa actttccatt   1320
aatggacagt gtatacctt ttgtgtattt aaaaaaaaa acactgaata tagtgccttt   1380
gtgacagggg agcttggttc ctgacaatgt cctcttgagc cttttttttt tttttgagat   1440
ggagtctcac tgtgtcaccc aggctggagt gcagtggcgc catcttggct cactgcaacc   1500
tccgcccccct gggttcaagt gattctcatt cctcagcttc ctaagtagct gggattacag   1560
gcacgcacca ccatgaccag ctaattttta tacttttagt agagacaggg ttttgccatg   1620
ttggctaggt tggtctcgaa ctcctgacct caagtaatcc acccaccatg gcctccccaa   1680
agtgctggga ttacaggcgt gagccatttc acccggcctc tcttccgtct ttgagctgtg   1740
aggaaatagc tacattacat gagctgctag atctgcctta tggtcagaaa tgaaggttga   1800
actctcagga acagtgacat atatacacac tgatatttcc aaagtacaat gccccaaatt   1860
gatccacaaa ggaattaagg tcatttgcaa caaaatcaca gaatagtaac aaataaatag   1920
aagataaata tggccaggga tgctgcaaac tgatatactg ccaagtttat cagttgggaa   1980
tcccaacagt gaaaagcata aaaatgaaag gaattttaag gagacttttt atagaagagt   2040
gggaaggatt ggaggagcca acaagtgatg gtgaggcaca cagggaagag cttcagtggg   2100
caccatcccc tctctggttt gaaggggtag ggaggggacc agagctggga ggagggggct   2160
ggaatactgc tggaggagcc actcccttcc agacctgctg tggccatcac agaatgcagc   2220
cactgccaga gcagcagccc gaggaaccag gcagggggag cacaagtacc ctagcctctc   2280
tctttctgtt tcttgcctgc cgatctcctc cactggctaa acccagctgg atgctaagag   2340
tacagtcagc ctgcctgctg aggagggacc accagggacc accatcagca agggatccaa   2400
tgtctttctg cctctgcaga atgaaggttg gggcgcgggg ggcgctctac ttcttaggga   2460
tattgtggga ataaaaggaa ataggcaaaa aatgtttttg aaaaacaaag cacatactgc   2520
```

-continued gcacccgtgg gccactactg cttttgaccc ctggctctgt ttcatgaagt aatgtcgtgt 2580
cattctcttt ttaggtgcta caggatttct ttaggtttgt tttctgtcca ccatatttca 2640
actcatgtgt gctgtttgtt gtgctaaaac aaatatttgc tgatgcctga gtgaatagtt 2700
gaatatttta tataagtcaa atttatacgt aatgattttt cttgtaactt agccgtttct 2760
cttttacaaa ctcagaaaac ctcagacttt gaaaaggcct tgaagttcct cacctgaaat 2820
ctgagaactt ggagcgcctt aaaaaatcta aaggaaaaca aaacagtgaa agaacatgat 2880
atagtcagtg tagagaataa aattatttat gtaattaata ttgaggatgc agataacaca 2940
ttgtgaaatc ttgcttgtaa aaaatctcga tctgctgaag aaagatgttc tctctagaga 3000
tctttgaaag cataattatt gagcttttaa aatgttagaa acaaaagtta gacccacaca 3060
tattctggcg tgtggaagat ttgcattcct tcccctgccc gccccgcccc cacacttgtg 3120
agttgtgcct gtgtacgcag ttcctgtagc actcggctgg gcagaaatca tctttcagca 3180
ctaagggaac atagttatga tctggacctt ctgggagtgg tcagtgccca agaacaggta 3240
tgggactcca gaaagttctg ctctcaaccc tattttgaaa tagagttaca cattgttcta 3300
caattatttg agttaataag cagctctttt caaacgtgat tatgcccttc caagtttaaa 3360
tacactagac tttagtgaaa gtaattgacc tcatctcatt tctctcctgt tatattaaga 3420
tcactttcag taaaaggtag aagcttttga agtggtgagg aggaggtaga ggagggacat 3480
agagcagata ggggctggaa agtggggtga ggaagagagt ggcttctctt tggcagagta 3540
ccaaggaaaa gccctatctg tacagaacct ttgtgcctgg gaacttgatg gctgcaacct 3600
gagcctcaac ctagtttgct tgcggagcca gaagagaagc taaaaacctt cagttaacca 3660
agccagacac caagaaagtt aaaccgaaag agaacccccc accccccgca aaaaaaagaa 3720
gtaaagtggg ttaaagtgat atcatgttag cacagaaaga gaacataagg gtcatctaag 3780
ttcatctgcc ccctcttcta tttcaaggtg cagaaactaa ggcacaaggg accccgtgtc 3840
ctgctcttga tcacatagct agtgggtgcc aagccaggtc tagaactctg ttctctgggg 3900
tcacaggctg gctcttcatc cctctagaga gatagctcat ctgtgtgcac ctgagcccgt 3960
tgtgtttcgg agtcaaagca aataaaggct caaactccaa gactgttttg cagaccggct 4020
gcagtagata tgggggagg agaaacctgc tttaaattgc ttcaagcaag ttgtttctgc 4080
aaaggtgttg actttttct ttcaactttc tagtgagtca ctgcagcctg agctgttatt 4140
tgtcattatg caataattca ggaactaact caagattctt ctttttaaat tatttgttta 4200
tttagagaca gagtcttgct ctgttgccca ggctggagtg cagtggtgtg atctcggctc 4260
actgcagcct ctgcctcctg ggttcaagca attctcatgt ctcagcctcc cgaatagctg 4320
gtattgcagg ctcgtgccac cacccctgc taatttttgt aattttagtg gagacacggt 4380
ttcgccatgt tggccgggct cgtcttgagc tcctggcctc aggtgatccg cccgcctcgg 4440
cctcccaaag tgctgggatt gcagccgtga gcctccacac ccggcctatt tatttatttt 4500
taaattggct gctcttagaa aggcatacca tgtttctgga tgggaaggct tattaattca 4560
ccctaattta atgtataaat ttgatgcaat catagtcaca gtcccagtgg aattttttaa 4620
cttggtaaga tgttctaaaa ttaatgagag aacttgaatt accaggtatt gaaacactgt 4680
aaagccacaa tcatgtaaac agtatgttat aaccatggga atagaggtct gtgatacagc 4740
agaaaaaagt gaaaaaaaga ataactgtat tcataaaaat ttaaatgtgg agtcactggg 4800
ggaaaggatt aaatattcga taatgtagaa acaactcaac tatttggaga aatgtaaatt 4860
tagagcctta tctcatgcca tataccaaaa tactatttag atttgattaa aaaataaaaa 4920

-continued aaaaaaaaaa aaaa 4934

<210> SEQ ID NO 108
<211> LENGTH: 2177
<212> TYPE: DNA
<213> ORGANISM: Homo sapiens

<400> SEQUENCE: 108
cgaacgcctt cgcgcgatcg ccctggaaac gcattctctg cgaccggcag ccgccaatgg 60
gaagggagtg agtgccacga acaggccaat aaggagggag cagtgcgggg tttaaatctg 120
aggctaggct ggctcttctc ggcgtgctgc ggcggaacgg ctgttggttt ctgctgggtg 180
taggtccttg gctggtcggg cctccggtgt tctgcttctc cccgctgagc tgctgcctgg 240
tgaagaggaa gccatggcgc tccgagtcac caggaactcg aaaattaatg ctgaaaataa 300
ggcgaagatc aacatggcag gcgcaaagcg cgttcctacg gcccctgctg caacctccaa 360
gcccggactg aggccaagaa cagctcttgg ggacattggt aacaaagtca gtgaacaact 420
gcaggccaaa atgcctatga agaaggaagc aaaaccttca gctactggaa aagtcattga 480
taaaaaacta ccaaaacctc ttgaaaaggt acctatgctg gtgccagtgc cagtgtctga 540
gccagtgcca gagccagaac ctgagccaga acctgagcct gttaaagaag aaaaactttc 600
gcctgagcct attttggttg atactgcctc tccaagccca atggaaacat ctggatgtgc 660
ccctgcagaa gaagacctgt gtcaggcttt ctctgatgta attcttgcag taaatgatgt 720
ggatgcagaa gatggagctg atccaaacct ttgtagtgaa tatgtgaaag atatttatgc 780
ttatctgaga caacttgagg aagagcaagc agtcagacca aaatacctac tgggtcggga 840
agtcactgga aacatgagag ccatcctaat tgactggcta gtacaggttc aaatgaaatt 900
caggttgttg caggagacca tgtacatgac tgtctccatt attgatcggt tcatgcagaa 960
taattgtgtg cccaagaaga tgctgcagct ggttggtgtc actgccatgt ttattgcaag 1020
caaatatgaa gaaatgtacc ctccagaaat tggtgacttt gcttttgtga ctgacaacac 1080
ttatactaag caccaaatca gacagatgga aatgaagatt ctaagagctt taaactttgg 1140
tctgggtcgg cctctacctt tgcacttcct tcggagagca tctaagattg gagaggttga 1200
tgtcgagcaa catactttgg ccaaatacct gatggaacta actatgttgg actatgacat 1260
ggtgcacttt cctccttctc aaattgcagc aggagctttt tgcttagcac tgaaaattct 1320
ggataatggt gaatggacac caactctaca acattacctg tcatatactg aagaatctct 1380
tcttccagtt atgcagcacc tggctaagaa tgtagtcatg gtaaatcaag gacttacaaa 1440
gcacatgact gtcaagaaca agtatgccac atcgaagcat gctaagatca gcactctacc 1500
acagctgaat tctgcactag ttcaagattt agccaaggct gtggcaaagg tgtaacttgt 1560
aaacttgagt tggagtacta tatttacaaa taaaattggc accatgtgcc atctgtacat 1620
attactgttg catttacttt taataaagct tgtggcccct tttacttttt tatagcttaa 1680
ctaatttgaa tgtggttact tcctactgta gggtagcgga aaagttgtct taaaaggtat 1740
ggtggggata tttttaaaaa ctccttttgg tttacctggg gatccaattg atgtatatgt 1800
ttatatactg ggttcttgtt ttatatacct ggcttttact ttattaatat gagttactga 1860
aggtgatgga ggtatttgaa aattttactt ccataggaca tactgcatgt aagccaagtc 1920
atggagaatc tgctgcatag ctctatttta aagtaaaagt ctaccaccga atccctagtc 1980
cccctgtttt ctgtttcttc ttgtgattgc tgccataatt ctaagttatt tacttttacc 2040

-continued actatttaag ttatcaactt tagctagtat cttcaaactt tcactttgaa aaatgagaat 2100
tttatattct aagccagttt tcattttggt tttgtgtttt ggttaataaa acaatactca 2160
aatacaaaaa aaaaaaa 2177

<210> SEQ ID NO 109
<211> LENGTH: 2011
<212> TYPE: DNA
<213> ORGANISM: Homo sapiens

<400> SEQUENCE: 109
gcggccgcca gcgcggtgta gggggcaggc gcggatcccg ccaccgccgc gcgctcggcc 60
cgccgactcc cggcgccgcc gccgccactg ccgtcgccgc cgccgcctgc cgggactgga 120
gcgcgccgtc cgccgcggac aagaccctgg cctcaggccg gagcagcccc atcatgccga 180
gggagcgcag ggagcgggat gcgaaggagc gggacaccat gaaggaggac ggcggcgcgg 240
agttctcggc tcgctccagg aagaggaagg caaacgtgac cgttttttttg caggatccag 300 atgaagaaat ggccaaaatc gacaggacgg cgagggacca gtgtgggagc cagccttggg 360
acaataatgc agtctgtgca gacccctgct ccctgatccc cacacctgac aaagaagatg 420
atgaccgggt ttacccaaac tcaacgtgca agcctcggat tattgcacca tccagaggct 480
ccccgctgcc tgtactgagc tgggcaaata gagaggaagt ctggaaaatc atgttaaaca 540
aggaaaagac atacttaagg gatcagcact ttcttgagca acaccctctt ctgcagccaa 600
aaatgcgagc aattcttctg gattggttaa tggaggtgtg tgaagtctat aaacttcaca 660
gggagacctt ttacttggca caagatttct ttgaccggta tatggcgaca caagaaaatg 720
ttgtaaaaac tcttttacag cttattggga tttcatcttt atttattgca gccaaacttg 780
aggaaatcta tcctccaaag ttgcaccagt ttgcgtatgt gacagatgga gcttgttcag 840
gagatgaaat tctcaccatg gaattaatga ttatgaaggc ccttaagtgg cgtttaagtc 900
ccctgactat tgtgtcctgg ctgaatgtat acatgcaggt tgcatatcta aatgacttac 960
atgaagtgct actgccgcag tatccccagc aaatctttat acagattgca gagctgttgg 1020
atctctgtgt cctggatgtt gactgccttg aatttcctta tggtatactt gctgcttcgg 1080
ccttgtatca tttctcgtca tctgaattga tgcaaaaggt ttcagggtat cagtggtgcg 1140
acatagagaa ctgtgtcaag tggatggttc catttgccat ggttataagg gagacgggga 1200
gctcaaaact gaagcacttc aggggcgtcg ctgatgaaga tgcacacaac atacagaccc 1260
acagagacag cttggatttg ctggacaaag cccgagcaaa gaaagccatg ttgtctgaac 1320
aaaatagggc ttctcctctc cccagtgggc tcctcacccc gccacagagc ggtaagaagc 1380
agagcagcgg gccggaaatg gcgtgaccac cccatccttc tccaccaaag acagttgcgc 1440
gcctgctcca cgttctcttc tgtctgttgc agcggaggcg tgcgtttgct tttacagata 1500
tctgaatgga agagtgtttc ttccacaaca gaagtatttc tgtggatggc atcaaacagg 1560
gcaaagtgtt ttttattgaa tgcttatagg tttttttttaa ataagtgggt caagtacacc 1620
agccacctcc agacaccagt gcgtgctccc gatgctgcta tggaaggtgc tacttgacct 1680
aagggactcc cacaacaaca aaagcttgaa gctgtggagg gccacggtgg cgtggctctc 1740
ctcgcaggtg ttctgggctc cgttgtacca agtggagcag gtggttgcgg gcaagcgttg 1800
tgcagagccc atagccagct gggcaggggg ctgccctctc cacattatca gttgacagtg 1860
tacaatgcct ttgatgaact gttttgtaag tgctgctata tctatccatt ttttaataaa 1920
gataatactg tttttgaaaa aaaaaaaaaa aaaaaaaaaa aaaaaaaaaa aaaaaaaaaa 1980
aaaaaaaaaa aaaaaaaaaa aaaaaaaaaa a 2011

<210> SEQ ID NO 110
<211> LENGTH: 1737
<212> TYPE: DNA
<213> ORGANISM: Homo sapiens

<400> SEQUENCE: 110
gagggcacgg gctccgtagg caccaactgc aaggacccct ccccctgcgg gcgctcccat 60
ggcacagttc gcgttcgaga gtgacctgca ctcgctgctt cagctggatg cacccatccc 120
caatgcaccc cctgcgcgct ggcagcgcaa agccaaggaa gccgcaggcc cggccccctc 180
acccatgcgg gccgccaacc gatcccacag cgccggcagg actccgggcc gaactcctgg 240
caaatccagt tccaaggttc agaccactcc tagcaaacct ggcggtgacc gctatatccc 300
ccatcgcagt gctgcccaga tggaggtggc cagcttcctc ctgagcaagg agaaccagcc 360
tgaaaacagc cagacgccca ccaagaagga acatcagaaa gcctgggctt tgaacctgaa 420
cggttttgat gtagaggaag ccaagatcct tcggctcagt ggaaaaacca caaaaatgcg 480
ccagagggtt atcacgaaca gactgaaagt actctacagc caaaaggcca ctcctggctc 540
cagccggaag acctgccgtt tacattcctt ccctgccaag accgtatcct ggatgcgcct 600
gaaatcgaat gactattaac tgaacctgtg ggactggcag tccggggaat gtccgggccg 660
ggccacggcc acgaggtgtt ccgtgtggag tgcaagctgg gacacaccgt gccgcttgtg 720
cacagggcca cgcggggaaa taatcccggg gcgcgcaaag cggcactggc gagagccgca 780
cgggccggtg ctgggggtgg tacaacaggc caaaacaaca cacaaggcca acaagacata 840
cgcgcgctga caccacggtg caaagcgctc agacgagtag taaccggcac tgtggttgct 900
gcctccccac ctctcccgct ctcagcgtaa gataaaagaa agaagagcaa aaagcaaaga 960
aagaagacga gacgagacac acaggaacga acagtaaagc aagctaaagc aaacgcaaga 1020
ccagacaaca gaaatagaaa gaaccaacag agaggagaca gaacaggacg ccagcaacat 1080
agcaacaaac gaacagaaga gagcactaaa caaaagcagc agcaagacga gacaggagag 1140
aaggaggaag gagggccgag cgagcaggga gcgcgagcag cgaggcgaag cagcagacaa 1200
gggcaggcga agggcaacga gaggaggcac cacacaaaaa ggagagggga caggagaagc 1260
agcgagagaa gcggaggagc aacaagagga agaaaaggag agggagagga gggagagagc 1320
ggaaggagga agaaacagca cgaggcgacg aagggggggag acgcgggggc aggaaaagac 1380
acaggaaggc agcgcggagg aggagaaggg gaagcaggaa ggagacggaa ggagaagagg 1440
gagaggacag cgcaagagag cgcgcgcggc gacagcgagg gacggagcga gagagaggaa 1500
acggaaagcg agagggaaga ggagaggcaa cgcagcgaac caaccgaaaa cagcagaaag 1560
agaggagaag gacgcgcaaa gaggcaagcg caagacgaca ggaaacgaag cgagagacga 1620
gaagccggtg acgagcagga gaaagggaag gcaggagaca ggacaggcgg aagagagaca 1680
cgcgagacgc aaagagtgag cagaacgaag cgaagagcaa cgcacgagag aaacgac 1737

<210> SEQ ID NO 111
<211> LENGTH: 3053
<212> TYPE: DNA
<213> ORGANISM: Homo sapiens

<400> SEQUENCE: 111
gagcgcggct ggagtttgct gctgccgctg tgcagtttgt tcaggggctt gtggtggtga 60

-continued

```
gtccgagagg ctgcgtgtga gagacgtgag aaggatcctg cactgaggag gtggaaagaa    120
gaggattgct cgaggaggcc tggggtctgt gaggcagcgg agctgggtga aggctgcggg    180
ttccggcgag gcctgagctg tgctgtcgtc atgcctcaaa cccgatccca ggcacaggct    240
acaatcagtt ttccaaaaag gaagctgtct cgggcattga acaaagctaa aaactccagt    300
gatgccaaac tagaaccaac aaatgtccaa accgtaacct gttctcctcg tgtaaaagcc    360
ctgcctctca gccccaggaa acgtctgggc gatgacaacc tatgcaacac tccccattta    420
cctccttgtt ctccaccaaa gcaaggcaag aaagagaatg gtccccctca ctcacataca    480
cttaagggac gaagattggt atttgacaat cagctgacaa ttaagtctcc tagcaaaaga    540
gaactagcca aagttcacca aaacaaaata ctttcttcag ttagaaaaag tcaagagatc    600
acaacaaatt ctgagcagag atgtccactg aagaaagaat ctgcatgtgt gagactattc    660
aagcaagaag gcacttgcta ccagcaagca aagctggtcc tgaacacagc tgtcccagat    720
cggctgcctg ccagggaaag ggagatggat gtcatcagga atttcttgag ggaacacatc    780
tgtgggaaaa aagctggaag cctttacctt tctggtgctc ctggaactgg aaaaactgcc    840
tgcttaagcc ggattctgca agacctcaag aaggaactga aaggctttaa aactatcatg    900
ctgaattgca tgtccttgag gactgcccag gctgtattcc cagctattgc tcaggagatt    960
tgtcaggaag aggtatccag gccagctggg aaggacatga tgaggaaatt ggaaaaacat   1020
atgactgcag agaagggccc catgattgtg ttggtattgg acgagatgga tcaactggac   1080
agcaaaggcc aggatgtatt gtacacgcta tttgaatggc catggctaag caattctcac   1140
ttggtgctga ttggtattgc taataccctg gatctcacag atagaattct acctaggctt   1200
caagctagag aaaaatgtaa gccacagctg ttgaacttcc caccttatac cagaaatcag   1260
atagtcacta ttttgcaaga tcgacttaat caggtatcta gagatcaggt tctggacaat   1320
gctgcagttc aattctgtgc ccgcaaagtc tctgctgttt caggagatgt tcgcaaagca   1380
ctggatgttt gcaggagagc tattgaaatt gtagagtcag atgtcaaaag ccagactatt   1440
ctcaaaccac tgtctgaatg taaatcacct tctgagcctc tgattcccaa gagggttggt   1500
cttattcaca tatcccaagt catctcagaa gttgatggta acaggatgac cttgagccaa   1560
gaaggagcac aagattcctt ccctcttcag cagaagatct tggtttgctc tttgatgctc   1620
ttgatcaggc agttgaaaat caaagaggtc actctgggga agttatatga agcctacagt   1680
aaagtctgtc gcaaacagca ggtggcggct gtggaccagt cagagtgttt gtcactttca   1740
gggctcttgg aagccagggg cattttagga ttaaagagaa acaaggaaac ccgtttgaca   1800
aaggtgtttt tcaagattga agagaaagaa atagaacatg ctctgaaaga taaagcttta   1860
attggaaata tcttagctac tggattgcct taaattcttc tcttacaccc cacccgaaag   1920
tattcagctg gcatttagag agctacagtc ttcattttag tgctttacac attcgggcct   1980
gaaaacaaat atgacctttt ttacttgaag ccaatgaatt ttaatctata gattctttaa   2040
tattagcaca gaataatatc tttgggtctt actattttta cccataaaag tgaccaggta   2100
gacccttttt aattacattc actacttcta ccacttgtgt atctctagcc aatgtgcttg   2160
caagtgtaca gatctgtgta gaggaatgtg tgtatattta cctcttcgtt tgctcaaaca   2220
tgagtgggta ttttttttgtt tgtttttttt gttgttgttg tttttgaggc gcgtctcacc   2280
ctgttgccca ggctggagtg caatggcgcg ttctctgctc actacagcac ccgcttccca   2340
ggttgaagtg attctcttgc ctcagcctcc cgagtagctg ggattacagg tgcccaccac   2400
cgcgcccagc taattttttta atttttagta gagacagggt tttaccatgt tggccaggct   2460
```

-continued

```
ggtcttgaac tcctgaccct caagtgatct gcccaccttg gcctccctaa gtgctgggat   2520

tataggcgtg agccaccatg ctcagccatt aaggtatttt gttaagaact ttaagtttag   2580

ggtaagaaga atgaaaatga tccagaaaaa tgcaagcaag tccacatgga gatttggagg   2640

acactggtta aagaatttat ttctttgtat agtatactat gttcatggtg cagatactac   2700

aacattgtgg cattttagac tcgttgagtt tcttgggcac tcccaagggc gttggggtca   2760

taaggagact ataactctac agattgtgaa tatatttatt ttcaagttgc attctttgtc   2820

tttttaagca atcagatttc aagagagctc aagctttcag aagtcaatgt gaaaattcct   2880

tcctaggctg tcccacagtc tttgctgccc ttagatgaag ccacttgttt caagatgact   2940

actttggggt tgggttttca tctaaacaca tttttccagt cttattagat aaattagtcc   3000

atatggttgg ttaatcaaga gccttctggg tttggtttgg tggcattaaa tgg          3053
```

<210> SEQ ID NO 112
<211> LENGTH: 1843
<212> TYPE: DNA
<213> ORGANISM: Homo sapiens

<400> SEQUENCE: 112

```
gcggaatggg gcgggacttc cagtaggagg cggcaagttt gaaaagtgat gacggttgac     60

gtttgctgat ttttgacttt gcttgtagct gctccccgaa ctcgccgtct tcctgtcggc    120

ggccggcact gtagattaac aggaaacttc caagatggaa actttgtctt tccccagata    180

taatgtagct gagattgtga ttcatattcg caataagatc ttaacaggag ctgatggtaa    240

aaacctcacc aagaatgatc tttatccaaa tccaaagcct gaagtcttgc acatgatcta    300

catgagagcc ttacaaatag tatatggaat tcgactggaa catttttaca tgatgccagt    360

gaactctgaa gtcatgtatc cacatttaat ggaaggcttc ttaccattca gcaatttagt    420

tactcatctg gactcatttt tgcctatctg ccgggtgaat gactttgaga ctgctgatat    480

tctatgtcca aaagcaaaac ggacaagtcg gtttttaagt ggcattatca actttattca    540

cttcagagaa gcatgccgtg aaacgtatat ggaatttctt tggcaatata aatcctctgc    600

ggacaaaatg caacagttaa acgccgcaca ccaggaggca ttaatgaaac tggagagact    660

tgattctgtt ccagttgaag agcaagaaga gttcaagcag ctttcagatg gaattcagga    720

gctacaacaa tcactaaatc aggattttca tcaaaaaacg atagtgctgc aagagggaaa    780

ttcccaaaag aagtcaaata tttcagagaa aaccaagcgt ttgaatgaac taaaattgtc    840

ggtggtttct ttgaaagaaa tacaagagag tttgaaaaca aaaattgtgg attctccaga    900

gaagttaaag aattataaag aaaaaatgaa agatacggtc cagaagctta aaaatgccag    960

acaagaagtg gtggagaaat atgaaatcta tggagactca gttgactgcc tgccttcatg   1020

tcagttggaa gtgcagttat atcaaaagaa aatacaggac ctttcagata atagggaaaa   1080

attagccagt atcttaaagg agagcctgaa cttggaggac caaattgaga gtgatgagtc   1140

agaactgaag aaattgaaga ctgaagaaaa ttcgttcaaa agactgatga ttgtgaagaa   1200

ggaaaaactt gccacagcac aattcaaaat aaataagaag catgaagatg ttaagcaata   1260

caaacgcaca gtaattgagg attgcaataa agttcaagaa aaaagaggtg ctgtctatga   1320

acgagtaacc acaattaatc aagaaatcca aaaaattaaa cttggaattc aacaactaaa   1380

agatgctgct gaaagggaga aactgaagtc ccaggaaata tttctaaact tgaaaactgc   1440

tttggagaaa taccacgacg gtattgaaaa ggcagcagag gactcctatg ctaagataga   1500
```

-continued tgagaagaca gctgaactga agaggaagat gttcaaaatg tcaacctgat taacaaaatt 1560
acatgtcttt ttgtaaatgg cttgccatct tttaattttc tatttagaaa gaaaagttga 1620
agcgaatgga agtatcagaa gtaccaaata atgttggctt catcagtttt tatacactct 1680
cataagtagt taataagatg aatttaatgt aggcttttat taatttataa ttaaaataac 1740
ttgtgcagct attcatgtct ctactctgcc ccttgttgta aatagtttga gtaaaacaaa 1800
actagttacc tttgaaatat atatattttt ttctgttact atc 1843

<210> SEQ ID NO 113
<211> LENGTH: 3686
<212> TYPE: DNA
<213> ORGANISM: Homo sapiens

<400> SEQUENCE: 113
ggctagcgcg ggaggtggag aaagaggctt gggcggcccc gctgtagccg cgtgtgggag 60
gacgcacggg cctgcttcaa agctttggga taacagcgcc tccgggggat aatgaatgcg 120
gagcctccgt tttcagtcga cttcagatgt gtctccactt ttttccgctg tagccgcaag 180
gcaaggaaac atttctcttc ccgtactgag gaggctgagg agtgcactgg gtgttctttt 240
ctcctctaac ccagaactgc gagacagagg ctgagtccct gtaaagaaca gctccagaaa 300
agccaggaga gcgcaggagg gcatccggga ggccaggagg ggttcgctgg ggcctcaacc 360
gcacccacat cggtcccacc tgcgaggggg cgggacctcg tggcgctgga ccaatcagca 420
cccacctgcg ctcacctggc ctcctcccgc tggctcccgg gggctgcggt gctcaaaggg 480
gcaagagctg agcggaacac cggcccgccg tcgcggcagc tgcttcaccc ctctctctgc 540
agccatgggg ctccctcgtg gacctctcgc gtctctcctc cttctccagg tttgctggct 600
gcagtgcgcg gcctccgagc cgtgccgggc ggtcttcagg gaggctgaag tgaccttgga 660
ggcgggaggc gcggagcagg agcccggcca ggcgctgggg aaagtattca tgggctgccc 720
tgggcaagag ccagctctgt ttagcactga taatgatgac ttcactgtgc ggaatggcga 780
gacagtccag gaaagaaggt cactgaagga aaggaatcca ttgaagatct tcccatccaa 840
acgtatctta cgaagacaca agagagattg ggtggttgct ccaatatctg tccctgaaaa 900
tggcaagggt cccttccccc agagactgaa tcagctcaag tctaataaag atagagacac 960
caagattttc tacagcatca cggggccggg ggcagacagc ccccctgagg gtgtcttcgc 1020
tgtagagaag gagacaggct ggttgttgtt gaataagcca ctggaccggg aggagattgc 1080
caagtatgag ctctttggcc acgctgtgtc agagaatggt gcctcagtgg aggaccccat 1140
gaacatctcc atcatagtga ccgaccagaa tgaccacaag cccaagttta cccaggacac 1200
cttccgaggg agtgtcttag agggagtcct accaggtact tctgtgatgc agatgacagc 1260
cacagatgag gatgatgcca tctacaccta caatggggtg gttgcttact ccatccatag 1320
ccaagaacca aaggacccac acgacctcat gttcacaatt caccggagca caggcaccat 1380
cagcgtcatc tccagtggcc tggaccggga aaaagtccct gagtacacac tgaccatcca 1440
ggccacagac atggatgggg acggctccac caccacggca gtggcagtag tggagatcct 1500
tgatgccaat gacaatgctc ccatgtttga cccccagaag tacgaggccc atgtgcctga 1560
gaatgcagtg ggccatgagg tgcagaggct gacggtcact gatctggacg cccccaactc 1620
accagcgtgg cgtgccacct accttatcat gggcggtgac gacggggacc attttaccat 1680
caccacccac cctgagagca accagggcat cctgacaacc aggaagggtt tggattttga 1740
ggccaaaaac cagcacaccc tgtacgttga agtgaccaac gaggcccctt ttgtgctgaa 1800
gctcccaacc tccacagcca ccatagtggt ccacgtggag gatgtgaatg aggcacctgt 1860
gtttgtccca ccctccaaag tcgttgaggt ccaggagggc atccccactg gggagcctgt 1920
gtgtgtctac actgcagaag accctgacaa ggagaatcaa aagatcagct accgcatcct 1980
gagagaccca gcagggtggc tagccatgga cccagacagt gggcaggtca cagctgtggg 2040
caccctcgac cgtgaggatg agcagtttgt gaggaacaac atctatgaag tcatggtctt 2100
ggccatggac aatggaagcc ctcccaccac tggcacggga acccttctgc taacactgat 2160
tgatgtcaac gaccatggcc cagtccctga gccccgtcag atcaccatct gcaaccaaag 2220
ccctgtgcgc caggtgctga acatcacgga caaggacctg tctccccaca cctcccccttt 2280 ccaggcccag ctcacagatg actcagacat ctactggacg gcagaggtca acgaggaagg 2340
tgacacagtg gtcttgtccc tgaagaagtt cctgaagcag gatacatatg acgtgcacct 2400
ttctctgtct gaccatggca acaaagagca gctgacggtg atcagggcca ctgtgtgcga 2460
ctgccatggc catgtcgaaa cctgccctgg accctggaaa ggaggtttca tcctccctgt 2520
gctgggggct gtcctggctc tgctgttcct cctgctggtg ctgcttttgt tggtgagaaa 2580
gaagcggaag atcaaggagc ccctcctact cccagaagat gacacccgtg acaacgtctt 2640
ctactatggc gaagaggggg gtggcgaaga ggaccaggac tatgacatca cccagctcca 2700
ccgaggtctg gaggccaggc cggaggtggt tctccgcaat gacgtggcac caaccatcat 2760
cccgacaccc atgtaccgtc ctaggccagc caacccagat gaaatcggca actttataat 2820
tgagaacctg aaggcggcta acacagaccc cacagccccg ccctacgaca ccctcttggt 2880
gttcgactat gagggcagcg gctccgacgc cgcgtccctg agctccctca cctcctccgc 2940
ctccgaccaa gaccaagatt acgattatct gaacgagtgg ggcagccgct tcaagaagct 3000
ggcagacatg tacggtggcg gggaggacga ctaggcggcc tgcctgcagg gctggggacc 3060
aaacgtcagg ccacagagca tctccaaggg gtctcagttc ccccttcagc tgaggacttc 3120
ggagcttgtc aggaagtggc cgtagcaact tggcggagac aggctatgag tctgacgtta 3180
gagtggttgc ttccttagcc tttcaggatg gaggaatgtg ggcagtttga cttcagcact 3240
gaaaacctct ccacctgggc cagggttgcc tcagaggcca agtttccaga agcctcttac 3300
ctgccgtaaa atgctcaacc ctgtgtcctg ggcctgggcc tgctgtgact gacctacagt 3360
ggactttctc tctggaatgg aaccttctta ggcctcctgg tgcaacttaa ttttttttt 3420 taatgctatc ttcaaaacgt tagagaaagt tcttcaaaag tgcagcccag agctgctggg 3480
cccactggcc gtcctgcatt tctggtttcc agaccccaat gcctcccatt cggatggatc 3540
tctgcgtttt tatactgagt gtgcctaggt tgccccttat tttttatttt ccctgttgcg 3600
ttgctataga tgaagggtga ggacaatcgt gtatatgtac tagaactttt ttattaaaga 3660
aacttttccc aaaaaaaaaa aaaaaa 3686

<210> SEQ ID NO 114
<211> LENGTH: 10316
<212> TYPE: DNA
<213> ORGANISM: Homo sapiens

<400> SEQUENCE: 114
gagaccagaa gcgggcgaat tgggcaccgg tggcggctgc gggcagtttg aattagactc 60
tgggctccag cccgccgaag ccgcgccaga actgtactct ccgagaggtc gttttcccgt 120
ccccgagagc aagtttattt acaaatgttg gagtaataaa gaaggcagaa caaaatgagc 180

-continued

```
tgggctttgg aagaatggaa agaagggctg cctacaagag ctcttcagaa aattcaagag    240
cttgaaggac agcttgacaa actgaagaag gaaaagcagc aaaggcagtt tcagcttgac    300
agtctcgagg ctgcgctgca gaagcaaaaa cagaaggttg aaaatgaaaa aaccgagggt    360
acaaacctga aaagggagaa tcaaagattg atggaaatat gtgaaagtct ggagaaaact    420
aagcagaaga tttctcatga acttcaagtc aaggagtcac aagtgaattt ccaggaagga    480
caactgaatt caggcaaaaa acaaatagaa aaactggaac aggaacttaa aaggtgtaaa    540
tctgagcttg aaagaagcca acaagctgcg cagtctgcag atgtctctct gaatccatgc    600
aatacaccac aaaaaatttt tacaactcca ctaacaccaa gtcaatatta tagtggttcc    660
aagtatgaag atctaaaaga aaaatataat aaagaggttg aagaacgaaa aagattagag    720
gcagaggtta aagccttgca ggctaaaaaa gcaagccaga ctcttccaca agccaccatg    780
aatcaccgcg acattgcccg gcatcaggct tcatcatctg tgttctcatg gcagcaagag    840
aagaccccaa gtcatctttc atctaattct caaagaactc caattaggag agatttctct    900
gcatcttact tttctgggga acaagaggtg actccaagtc gatcaacttt gcaaataggg    960
aaaagagatg ctaatagcag tttctttgac aattctagca gtcctcatct tttggatcaa   1020
ttaaaagcgc agaatcaaga gctaagaaac aagattaatg agttggaact acgcctgcaa   1080
ggacatgaaa aagaaatgaa aggccaagtg aataagtttc aagaactcca actccaactg   1140
gagaaagcaa aagtggaatt aattgaaaaa gagaaagttt tgaacaaatg tagggatgaa   1200
ctagtgagaa caacagcaca atacgaccag gcgtcaacca agtatactgc attggaacaa   1260
aaactgaaaa aattgacgga agatttgagt tgtcagcgac aaaatgcaga aagtgccaga   1320
tgttctctgg aacagaaaat taaggaaaaa gaaaaggagt ttcaagagga gctctcccgt   1380
caacagcgtt ctttccaaac actggaccag gagtgcatcc agatgaaggc cagactcacc   1440
caggagttac agcaagccaa gaatatgcac aacgtcctgc aggctgaact ggataaactc   1500
acatcagtaa agcaacagct agaaaacaat ttggaagagt ttaagcaaaa gttgtgcaga   1560
gctgaacagg cgttccaggc gagtcagatc aaggagaatg agctgaggag aagcatggag   1620
gaaatgaaga aggaaaacaa cctccttaag agtcactctg agcaaaaggc cagagaagtc   1680
tgccacctgg aggcagaact caagaacatc aaacagtgtt taaatcagag ccagaatttt   1740
gcagaagaaa tgaaagcgaa gaatacctct caggaaacca tgttaagaga tcttcaagaa   1800
aaaataaatc agcaagaaaa ctccttgact ttagaaaaac tgaagcttgc tgtggctgat   1860
ctggaaaagc agcgagattg ttctcaagac cttttgaaga aaagagaaca tcacattgaa   1920
caacttaatg ataagttaag caagacagag aaagagtcca aagccttgct gagtgcttta   1980
gagttaaaaa agaaagaata tgaagaattg aaagaagaga aaactctgtt ttcttgttgg   2040
aaaagtgaaa acgaaaaact tttaactcag atggaatcag aaaaggaaaa cttgcagagt   2100
aaaattaatc acttggaaac ttgtctgaag acacagcaaa taaaaagtca tgaatacaac   2160
gagagagtaa gaacgctgga gatggacaga gaaaacctaa gtgtcgagat cagaaacctt   2220
cacaacgtgt tagacagtaa gtcagtggag gtagagaccc agaaactagc ttatatggag   2280
ctacagcaga aagctgagtt ctcagatcag aaacatcaga aggaaataga aaatatgtgt   2340
ttgaagactt ctcagcttac tgggcaagtt gaagatctag aacacaagct tcagttactg   2400
tcaaatgaaa taatggacaa agaccggtgt taccaagact tgcatgccga atatgagagc   2460
ctcagggatc tgctaaaatc caaagatgct tctctggtga caaatgaaga tcatcagaga   2520
agtcttttgg cttttgatca gcagcctgcc atgcatcatt cctttgcaaa tataattgga   2580
```

-continued

```
gaacaaggaa gcatgccttc agagaggagt gaatgtcgtt tagaagcaga ccaaagtccg   2640
aaaaattctg ccatcctaca aaatagagtt gattcacttg aattttcatt agagtctcaa   2700
aaacagatga actcagacct gcaaaagcag tgtgaagagt tggtgcaaat caaaggagaa   2760
atagaagaaa atctcatgaa agcagaacag atgcatcaaa gttttgtggc tgaaacaagt   2820
cagcgcatta gtaagttaca ggaagacact tctgctcacc agaatgttgt tgctgaaacc   2880
ttaagtgccc ttgagaacaa ggaaaaagag ctgcaacttt taaatgataa ggtagaaact   2940
gagcaggcag agattcaaga attaaaaaag agcaaccatc tacttgaaga ctctctaaag   3000
gagctacaac ttttatccga aaccctaagc ttggagaaga aagaaatgag ttccatcatt   3060
tctctaaata aaagggaaat tgaagagctg acccaagaga atgggactct taaggaaatt   3120
aatgcatcct taaatcaaga gaagatgaac ttaatccaga aaagtgagag ttttgcaaac   3180
tatatagatg aaagggagaa aagcatttca gagttatctg atcagtacaa gcaagaaaaa   3240
cttattttac tacaaagatg tgaagaaacc ggaaatgcat atgaggatct tagtcaaaaa   3300
tacaaagcag cacaggaaaa gaattctaaa ttagaatgct tgctaaatga atgcactagt   3360
ctttgtgaaa ataggaaaaa tgagttggaa cagctaaagg aagcatttgc aaaggaacac   3420
caagaattct taacaaaatt agcatttgct gaagaaagaa atcagaatct gatgctagag   3480
ttggagacag tgcagcaagc tctgagatct gagatgacag ataaccaaaa caattctaag   3540
agcgaggctg gtggtttaaa gcaagaaatc atgactttaa aggaagaaca aaacaaaatg   3600
caaaaggaag ttaatgactt attacaagag aatgaacagc tgatgaaggt aatgaagact   3660
aaacatgaat gtcaaaatct agaatcagaa ccaattagga actctgtgaa agaaagagag   3720
agtgagagaa atcaatgtaa ttttaaacct cagatggatc ttgaagttaa agaaatttct   3780
ctagatagtt ataatgcgca gttggtgcaa ttagaagcta tgctaagaaa taaggaatta   3840
aaacttcagg aaagtgagaa ggagaaggag tgcctgcagc atgaattaca gacaattaga   3900
ggagatcttg aaaccagcaa tttgcaagac atgcagtcac aagaaattag tggccttaaa   3960
gactgtgaaa tagatgcgga agaaaagtat atttcagggc ctcatgagtt gtcaacaagt   4020
caaaacgaca atgcacacct tcagtgctct ctgcaaacaa caatgaacaa gctgaatgag   4080
ctagagaaaa tatgtgaaat actgcaggct gaaaagtatg aactcgtaac tgagctgaat   4140
gattcaaggt cagaatgtat cacagcaact aggaaaatgg cagaagaggt agggaaacta   4200
ctaaatgaag ttaaaatatt aaatgatgac agtggtcttc tccatggtga gttagtggaa   4260
gacataccag gaggtgaatt tggtgaacaa ccaaatgaac agcaccctgt gtctttggct   4320
ccattggacg agagtaattc ctacgagcac ttgacattgt cagacaaaga agttcaaatg   4380
cactttgccg aattgcaaga gaaattctta tctttacaaa gtgaacacaa aattttacat   4440
gatcagcact gtcagatgag ctctaaaatg tcagagctgc agacctatgt tgactcatta   4500
aaggccgaaa atttggtctt gtcaacgaat ctgagaaact ttcaaggtga cttggtgaag   4560
gagatgcagc tgggcttgga ggagggggctc gttccatccc tgtcatcctc ttgtgtgcct   4620
gacagctcta gtcttagcag tttgggagac tcctcctttt acagagctct tttagaacag   4680
acaggagata tgtctctttt gagtaattta gaaggggctg tttcagcaaa ccagtgcagt   4740
gtagatgaag tattttgcag cagtctgcag gaggagaatc tgaccaggaa agaaacccct   4800
tcggccccag cgaagggtgt tgaagagctt gagtccctct gtgaggtgta ccggcagtcc   4860
ctcgagaagc tagaagagaa aatggaaagt caagggatta tgaaaaataa ggaaattcaa   4920
```

-continued gagctcgagc agttattaag ttctgaaagg caagagcttg actgccttag gaagcagtat 4980
ttgtcagaaa atgaacagtg gcaacagaag ctgacaagcg tgactctgga gatggagtcc 5040
aagttggcgg cagaaaagaa acagacggaa caactgtcac ttgagctgga agtagcacga 5100
ctccagctac aaggtctgga cttaagttct cggtctttgc ttggcatcga cacagaagat 5160
gctattcaag gccgaaatga gagctgtgac atatcaaaag aacatacttc agaaactaca 5220
gaaagaacac caaagcatga tgttcatcag atttgtgata aagatgctca gcaggacctc 5280
aatctagaca ttgagaaaat aactgagact ggtgcagtga aacccacagg agagtgctct 5340
ggggaacagt ccccagatac caattatgag cctccagggg aagataaaac ccagggctct 5400
tcagaatgca tttctgaatt gtcattttct ggtcctaatg ctttggtacc tatggatttc 5460
ctggggaatc aggaagatat ccataatctt caactgcggg taaaagagac atcaaatgag 5520
aatttgagat tacttcatgt gatagaggac cgtgacagaa aagttgaaag tttgctaaat 5580
gaaatgaaag aattagactc aaaactccat ttacaggagg tacaactaat gaccaaaatt 5640
gaagcatgca tagaattgga aaaaatagtt ggggaactta agaaagaaaa ctcagattta 5700
agtgaaaaat tggaatattt ttcttgtgat caccaggagt tactccagag agtagaaact 5760
tctgaaggcc tcaattctga tttagaaatg catgcagata aatcatcacg tgaagatatt 5820
ggagataatg tggccaaggt gaatgacagc tggaaggaga gatttcttga tgtggaaaat 5880
gagctgagta ggatcagatc ggagaaagct agcattgagc atgaagccct ctacctggag 5940
gctgacttag aggtagttca aacagagaag ctatgtttag aaaaagacaa tgaaaataag 6000
cagaaggtta ttgtctgcct tgaagaagaa ctctcagtgg tcacaagtga gagaaaccag 6060
cttcgtggag aattagatac tatgtcaaaa aaaaccacgg cactggatca gttgtctgaa 6120
aaaatgaagg agaaaacaca agagcttgag tctcatcaaa gtgagtgtct ccattgcatt 6180
caggtggcag aggcagaggt gaaggaaaag acggaactcc ttcagacttt gtcctctgat 6240
gtgagtgagc tgttaaaaga caaaactcat ctccaggaaa agctgcagag tttggaaaag 6300
gactcacagg cactgtcttt gacaaaatgt gagctggaaa accaaattgc acaactgaat 6360
aaagagaaag aattgcttgt caaggaatct gaaagcctgc aggccagact gagtgaatca 6420
gattatgaaa agctgaatgt ctccaaggcc ttggaggccg cactggtgga gaaaggtgag 6480
ttcgcattga ggctgagctc aacacaggag gaagtgcatc agctgagaag aggcatcgag 6540
aaactgagag ttcgcattga ggccgatgaa aagaagcagc tgcacatcgc agagaaactg 6600
aaagaacgcg agcgggagaa tgattcactt aaggataaag ttgagaacct tgaaagggaa 6660
ttgcagatgt cagaagaaaa ccaggagcta gtgattcttg atgccgagaa ttccaaagca 6720
gaagtagaga ctctaaaaac acaaatagaa gagatggcca gaagcctgaa agtttttgaa 6780
ttagaccttg tcacgttaag gtctgaaaaa gaaaatctga caaaacaaat acaagaaaaa 6840
caaggtcagt tgtcagaact agacaagtta ctctcttcat ttaaaagtct gttagaagaa 6900
aaggagcaag cagagataca gatcaaagaa gaatctaaaa ctgcagtgga gatgcttcag 6960
aatcagttaa aggagctaaa tgaggcagta gcagccttgt gtggtgacca agaaattatg 7020
aaggccacag aacagagtct agacccacca atagaggaag agcatcagct gagaaatagc 7080
attgaaaagc tgagagcccg cctagaagct gatgaaaaga agcagctctg tgtcttacaa 7140
caactgaagg aaagtgagca tcatgcagat ttacttaagg gtagagtgga gaaccttgaa 7200
agagagctag agatagccag gacaaaccaa gagcatgcag ctcttgaggc agagaattcc 7260
aaaggagagg tagagaccct aaaagcaaaa atagaaggga tgacccaaag tctgagaggt 7320

-continued ctggaattag atgttgttac tataaggtca gaaaaagaaa atctgacaaa tgaattacaa 7380
aaagagcaag agcgaatatc tgaattagaa ataataaatt catcatttga aaatattttg 7440
caagaaaaag agcaagagaa agtacagatg aaagaaaaat caagcactgc catggagatg 7500
cttcaaacac aattaaaaga gctcaatgag agagtggcag ccctgcataa tgaccaagaa 7560
gcctgtaagg ccaaagagca gaatcttagt agtcaagtag agtgtcttga acttgagaag 7620
gctcagttgc tacaaggcct tgatgaggcc aaaaataatt atattgtttt gcaatcttca 7680
gtgaatggcc tcattcaaga agtagaagat ggcaagcaga aactggagaa gaaggatgaa 7740
gaaatcagta gactgaaaaa tcaaattcaa gaccaagagc agcttgtctc taaactgtcc 7800
caggtggaag gagagcacca actttggaag gagcaaaact tagaactgag aaatctgaca 7860
gtggaattgg agcagaagat ccaagtgcta caatccaaaa atgcctcttt gcaggacaca 7920
ttagaagtgc tgcagagttc ttacaagaat ctagagaatg agcttgaatt gacaaaaatg 7980
gacaaaatgt cctttgttga aaaagtaaac aaaatgactg caaaggaaac tgagctgcag 8040
agggaaatgc atgagatggc acagaaaaca gcagagctgc aagaagaact cagtggagag 8100
aaaaataggc tagctggaga gttgcagtta ctgttggaag aaataaagag cagcaaagat 8160
caattgaagg agctcacact agaaaatagt gaattgaaga agagcctaga ttgcatgcac 8220
aaagaccagg tggaaaagga agggaaagtg agagaggaaa tagctgaata tcagctacgg 8280
cttcatgaag ctgaaaagaa acaccaggct ttgcttttgg acacaaacaa acagtatgaa 8340
gtagaaatcc agacataccg agagaaattg acttctaaag aagaatgtct cagttcacag 8400
aagctggaga tagacctttt aaagtctagt aaagaagagc tcaataattc attgaaagct 8460
actactcaga ttttggaaga attgaagaaa accaagatgg acaatctaaa atatgtaaat 8520
cagttgaaga aggaaaatga acgtgcccag gggaaaatga agttgttgat caaatcctgt 8580
aaacagctgg aagaggaaaa ggagatactg cagaaagaac tctctcaact tcaagctgca 8640
caggagaagc agaaaacagg tactgttatg gataccaagg tcgatgaatt aacaactgag 8700
atcaaagaac tgaaagaaac tcttgaagaa aaaaccaagg aggcagatga atacttggat 8760
aagtactgtt ccttgcttat aagccatgaa aagttagaga aagctaaaga gatgttagag 8820
acacaagtgg cccatctgtg ttcacagcaa tctaaacaag attcccgagg gtctcctttg 8880
ctaggtccag ttgttccagg accatctcca atcccttctg ttactgaaaa gaggttatca 8940
tctggccaaa ataaagcttc aggcaagagg caaagatcca gtggaatatg ggagaatggt 9000
agaggaccaa cacctgctac cccagagagc ttttctaaaa aaagcaagaa agcagtcatg 9060
agtggtattc accctgcaga agacacggaa ggtactgagt ttgagccaga gggacttcca 9120
gaagttgtaa agaaagggtt tgctgacatc ccgacaggaa agactagccc atatatcctg 9180
cgaagaacaa ccatggcaac tcggaccagc cccgcctgg ctgcacagaa gttagcgcta 9240
tccccactga gtctcggcaa agaaaatctt gcagagtcct ccaaaccaac agctggtggc 9300
agcagatcac aaaaggtcaa agttgctcag cggagcccag tagattcagg caccatcctc 9360
cgagaaccca ccacgaaatc cgtcccagtc aataatcttc ctgagagaag tccgactgac 9420
agccccagag agggcctgag ggtcaagcga ggccgacttg tccccagccc caaagctgga 9480
ctggagtcca acggcagtga gaactgtaag gtccagtgaa ggcactttgt gtgtcagtac 9540
ccctgggagg tgccagtcat tgaatagata aggctgtgcc tacaggactt ctctttagtc 9600
agggcatgct ttattagtga ggagaaaaca attccttaga agtcttaaat atattgtact 9660

```
ctttagatct cccatgtgta ggtattgaaa aagtttggaa gcactgatca cctgttagca   9720

ttgccattcc tctactgcaa tgtaaatagt ataaagctat gtatataaag ctttttggta   9780

atatgttaca attaaaatga caagcactat atcacaatct ctgtttgtat gtgggtttta   9840

cactaaaaaa atgcaaaaca cattttattc ttctaattaa cagctcctag gaaaatgtag   9900

acttttgctt tatgatattc tatctgtagt atgaggcatg gaatagtttt gtatcgggaa   9960

tttctcagag ctgagtaaaa tgaaggaaaa gcatgttatg tgtttttaag gaaaatgtgc  10020

acacatatac atgtaggagt gtttatcttt ctcttacaat ctgttttaga catctttgct  10080

tatgaaacct gtacatatgt gtgtgtgggt atgtgtttat ttccagtgag ggctgcaggc  10140

ttcctagagg tgtgctatac catgcgtctg tcgttgtgct tttttctgtt tttagaccaa  10200

ttttttacag ttctttggta agcattgtcg tatctggtga tggattaaca tatagccttt  10260

gttttctaat aaaatagtcg ccttcgtttt ctgtaaaaaa aaaaaaaaaa aaaaaa      10316
```

<210> SEQ ID NO 115
<211> LENGTH: 2639
<212> TYPE: DNA
<213> ORGANISM: Homo sapiens

<400> SEQUENCE: 115

```
ggcacgaggg gccgacgcga gcgccgcgct tcgcttcagc tgctagctgg cccaagggag     60

gcgaccgcgg agggtggcga ggggcggcca ggacccgcag ccccggggcc gggccggtcc    120

ggaccgccag ggagggcagg tcagtgggca gatcgcgtcc gcgggattca atctctgccc    180

gctctgataa cagtcctttt ccctggcgct cacttcgtgc ctggcacccg gctgggcgcc    240

tcaagaccgt tgtctcttcg atcgcttctt tggacttggc gaccatttca gagatgtctt    300

ccagaagtac caaagattta attaaaagta agtggggatc gaagcctagt aactccaaat    360

ccgaaactac attagaaaaa ttaaagggag aaattgcaca cttaaagaca tcagtggatg    420

aaatcacaag tgggaaagga aagctgactg ataaagagag acacagactt ttggagaaaa    480

ttcgagtcct tgaggctgag aaggagaaga atgcttatca actcacagag aaggacaaag    540

aaatacagcg actgagagac caactgaagg ccagatatag tactaccgca ttgcttgaac    600

agctggaaga gacaacgaga gaaggagaaa ggagggagca ggtgttgaaa gccttatctg    660

aagagaaaga cgtattgaaa caacagttgt ctgctgcaac ctcacgaatt gctgaacttg    720

aaagcaaaac caatacactc cgtttatcac agactgtggc tccaaactgc ttcaactcat    780

caataaataa tattcatgaa atggaaatac agctgaaaga tgctctggag aaaaatcagc    840

agtggctcgt gtatgatcag cagcgggaag tctatgtaaa aggactttta gcaaagatct    900

ttgagttgga aaagaaaacg gaaacagctg ctcattcact cccacagcag acaaaaaagc    960

ctgaatcaga aggttatctt caagaagaga agcagaaatg ttacaacgat ctcttggcaa   1020

gtgcaaaaaa agatcttgag gttgaacgac aaaccataac tcagctgagt tttgaactga   1080

gtgaatttcg aagaaaatat gaagaaaccc aaaaagaagt tcacaattta aatcagctgt   1140

tgtattcaca aagaagggca gatgtgcaac atctggaaga tgataggcat aaaacagaga   1200

agatacaaaa actcagggaa gagaatgata ttgctagggg aaaacttgaa gaagagaaga   1260

agagatccga agagctctta tctcaggtcc agtttcttta cacatctctg ctaaagcagc   1320

aagaagaaca aacaagggta gctctgttgg aacaacagat gcaggcatgt actttagact   1380

ttgaaaatga aaaactcgac cgtcaacatg tgcagcatca attgcatgta attcttaagg   1440

agctccgaaa agcaagaaat caaataacac agttggaatc cttgaaacag cttcatgagt   1500
```

-continued ttgccatcac agagccatta gtcactttcc aaggagagac tgaaaacaga gaaaaagttg 1560
ccgcctcacc aaaaagtccc actgctgcac tcaatgaaag cctggtggaa tgtcccaagt 1620
gcaatataca gtatccagcc actgagcatc gcgatctgct tgtccatgtg gaatactgtt 1680
caaagtagca aaataagtat ttgttttgat attaaaagat tcaatactgt attttctgtt 1740
agcttgtggg cattttgaat tatatatttc acattttgca taaaactgcc tatctacctt 1800
tgacactcca gcatgctagt gaatcatgta tcttttaggc tgctgtgcat ttctcttggc 1860
agtgatacct ccctgacatg gttcatcatc aggctgcaat gacagaatgt ggtgagcagc 1920
gtctactgag actactaaca ttttgcactg tcaaaatact tggtgaggaa aagatagctc 1980
aggttattgc taatgggtta atgcaccagc aagcaaaata ttttatgttt tgggggtttg 2040
aaaaatcaaa gataattaac caaggatctt aactgtgttc gcattttttta tccaagcact 2100 tagaaaacct acaatcctaa ttttgatgtc cattgttaag aggtggtgat agatactatt 2160 tttttttca tattgtatag cggttattag aaaagttggg gattttcttg atctttattg 2220
ctgcttacca ttgaaactta acccagctgt gttccccaac tctgttctgc gcacgaaaca 2280
gtatctgttt gaggcataat cttaagtggc cacacacaat gttttctctt atgttatctg 2340
gcagtaactg taacttgaat tacattagca cattctgctt agctaaaatt gttaaaataa 2400
actttaataa acccatgtag ccctctcatt tgattgacag tattttagtt atttttggca 2460
ttcttaaagc tgggcaatgt aatgatcaga tctttgtttg tctgaacagg tattttata 2520 catgcttttt gtaaaccaaa aactttaaa tttcttcagg ttttctaaca tgcttaccac 2580
tgggctactg taaatgagaa aagaataaaa ttatttaatg ttttaaaaaa aaaaaaaaa 2639

<210> SEQ ID NO 116
<211> LENGTH: 2632
<212> TYPE: DNA
<213> ORGANISM: Homo sapiens

<400> SEQUENCE: 116
ggcggctgag cctgagcggg gatgtagagg cggcggcagc agaggcggca ctggcggcaa 60
gagcagacgc ccgagccgag cgagaagagc ggcagagcct tatcccctga agccgggccc 120
cgcgtcccag ccctgcccag cccgcgccca gccatgcgcg ccgcctgctg agtccgggcg 180
ccgcacgctg agccctccgc ccgcgagccg cgctcagctc gggggtgatt agttgctttt 240
tgttgttttt taatttgggc cgcggggagg gggaggaggg gcaggtgctg caggctcccc 300
cccctccccg cctcgggcca gccgcggcgg cgcgactcgg gctccggacc cgggcactgc 360
tggcggctgg agcggagcgc accgcggcgg tggtgcccag agcggagcgc agctccctgc 420
cccgcccctc cccctcggcc tcgcggcgac ggcggcggtg gcggcttgga cgactcggag 480
agccgagtga agacatttcc acctggacac ctgaccatgt gcctgccctg agcagcgagg 540
cccaccaggc atctctgttg tgggcagcag ggccaggtcc tggtctgtgg accctcggca 600
gttggcaggc tccctctgca gtggggtctg ggcctcggcc ccaccatgtc gagcctcggc 660
ggtggctccc aggatgccgg cggcagtagc agcagcagca ccaatggcag cggtggcagt 720
ggcagcagtg gcccaaaggc aggagcagca gacaagagtg cagtggtggc tgccgccgca 780
ccagcctcag tggcagatga cacaccaccc cccgagcgtc ggaacaagag cggtatcatc 840
agtgagcccc tcaacaagag cctgcgccgc tcccgcccgc tctcccacta ctcttctttt 900
ggcagcagtg gtggtagtgg cggtggcagc atgatgggcg gagagtctgc tgacaaggcc 960
actgcggctg cagccgctgc ctccctgttg gccaatgggc atgacctggc ggcggccatg 1020
gcggtggaca aaagcaaccc tacctcaaag cacaaaagtg gtgctgtggc cagcctgctg 1080
agcaaggcag agcgggccac ggagctggca gccgagggac agctgacgct gcagcagttt 1140
gcgcagtcca cagagatgct gaagcgcgtg gtgcaggagc atctcccgct gatgagcgag 1200
gcgggtgctg gcctgcctga catggaggct gtggcaggtg ccgaagccct caatggccag 1260
tccgacttcc cctacctggg cgctttcccc atcaacccag gcctcttcat tatgaccccg 1320
gcaggtgtgt tcctggccga gagcgcgctg cacatggcgg gcctggctga gtaccccatg 1380
cagggagagc tggcctctgc catcagctcc ggcaagaaga agcggaaacg ctgcggcatg 1440
tgcgcgccct gccggcggcg catcaactgc gagcagtgca gcagttgtag gaatcgaaag 1500
actggccatc agatttgcaa attcagaaaa tgtgaggaac tcaaaaagaa gccttccgct 1560
gctctggaga aggtgatgct tccgacggga gccgccttcc ggtggtttca gtgacggcgg 1620
cggaacccaa agctgccctc tccgtgcaat gtcactgctc gtgtggtctc cagcaaggga 1680
ttcgggcgaa gacaaacgga tgcacccgtc tttagaacca aaaatattct ctcacagatt 1740
tcattcctgt ttttatatat atattttttg ttgtcgtttt aacatctcca cgtccctagc 1800
ataaaaagaa aaagaaaaaa atttaaactg ctttttcgga agaacaacaa caaaaaagag 1860
gtaaagacga atctataaag taccgagact tcctgggcaa agaatggaca atcagtttcc 1920
ttcctgtgtc gatgtcgatg ttgtctgtgc aggagatgca gtttttgtgt agagaatgta 1980
aattttctgt aaccttttga aatctagtta ctaataagca ctactgtaat ttagcacagt 2040
ttaactccac cctcatttaa acttcctttg attctttccg accatgaaat agtgcatagt 2100
ttgcctggag aatccactca cgttcataaa gagaatgttg atggcgccgt gtagaagccg 2160
ctctgtatcc atccacgcgt gcagagctgc cagcagggag ctcacagaag ggagagggagc 2220 accaggccag ctgagctgca cccacagtcc cgagactggg atcccccacc ccaacagtga 2280
ttttggaaaa aaaaatgaaa gttctgttcg tttatccatt gcgatctggg gagccccatc 2340
tcgatatttc caatcctggc tacttttctt agagaaaata agtccttttt ttctggcctt 2400
gctaatggca acagaagaaa gggcttcttt gcgtggtccc ctgctggtgg gggtgggtcc 2460
ccagggggcc ccctgcggcc tgggcccccc tgcccacggc cagcttcctg ctgatgaaca 2520
tgctgtttgt attgttttag gaaaccaggc tgttttgtga ataaaacgaa tgcatgtttg 2580
tgtcacgaaa aaaaaaaaaa aaaaaaaaaa aaaaaaaaaa aaaaaaaaaa aa 2632

<210> SEQ ID NO 117
<211> LENGTH: 5616
<212> TYPE: DNA
<213> ORGANISM: Homo sapiens

<400> SEQUENCE: 117
ccccggcgca gcgcggccgc agcagcctcc gccccccgca cggtgtgagc gcccgacgcg 60
gccgaggcgg ccggagtccc gagctagccc cggcggccgc cgccgcccag accggacgac 120
aggccacctc gtcggcgtcc gcccgagtcc ccgcctcgcc gccaacgcca caaccaccgc 180
gcacggcccc ctgactccgt ccagtattga tcgggagagc cggagcgagc tcttcgggga 240
gcagcgatgc gaccctccgg gacggccggg gcagcgctcc tggcgctgct ggctgcgctc 300
tgcccggcga gtcgggctct ggaggaaaag aaagtttgcc aaggcacgag taacaagctc 360
acgcagttgg gcacttttga agatcatttt ctcagcctcc agaggatgtt caataactgt 420
gaggtggtcc ttgggaattt ggaaattacc tatgtgcaga ggaattatga tctttccttc 480

-continued

```
ttaaagacca tccaggaggt ggctggttat gtcctcattg ccctcaacac agtggagcga    540
attcctttgg aaaacctgca gatcatcaga ggaaatatgt actacgaaaa ttcctatgcc    600
ttagcagtct tatctaacta tgatgcaaat aaaaccggac tgaaggagct gcccatgaga    660
aatttacagg aaatcctgca tggcgccgtg cggttcagca acaaccctgc cctgtgcaac    720
gtggagagca tccagtggcg ggacatagtc agcagtgact ttctcagcaa catgtcgatg    780
gacttccaga accacctggg cagctgccaa aagtgtgatc caagctgtcc caatgggagc    840
tgctggggtg caggagagga gaactgccag aaactgacca aaatcatctg tgcccagcag    900
tgctccgggc gctgccgtgg caagtccccc agtgactgct gccacaacca gtgtgctgca    960
ggctgcacag gcccccggga gagcgactgc ctggtctgcc gcaaattccg agacgaagcc   1020
acgtgcaagg acacctgccc cccactcatg ctctacaacc ccaccacgta ccagatggat   1080
gtgaaccccg agggcaaata cagctttggt gccacctgcg tgaagaagtg tccccgtaat   1140
tatgtggtga cagatcacgg ctcgtgcgtc cgagcctgtg ggccgacag ctatgagatg    1200
gaggaagacg gcgtccgcaa gtgtaagaag tgcgaagggc cttgccgcaa agtgtgtaac   1260
ggaataggta ttggtgaatt taaagactca ctctccataa atgctacgaa tattaaacac   1320
ttcaaaaact gcacctccat cagtggcgat ctccacatcc tgccggtggc atttaggggt   1380
gactccttca cacatactcc tcctctggat ccacaggaac tggatattct gaaaaccgta   1440
aaggaaatca cagggttttt gctgattcag gcttggcctg aaaacaggac ggacctccat   1500
gcctttgaga acctagaaat catacgcggc aggaccaagc aacatggtca gttttctctt   1560
gcagtcgtca gcctgaacat aacatccttg ggattacgct ccctcaagga gataagtgat   1620
ggagatgtga taatttcagg aaacaaaaat ttgtgctatg caaatacaat aaactggaaa   1680
aaactgtttg ggacctccgg tcagaaaacc aaaattataa gcaacagagg tgaaaacagc   1740
tgcaaggcca caggccaggt ctgccatgcc ttgtgctccc ccgagggctg ctggggcccg   1800
gagcccaggg actgcgtctc ttgccggaat gtcagccgag gcagggaatg cgtggacaag   1860
tgcaaccttc tggagggtga gccaagggag tttgtggaga actctgagtg catacagtgc   1920
cacccagagt gcctgcctca ggccatgaac atcacctgca caggacgggg accagacaac   1980
tgtatccagt gtgcccacta cattgacggc ccccactgcg tcaagacctg cccggcagga   2040
gtcatgggag aaaacaacac cctggtctgg aagtacgcag acgccggcca tgtgtgccac   2100
ctgtgccatc caaactgcac ctacggatgc actgggccag gtcttgaagg ctgtccaacg   2160
aatgggccta agatcccgtc catcgccact gggatggtgg gggccctcct cttgctgctg   2220
gtggtggccc tggggatcgg cctcttcatg cgaaggcgcc acatcgttcg gaagcgcacg   2280
ctgcggaggc tgctgcagga gagggagctt gtggagcctc ttacacccag tggagaagct   2340
cccaaccaag ctctcttgag gatcttgaag gaaactgaat tcaaaaagat caaagtgctg   2400
ggctccggtg cgttcggcac ggtgtataag ggactctgga tcccagaagg tgagaaagtt   2460
aaaattcccg tcgctatcaa ggaattaaga gaagcaacat ctccgaaagc caacaaggaa   2520
atcctcgatg aagcctacgt gatggccagc gtggacaacc cccacgtgtg ccgcctgctg   2580
ggcatctgcc tcacctccac cgtgcagctc atcacgcagc tcatgccctt cggctgcctc   2640
ctggactatg tccgggaaca caaagacaat attggctccc agtacctgct caactggtgt   2700
gtgcagatcg caaagggcat gaactacttg gaggaccgtc gcttggtgca ccgcgacctg   2760
gcagccagga acgtactggt gaaaacaccg cagcatgtca agatcacaga ttttgggctg   2820
```

gccaaactgc tgggtgcgga agagaaagaa taccatgcag aaggaggcaa agtgcctatc 2880
aagtggatgg cattggaatc aattttacac agaatctata cccaccagag tgatgtctgg 2940
agctacgggg tgaccgtttg ggagttgatg acctttggat ccaagccata tgacggaatc 3000
cctgccagcg agatctcctc catcctggag aaaggagaac gcctccctca gccacccata 3060
tgtaccatcg atgtctacat gatcatggtc aagtgctgga tgatagacgc agatagtcgc 3120
ccaaagttcc gtgagttgat catcgaattc tccaaaatgg cccgagaccc ccagcgctac 3180
cttgtcattc agggggatga aagaatgcat ttgccaagtc ctacagactc caacttctac 3240
cgtgccctga tggatgaaga agacatggac gacgtggtgg atgccgacga gtacctcatc 3300
ccacagcagg gcttcttcag cagcccctcc acgtcacgga ctcccctcct gagctctctg 3360
agtgcaacca gcaacaattc caccgtggct tgcattgata gaaatgggct gcaaagctgt 3420
cccatcaagg aagacagctt cttgcagcga tacagctcag accccacagg cgccttgact 3480
gaggacagca tagacgacac cttcctccca gtgcctgaat acataaacca gtccgttccc 3540
aaaaggcccg ctggctctgt gcagaatcct gtctatcaca atcagcctct gaaccccgcg 3600
cccagcagag acccacacta ccaggacccc cacagcactg cagtgggcaa ccccgagtat 3660
ctcaacactg tccagcccac ctgtgtcaac agcacattcg acagccctgc ccactgggcc 3720
cagaaaggca gccaccaaat tagcctggac aaccctgact accagcagga cttctttccc 3780
aaggaagcca agccaaatgg catctttaag ggctccacag ctgaaaatgc agaataccta 3840
agggtcgcgc cacaaagcag tgaatttatt ggagcatgac cacggaggat agtatgagcc 3900
ctaaaaatcc agactctttc gatacccagg accaagccac agcaggtcct ccatcccaac 3960
agccatgccc gcattagctc ttagacccac agactggttt tgcaacgttt acaccgacta 4020
gccaggaagt acttccacct cgggcacatt ttgggaagtt gcattccttt gtcttcaaac 4080
tgtgaagcat ttacagaaac gcatccagca agaatattgt ccctttgagc agaaatttat 4140
ctttcaaaga ggtatatttg aaaaaaaaaa aaagtatatg tgaggatttt tattgattgg 4200
ggatcttgga gtttttcatt gtcgctattg atttttactt caatgggctc ttccaacaag 4260
gaagaagctt gctggtagca cttgctaccc tgagttcatc caggcccaac tgtgagcaag 4320
gagcacaagc cacaagtctt ccagaggatg cttgattcca gtggttctgc ttcaaggctt 4380
ccactgcaaa acactaaaga tccaagaagg ccttcatggc cccagcaggc cggatcggta 4440
ctgtatcaag tcatggcagg tacagtagga taagccactc tgtcccttcc tgggcaaaga 4500
agaaacggag gggatggaat tcttccttag acttactttt gtaaaaatgt ccccacggta 4560
cttactcccc actgatggac cagtggtttc cagtcatgag cgttagactg acttgtttgt 4620
cttccattcc attgttttga aactcagtat gctgcccctg tcttgctgtc atgaaatcag 4680
caagagagga tgacacatca aataataact cggattccag cccacattgg attcatcagc 4740
atttggacca atagcccaca gctgagaatg tggaatacct aaggatagca ccgcttttgt 4800
tctcgcaaaa acgtatctcc taatttgagg ctcagatgaa atgcatcagg tcctttgggg 4860
catagatcag aagactacaa aaatgaagct gctctgaaat ctcctttagc catcacccca 4920
accccccaaa attagtttgt gttacttatg gaagatagtt ttctcctttt acttcacttc 4980
aaaagctttt tactcaaaga gtatatgttc cctccaggtc agctgccccc aaaccccctc 5040
cttacgcttt gtcacacaaa aagtgtctct gccttgagtc atctattcaa gcacttacag 5100
ctctggccac aacagggcat tttacaggtg cgaatgacag tagcattatg agtagtgtgg 5160
aattcaggta gtaaatatga aactagggtt tgaaattgat aatgctttca caacatttgc 5220

-continued agatgtttta gaaggaaaaa agttccttcc taaaataatt tctctacaat tggaagattg 5280
gaagattcag ctagttagga gcccaccttt tttcctaatc tgtgtgtgcc ctgtaacctg 5340
actggttaac agcagtcctt tgtaaacagt gttttaaact ctcctagtca atatccaccc 5400
catccaattt atcaaggaag aaatggttca gaaaatattt tcagcctaca gttatgttca 5460
gtcacacaca catacaaaat gttccttttg cttttaaagt aatttttgac tcccagatca 5520
gtcagagccc ctacagcatt gttaagaaag tatttgattt ttgtctcaat gaaaataaaa 5580
ctatattcat ttccactcta aaaaaaaaaa aaaaaa 5616

<210> SEQ ID NO 118
<211> LENGTH: 4816
<212> TYPE: DNA
<213> ORGANISM: Homo sapiens

<400> SEQUENCE: 118
gttcccggat ttttgtgggc gcctgccccg cccctcgtcc ccctgctgtg tccatatatc 60
gaggcgatag ggttaaggga aggcggacgc ctgatgggtt aatgagcaaa ctgaagtgtt 120
ttccatgatc ttttttgagt cgcaattgaa gtaccacctc ccgagggtga ttgcttcccc 180
atgcggggta gaacctttgc tgtcctgttc accactctac ctccagcaca gaatttggct 240
tatgcctact caatgtgaag atgatgagga tgaaaacctt tgtgatgatc cacttccact 300
taatgaatgg tggcaaagca aagctatatt caagaccaca tgcaaagcta ctccctgagc 360
aaagagtcac agataaaacg ggggcaccag tagaatggcc aggacaaacg cagtgcagca 420
cagagactca gaccctggca gccatgcctg cgcaggcagt gatgagagtg acatgtactg 480
ttgtggacat gcacaaaagt gagtgtgcac cggcacagac atgaagctgc ggctccctgc 540
cagtcccgag acccacctgg acatgctccg ccacctctac cagggctgcc aggtggtgca 600
gggaaacctg gaactcacct acctgcccac caatgccagc ctgtccttcc tgcaggatat 660
ccaggaggtg cagggctacg tgctcatcgc tcacaaccaa gtgaggcagg tcccactgca 720
gaggctgcgg attgtgcgag gcacccagct ctttgaggac aactatgccc tggccgtgct 780
agacaatgga gacccgctga acaataccac ccctgtcaca ggggcctccc caggaggcct 840
gcgggagctg cagcttcgaa gcctcacaga gatcttgaaa ggaggggtct tgatccagcg 900
gaacccccag ctctgctacc aggacacgat tttgtggaag gacatcttcc acaagaacaa 960
ccagctggct ctcacactga tagacaccaa ccgctctcgg gcctgccacc cctgttctcc 1020
gatgtgtaag ggctcccgct gctggggaga gagttctgag gattgtcaga gcctgacgcg 1080
cactgtctgt gccggtggct gtgcccgctg caaggggcca ctgcccactg actgctgcca 1140
tgagcagtgt gctgccggct gcacgggccc caagcactct gactgcctgg cctgcctcca 1200
cttcaaccac agtggcatct gtgagctgca ctgcccagcc ctggtcacct acaacacaga 1260
cacgtttgag tccatgccca atcccgaggg ccggtataca ttcggcgcca gctgtgtgac 1320
tgcctgtccc tacaactacc tttctacgga cgtgggatcc tgcaccctcg tctgccccct 1380
gcacaaccaa gaggtgacag cagaggatgg aacacagcgg tgtgagaagt gcagcaagcc 1440
ctgtgcccga gtgtgctatg gtctgggcat ggagcacttg cgagaggtga gggcagttac 1500
cagtgccaat atccaggagt ttgctggctg caagaagatc tttgggagcc tggcatttct 1560
gccggagagc tttgatgggg acccagcctc caacactgcc ccgctccagc cagagcagct 1620
ccaagtgttt gagactctgg aagagatcac aggttaccta tacatctcag catggccgga 1680

-continued

```
cagcctgcct gacctcagcg tcttccagaa cctgcaagta atccggggac gaattctgca   1740
caatggcgcc tactcgctga ccctgcaagg gctgggcatc agctggctgg ggctgcgctc   1800
actgagggaa ctgggcagtg gactggccct catccaccat aacacccacc tctgcttcgt   1860
gcacacggtg ccctgggacc agctctttcg gaacccgcac caagctctgc tccacactgc   1920
caaccggcca gaggacgagt gtgtgggcga gggcctggcc tgccaccagc tgtgcgcccg   1980
agggcactgc tggggtccag ggcccaccca gtgtgtcaac tgcagccagt tccttcgggg   2040
ccaggagtgc gtggaggaat gccgagtact gcaggggctc cccagggagt atgtgaatgc   2100
caggcactgt ttgccgtgcc accctgagtg tcagccccag aatggctcag tgacctgttt   2160
tggaccggag gctgaccagt gtgtggcctg tgcccactat aaggaccctc ccttctgcgt   2220
ggcccgctgc cccagcggtg tgaaacctga cctctcctac atgcccatct ggaagtttcc   2280
agatgaggag ggcgcatgcc agccttgccc catcaactgc acccactcct gtgtggacct   2340
ggatgacaag ggctgccccg ccgagcagag agccagccct ctgacgtcca tcatctctgc   2400
ggtggttggc attctgctgg tcgtggtctt gggggtggtc tttgggatcc tcatcaagcg   2460
acggcagcag aagatccgga agtacacgat gcggagactg ctgcaggaaa cggagctggt   2520
ggagccgctg acacctagcg gagcgatgcc caaccaggcg cagatgcgga tcctgaaaga   2580
gacggagctg aggaaggtga aggtgcttgg atctggcgct tttggcacag tctacaaggg   2640
catctggatc cctgatgggg agaatgtgaa aattccagtg gccatcaaag tgttgaggga   2700
aaacacatcc cccaaagcca acaaagaaat cttagacgaa gcatacgtga tggctggtgt   2760
gggctcccca tatgtctccc gccttctggg catctgcctg acatccacgg tgcagctggt   2820
gacacagctt atgccctatg gctgcctctt agaccatgtc cgggaaaacc gcggacgcct   2880
gggctcccag gacctgctga actggtgtat gcagattgcc aaggggatga gctacctgga   2940
ggatgtgcgg ctcgtacaca gggacttggc cgctcggaac gtgctggtca agagtcccaa   3000
ccatgtcaaa attacagact tcgggctggc tcggctgctg gacattgacg agacagagta   3060
ccatgcagat gggggcaagg tgcccatcaa gtggatggcg ctggagtcca ttctccgccg   3120
gcggttcacc caccagagtg atgtgtggag ttatggtgtg actgtgtggg agctgatgac   3180
ttttggggcc aaaccttacg atgggatccc agcccgggag atccctgacc tgctggaaaa   3240
gggggagcgg ctgccccagc cccccatctg caccattgat gtctacatga tcatggtcaa   3300
atgttggatg attgactctg aatgtcggcc aagattccgg gagttggtgt ctgaattctc   3360
ccgcatggcc agggaccccc agcgctttgt ggtcatccag aatgaggact tgggcccagc   3420
cagtcccttg gacagcacct tctaccgctc actgctggag gacgatgaca tgggggacct   3480
ggtggatgct gaggagtatc tggtacccca gcagggcttc ttctgtccag accctgcccc   3540
gggcgctggg ggcatggtcc accacaggca ccgcagctca tctaccagga gtggcggtgg   3600
ggacctgaca ctagggctgg agccctctga agaggaggcc cccaggtctc cactggcacc   3660
ctccgaaggg gctggctccg atgtatttga tggtgacctg ggaatggggg cagccaaggg   3720
gctgcaaagc ctccccacac atgaccccag ccctctacag cggtacagtg aggaccccac   3780
agtacccctg ccctctgaga ctgatggcta cgttgccccc ctgacctgca gcccccagcc   3840
tgaatatgtg aaccagccag atgttcggcc ccagcccccct tcgccccgag agggccctct   3900
gcctgctgcc cgacctgctg gtgccactct ggaaaggccc aagactctct ccccagggaa   3960
gaatggggtc gtcaaagacg tttttgcctt tgggggtgcc gtggagaacc ccgagtactt   4020
gacaccccag ggaggagctg cccctcagcc ccaccctcct cctgccttca gcccagcctt   4080
```

-continued

```
cgacaacctc tattactggg accaggaccc accagagcgg ggggctccac ccagcacctt   4140

caaagggaca cctacggcag agaacccaga gtacctgggt ctggacgtgc cagtgtgaac   4200

cagaaggcca agtccgcaga agccctgatg tgtcctcagg gagcagggaa ggcctgactt   4260

ctgctggcat caagaggtgg gagggccctc cgaccacttc caggggaacc tgccatgcca   4320

ggaacctgtc ctaaggaacc ttccttcctg cttgagttcc cagatggctg gaaggggtcc   4380

agcctcgttg gaagaggaac agcactgggg agtctttgtg gattctgagg ccctgcccaa   4440

tgagactcta gggtccagtg gatgccacag cccagcttgg ccctttcctt ccagatcctg   4500

ggtactgaaa gccttaggga agctggcctg agaggggaag cggccctaag ggagtgtcta   4560

agaacaaaag cgacccattc agagactgtc cctgaaacct agtactgccc cccatgagga   4620

aggaacagca atggtgtcag tatccaggct ttgtacagag tgcttttctg tttagttttt   4680

actttttttg ttttgttttt ttaaagatga aataaagacc caggggggaga atgggtgttg   4740

tatggggagg caagtgtggg gggtccttct ccacacccac tttgtccatt tgcaaatata   4800

ttttggaaaa cagcta                                                   4816
```

<210> SEQ ID NO 119
<211> LENGTH: 6466
<212> TYPE: DNA
<213> ORGANISM: Homo sapiens

<400> SEQUENCE: 119

```
atggtcataa cagcctcctg tctaccgact cagaacggat tttaccaaaa ctgaaaatgc     60

aggctccatg ctcagaagct ctttaacagg ctcgaaaggt ccatgctcct ttctcctgcc    120

cattctatag cataagaaga cagtctctga gtgataatct tctcttcaag aagaagaaaa    180

ctaggaagga gtaagcacaa agatctcttc acattctccg ggactgcggt accaaatatc    240

agcacagcac ttcttgaaaa aggatgtaga ttttaatctg aactttgaac catcactgag    300

gtggcccgcc ggtttctgag ccttctgccc tgcggggaca cggtctgcac cctgcccgcg    360

gccacggacc atgaccatga ccctccacac caaagcatct gggatggccc tactgcatca    420

gatccaaggg aacgagctgg agcccctgaa ccgtccgcag ctcaagatcc ccctggagcg    480

gcccctgggc gaggtgtacc tggacagcag caagcccgcc gtgtacaact accccgaggg    540

cgccgcctac gagttcaacg ccgcggccgc cgccaacgcg caggtctacg gtcagaccgg    600

cctcccctac ggccccgggt ctgaggctgc ggcgttcggc tccaacggcc tggggggttt    660

ccccccactc aacagcgtgt ctccgagccc gctgatgcta ctgcacccgc cgccgcagct    720

gtcgcctttc ctgcagcccc acggccagca ggtgccctac tacctggaga acgagcccag    780

cggctacacg gtgcgcgagg ccggcccgcc ggcattctac aggccaaatt cagataatcg    840

acgccagggt ggcagagaaa gattggccag taccaatgac aagggaagta tggctatgga    900

atctgccaag gagactcgct actgtgcagt gtgcaatgac tatgcttcag gctaccatta    960

tggagtctgg tcctgtgagg gctgcaaggc cttcttcaag agaagtattc aaggacataa   1020

cgactatatg tgtccagcca ccaaccagtg caccattgat aaaaacagga ggaagagctg   1080

ccaggcctgc cggctccgca aatgctacga agtgggaatg atgaaaggtg ggatacgaaa   1140

agaccgaaga ggagggagaa tgttgaaaca caagcgccag agagatgatg gggagggcag   1200

gggtgaagtg gggtctgctg gagacatgag agctgccaac ctttggccaa gcccgctcat   1260

gatcaaacgc tctaagaaga acagcctggc cttgtccctg acggccgacc agatggtcag   1320
```

-continued

```
tgccttgttg gatgctgagc cccccatact ctattccgag tatgatccta ccagaccctt   1380
cagtgaagct tcgatgatgg gcttactgac caacctggca gacagggagc tggttcacat   1440
gatcaactgg gcgaagaggg tgccaggctt tgtggatttg accctccatg atcaggtcca   1500
ccttctagaa tgtgcctggc tagagatcct gatgattggt ctcgtctggc gctccatgga   1560
gcacccaggg aagctactgt ttgctcctaa cttgctcttg gacaggaacc agggaaaatg   1620
tgtagagggc atggtggaga tcttcgacat gctgctggct acatcatctc ggttccgcat   1680
gatgaatctg cagggagagg agtttgtgtg cctcaaatct attattttgc ttaattctgg   1740
agtgtacaca tttctgtcca gcaccctgaa gtctctggaa gagaaggacc atatccaccg   1800
agtcctggac aagatcacag acactttgat ccacctgatg gccaaggcag gcctgaccct   1860
gcagcagcag caccagcggc tggcccagct cctcctcatc ctctcccaca tcaggcacat   1920
gagtaacaaa ggcatggagc atctgtacag catgaagtgc aagaacgtgg tgcccctcta   1980
tgacctgctg ctggagatgc tggacgccca ccgcctacat gcgcccacta gccgtggagg   2040
ggcatccgtg gaggagacgg accaaagcca cttggccact gcgggctcta cttcatcgca   2100
ttccttgcaa aagtattaca tcacggggga ggcagagggt ttccctgcca cggtctgaga   2160
gctccctggc tcccacacgg ttcagataat ccctgctgca ttttaccctc atcatgcacc   2220
actttagcca aattctgtct cctgcataca ctccggcatg catccaacac caatggcttt   2280
ctagatgagt ggccattcat ttgcttgctc agttcttagt ggcacatctt ctgtcttctg   2340
ttgggaacag ccaaagggat tccaaggcta aatctttgta acagctctct ttcccccttg   2400
ctatgttact aagcgtgagg attcccgtag ctcttcacag ctgaactcag tctatgggtt   2460
ggggctcaga taactctgtg catttaagct acttgtagag acccaggcct ggagagtaga   2520
cattttgcct ctgataagca ctttttaaat ggctctaaga ataagccaca gcaaagaatt   2580
taaagtggct cctttaattg gtgacttgga gaaagctagg tcaagggttt attatagcac   2640
cctcttgtat tcctatggca atgcatcctt ttatgaaagt ggtacacctt aaagctttta   2700
tatgactgta gcagagtatc tggtgattgt caattcattc cccctatagg aatacaaggg   2760
gcacacaggg aaggcagatc ccctagttgg caagactatt ttaacttgat acactgcaga   2820
ttcagatgtg ctgaaagctc tgcctctggc tttccggtca tgggttccag ttaattcatg   2880
cctcccatgg acctatggag agcagcaagt tgatcttagt taagtctccc tatatgaggg   2940
ataagttcct gatttttgtt tttatttttg tgttacaaaa gaaagccctc cctccctgaa   3000
cttgcagtaa ggtcagcttc aggacctgtt ccagtgggca ctgtacttgg atcttcccgg   3060
cgtgtgtgtg ccttacacag gggtgaactg ttcactgtgg tgatgcatga tgagggtaaa   3120
tggtagttga aaggagcagg ggccctggtg ttgcatttag ccctggggca tggagctgaa   3180
cagtacttgt gcaggattgt tgtggctact agagaacaag agggaaagta gggcagaaac   3240
tggatacagt tctgaggcac agccagactt gctcagggtg gccctgccac aggctgcagc   3300
tacctaggaa cattccttgc agaccccgca ttgccctttg gggtgccct gggatccctg   3360
gggtagtcca gctcttcttc atttcccagc gtggccctgg ttggaagaag cagctgtcac   3420
agctgctgta gacagctgtg ttcctacaat tggcccagca ccctggggca cgggagaagg   3480
gtggggaccg ttgctgtcac tactcaggct gactggggcc tggtcagatt acgtatgccc   3540
ttggtggttt agagataatc caaaatcagg gtttggtttg gggaagaaaa tcctccccct   3600
tcctcccccg ccccgttccc taccgcctcc actcctgcca gctcatttcc ttcaatttcc   3660
tttgacctat aggctaaaaa agaaaggctc attccagcca cagggcagcc ttccctgggc   3720
```

ctttgcttct ctagcacaat tatgggttac ttcctttttc ttaacaaaaa agaatgtttg 3780
atttcctctg ggtgacctta ttgtctgtaa ttgaaaccct attgagaggt gatgtctgtg 3840
ttagccaatg acccaggtga gctgctcggg cttctcttgg tatgtcttgt ttggaaaagt 3900
ggatttcatt catttctgat tgtccagtta agtgatcacc aaaggactga gaatctggga 3960
gggcaaaaaa aaaaaaaaag tttttatgtg cacttaaatt tggggacaat tttatgtatc 4020
tgtgttaagg atatgtttaa gaacataatt cttttgttgc tgtttgttta agaagcacct 4080
tagtttgttt aagaagcacc ttatatagta taatatatat ttttttgaaa ttacattgct 4140
tgtttatcag acaattgaat gtagtaattc tgttctggat ttaatttgac tgggttaaca 4200
tgcaaaaacc aaggaaaaat atttagtttt tttttttttt tttgtatact tttcaagcta 4260
ccttgtcatg tatacagtca tttatgccta aagcctggtg attattcatt taaatgaaga 4320
tcacatttca tatcaacttt tgtatccaca gtagacaaaa tagcactaat ccagatgcct 4380
attgttggat actgaatgac agacaatctt atgtagcaaa gattatgcct gaaaaggaaa 4440
attattcagg gcagctaatt ttgcttttac caaaatatca gtagtaatat ttttggacag 4500
tagctaatgg gtcagtgggt tctttttaat gtttatactt agattttctt ttaaaaaaat 4560
taaaataaaa caaaaaaaaa tttctaggac tagacgatgt aataccagct aaagccaaac 4620
aattatacag tggaaggttt tacattattc atccaatgtg tttctattca tgttaagata 4680
ctactacatt tgaagtgggc agagaacatc agatgattga aatgttcgcc caggggtctc 4740
cagcaacttt ggaaatctct ttgtattttt acttgaagtg ccactaatgg acagcagata 4800
ttttctggct gatgttggta ttgggtgtag gaacatgatt taaaaaaaaa ctcttgcctc 4860
tgctttcccc cactctgagg caagttaaaa tgtaaaagat gtgatttatc tggggggctc 4920
aggtatggtg gggaagtgga ttcaggaatc tggggaatgg caaatatatt aagaagagta 4980
ttgaaagtat ttggaggaaa atggttaatt ctgggtgtgc accagggttc agtagagtcc 5040
acttctgccc tggagaccac aaatcaacta gctccattta cagccatttc taaaatggca 5100
gcttcagttc tagagaagaa agaacaacat cagcagtaaa gtccatggaa tagctagtgg 5160
tctgtgtttc ttttcgccat tgcctagctt gccgtaatga ttctataatg ccatcatgca 5220
gcaattatga gaggctaggt catccaaaga gaagacccta tcaatgtagg ttgcaaaatc 5280
taacccctaa ggaagtgcag tctttgattt gatttcccta gtaaccttgc agatatgttt 5340
aaccaagcca tagcccatgc cttttgaggg ctgaacaaat aagggactta ctgataattt 5400
acttttgatc acattaaggt gttctcacct tgaaatctta tacactgaaa tggccattga 5460
tttaggccac tggcttagag tactccttcc cctgcatgac actgattaca aatactttcc 5520
tattcatact ttccaattat gagatggact gtgggtactg ggagtgatca ctaacaccat 5580
agtaatgtct aatattcaca ggcagatctg cttggggaag ctagttatgt gaaaggcaaa 5640
tagagtcata cagtagctca aaaggcaacc ataattctct ttggtgcagg tcttgggagc 5700
gtgatctaga ttacactgca ccattcccaa gttaatcccc tgaaaactta ctctcaactg 5760
gagcaaatga actttggtcc caaatatcca tcttttcagt agcgttaatt atgctctgtt 5820
tccaactgca tttcctttcc aattgaatta aagtgtggcc tcgtttttag tcatttaaaa 5880
ttgttttcta agtaattgct gcctctatta tggcacttca attttgcact gtcttttgag 5940
attcaagaaa aatttctatt cttttttttg catccaattg tgcctgaact tttaaaatat 6000
gtaaatgctg ccatgttcca aacccatcgt cagtgtgtgt gtttagagct gtgcacccta 6060

-continued gaaacaacat attgtcccat gagcaggtgc ctgagacaca gacccctttg cattcacaga 6120
gaggtcattg gttatagaga cttgaattaa taagtgacat tatgccagtt tctgttctct 6180
cacaggtgat aaacaatgct ttttgtgcac tacatactct tcagtgtaga gctcttgttt 6240
tatgggaaaa ggctcaaatg ccaaattgtg tttgatggat taatatgccc ttttgccgat 6300
gcatactatt actgatgtga ctcggttttg tcgcagcttt gctttgttta atgaaacaca 6360
cttgtaaacc tcttttgcac tttgaaaaag aatccagcgg gatgctcgag cacctgtaaa 6420
caattttctc aacctatttg atgttcaaat aaagaattaa actaaa 6466

<210> SEQ ID NO 120
<211> LENGTH: 3478
<212> TYPE: DNA
<213> ORGANISM: Homo sapiens

<400> SEQUENCE: 120
aaattgaaag gtcagccttt cgcgcgctgt gtaggcaagt tacccgtgtt ctgcgttgcc 60
ggccgtgggt gctctggcca cagtgagtta ggggcgtcgg agcgggtttc tccaaccgca 120
atcggctccg ctcaagggga ggaggagagt cccttctcgg aaggcctaag gaaacgtgtc 180
gtctggaatg ggcttggggg ccacgcctgc acatctccgc gagacagagg gataaagtga 240
agatggtgct gttattgtta cctcgagtgc cacatgcgac ctctgagata tgtacacagt 300
cattcttact atcgcactca gccattctta ctacgctaaa gaagaaataa ttattcgagg 360
atatttgcct ggcccagaag aaacttatgt aaatttcatg aactattata tccgttttcc 420
tcggagtgag agaaaactct tttagatat catctgagag aactagtgaa tcccagtcac 480
tgagtggagt tgagagtcta agaacctctg aaatttgaga actgctggac cagagccttt 540
agagctctga taaggtgtca acagggtagt taatttggca ccatggggat acagggattg 600
ctacaattta tcaaagaagc ttcagaaccc atccatgtga ggaagtataa agggcaggta 660
gtagctgtgg atacatattg ctggcttcac aaaggagcta ttgcttgtgc tgaaaaacta 720
gccaaaggtg aacctactga taggtatgta ggattttgta tgaaatttgt aaatatgtta 780
ctatctcatg ggatcaagcc tattctcgta tttgatggat gtactttacc ttctaaaaag 840
gaagtagaga gatctagaag agaaagacga caagccaatc ttcttaaggg aaagcaactt 900
cttcgtgagg ggaaagtctc ggaagctcga gagtgtttca cccggtctat caatatcaca 960
catgccatgg cccacaaagt aattaaagct gcccggtctc agggggtaga ttgcctcgtg 1020
gctccctatg aagctgatgc gcagttggcc tatcttaaca aagcgggaat tgtgcaagcc 1080
ataattacag aggactcgga tctcctagct tttggctgta aaaaggtaat tttaaagatg 1140
gaccagtttg gaaatggact tgaaattgat caagctcggc taggaatgtg cagacagctt 1200
ggggatgtat tcacggaaga gaagtttcgt tacatgtgta ttctttcagg ttgtgactac 1260
ctgtcatcac tgcgtgggat tggattagca aaggcatgca aagtcctaag actagccaat 1320
aatccagata tagtaaaggt tatcaagaaa attggacatt atctcaagat gaatatcacg 1380
gtaccagagg attacatcaa cgggtttatt cgggccaaca ataccttcct ctatcagcta 1440
gtttttgatc ccatcaaaag gaaacttatt cctctgaacg cctatgaaga tgatgttgat 1500
cctgaaacac taagctacgc tgggcaatat gttgatgatt ccatagctct tcaaatagca 1560
cttggaaata aagatataaa tacttttgaa cagatcgatg actacaatcc agacactgct 1620
atgcctgccc attcaagaag tcatagttgg gatgacaaaa catgtcaaaa gtcagctaat 1680
gttagcagca tttggcatag gaattactct cccagaccag agtcgggtac tgtttcagat 1740
gccccacaat tgaaggaaaa tccaagtact gtgggagtgg aacgagtgat tagtactaaa 1800
gggttaaatc tcccaaggaa atcatccatt gtgaaaagac caagaagtgc agagctgtca 1860
gaagatgacc tgttgagtca gtattctctt tcatttacga agaagaccaa gaaaaatagc 1920
tctgaaggca ataaatcatt gagcttttct gaagtgtttg tgcctgacct ggtaaatgga 1980
cctactaaca aaaagagtgt aagcactcca cctaggacga gaaataaatt tgcaacattt 2040
ttacaaagga aaaatgaaga aagtggtgca gttgtggttc cagggaccag aagcaggttt 2100
ttttgcagtt cagattctac tgactgtgta tcaaacaaag tgagcatcca gcctctggat 2160
gaaactgctg tcacagataa agagaacaat ctgcatgaat cagagtatgg agaccaagaa 2220
ggcaagagac tggttgacac agatgtagca cgtaattcaa gtgatgacat tccgaataat 2280
catattccag gtgatcatat tccagacaag gcaacagtgt ttacagatga agagtcctac 2340
tcttttgaga gcagcaaatt tacaaggacc atttcaccac ccactttggg aacactaaga 2400
agttgtttta gttggtctgg aggtcttgga gatttttcaa gaacgccgag cccctctcca 2460
agcacagcat tgcagcagtt ccgaagaaag agcgattccc ccacctcttt gcctgagaat 2520
aatatgtctg atgtgtcgca gttaaagagc gaggagtcca gtgacgatga gtctcatccc 2580
ttacgagaag aggcatgttc ttcacagtcc caggaaagtg gagaattctc actgcagagt 2640
tcaaatgcat caaagctttc tcagtgctct agtaaggact ctgattcaga ggaatctgat 2700
tgcaatatta agttacttga cagtcaaagt gaccagacct ccaagctacg tttatctcat 2760
ttctcaaaaa aagacacacc tctaaggaac aaggttcctg ggctatataa gtccagttct 2820
gcagactctc tttctacaac caagatcaaa cctctaggac ctgccagagc cagtgggctg 2880
agcaagaagc cggcaagcat ccagaagaga aagcatcata atgccgagaa caagccgggg 2940
ttacagatca aactcaatga gctctggaaa aactttggat ttaaaaaaga ttctgaaaag 3000
cttcctcctt gtaagaaacc cctgtcccca gtcagagata acatccaact aactccagaa 3060
gcggaagagg atatatttaa caaacctgaa tgtggccgtg ttcaaagagc aatattccag 3120
taaatgcaga ctgctgcaaa gcttttgcct gcaagagaat ctgatcaatt tgaagtccct 3180
gtttgggaat gaggcactta tcagcatgaa gaatttttc tcattctgtg ccattttaaa 3240
aatagaatac attttgtata ttaactttat aattgggttg tggtttttt gctcagcttt 3300 ttatattttt ataagaagct aaatagaaga ataattgtat ctctgacagg tttttggagg 3360
ttttagtgtt aattgggaaa atcctctgga gtttataaaa gtctactcta aatatttctg 3420
taatgttgtc aagtagaaag atagtaaatg gagaaactac aaaaaaaaaa aaaaaaaa 3478

<210> SEQ ID NO 121
<211> LENGTH: 5192
<212> TYPE: DNA
<213> ORGANISM: Homo sapiens

<400> SEQUENCE: 121
ccatgacctg ccttgagaag gggcagggga agccagatgg actggaagtg gagtggcagt 60
gaccaaggag gaggaggtgt gataggcttc ccacgcaggg tagatccaga gacaccagtg 120
ccacccatag gcccctagga ctgcagtggt cacccgattc ctttgtccca gctgagactc 180
agttctgagt gttctatttt ggggaacaga ggcgtccttg gtagcatttg gaagaggata 240
gccagctggg gtgtgtgtac atcacagcct gacagtaaca gcatccgaac cagaggtgac 300
tggctaaggg cagacccagg gcaacaggtt aaccgttcta gggccgggca cagggaggag 360

-continued

```
aacattccaa cactctgtgt gcccagtgcc gacgcacgtt ctctctttta tcctcaaaac    420
agtcctatga ggatataagc cagagagaga cagagacaag gaattacaag ttggtgagag    480
tcaggatttg aacttggctc tggcagatgg aaaattaggg tctgtattct ttacaaaacc    540
gtgtgtgcct cagatggagt tggtgcataa caagcagagg tatccagggt cgcggtcctg    600
cttgccacgg aaggggccgc cttgtcagtt gtgaccaccc agccctggaa atgtcagtaa    660
tgctgtaagg agtggggatc ggatcagatg ccatccagat gctgaagttt gaccttgtgt    720
catttttcac tttctttttt ggctcttctg caatcaattc atttatttag caaaaaagaa    780
attatgtgtg ccgagagcat gcagaagata tgtctccgtt ctctgcttcc ctccaaaaaa    840
gaatcccaaa actgctttct gtgaacgtgt gccagggtcc cagcaggact cagggagagc    900
aggaagccca gcccagaccc cttgcacaac ctaccgtggg gaggccttag gctctggcta    960
ctacagagct ggttccagtc tgcactgcca cagcctggcc agggacttgg acacatctgc   1020
tggccacttc ctgtctcagt ttccttatct gcaaaataag ggaaaagccc ccacaaaggt   1080
gcacgtgtag caggagctct tttccctccc tattttagga aggcagttgg tgggaagtcc   1140
agcttgggtc cctgagagct gtgagaagga gatgcggctg ctgctggccc tgttgggggt   1200
cctgctgagt gtgcctgggc ctccagtctt gtccctggag gcctctgagg aagtggagct   1260
tggtatggct tctgaggtgg gagagggtgg caggggtggg aagagtgggc accaggaggg   1320
ggctgctggg ctgagcaaag ctggaaagga tccttgccca ggccctgaga aggtggcggc   1380
agggcagggc tcaaccactg agactcagtc agtgcctggc ttccagcaag cattcatcta   1440
tcactgtgtc tgcgagagag gactggcctt gcagggcgca gggccctaag ctgggctgca   1500
gagctggtgg tgagctcctt gcctgggtgt gtgtgcgtgt gtgtgtgtgt tctgtgcact   1560
gggtgtgtga cctaggaggt ccaggcagca tgtgtggtat aagcattatg agggtgatat   1620
gccccggtgc agcatgaccc tgtatgtggc accaacagca tgtgccttgt gtgtgtgtgt   1680
gtccgtatgt gtgtgtgtgt atgcgtgtgt gtgtgtgtgt gtgtgtgtct tggccactgt   1740
catgtgcact aaatgctgtg tgtgtgacat gccccaagag tgtggcattt gccctgggtg   1800
tggcatccgc agcatgtggc tgtgtgggtg tcaaggagtg gtggctcctt cagcatgcgt   1860
tgcgaagtgc ttgtgccctg catgtgcggt gtgttctctg tacacaggag gctgcctcag   1920
atggggctgc ggggtctgct gacctctgcc ctctgcccac agagccctgc ctggctccca   1980
gcctggagca gcaagagcag gagctgacag tagcccttgg gcagcctgtg cggctgtgct   2040
gtgggcgggc tgagcgtggt ggccactggt acaaggaggg cagtcgcctg gcacctgctg   2100
gccgtgtacg gggctggagg ggccgcctag agattgccag cttcctacct gaggatgctg   2160
gccgctacct ctgcctggca cgaggctcca tgatcgtcct gcagaatctc accttgatta   2220
caggtgactc cttgacctcc agcaacgatg atgaggaccc caagtcccat agggacctct   2280
cgaataggca cagttacccc cagcaaggtc agtaggtctc caaggacttg tgtccccgct   2340
gctgctcatc tgatcactga gaagaggagg cctgtgtggg aacacacggt cattctaggg   2400
gccttcccct gccctccagc accctactgg acacaccccc agcgcatgga gaagaaactg   2460
catgcagtac ctgcggggaa caccgtcaag ttccgctgtc cagctgcagg caaccccacg   2520
cccaccatcc gctggcttaa ggatggacag gcctttcatg gggagaaccg cattggaggc   2580
attcggctgc gccatcagca ctggagtctc gtgatggaga gcgtggtgcc ctcggaccgc   2640
ggcacataca cctgcctggt agagaacgct gtgggcagca tccgttataa ctacctgcta   2700
gatgtgctgg agcggtcccc gcaccggccc atcctgcagg ccgggctccc ggccaacacc   2760
```

-continued acagccgtgg tgggcagcga cgtggagctg ctgtgcaagg tgtacagcga tgcccagccc 2820
cacatccagt ggctgaagca catcgtcatc aacggcagca gcttcggagc cgacggtttc 2880
ccctatgtgc aagtcctaaa gactgcagac atcaatagct cagaggtgga ggtcctgtac 2940
ctgcggaacg tgtcagccga ggacgcaggc gagtacacct gcctcgcagg caattccatc 3000
ggcctctcct accagtctgc ctggctcacg gtgctgccag gtgagcacct gaagggccag 3060
gagatgctgc gagatgcccc tctgggccag cagtgggggc tgtggcctgt tgggtggtca 3120
gtctctgttg gcctgtgggg tctggcctgg ggggcagtgt gtggatttgt gggtttgagc 3180
tgtatgacag cccctctgtg cctctccaca cgtggccgtc catgtgaccg tctgctgagg 3240
tgtgggtgcc tgggactggg cataactaca gcttcctccg tgtgtgtccc cacatatgtt 3300
gggagctggg agggactgag ttagggtgca cggggcggcc agtctcacca ctgaccagtt 3360
tgtctgtctg tgtgtgtcca tgtgcgaggg cagaggagga ccccacatgg accgcagcag 3420
cgcccgaggc caggtatacg gacatcatcc tgtacgcgtc gggctccctg gccttggctg 3480
tgctcctgct gctggccagg ctgtatcgag ggcaggcgct ccacggccgg cacccccgcc 3540
cgcccgccac tgtgcagaag ctctcccgct tccctctggc ccgacagttc tccctggagt 3600
caggctcttc cggcaagtca agctcatccc tggtacgagg cgtgcgtctc tcctccagcg 3660
gccccgcctt gctcgccggc ctcgtgagtc tagatctacc tctcgaccca ctatgggagt 3720
tcccccggga caggctggtg cttgggaagc ccctaggcga gggctgcttt ggccaggtag 3780
tacgtgcaga ggcctttggc atggaccctg cccggcctga ccaagccagc actgtggccg 3840
tcaagatgct caaagacaac gcctctgaca aggacctggc cgacctggtc tcggagatgg 3900
aggtgatgaa gctgatcggc cgacacaaga acatcatcaa cctgcttggt gtctgcaccc 3960
aggaagggcc cctgtacgtg atcgtggagt gcgccgccaa gggaaacctg cgggagttcc 4020
tgcgggcccg gcgcccccca ggccccgacc tcagccccga cggtcctcgg agcagtgagg 4080
ggccgctctc cttcccagtc ctggtctcct gcgcctacca ggtggcccga ggcatgcagt 4140
atctggagtc ccggaagtgt atccaccggg acctggctgc ccgcaatgtg ctggtgactg 4200
aggacaatgt gatgaagatt gctgactttg ggctggcccg cggcgtccac cacattgact 4260
actataagaa aaccagcaac ggccgcctgc ctgtgaagtg gatggcgccc gaggccttgt 4320
ttgaccgggt gtacacacac cagagtgacg tgtggtcttt tgggatcctg ctatgggaga 4380
tcttcaccct cgggggctcc ccgtatcctg gcatcccggt ggaggagctg ttctcgctgc 4440
tgcgggaggg acatcggatg gaccgacccc cacactgccc cccagagctg tacgggctga 4500
tgcgtgagtg ctggcacgca gcgccctccc agaggcctac cttcaagcag ctggtggagg 4560
cgctggacaa ggtcctgctg gccgtctctg aggagtacct cgacctccgc ctgaccttcg 4620
gaccctattc cccctctggt ggggacgcca gcagcacctg ctcctccagc gattctgtct 4680
tcagccacga ccccctgcca ttgggatcca gctccttccc cttcgggtct ggggtgcaga 4740
catgagcaag gctcaaggct gtgcaggcac ataggctggt ggccttgggc cttggggctc 4800
agccacagcc tgacacagtg ctcgaccttg atagcatggg gcccctggcc cagagttgct 4860
gtgccgtgtc caagggccgt gcccttgccc ttggagctgc cgtgcctgtg tcctgatggc 4920
ccaaatgtca gggttctgct cggcttcttg gaccttggcg cttagtcccc atcccgggtt 4980
tggctgagcc tggctggaga gctgctatgc taaacctcct gcctcccaat accagcagga 5040
ggttctgggc ctctgaaccc cctttcccca cacctccccc tgctgctgct gccccagcgt 5100

-continued

```
cttgacggga gcattggccc ctgagcccag agaagctgga agcctgccga aaacaggagc   5160

aaatggcgtt ttataaatta ttttttgaa at                                 5192


<210> SEQ ID NO 122
<211> LENGTH: 3124
<212> TYPE: DNA
<213> ORGANISM: Homo sapiens

<400> SEQUENCE: 122

taagatccac atcagctcaa ctgcacttgc ctcgcagagg cagcccgctc acttcccgcg     60

gaggcgctcc ccggcgccgc gctccgcggc agccgcctgc cccggcgct gcccccgccc    120

gccgcgccgc cgccgccgcc gcgcacgccg cgccccgcag ctctgggctt cctcttcgcc    180

cgggtggcgt tgggcccgcg cgggcgctcg ggtgactgca gctgctcagc tcccctcccc    240

cgccccgcgc cgcgcggccg cccgtcgctt cgcacagggc tggatggttg tattgggcag    300

ggtggctcca ggatgttagg aactgtgaag atggaagggc atgaaaccag cgactggaac    360

agctactacg cagacacgca ggaggcctac tcctccgtcc cggtcagcaa catgaactca    420

ggcctgggct ccatgaactc catgaacacc tacatgacca tgaacaccat gactacgagc    480

ggcaacatga ccccggcgtc cttcaacatg tcctatgcca acccgggcct aggggccggc    540

ctgagtcccg gcgcagtagc cggcatgccg gggggctcgg cgggcgccat gaacagcatg    600

actgcggccg gcgtgacggc catgggtacg gcgctgagcc cgagcggcat gggcgccatg    660

ggtgcgcagc aggcggcctc catgaatggc ctgggcccct acgcggccgc catgaacccg    720

tgcatgagcc ccatggcgta cgcgccgtcc aacctgggcc gcagccgcgc gggcggcggc    780

ggcgacgcca agacgttcaa gcgcagctac ccgcacgcca agccgcccta ctcgtacatc    840

tcgctcatca ccatggccat ccagcaggcg cccagcaaga tgctcacgct gagcgagatc    900

taccagtgga tcatggacct cttcccctat taccggcaga accagcagcg ctggcagaac    960

tccatccgcc actcgctgtc cttcaatgac tgcttcgtca aggtggcacg ctccccggac   1020

aagccgggca agggctccta ctggacgctg cacccggact ccggcaacat gttcgagaac   1080

ggctgctact tgcgccgcca gaagcgcttc aagtgcgaga agcagccggg ggccggcggc   1140

gggggcggga gcggaagcgg gggcagcggc gccaagggcg gccctgagag ccgcaaggac   1200

ccctctggcg cctctaaccc cagcgccgac tcgcccctcc atcggggtgt gcacgggaag   1260

accggccagc tagagggcgc gccggccccc gggcccgccg ccagccccca gactctggac   1320

cacagtgggg cgacggcgac agggggcgcc tcggagttga agactccagc ctcctcaact   1380

gcgcccccca taagctccgg gcccggggcg ctggcctctg tgcccgcctc tcacccggca   1440

cacggcttgg caccccacga gtcccagctg cacctgaaag gggacccccca ctactccttc   1500

aaccacccgt tctccatcaa caacctcatg tcctcctcgg agcagcagca taagctggac   1560

ttcaaggcat acgaacaggc actgcaatac tcgccttacg gctctacgtt gcccgccagc   1620

ctgcctctag gcagcgcctc ggtgaccacc aggagcccca tcgagccctc agccctggag   1680

ccggcgtact accaaggtgt gtattccaga cccgtcctaa acacttccta gctcccggga   1740

ctggggggtt tgtctggcat agccatgctg gtagcaagag agaaaaaatc aacagcaaac   1800

aaaaccacac aaaccaaacc gtcaacagca taataaaatc ccaacaacta tttttatttc   1860

atttttcatg cacaaccttt cccccagtgc aaaagactgt tactttatta ttgtattcaa   1920

aattcattgt gtatattact acaaagacaa ccccaaacca attttttttcc tgcgaagttt   1980

aatgatccac aagtgtatat atgaaattct cctccttcct tgcccccctc tctttcttcc   2040
```

ctctttcccc tccagacatt ctagtttgtg gagggttatt taaaaaaaca aaaaaggaag 2100
atggtcaagt ttgtaaaata tttgtttgtg ctttttcccc ctccttacct gaccccctac 2160
gagtttacag gtctgtggca atactcttaa ccataagaat tgaaatggtg aagaaacaag 2220
tatacactag aggctcttaa aagtattgaa agacaatact gctgttatat agcaagacat 2280
aaacagatta taaacatcag agccatttgc ttctcagttt acatttctga tacatgcaga 2340
tagcagatgt ctttaaatga aatacatgta tattgtgtat ggacttaatt atgcacatgc 2400
tcagatgtgt agacatcctc cgtatattta cataacatat agaggtaata gataggtgat 2460
atacatgata cattctcaag agttgcttga ccgaaagtta caaggacccc aacccctttg 2520
tcctctctac ccacagatgg ccctgggaat caattcctca ggaattgccc tcaagaactc 2580
tgcttcttgc tttgcagagt gccatggtca tgtcattctg aggtcacata acacataaaa 2640
ttagtttcta tgagtgtata ccatttaaag aatttttttt tcagtaaaag ggaatattac 2700
aatgttggag gagagataag ttatagggag ctggatttca aaacgtggtc caagattcaa 2760
aaatcctatt gatagtggcc attttaatca ttgccatcgt gtgcttgttt catccagtgt 2820
tatgcacttt ccacagttgg acatggtgtt agtatagcca gacgggtttc attattattt 2880
ctctttgctt tctcaatgtt aatttattgc atggtttatt ctttttcttt acagctgaaa 2940
ttgctttaaa tgatggttaa aattacaaat taaattgtta atttttatca atgtgattgt 3000
aattaaaaat attttgattt aaataacaaa aataatacca gattttaagc cgtggaaaat 3060
gttcttgatc atttgcagtt aaggacttta aataaatcaa atgttaacaa aaaaaaaaaa 3120
aaaa 3124

<210> SEQ ID NO 123
<211> LENGTH: 3452
<212> TYPE: DNA
<213> ORGANISM: Homo sapiens

<400> SEQUENCE: 123
atgcaggcgc gctactccgt gtccagcccc aactccctgg gagtggtgcc ctacctcggc 60
ggcgagcaga gctactaccg cgcggcggcc gcggcggccg ggggcggcta caccgccatg 120
ccggccccca tgagcgtgta ctcgcaccct gcgcacgccg agcagtaccc gggcggcatg 180
gcccgcgcct acgggcccta cacgccgcag ccgcagccca aggacatggt gaagccgccc 240
tatagctaca tcgcgctcat caccatggcc atccagaacg ccccggacaa gaagatcacc 300
ctgaacggca tctaccagtt catcatggac cgcttcccct tctaccggga caacaagcag 360
ggctggcaga acagcatccg ccacaacctc tcgctcaacg agtgcttcgt caaggtgccg 420
cgcgacgaca agaagccggg caagggcagc tactggacgc tggacccgga ctcctacaac 480
atgttcgaga acggcagctt cctgcggcgg cggcggcgct tcaagaagaa ggacgcggtg 540
aaggacaagg aggagaagga caggctgcac ctcaaggagc cgcccccgcc cggccgccag 600
cccccgcccg cgccgccgga gcaggccgac ggcaacgcgc ccggtccgca gccgccgccc 660
gtgcgcatcc aggacatcaa gaccgagaac ggtacgtgcc cctcgccgcc ccagcccctg 720
tccccggccg ccgccctggg cagcggcagc gccgccgcgg tgcccaagat cgagagcccc 780
gacagcagca gcagcagcct gtccagcggg agcagccccc cgggcagcct gccgtcggcg 840
cggccgctca gcctggacgg tgcggattcc gcgccgccgc cgcccgcgcc ctccgccccg 900
ccgccgcacc atagccaggg cttcagcgtg gacaacatca tgacgtcgct gcgggggtcg 960

-continued

```
ccgcagagcg cggccgcgga gctcagctcc ggccttctgg cctcggcggc cgcgtcctcg   1020
cgcgcgggga tcgcaccccc gctggcgctc ggcgcctact cgcccggcca gagctccctc   1080
tacagctccc cctgcagcca gacctccagc gcgggcagct cgggcggcgg cggcggcggc   1140
gcgggggccg cggggggcgc gggcggcgcc gggacctacc actgcaacct gcaagccatg   1200
agcctgtacg cggccggcga gcgcgggggc cacttgcagg gcgcgcccgg gggcgcgggc   1260
ggctcggccg tggacgaccc cctgcccgac tactctctgc ctccggtcac cagcagcagc   1320
tcgtcgtccc tgagtcacgg cggcggcggc ggcggcggcg ggggaggcca ggaggccggc   1380
caccaccctg cggcccacca aggccgcctc acctcgtggt acctgaacca ggcgggcgga   1440
gacctgggcc acttggcgag cgcggcggcg gcggcggcgg ccgcaggcta cccgggccag   1500
cagcagaact tccactcggt gcgggagatg ttcgagtcac agaggatcgg cttgaacaac   1560
tctccagtga acgggaatag tagctgtcaa atggccttcc cttccagcca gtctctgtac   1620
cgcacgtccg gagctttcgt ctacgactgt agcaagtttt gacacaccct caaagccgaa   1680
ctaaatcgaa ccccaaagca ggaaaagcta aaggaaccca tcaaggcaaa atcgaaacta   1740
aaaaaaaaaa atccaattaa aaaaaacccc tgagaatatt caccacacca gcgaacagaa   1800
tatccctcca aaaattcagc tcaccagcac cagcacgaag aaaactctat tttcttaacc   1860
gattaattca gagccacctc cactttgcct tgtctaaata aacaaacccg taaactgttt   1920
tatacagaga cagcaaaatc ttggtttatt aaaggacagt gttactccag ataacacgta   1980
agtttcttct tgcttttcag agacctgctt tcccctcctc ccgtctcccc tctcttgcct   2040
tcttccttgc ctctcacctg taagatatta ttttatccta tgttgaaggg agggggaaag   2100
tccccgttta tgaaagtcgc tttcttttta ttcatggact tgttttaaaa tgtaaattgc   2160
aacatagtaa tttattttta atttgtagtt ggatgtcgtg gaccaaacgc cagaaagtgt   2220
tcccaaaacc tgacgttaaa ttgcctgaaa ctttaaattg tgcttttttt ctcattataa   2280
aaagggaaac tgtattaatc ttattctatc ctcttttctt tctttttgtt gaacatattc   2340
attgtttgtt tattaataaa ttaccattca gtttgaatga gacctatatg tctggatact   2400
ttaatagagc tttaattatt acgaaaaaag atttcagaga taaaacacta gaagttacct   2460
attctccacc taaatctctg aaaaatggag aaaccctctg actagtccat gtcaaatttt   2520
actaaaagtc tttttgttta gatttatttt cctgcagcat cttctgcaaa atgtactata   2580
tagtcagctt gctttgaggc tagtaaaaag atatttttct aaacagattg gagttggcat   2640
ataaacaaat acgttttctc actaatgaca gtccatgatt cggaaatttt aagcccatga   2700
atcagccgcg gtcttaccac ggtgatgcct gtgtgccgag agatgggact gtgcggccag   2760
atatgcacag ataaatattt ggcttgtgta ttccatataa aattgcagtg catattatac   2820
atccctgtga gccagatgct gaatagatat tttcctatta tttcagtcct ttataaaagg   2880
aaaaataaac cagtttttaa atgtatgtat ataattctcc cccatttaca atccttcatg   2940
tattacatag aaggattgct tttttaaaaa tatactgcgg gttggaaagg gatatttaat   3000
ctttgagaaa ctattttaga aaatatgttt gtagaacaat tatttttgaa aaagatttaa   3060
agcaataaca agaaggaagg cgagaggagc agaacatttt ggtctagggt ggtttctttt   3120
taaaccattt tttcttgtta atttacagtt aaacctaggg gacaatccgg attggccctc   3180
ccccttttgt aaataaccca ggaaatgtaa taaattcatt atcttagggt gatctgccct   3240
gccaatcaga ctttggggag atggcgattt gattacagac gttcgggggg gtgggggggct   3300
tgcagtttgt tttggagata atacagtttc ctgctatctg ccgctcctat ctagaggcaa   3360
```

cacttaagca gtaattgctg ttgcttgttg tcaaaatttg atcattgtta aaggattgct 3420
gcaaataaat acactttaat ttcagtcaaa aa 3452

<210> SEQ ID NO 124
<211> LENGTH: 1749
<212> TYPE: DNA
<213> ORGANISM: Homo sapiens

<400> SEQUENCE: 124
gtggcctcga ggtggtggca gggccgcccc ctgcagtccg gagacgaacg cacggaccgg 60
gcctccggag gcaggttcgg ctggaaggaa ccgctctcgc ttcgtcctac acttgcgcaa 120
atgtctccga gcttactcac atagcatatt ggtatatcaa aatgaaatgc aaggaaccaa 180
aaataacata attgaaggca gtaaaagtga aattaaatag gaagatcatc agtcaaggaa 240
gacccactgg agaggacaga aaatgaagca gtgttttatc atgtgtattt cagcaggtct 300
tcttgaaatt taactaaaaa tatgactgct ctctcttcag agaactgctc ttttcagtac 360
cagttacgtc aaacaaacca gcccctagac gttaactatc tgctattctt gatcatactt 420
gggaaaatat tattaaatat ccttacacta ggaatgagaa gaaaaaacac ctgtcaaaat 480
tttatggaat atttttgcat ttcactagca ttcgttgatc ttttactttt ggtaaacatt 540
tccattatat tgtatttcag ggattttgta cttttaagca ttaggttcac taaataccac 600
atctgcctat ttactcaaat tatttccttt acttatggct tttgcatta tccagttttc 660 ctgacagctt gtatagatta ttgcctgaat ttctctaaaa caaccaagct ttcatttaag 720
tgtcaaaaat tattttattt ctttacagta attttaattt ggatttcagt ccttgcttat 780
gttttgggag acccagccat ctaccaaagc ctgaaggcac agaatgctta ttctcgtcac 840
tgtcctttct atgtcagcat tcagagttac tggctgtcat tttcatggt gatgatttta 900 tttgtagctt tcataacctg ttgggaagaa gttactactt tggtacaggc tatcaggata 960
acttcctata tgaatgaaac tatcttatat tttcctttt catcccactc cagttatact 1020
gtgagatcta aaaaaatatt cttatccaag ctcattgtct gttttctcag tacctggtta 1080
ccatttgtac tacttcaggt aatcattgtt ttacttaaag ttcagattcc agcatatatt 1140
gagatgaata ttccctggtt atactttgtc aatagttttc tcattgctac agtgtattgg 1200
tttaattgtc acaagcttaa tttaaaagac attggattac ctttggatcc atttgtcaac 1260
tggaagtgct gcttcattcc acttacaatt cctaatcttg agcaaattga aaagcctata 1320
tcaataatga tttgttaata ttattaatta aaagttacag ctgtcataag atcataattt 1380
tatgaacaga aagaactcag gacatattaa aaaataaact gaactaaaac aacttttgcc 1440
ccctgactga tagcatttca gaatgtgtct tttgaagggc tataccagtt attaaatagt 1500
gttttatttt aaaaacaaaa taattccaag aagtttttat agttattcag ggacactata 1560
ttacaaatat tactttgtta ttaacacaaa aagtgataag agttaacatt tggctatact 1620
gatgtttgtg ttactcaaaa aaactactgg atgcaaactg ttatgtaaat ctgagatttc 1680
actgacaact ttaagatatc aacctaaaca tttttattaa atgttcaaat gtaagcaaga 1740
aaaaaaaaa 1749

<210> SEQ ID NO 125
<211> LENGTH: 2285
<212> TYPE: DNA
<213> ORGANISM: Homo sapiens -continued

<400> SEQUENCE: 125

```
acccgccccc atctgcccaa gataatttta gtttccttgg gcctggaatc tggacacaca     60
gggctccccc ccgcctctga cttctctgtc cgaagtcggg acaccctcct accacctgta    120
gagaagcggg agtggatctg aaataaaatc caggaatctg ggggttccta gacggagcca    180
gacttcggaa cgggtgtcct gctactcctg ctggggctcc tccaggacaa gggcacacaa    240
ctggttccgt taagcccctc tctcgctcag acgccatgga gctggatctg tctccacctc    300
atcttagcag ctctccggaa gacctttgcc cagcccctgg gacccctcct gggactcccc    360
ggcccccctga taccccctctg cctgaggagg taaagaggtc ccagcctctc ctcatcccaa    420
ccaccggcag gaaacttcga gaggaggaga ggcgtgccac ctccctcccc tctatcccca    480
acccccttccc tgagctctgc agtcctccct cacagagccc aattctcggg ggcccctcca    540
gtgcaagggg gctgctcccc cgcgatgcca gccgccccca tgtagtaaag gtgtacagtg    600
aggatggggc ctgcaggtct gtggaggtgg cagcaggtgc cacagctcgc cacgtgtgtg    660
aaatgctggt gcagcgagct cacgccttga gcgacgagac ctgggggctg gtggagtgcc    720
acccccacct agcactggag cggggtttgg aggaccacga gtccgtggtg gaagtgcagg    780
ctgcctggcc cgtgggcgga gatagccgct tcgtcttccg gaaaaacttc gccaagtacg    840
aactgttcaa gagctcccca cactccctgt tcccagaaaa aatggtctcc agctgtctcg    900
atgcacacac tggtatatcc catgaagacc tcatccagaa cttcctgaat gctggcagct    960
ttcctgagat ccagggcttt ctgcagctgc ggggttcagg acggaagctt tggaaacgct   1020
ttttctgctt cttgcgccga tctggcctct attactccac caagggcacc tctaaggatc   1080
cgaggcacct gcagtacgtg gcagatgtga acgagtccaa cgtgtacgtg gtgacgcagg   1140
gccgcaagct ctacgggatg cccactgact tcggtttctg tgtcaagccc aacaagcttc   1200
gaaatggcca caaggggctt cggatcttct gcagtgaaga tgagcagagc cgcacctgct   1260
ggctggctgc cttccgcctc ttcaagtacg gggtgcagct gtacaagaat taccagcagg   1320
cacagtctcg ccatctgcat ccatcttgtt tgggctcccc acccttgaga agtgcctcag   1380
ataataccct ggtggccatg gacttctctg gccatgctgg gcgtgtcatt gagaaccccc   1440
gggaggctct gagtgtggcc ctggaggagg cccaggcctg gaggaagaag acaaaccacc   1500
gcctcagcct gcccatgcca gcctccggca cgagcctcag tgcagccatc caccgcaccc   1560
aactctggtt ccacgggcgc atttcccgtg aggagagcca gcggcttatt ggacagcagg   1620
gcttggtaga cggcctgttc ctggtccggg agagtcagcg gaacccccag ggctttgtcc   1680
tctctttgtg ccacctgcag aaagtgaagc attatctcat cctgccgagc gaggaggagg   1740
gccgcctgta cttcagcatg gatgatggcc agacccgctt cactgacctg ctgcagctcg   1800
tggagttcca ccagctgaac cgcggcatcc tgccgtgctt gctgcgccat tgctgcacgc   1860
gggtggccct ctgaccaggc cgtggactgg ctcatgcctc agcccgcctt caggctgccc   1920
gccgccccctc cacccatcca gtggactctg gggcgcggcc acaggggacg ggatgaggag   1980
cgggagggtt ccgccactcc agttttctcc tctgcttctt tgcctccctc agatagaaaa   2040
cagcccccac tccagtccac tcctgacccc tctcctcaag ggaaggcctt gggtggcccc   2100
ctctccttct cctagctctg gaggtgctgc tctagggcag ggaattatgg gagaagtggg   2160
ggcagcccag gcggtttcac gccccacact ttgtacagac cgagaggcca gttgatctgc   2220
tctgttttat actagtgaca ataaagatta ttttttgata caaaaaaaaa aaaaaaaaaa   2280
aaaaa                                                                2285
```

<210> SEQ ID NO 126
<211> LENGTH: 935
<212> TYPE: DNA
<213> ORGANISM: Homo sapiens

<400> SEQUENCE: 126
agtcagaggt cgcgcaggcg ctggtacccc gttggtccgc gcgttgctgc gttgtgaggg 60
gtgtcagctc agtgcatccc aggcagctct tagtgtggag cagtgaactg tgtgtggttc 120
cttctacttg gggatcatgc agagagcttc acgtctgaag agagagctgc acatgttagc 180
cacagagcca cccccaggca tcacatgttg gcaagataaa gaccaaatgg atgacctgcg 240
agctcaaata ttaggtggag ccaacacacc ttatgagaaa ggtgttttta agctagaagt 300
tatcattcct gagaggtacc catttgaacc tcctcagatc cgatttctca ctccaattta 360
tcatccaaac attgattctg ctggaaggat ttgtctggat gttctcaaat tgccaccaaa 420
aggtgcttgg agaccatccc tcaacatcgc aactgtgttg acctctattc agctgctcat 480
gtcagaaccc aaccctgatg acccgctcat ggctgacata tcctcagaat ttaaatataa 540
taagccagcc ttcctcaaga atgccagaca gtggacagag aagcatgcaa gacagaaaca 600
aaaggctgat gaggaagaga tgcttgataa tctaccagag gctggtgact ccagagtaca 660
caactcaaca cagaaaagga aggccagtca gctagtaggc atagaaaaga aatttcatcc 720
tgatgtttag gggacttgtc ctggttcatc ttagttaatg tgttctttgc caaggtgatc 780
taagttgcct accttgaatt ttttttaaa tatatttgat gacataattt ttgtgtagtt 840
tatttatctt gtacatatgt attttgaaat cttttaaacc tgaaaaataa atagtcattt 900
aatgttgaaa aaaaaaaaaa aaaaaaaaaa aaaaa 935

<210> SEQ ID NO 127
<211> LENGTH: 2896
<212> TYPE: DNA
<213> ORGANISM: Homo sapiens

<400> SEQUENCE: 127
acgcttgcgc gcgggattta aactgcggcg gtttacgcgg cgttaagact tcgtagggtt 60
agcgaaattg aggtttcttg gtattgcgcg tttctcttcc ttgctgactc tccgaatggc 120
catggactcg tcgcttcagg cccgcctgtt tcccggtctc gctatcaaga tccaacgcag 180
taatggttta attcacagtg ccaatgtaag gactgtgaac ttggagaaat cctgtgtttc 240
agtggaatgg gcagaaggag gtgccacaaa gggcaaagag attgattttg atgatgtggc 300
tgcaataaac ccagaactct tacagcttct tcccttacat ccgaaggaca atctgccctt 360
gcaggaaaat gtaacaatcc agaaacaaaa acggagatcc gtcaactcca aaattcctgc 420
tccaaaagaa agtcttcgaa gccgctccac tcgcatgtcc actgtctcag agcttcgcat 480
cacggctcag gagaatgaca tggaggtgga gctgcctgca gctgcaaact cccgcaagca 540
gttttcagtt cctcctgccc ccactaggcc ttcctgccct gcagtggctg aaataccatt 600
gaggatggtc agcgaggaga tggaagagca agtccattcc atccgaggca gctcttctgc 660
aaaccctgtg aactcagttc ggaggaaatc atgtcttgtg aaggaagtgg aaaaaatgaa 720
gaacaagcga gaagagaaga aggcccagaa ctctgaaatg agaatgaaga gagctcagga 780
gtatgacagt agttttccaa actgggaatt tgcccgaatg attaaagaat ttcgggctac 840
tttggaatgt catccactta ctatgactga tcctatcgaa gagcacagaa tatgtgtctg 900

-continued

```
tgttaggaaa cgcccactga ataagcaaga attggccaag aaagaaattg atgtgatttc    960

cattcctagc aagtgtctcc tcttggtaca tgaacccaag ttgaaagtgg acttaacaaa   1020

gtatctggag aaccaagcat tctgctttga ctttgcattt gatgaaacag cttcgaatga   1080

agttgtctac aggttcacag caaggccact ggtacagaca atctttgaag gtggaaaagc   1140

aacttgtttt gcatatggcc agacaggaag tggcaagaca catactatgg gcggagacct   1200

ctctgggaaa gcccagaatg catccaaagg gatctatgcc atggcctccc gggacgtctt   1260

cctcctgaag aatcaaccct gctaccggaa gttgggcctg gaagtctatg tgacattctt   1320

cgagatctac aatgggaagc tgtttgacct gctcaacaag aaggccaagc tgcgcgtgct   1380

ggaggacggc aagcaacagg tgcaagtggt ggggctgcag gagcatctgg ttaactctgc   1440

tgatgatgtc atcaagatga tcgacatggg cagcgcctgc agaacctctg ggcagacatt   1500

tgccaactcc aattcctccc gctcccacgc gtgcttccaa attattcttc gagctaaagg   1560

gagaatgcat ggcaagttct ctttggtaga tctggcaggg aatgagcgag gcgcggacac   1620

ttccagtgct gaccggcaga cccgcatgga gggcgcagaa atcaacaaga gtctcttagc   1680

cctgaaggag tgcatcaggg ccctgggaca gaacaaggct cacaccccgt tccgtgagag   1740

caagctgaca caggtgctga gggactcctt cattggggag aactctagga cttgcatgat   1800

tgccacgatc tcaccaggca taagctcctg tgaatatact ttaaacaccc tgagatatgc   1860

agacagggtc aaggagctga gcccccacag tgggcccagt ggagagcagt tgattcaaat   1920

ggaaacagaa gagatggaag cctgctctaa cggggcgctg attccaggca atttatccaa   1980

ggaagaggag gaactgtctt cccagatgtc cagctttaac gaagccatga ctcagatcag   2040

ggagctggag gagaaggcta tggaagagct caaggagatc atacagcaag gaccagactg   2100

gcttgagctc tctgagatga ccgagcagcc agactatgac ctggagacct ttgtgaacaa   2160

agcggaatct gctctggccc agcaagccaa gcatttctca gccctgcgag atgtcatcaa   2220

ggccttgcgc ctggccatgc agctggaaga gcaggctagc agacaaataa gcagcaagaa   2280

acggccccag tgacgactgc aaataaaaat ctgtttggtt tgacacccag cctcttccct   2340

ggccctcccc agagaacttt gggtacctgg tgggtctagg cagggtctga gctgggacag   2400

gttctggtaa atgccaagta tgggggcatc tgggcccagg gcagctgggg agggggtcag   2460

agtgacatgg gacactcctt ttctgttcct cagttgtcgc cctcacgaga ggaaggagct   2520

cttagttacc cttttgtgtt gcccttcttt ccatcaaggg gaatgttctc agcatagagc   2580

tttctccgca gcatcctgcc tgcgtggact ggctgctaat ggagagctcc ctggggttgt   2640

cctggctctg gggagagaga cggagccttt agtacagcta tctgctggct ctaaaccttc   2700

tacgcctttg ggccgagcac tgaatgtctt gtactttaaa aaaatgtttc tgagacctct   2760

ttctacttta ctgtctccct agagatccta gaggatccct actgttttct gttttatgtg   2820

tttatacatt gtatgtaaca ataaagagaa aaaataaatc agctgtttaa gtgtgtggaa   2880

aaaaaaaaaa aaaaaa                                                   2896
```

<210> SEQ ID NO 128
<211> LENGTH: 2209
<212> TYPE: DNA
<213> ORGANISM: Homo sapiens

<400> SEQUENCE: 128

```
actgcgcgcg tcgtgcgtaa tgacgtcagc gccggcggag aatttcaaat tcgaacggct     60

ttggcgggcc gaggaaggac ctggtgtttt gatgaccgct gtcctgtcta gcagatactt    120
```

-continued

```
gcacggttta cagaaattcg gtccctgggt cgtgtcagga aactggaaaa aaggtcataa     180
gcatgaagcg cagttcagtt tccagcggtg gtgctggccg cctctccatg caggagttaa     240
gatcccagga tgtaaataaa caaggcctct ataccccctca aaccaaagag aaaccaacct     300
ttggaaagtt gagtataaac aaaccgacat ctgaaagaaa agtctcgcta tttggcaaaa     360
gaactagtgg acatggatcc cggaatagtc aacttggtat attttccagt tctgagaaaa     420
tcaaggaccc gagaccactt aatgacaaag cattcattca gcagtgtatt cgacaactct     480
gtgagtttct tacagaaaat ggttatgcac ataatgtgtc catgaaatct ctacaagctc     540
cctctgttaa agacttcctg aagatcttca catttcttta tggcttcctg tgcccctcat     600
acgaacttcc tgacacaaag tttgaagaag aggttccaag aatctttaaa gaccttgggt     660
atccttttgc actatccaaa agctccatgt acacagtggg ggctcctcat acatggcctc     720
acattgtggc agccttagtt tggctaatag actgcatcaa gatacatact gccatgaaag     780
aaagctcacc tttatttgat gatgggcagc cttggggaga agaaactgaa gatggaatta     840
tgcataataa gttgttttttg gactacacca taaaatgcta tgagagtttt atgagtggtg     900
ccgacagctt tgatgagatg aatgcagagc tgcagtcaaa actgaaggat ttatttaatg     960
tggatgcttt taagctggaa tcattagaag caaaaaacag agcattgaat gaacagattg    1020
caagattgga acaagaaaga gaaaaagaac cgaatcgtct agagtcgttg agaaaactga    1080
aggcttcctt acaaggagat gttcaaaagt atcaggcata catgagcaat ttggagtctc    1140
attcagccat tcttgaccag aaattaaatg gtctcaatga ggaaattgct agagtagaac    1200
tagaatgtga aacaataaaa caggagaaca ctcgactaca gaatatcatt gacaaccaga    1260
agtactcagt tgcagacatt gagcgaataa atcatgaaag aaatgaattg cagcagacta    1320
ttaataaatt aaccaaggac ctggaagctg aacaacagaa gttgtggaat gaggagttaa    1380
aatatgccag aggcaaagaa gcgattgaaa cacaattagc agagtatcac aaattggcta    1440
gaaaattaaa acttattcct aaaggtgctg agaattccaa aggttatgac tttgaaatta    1500
agtttaatcc cgaggctggt gccaactgcc ttgtcaaata cagggctcaa gtttatgtac    1560
ctcttaagga actcctgaat gaaactgaag aagaaattaa taaagcccta aataaaaaaa    1620
tgggtttgga ggatacttta gaacaattga atgcaatgat aacagaaagc aagagaagtg    1680
tgagaactct gaaagaagaa gttcaaaagc tggatgatct ttaccaacaa aaaattaagg    1740
aagcagagga agaggatgaa aaatgtgcca gtgagcttga gtccttggag aaacacaagc    1800
acctgctaga aagtactgtt aaccaggggc tcagtgaagc tatgaatgaa ttagatgctg    1860
ttcagcggga ataccaacta gttgtgcaaa ccacgactga agaaagacga aaagtgggaa    1920
ataacttgca acgtctgtta gagatggttg ctacacatgt tgggtctgta gagaaacatc    1980
ttgaggagca gattgctaaa gttgatagag aatatgaaga atgcatgtca gaagatctct    2040
cggaaaatat taaagagatt agagataagt atgagaagaa agctactcta attaagtctt    2100
ctgaagaatg aagataaaat gttgatcatg tatatatatc catagtgaat aaaattgtct    2160
cagtaaagtg taaaaaaaaa aaaaaaaaaa aaaaaaaaaa aaaaaaaaa               2209
```

<210> SEQ ID NO 129
<211> LENGTH: 1740
<212> TYPE: DNA
<213> ORGANISM: Homo sapiens

<400> SEQUENCE: 129

-continued

```
ctccctcctc tgcaccatga ctacctgcag ccgccagttc acctcctcca gctccatgaa     60

gggctcctgc ggcatcgggg gcggcatcgg gggcggctcc agccgcatct cctccgtcct    120

ggccggaggg tcctgccgcg cccccagcac ctacgggggc ggcctgtctg tctcatcctc    180

ccgcttctcc tctgggggag cctatgggtt ggggggcggc tatggcggtg gcttcagcag    240

cagcagcagc agctttggta gtggctttgg gggaggatat ggtggtggcc ttggtgctgg    300

cttgggtggt ggctttggtg gtggctttgc tggtggtgat gggcttctgg tgggcagtga    360

gaaggtgacc atgcagaacc tcaacgaccg cctggcctcc tacctggaca aggtgcgtgc    420

tctggaggag gccaacgccg acctggaagt gaagatccgt gactggtacc agaggcagcg    480

gcctgctgag atcaaagact acagtcccta cttcaagacc attgaggacc tgaggaacaa    540

gattctcaca gccacagtgg acaatgccaa tgtccttctg cagattgaca atgcccgtct    600

ggccgcggat gacttccgca ccaagtatga gacagagttg aacctgcgca tgagtgtgga    660

agccgacatc aatggcctgc gcagggtgct ggacgaactg accctggcca gagctgacct    720

ggagatgcag attgagagcc tgaaggagga gctggcctac ctgaagaaga accacgagga    780

ggagatgaat gccctgagag gccaggtggg tggagatgtc aatgtggaga tggacgctgc    840

acctggcgtg gacctgagcc gcattctgaa cgagatgcgt gaccagtatg agaagatggc    900

agagaagaac cgcaaggatg ccgaggaatg gttcttcacc aagacagagg agctgaaccg    960

cgaggtggcc accaacagcg agctggtgca gagcggcaag agcgagatct cggagctccg   1020

gcgcaccatg cagaacctgg agattgagct gcagtcccag ctcagcatga aagcatccct   1080

ggagaacagc ctggaggaga ccaaaggtcg ctactgcatg cagctggccc agatccagga   1140

gatgattggc agcgtggagg agcagctggc ccagctccgc tgcgagatgg agcagcagaa   1200

ccaggagtac aagatcctgc tggacgtgaa gacgcggctg gagcaggaga tcgccaccta   1260

ccgccgcctg ctggagggcg aggacgccca cctctcctcc tcccagttct cctctggatc   1320

gcagtcatcc agagatgtga cctcctccag ccgccaaatc cgcaccaagg tcatggatgt   1380

gcacgatggc aaggtggtgt ccacccacga gcaggtcctt cgcaccaaga actgaggctg   1440

cccagccccg ctcaggccta ggaggccccc cgtgtggaca cagatcccac tggaagatcc   1500

cctctcctgc ccaagcactt cacagctgga ccctgcttca ccctcacccc ctcctggcaa   1560

tcaatacagc ttcattatct gagttgcata aaaaaaaaaa aaaaaaaaaa aaaaaaaaaa   1620

aaaaaaaaaa aaaaaaaaaa aaaaaaaaaa aaaaaaaaaa aaaaaaaaaa aaaaaaaaaa   1680

aaaaaaaaaa aaaaaaaaaa aaaaaaaaaa aaaaaaaaaa aaaaaaaaaa aaaaaaaaaa   1740
```

<210> SEQ ID NO 130
<211> LENGTH: 2895
<212> TYPE: DNA
<213> ORGANISM: Homo sapiens

<400> SEQUENCE: 130

```
ctcttttgca ggggccgttc ctcggggcat gacgctggct cctgcacaga tcctgctcct     60

ctgtggcctt cctgggctgc cctcccctcc tccgggactg ctctggactg acactgctca    120

ggttcggatt ccctcaaaga ctttgggaga caagacttgg tccccctttt acaaacaagg    180

gaacggaggc tctagaactg acttcctgaa aggcttggat ccaaagctcc ctcagttcag    240

cggccacgtc tatttccctc agacacaggg atccttgaac ctgtgggctg tatctccccg    300

cggacttgga agaatcccaa gagagtgggg ctcccacagg ctggagtgca atggtgtgat    360

ctcggctcac tgcaacctcc acctcccagg ttcaagctat tctcctgcct cagcctcctg    420
```

-continued

```
agtagctggg attacagatc ctggtggctg tggtcggtaa ttccagcttc gtgctggcta    480
caggtggatg atgcccacct ggctgccgat gacctctgca ccaagtgagg ctgggtctct    540
ggagctgccc caggggctgg acaagctgac cctggccggg gccaacctgg agatgcagat    600
tgagaacctc aaggaggacc tggtctacct gaagaagaac cacaagcagg aaatgaacgt    660
cctttgaggt caggtggatg aggatgtcag tgtgaagatg gacactgtgc ctggagtgaa    720
cctgagctgc atcctgaatg agatgcgtga ccaggacaag acattggtgg agaagagctg    780
caaggatgcc gagggctggt tcttcagcat ggtgggtggc cgtgcgtaag caggtgtgta    840
cacgtgtggg cacatgtgct gcatgctggt gcagctggag cactggcaga tccacaggct    900
gtcccagttg gaaggacttt tggaaaccag ttggaccagc ccctcatgtt ttagatgtaa    960
aacgtgaggc tcagagagga ctcaagctca cacagccctt cactgtggcc tgcaaaatag   1020
atccaggtct ctacaagtct ggtcttgggt ttccaccaca gctgtttaca ggatgtgcgt   1080
atttgaatac atatgtatac ccttggcaag cacaggctga gtatctccgg tatcctaggg   1140
acagcaacag gcgcaaaaga ataacaccca gtgcctgtct ttgaggtgct gcagttcagt   1200
aggaaaaaga aatgcaaatg accgcagagc aggctgaatt cctccaagtt ccaatgtggg   1260
tgcagaggct ctctgtgtgc agaaagaggg gctgaactgc gaggtggcca ccaacacaga   1320
ggccctgcag agtggctgga tagagatatg gagctctacg tctctgtgca gaacctgagc   1380
cgtcccagct cagcaagaaa gcatcgctgg agggcagcct ggtggagatg gaggtgtgtt   1440
acaggaccct gccggcccag ctgcaggggc ttaacagaag catggagcag cagctgtgcg   1500
agctctgctg cgacacggag caccaggacc acaagcacag gtccttctgg acgtgaagac   1560
gtggctggag caggagatcg ccacctaccg ccgcttgctg gaggttgagg acgcccagag   1620
gtgatactga cgatgcaggc tggagtctgg ctgaggagcc ttgaatgcca agttaaagcg   1680
tctggactag atcacgtagg caatggggag ccatggaggg atttggagca ggagagtgaa   1740
atgaacatca agagatttta gaacattcac tctggctgca gagggagaaa tggatcagag   1800
gggtcagggc ggggccagag agatgtgtca gggggctgga gcagggagtc tggccagaga   1860
agtcccgtgc ggtggtgggt agtggggcag gggaaggaag gtggtgcacg cagaagagag   1920
gttatagctc aaaacagcgg gactggatgc ctggatctcg gggtaagcat ggctcacagt   1980
caggactcag taagtgtcgg gagaacacat gaaggagcag gcattgatgg ccctgggttt   2040
ctggttctga tgactgtgtg agtggtgaag agcaaggtgg gtggtggttg ggtttgcagt   2100
tgggaagggt gatcaggcct tcagctgaga gtgtcccgga gtctccatgc ttagtcacac   2160
gttgcagctt tttgctcccc ggaaatggtg aagtccatct atagtctaac aacagtctct   2220
cctgctttaa ttgggtctat ttgttgggcc ctctgggtta tggaaaaacc acttgctcag   2280
cttctccttg taaattcctg gtgagtagcc acagagtgcc gccagaccta ctgctgtgct   2340
gtttcttttt cttcttcctg ctgtgctgaa cccctgccct ttcattcttg ggcctgcgct   2400
aatttctgtg cattcccaac tgtgattttt caccaattta ggggaacctc ctctgccagg   2460
gcctacttct ccccagcagt gcttgcaggt gcctgggctg gctggcatcc ctgggctgat   2520
gggtgcttct ctccctgcag gctggccact cagtactcct tgtccctggc ctcgcagccc   2580
acccgggaag ccacagtgac cagccaccag gtgtgccatc gtggaggaag tccaggttgg   2640
agaggtggtc ttcttctgtg agcaggtcca cttctccacc cactgagacc cctttctgtc   2700
tgcgacagcc ccacctcgag ggccacggca cagccatcag ctccagctcc cagcatgcta   2760
```

-continued

```
ctgccacgcc ccgagtgtcc gtctgggccc cggtgcatgg cctgttgtct ttctgtatct   2820

actttctgca gcccctcact gaggaggcct cctgggtttg tccagtgcct actattaaag   2880

ctttgctcca agttc                                                    2895


<210> SEQ ID NO 131
<211> LENGTH: 2529
<212> TYPE: DNA
<213> ORGANISM: Homo sapiens

<400> SEQUENCE: 131

gcatcctttt tgggctgctc acagccccca gcctctatgg tgaagacata cttgctagca     60

gcgtcaccaa cttgctgcca agagatcagt gctgcaaggc aaggttattt ctaactgagc    120

agagcctgcc aggaagaaag cgtttgcacc ccacaccact gtgcaggtgt gaccggtgag    180

ctcacagctg ccccccaggc atgcccagcc cacttaatca ttcacagctc gacagctctc    240

tcgcccagcc cagttctgga agggataaaa agggggcatc accgttcctg ggtaacagag    300

ccaccttctg cgtcctgctg agctctgttc tctccagcac ctcccaaccc actagtgcct    360

ggttctcttg ctccaccagg aacaagccac catgtctcgc cagtcaagtg tgtccttccg    420

gagcgggggc agtcgtagct tcagcaccgc ctctgccatc accccgtctg tctcccgcac    480

cagcttcacc tccgtgtccc ggtccggggg tggcggtggt ggtggcttcg gcagggtcag    540

ccttgcgggt gcttgtggag tgggtggcta tggcagccgg agcctctaca acctgggggg    600

ctccaagagg atatccatca gcactagagg aggcagcttc aggaaccggt ttggtgctgg    660

tgctggaggc ggctatggct ttggaggtgg tgccggtagt ggatttggtt tcggcggtgg    720

agctggtggt ggctttgggc tcggtggcgg agctggcttt ggaggtggct tcggtggccc    780

tggctttcct gtctgccctc ctggaggtat ccaagaggtc actgtcaacc agagtctcct    840

gactcccctc aacctgcaaa tcgaccccag catccagagg gtgaggaccg aggagcgcga    900

gcagatcaag accctcaaca ataagtttgc ctccttcatc gacaaggtgc ggttcctgga    960

gcagcagaac aaggttctgg acaccaagtg gaccctgctg caggagcagg gcaccaagac   1020

tgtgaggcag aacctggagc cgttgttcga gcagtacatc aacaacctca ggaggcagct   1080

ggacagcatc gtgggggaac ggggccgcct ggactcagag ctgagaaaca tgcaggacct   1140

ggtggaagac ttcaagaaca agtatgagga tgaaatcaac aagcgtacca ctgctgagaa   1200

tgagtttgtg atgctgaaga aggatgtaga tgctgcctac atgaacaagg tggagctgga   1260

ggccaaggtt gatgcactga tggatgagat taacttcatg aagatgttct ttgatgcgga   1320

gctgtcccag atgcagacgc atgtctctga cacctcagtg gtcctctcca tggacaacaa   1380

ccgcaacctg gacctggata gcatcatcgc tgaggtcaag gcccagtatg aggagattgc   1440

caaccgcagc cggacagaag ccgagtcctg gtatcagacc aagtatgagg agctgcagca   1500

gacagctggc cggcatggcg atgacctccg caacaccaag catgagatca cagagatgaa   1560

ccggatgatc cagaggctga gagccgagat tgacaatgtc aagaaacagt gcgccaatct   1620

gcagaacgcc attgcggatg ccgagcagcg tggggagctg gccctcaagg atgccaggaa   1680

caagctggcc gagctggagg aggccctgca gaaggccaag caggacatgg cccggctgct   1740

gcgtgagtac caggagctca tgaacaccaa gctggccctg gacgtggaga tcgccactta   1800

ccgcaagctg ctggagggcg aggaatgcag actcagtgga gaaggagttg gaccagtcaa   1860

catctctgtt gtcacaagca gtgtttcctc tggatatggc agtggcagtg gctatggcgg   1920

tggcctcggt ggaggtcttg gcggcggcct cggtggaggt cttgccggag gtagcagtgg   1980
```

aagctactac tccagcagca gtgggggtgt cggcctaggt ggtgggctca gtgtgggggg 2040
ctctggcttc agtgcaagca gtggccgagg gctgggggtg ggctttggca gtggcggggg 2100
tagcagctcc agcgtcaaat ttgtctccac cacctcctcc tcccggaaga gcttcaagag 2160
ctaagaacct gctgcaagtc actgccttcc aagtgcagca acccagccca tggagattgc 2220
ctcttctagg cagttgctca agccatgttt tatccttttc tggagagtag tctagaccaa 2280
gccaattgca gaaccacatt ctttggttcc caggagagcc ccattcccag cccctggtct 2340
cccgtgccgc agttctatat tctgcttcaa atcagccttc aggtttccca cagcatggcc 2400
cctgctgaca cgagaaccca aagttttccc aaatctaaat catcaaaaca gaatccccac 2460
cccaatccca aattttgttt tggttctaac tacctccaga atgtgttcaa taaaatgctt 2520
ttataatat 2529

<210> SEQ ID NO 132
<211> LENGTH: 6816
<212> TYPE: DNA
<213> ORGANISM: Homo sapiens

<400> SEQUENCE: 132
ggacggccga gcggcagggc gctcgcgcgc gcccactagt ggccggagga gaaggctccc 60
gcggaggccg cgctgcccgc cccctcccct ggggaggctc gcgttcccgc tgctcgcgcc 120
tgcgccgccc gccggcctca ggaacgcgcc ctcttcgccg gcgcgcgccc tcgcagtcac 180
cgccacccac cagctccggc accaacagca gcgccgctgc caccgcccac cttctgccgc 240
cgccaccaca gccaccttct cctcctccgc tgtcctctcc cgtcctcgcc tctgtcgact 300
atcaggtgaa ctttgaacca ggatggctga gccccgccag gagttcgaag tgatggaaga 360
tcacgctggg acgtacgggt tgggggacag gaaagatcag gggggctaca ccatgcacca 420
agaccaagag ggtgacacgg acgctggcct gaaagaatct cccctgcaga cccccactga 480
ggacggatct gaggaaccgg gctctgaaac ctctgatgct aagagcactc caacagcgga 540
agatgtgaca gcacccttag tggatgaggg agctcccggc aagcaggctg ccgcgcagcc 600
ccacacggag atcccagaag gaaccacagc tgaagaagca ggcattggag acacccccag 660
cctggaagac gaagctgctg gtcacgtgac ccaagagcct gaaagtggta aggtggtcca 720
ggaaggcttc ctccgagagc caggcccccc aggtctgagc caccagctca tgtccggcat 780
gcctggggct cccctcctgc ctgagggccc cagagaggcc acacgccaac cttcggggac 840
aggacctgag gacacagagg gcggccgcca cgcccctgag ctgctcaagc accagcttct 900
aggagacctg caccaggagg ggccgccgct gaagggggca gggggcaaag agaggccggg 960
gagcaaggag gaggtggatg aagaccgcga cgtcgatgag tcctccccc aagactcccc 1020 tccctccaag gcctccccag cccaagatgg gcggcctccc cagacagccg ccagagaagc 1080
caccagcatc ccaggcttcc cagcggaggg tgccatcccc ctccctgtgg atttcctctc 1140
caaagtttcc acagagatcc cagcctcaga gcccgacggg cccagtgtag ggcgggccaa 1200
agggcaggat gccccctgg agttcacgtt tcacgtggaa atcacaccca acgtgcagaa 1260
ggagcaggcg cactcggagg agcatttggg aagggctgca tttccagggg cccctggaga 1320
ggggccagag gcccggggcc cctctttggg agaggacaca aaagaggctg accttccaga 1380
gccctctgaa aagcagcctg ctgctgctcc gcgggggaag cccgtcagcc gggtccctca 1440
actcaaagct cgcatggtca gtaaaagcaa agacgggact ggaagcgatg acaaaaaagc 1500

-continued

```
caagacatcc acacgttcct ctgctaaaac cttgaaaaat aggccttgcc ttagccccaa   1560
acaccccact cctggtagct cagaccctct gatccaaccc tccagccctg ctgtgtgccc   1620
agagccacct tcctctccta aatacgtctc ttctgtcact tcccgaactg gcagttctgg   1680
agcaaaggag atgaaactca agggggctga tggtaaaacg aagatcgcca caccgcgggg   1740
agcagcccct ccaggccaga agggccaggc caacgccacc aggattccag caaaaacccc   1800
gcccgctcca aagacaccac ccagctctgc gactaagcaa gtccagagaa gaccaccccc   1860
tgcagggccc agatctgaga gaggtgaacc tccaaaatca ggggatcgca gcggctacag   1920
cagccccggc tccccaggca ctcccggcag ccgctcccgc accccgtccc ttccaacccc   1980
acccacccgg gagcccaaga aggtggcagt ggtccgtact ccacccaagt cgccgtcttc   2040
cgccaagagc cgcctgcaga cagcccccgt gcccatgcca gacctgaaga atgtcaagtc   2100
caagatcggc tccactgaga acctgaagca ccagccggga ggcgggaagg tgcagataat   2160
taataagaag ctggatctta gcaacgtcca gtccaagtgt ggctcaaagg ataatatcaa   2220
acacgtcccg ggaggcggca gtgtgcaaat agtctacaaa ccagttgacc tgagcaaggt   2280
gacctccaag tgtggctcat taggcaacat ccatcataaa ccaggaggtg gccaggtgga   2340
agtaaaatct gagaagcttg acttcaagga cagagtccag tcgaagattg ggtccctgga   2400
caatatcacc cacgtccctg gcggaggaaa taaaaagatt gaaacccaca agctgacctt   2460
ccgcgagaac gccaaagcca agacagacca cggggcggag atcgtgtaca agtcgccagt   2520
ggtgtctggg gacacgtctc cacggcatct cagcaatgtc tcctccaccg gcagcatcga   2580
catggtagac tcgccccagc tcgccacgct agctgacgag gtgtctgcct ccctggccaa   2640
gcagggtttg tgatcaggcc cctggggcgg tcaataattg tggagaggag agaatgagag   2700
agtgtggaaa aaaaaagaat aatgacccgg cccccgccct ctgcccccag ctgctcctcg   2760
cagttcggtt aattggttaa tcacttaacc tgcttttgtc actcggcttt ggctcgggac   2820
ttcaaaatca gtgatgggag taagagcaaa tttcatcttt ccaaattgat gggtgggcta   2880
gtaataaaat atttaaaaaa aaacattcaa aaacatggcc acatccaaca tttcctcagg   2940
caattccttt tgattctttt ttcttccccc tccatgtaga agagggagaa ggagaggctc   3000
tgaaagctgc ttctggggga tttcaaggga ctgggggtgc caaccacctc tggccctgtt   3060
gtgggggtgt cacagaggca gtggcagcaa caaaggattt gaaacttggt gtgttcgtgg   3120
agccacaggc agacgatgtc aaccttgtgt gagtgtgacg ggggttgggg tggggcggga   3180
ggccacgggg gaggccgagg caggggctgg gcagagggga gaggaagcac aagaagtggg   3240
agtgggagag gaagccacgt gctggagagt agacatcccc ctccttgccg ctgggagagc   3300
caaggcctat gccacctgca gcgtctgagc ggccgcctgt ccttggtggc cgggggtggg   3360
ggcctgctgt gggtcagtgt gccaccctct gcagggcagc ctgtgggaga agggacagcg   3420
ggtaaaaaga gaaggcaagc tggcaggagg gtggcacttc gtggatgacc tccttagaaa   3480
agactgacct tgatgtcttg agagcgctgg cctcttcctc cctccctgca gggtaggggg   3540
cctgagttga ggggcttccc tctgctccac agaaaccctg ttttattgag ttctgaaggt   3600
tggaactgct gccatgattt tggccacttt gcagacctgg gactttaggg ctaaccagtt   3660
ctctttgtaa ggacttgtgc ctcttgggag acgtccaccc gtttccaagc ctgggccact   3720
ggcatctctg gagtgtgtgg gggtctggga ggcaggtccc gagcccccctg tccttcccac   3780
ggccactgca gtcaccccgt ctgcgccgct gtgctgttgt ctgccgtgag agcccaatca   3840
ctgcctatac ccctcatcac acgtcacaat gtcccgaatt cccagcctca ccaccccttc   3900
```

```
tcagtaatga ccctggttgg ttgcaggagg tacctactcc atactgaggg tgaaattaag   3960
ggaaggcaaa gtccaggcac aagagtggga ccccagcctc tcactctcag ttccactcat   4020
ccaactggga ccctcaccac gaatctcatg atctgattcg gttccctgtc tcctcctccc   4080
gtcacagatg tgagccaggg cactgctcag ctgtgaccct aggtgtttct gccttgttga   4140
catggagaga gccctttccc ctgagaaggc ctggcccctt cctgtgctga gcccacagca   4200
gcaggctggg tgtcttggtt gtcagtggtg gcaccaggat ggaagggcaa ggcacccagg   4260
gcaggcccac agtcccgctg tcccccactt gcaccctagc ttgtagctgc caacctccca   4320
gacagcccag cccgctgctc agctccacat gcatagtatc agccctccac acccgacaaa   4380
ggggaacaca ccccccttgga aatggttctt ttcccccagt cccagctgga agccatgctg   4440
tctgttctgc tggagcagct gaacatatac atagatgttg ccctgccctc cccatctgca   4500
ccctgttgag ttgtagttgg atttgtctgt ttatgcttgg attcaccaga gtgactatga   4560
tagtgaaaag aaaaaaaaaa aaaaaaaagg acgcatgtat cttgaaatgc ttgtaaagag   4620
gtttctaacc caccctcacg aggtgtctct cacccccaca ctgggactcg tgtggcctgt   4680
gtggtgccac cctgctgggg cctcccaagt tttgaaaggc tttcctcagc acctgggacc   4740
caacagagac cagcttctag cagctaagga ggccgttcag ctgtgacgaa ggcctgaagc   4800
acaggattag gactgaagcg atgatgtccc cttccctact tccccttggg gctccctgtg   4860
tcagggcaca gactaggtct tgtggctggt ctggcttgcg gcgcgaggat ggttctctct   4920
ggtcatagcc cgaagtctca tggcagtccc aaaggaggct tacaactcct gcatcacaag   4980
aaaaaggaag ccactgccag ctggggggat ctgcagctcc cagaagctcc gtgagcctca   5040
gccacccctc agactgggtt cctctccaag ctcgccctct ggaggggcag cgcagcctcc   5100
caccaagggc cctgcgacca cagcagggat tgggatgaat tgcctgtcct ggatctgctc   5160
tagaggccca agctgcctgc ctgaggaagg atgacttgac aagtcaggag acactgttcc   5220
caaagccttg accagagcac ctcagcccgc tgaccttgca caaactccat ctgctgccat   5280
gagaaaaggg aagccgcctt tgcaaaacat tgctgcctaa agaaactcag cagcctcagg   5340
cccaattctg ccacttctgg tttgggtaca gttaaaggca accctgaggg acttggcagt   5400
agaaatccag ggcctcccct ggggctggca gcttcgtgtg cagctagagc tttacctgaa   5460
aggaagtctc tgggcccaga actctccacc aagagcctcc ctgccgttcg ctgagtccca   5520
gcaattctcc taagttgaag ggatctgaga aggagaagga aatgtggggt agatttggtg   5580
gtggttagag atatgccccc ctcattactg ccaacagttt cggctgcatt tcttcacgca   5640
cctcggttcc tcttcctgaa gttcttgtgc cctgctcttc agcaccatgg gccttcttat   5700
acggaaggct ctgggatctc cccttgtgg ggcaggctct tggggccagc ctaagatcat   5760
ggtttagggt gatcagtgct ggcagataaa ttgaaaaggc acgctggctt gtgatcttaa   5820
atgaggacaa tccccccagg gctgggcact cctcccctcc cctcacttct cccacctgca   5880
gagccagtgt ccttgggtgg gctagatagg atatactgta tgccggctcc ttcaagctgc   5940
tgactcactt tatcaatagt tccatttaaa ttgacttcag tggtgagact gtatcctgtt   6000
tgctattgct tgttgtgcta tggggggagg ggggaggaat gtgtaagata gttaacatgg   6060
gcaaagggag atcttggggt gcagcactta aactgcctcg taaccctttt catgatttca   6120
accacatttg ctagagggag ggagcagcca cggagttaga ggcccttggg gtttctcttt   6180
tccactgaca ggctttccca ggcagctggc tagttcattc cctccccagc caggtgcagg   6240
```

```
cgtaggaata tggacatctg gttgctttgg cctgctgccc tctttcaggg gtcctaagcc   6300
cacaatcatg cctccctaag accttggcat ccttccctct aagccgttgg cacctctgtg   6360
ccacctctca cactggctcc agacacacag cctgtgcttt tggagctgag atcactcgct   6420
tcaccctcct catctttgtt ctccaagtaa agccacgagg tcggggcgag ggcagaggtg   6480
atcacctgcg tgtcccatct acagacctgc agcttcataa aacttctgat ttctcttcag   6540
ctttgaaaag ggttaccctg ggcactggcc tagagcctca cctcctaata gacttagccc   6600
catgagtttg ccatgttgag caggactatt tctggcactt gcaagtccca tgatttcttc   6660
ggtaattctg agggtggggg gagggacatg aaatcatctt agcttagctt tctgtctgtg   6720
aatgtctata tagtgtattg tgtgttttaa caaatgattt acactgactg ttgctgtaaa   6780
agtgaatttg gaaataaagt tattactctg attaaa                            6816
```

<210> SEQ ID NO 133
<211> LENGTH: 2372
<212> TYPE: DNA
<213> ORGANISM: Homo sapiens

<400> SEQUENCE: 133

```
gcaccgcgcg agcttggctg cttctggggc ctgtgtggcc ctgtgtgtcg gaaagatgga     60
gcaagaagcc gagcccgagg ggcggccgcg acccctctga ccgagatcct gctgctttcg    120
cagccaggag caccgtccct ccccggatta gtgcgtacga gcgcccagtg ccctggcccg    180
gagagtggaa tgatccccga ggcccagggc gtcgtgcttc cgcagtagtc agtccccgtg    240
aaggaaactg gggagtcttg agggaccccc gactccaagc gcgaaaaccc cggatggtga    300
ggagcaggca aatgtgcaat accaacatgt ctgtacctac tgatggtgct gtaaccacct    360
cacagattcc agcttcggaa caagagaccc tggttagacc aaagccattg cttttgaagt    420
tattaaagtc tgttggtgca caaaaagaca cttatactat gaaagaggtt ctttttttatc    480
ttggccagta tattatgact aaacgattat atgatgagaa gcaacaacat attgtatatt    540
gttcaaatga tcttctagga gatttgtttg gcgtgccaag cttctctgtg aaagagcaca    600
ggaaaatata taccatgatc tacaggaact tggtagtagt caatcagcag gaatcatcgg    660
actcaggtac atctgtgagt gagaacaggt gtcaccttga aggtgggagt gatcaaaagg    720
accttgtaca agagcttcag gaagagaaac cttcatcttc acatttggtt tctagaccat    780
ctacctcatc tagaaggaga gcaattagtg agacagaaga aaattcagat gaattatctg    840
gtgaacgaca aagaaaacgc cacaaatctg atagtatttc cctttccttt gatgaaagcc    900
tggctctgtg tgtaataagg gagatatgtt gtgaaagaag cagtagcagt gaatctacag    960
ggacgccatc gaatccggat cttgatgctg gtgtaagtga acattcaggt gattggttgg   1020
atcaggattc agtttcagat cagtttagtg tagaatttga agttgaatct ctcgactcag   1080
aagattatag ccttagtgaa gaaggacaag aactctcaga tgaagatgat gaggtatatc   1140
aagttactgt gtatcaggca ggggagagtg atacagattc atttgaagaa gatcctgaaa   1200
tttccttagc tgactattgg aaatgcactt catgcaatga aatgaatccc ccccttccat   1260
cacattgcaa cagatgttgg gcccttcgtg agaattggct tcctgaagat aaagggaaag   1320
ataaagggga aatctctgag aaagccaaac tggaaaactc aacacaagct gaagagggct   1380
ttgatgttcc tgattgtaaa aaaactatag tgaatgattc cagagagtca tgtgttgagg   1440
aaaatgatga taaaattaca caagcttcac aatcacaaga aagtgaagac tattctcagc   1500
catcaacttc tagtagcatt atttatagca gccaagaaga tgtgaaagag tttgaaaggg   1560
```

-continued

```
aagaaaccca agacaaagaa gagagtgtgg aatctagttt gccccttaat gccattgaac   1620
cttgtgtgat ttgtcaaggt cgacctaaaa atggttgcat tgtccatggc aaaacaggac   1680
atcttatggc ctgctttaca tgtgcaaaga agctaaagaa aaggaataag ccctgcccag   1740
tatgtagaca accaattcaa atgattgtgc taacttattt cccctagttg acctgtctat   1800
aagagaatta tatatttcta actatataac cctaggaatt tagacaacct gaaatttatt   1860
cacatatatc aaagtgagaa aatgcctcaa ttcacataga tttcttctct ttagtataat   1920
tgacctactt tggtagtgga atagtgaata cttactataa tttgacttga atatgtagct   1980
catcctttac accaactcct aattttaaat aatttctact ctgtcttaaa tgagaagtac   2040
ttggtttttt ttttcttaaa tatgtatatg acatttaaat gtaacttatt attttttttg   2100
agaccgagtc ttgctctgtt acccaggctg gagtgcagtg ggtgatcttg gctcactgca   2160
agctctgccc tccccgggtt cgcaccattc tcctgcctca gcctcccaat tagcttggcc   2220
tacagtcatc tgccaccaca cctggctaat tttttgtact tttagtagag acagggtttc   2280
accgtgttag ccaggatggt ctcgatctcc tgacctcgtg atccgcccac ctcggcctcc   2340
caaagtgctg ggattacagg catgagccac cg                                 2372
```

<210> SEQ ID NO 134
<211> LENGTH: 2486
<212> TYPE: DNA
<213> ORGANISM: Homo sapiens

<400> SEQUENCE: 134

```
gagatttgat tcccttggcg ggcggaagcg gccacaaccc ggcgatcgaa aagattctta     60
ggaacgccgt accagccgcg tctctcagga cagcaggccc ctgtccttct gtcgggcgcc    120
gctcagccgt gccctccgcc cctcaggttc tttttctaat tccaaataaa cttgcaagag    180
gactatgaaa gattatgatg aacttctcaa atattatgaa ttacatgaaa ctattgggac    240
aggtggcttt gcaaaggtca aacttgcctg ccatatcctt actggagaga tggtagctat    300
aaaaatcatg gataaaaaca cactagggag tgatttgccc cggatcaaaa cggagattga    360
ggccttgaag aacctgagac atcagcatat atgtcaactc taccatgtgc tagagacagc    420
caacaaaata ttcatggttc ttgagtactg ccctggagga gagctgtttg actatataat    480
ttcccaggat cgcctgtcag aagaggagac ccgggttgtc ttccgtcaga tagtatctgc    540
tgttgcttat gtgcacagcc agggctatgc tcacagggac ctcaagccag aaaatttgct    600
gtttgatgaa tatcataaat taaagctgat tgactttggt ctctgtgcaa aacccaaggg    660
taacaaggat taccatctac agacatgctg tgggagtctg gcttatgcag cacctgagtt    720
aatacaaggc aaatcatatc ttggatcaga ggcagatgtt tggagcatgg gcatactgtt    780
atatgttctt atgtgtggat ttctaccatt tgatgatgat aatgtaatgg ctttatacaa    840
gaagattatg agaggaaaat atgatgttcc caagtggctc tctcccagta gcattctgct    900
tcttcaacaa atgctgcagg tggacccaaa gaaacggatt tctatgaaaa atctattgaa    960
ccatccctgg atcatgcaag attacaacta tcctgttgag tggcaaagca agaatccttt   1020
tattcacctc gatgatgatt gcgtaacaga actttctgta catcacagaa acaacaggca   1080
aacaatggag gatttaattt cactgtggca gtatgatcac ctcacggcta cctatcttct   1140
gcttctagcc aagaaggctc ggggaaaacc agttcgttta aggctttctt ctttctcctg   1200
tggacaagcc agtgctaccc cattcacaga catcaagtca aataattgga gtctggaaga   1260
```

tgtgaccgca agtgataaaa attatgtggc gggattaata gactatgatt ggtgtgaaga 1320
tgatttatca acaggtgctg ctactccccg aacatcacag tttaccaagt actggacaga 1380
atcaaatggg gtggaatcta aatcattaac tccagcctta tgcagaacac ctgcaaataa 1440
attaaagaac aaagaaaatg tatatactcc taagtctgct gtaaagaatg aagagtactt 1500
tatgtttcct gagccaaaga ctccagttaa taagaaccag cataagagag aaatactcac 1560
tacgccaaat cgttacacta caccctcaaa agctagaaac cagtgcctga aagaaactcc 1620
aattaaaata ccagtaaatt caacaggaac agacaagtta atgacaggtg tcattagccc 1680
tgagaggcgg tgccgctcag tggaattgga tctcaaccaa gcacatatgg aggagactcc 1740
aaaaagaaag ggagccaaag tgtttgggag ccttgaaagg gggttggata aggttatcac 1800
tgtgctcacc aggagcaaaa ggaagggttc tgccagagac gggcccagaa gactaaagct 1860
tcactataac gtgactacaa ctagattagt gaatccagat caactgttga atgaaataat 1920
gtctattctt ccaaagaagc atgttgactt tgtacaaaag ggttatacac tgaagtgtca 1980
aacacagtca gattttggga aagtgacaat gcaatttgaa ttagaagtgt gccagcttca 2040
aaaacccgat gtggtgggta tcaggaggca gcggcttaag ggcgatgcct gggtttacaa 2100
aagattagtg gaagacatcc tatctagctg caaggtataa ttgatggatt cttccatcct 2160
gccggatgag tgtgggtgtg atacagccta cataaagact gttatgatcg ctttgatttt 2220
aaagttcatt ggaactacca acttgtttct aaagagctat cttaagacca atatctcttt 2280
gtttttaaac aaaagatatt attttgtgta tgaatctaaa tcaagcccat ctgtcattat 2340
gttactgtct tttttaatca tgtggttttg tatattaata attgttgact ttcttagatt 2400
cacttccata tgtgaatgta agctcttaac tatgtctctt tgtaatgtgt aatttctttc 2460
tgaaataaaa ccatttgtga atatag 2486

<210> SEQ ID NO 135
<211> LENGTH: 1140
<212> TYPE: DNA
<213> ORGANISM: Homo sapiens
<220> FEATURE:
<221> NAME/KEY: misc_feature
<222> LOCATION: (1140)..(1140)
<223> OTHER INFORMATION: n is a, c, g, or t

<400> SEQUENCE: 135
gcagcggagg agcccagtcc acgatggccc ggtccctggt gtgccttggt gtcatcatct 60
tgctgtctgc cttctccgga cctggtgtca ggggtggtcc tatgcccaag ctggctgacc 120
ggaagctgtg tgcggaccag gagtgcagcc accctatctc catggctgtg gcccttcagg 180
actacatggc ccccgactgc cgattcctga ccattcaccg ggccaagtg gtgtatgtct 240 tctccaagct gaagggccgt gggcggctct tctggggagg cagcgttcag ggagattact 300
atggagatct ggctgctcgc ctgggctatt tccccagtag cattgtccga gaggaccaga 360
ccctgaaacc tggcaaagtc gatgtgaaga cagacaaatg ggatttctac tgccagtgag 420
ctcagcctac cgctggccct gccgtttccc ctccttgggt ttatgcaaat acaatcagcc 480
cagtgcaaaa aaaaaaaaaa aaaaaaaaaa cttcggagaa gagatagcaa caaaaggccg 540
cttgtgtgaa ggcgccaaaa gttttcgccc aagagacctt cggcctcccc cagggcgcgc 600
gcaaaggcgc cttgttttga caacctcttg gacaaccgga ggggctaccg cccggagacc 660
cctgtggtgg accccccggg caacccggtg tgacagggta ctcacccccca cggctttgtc 720 gggggtccca ccaaaggccc caaagaggct ctttcaaggc actattcctt gttgtagacc 780

-continued

```
ttgtgtgtgc cacaggcgcc aaagaaacct cggggggcta acaaacgcac gtgcttggca     840

gctccgagaa ggctctctcc cacccgaggg gtggacgcaa caggggggaat gggccatcat    900

attgttgccc ccggtgggca ccaactcttt ttcccccata gagaggcctt agcacactat     960

gtggggcacg ttattgccgc ctagagaaac cgagcgccag aaaatttcga aggggggggc   1020

gcttctcatc attttgcgca aaaccccctt gtgggagtat gccccgaact cctctggaac   1080

acacaagcga cacttgcgcg gggtctgcaa aaaacctcct gttgggaagc cggcttcacn   1140
```

<210> SEQ ID NO 136
<211> LENGTH: 12507
<212> TYPE: DNA
<213> ORGANISM: Homo sapiens

<400> SEQUENCE: 136

```
taccgggcgg aggtgagcgc ggcgccggct cctcctgcgg cggactttgg gtgcgacttg      60

acgagcggtg gttcgacaag tggccttgcg ggccggatcg tcccagtgga agagttgtaa     120

atttgcttct ggccttcccc tacggattat acctggcctt cccctacgga ttatactcaa     180

cttactgttt agaaaatgtg gcccacgaga cgcctggtta ctatcaaaag gagcggggtc     240

gacggtcccc actttcccct gagcctcagc acctgcttgt ttggaagggg tattgaatgt     300

gacatccgta tccagcttcc tgttgtgtca aaacaacatt gcaaaattga aatccatgag     360

caggaggcaa tattacataa tttcagttcc acaaatccaa cacaagtaaa tgggtctgtt     420

attgatgagc ctgtacggct aaaacatgga gatgtaataa ctattattga tcgttccttc     480

aggtatgaaa atgaaagtct tcagaatgga aggaagtcaa ctgaatttcc aagaaaaata     540

cgtgaacagg agccagcacg tcgtgtctca agatctagct tctcttctga ccctgatgag     600

aaagctcaag attccaaggc ctattcaaaa atcactgaag gaaaagtttc aggaaatcct     660

caggtacata tcaagaatgt caaagaagac agtaccgcag atgactcaaa agacagtgtt     720

gctcagggaa caactaatgt tcattcctca gaacatgctg gacgtaatgg cagaaatgca     780

gctgatccca tttctgggga ttttaaagaa atttccagcg ttaaattagt gagccgttat     840

ggagaattga agtctgttcc cactacacaa tgtcttgaca atagcaaaaa aaatgaatct     900

ccctttttgga agctttatga gtcagtgaag aaagagttgg atgtaaaatc acaaaaagaa    960

aatgtcctac agtattgtag aaaatctgga ttacaaactg attacgcaac agagaaagaa    1020

agtgctgatg gtttacaggg ggagacccaa ctgttggtct cgcgtaagtc aagaccaaaa    1080

tctggtggga gcggccacgc tgtggcagag cctgcttcac ctgaacaaga gcttgaccag    1140

aacaagggga agggaagaga cgtggagtct gttcagactc ccagcaaggc tgtgggcgcc    1200

agctttcctc tctatgagcc ggctaaaatg aagacccctg tacaatattc acagcaacaa    1260

aattctccac aaaaacataa gaacaaagac ctgtatacta ctggtagaag agaatctgtg    1320

aatctgggta aaagtgaagg cttcaaggct ggtgataaaa ctcttactcc caggaagctt    1380

tcaactagaa atcgaacacc agctaaagtt gaagatgcag ctgactctgc cactaagcca    1440

gaaaatctct cttccaaaac cagaggaagt attcctacag atgtggaagt tctgcctacg    1500

gaaactgaaa ttcacaatga gccattttta actctgtggc tcactcaagt tgagaggaag    1560

atccaaaagg attccctcag caagcctgag aaattgggca ctacagctgg acagatgtgc    1620

tctgggttac ctggtcttag ttcagttgat atcaacaact ttggtgattc cattaatgag    1680

agtgagggaa tacctttgaa aagaaggcgt gtgtcctttg gtgggcacct aagacctgaa    1740
```

-continued

```
ctatttgatg aaaacttgcc tcctaatacg cctctcaaaa ggggagaagc cccaaccaaa   1800
agaaagtctc tggtaatgca cactccacct gtcctgaaga aaatcatcaa ggaacagcct   1860
caaccatcag gaaaacaaga gtcaggttca gaaatccatg tggaagtgaa ggcacaaagc   1920
ttggttataa gccctccagc tcctagtcct aggaaaactc cagttgccag tgatcaacgc   1980
cgtaggtcct gcaaaacagc ccctgcttcc agcagcaaat ctcagacaga ggttcctaag   2040
agaggaggga gaaagagtgg caacctgcct tcaaagagag tgtctatcag ccgaagtcaa   2100
catgatattt tacagatgat atgttccaaa agaagaagtg gtgcttcgga agcaaatctg   2160
attgttgcaa aatcatgggc agatgtagta aaacttggtg caaaacaaac acaaactaaa   2220
gtcataaaac atggtcctca aaggtcaatg aacaaaaggc aaagaagacc tgctactcca   2280
aagaagcctg tgggcgaagt tcacagtcaa tttagtacag gccacgcaaa ctctccttgt   2340
accataataa tagggaaagc tcatactgaa aaagtacatg tgcctgctcg accctacaga   2400
gtgctcaaca acttcatttc caaccaaaaa atggacttta aggaagatct ttcaggaata   2460
gctgaaatgt tcaagacccc agtgaaggag caaccgcagt tgacaagcac atgtcacatc   2520
gctatttcaa attcagagaa tttgcttgga aaacagtttc aaggaactga ttcaggagaa   2580
gaacctctgc tccccacctc agagagtttt ggaggaaatg tgttcttcag tgcacagaat   2640
gcagcaaaac agccatctga taaatgctct gcaagccctc ccttaagacg gcagtgtatt   2700
agagaaaatg gaaacgtagc aaaaacgccc aggaacacct acaaaatgac ttctctggag   2760
acaaaaactt cagatactga gacagagcct tcaaaaacag tatccactgc aaacaggtca   2820
ggaaggtcta cagagttcag gaatatacag aagctacctg tggaaagtaa gagtgaagaa   2880
acaaatacag aaattgttga gtgcatccta aaaagaggtc agaaggcaac actactacaa   2940
caaaggagag aaggagagat gaaggaaata gaaagacctt ttgagacata taaggaaaat   3000
attgaattaa aagaaaacga tgaaaagatg aaagcaatga agagatcaag aacttggggg   3060
cagaaatgtg caccaatgtc tgacctgaca gacctcaaga gcttgcctga tacagaactc   3120
atgaaagaca cggcacgtgg ccagaatctc ctccaaaccc aagatcatgc caaggcacca   3180
aagagtgaga aaggcaaaat cactaaaatg ccctgccagt cattacaacc agaaccaata   3240
aacaccccaa cacacacaaa acaacagttg aaggcatccc tggggaaagt aggtgtgaaa   3300
gaagagctcc tagcagtcgg caagttcaca cggacgtcag gggagaccac gcacacgcac   3360
agagagccag caggagatgg caagagcatc agaacgttta aggagtctcc aaagcagatc   3420
ctggacccag cagcccgtgt aactggaatg aagaagtggc caagaacgcc taaggaagag   3480
gcccagtcac tagaagacct ggctggcttc aaagagctct tccagacacc aggtccctct   3540
gaggaatcaa tgactgatga gaaaactacc aaaatagcct gcaaatctcc accaccagaa   3600
tcagtggaca ctccaacaag cacaaagcaa tggcctaaga gaagtctcag gaaagcagat   3660
gtagaggaag aattcttagc actcaggaaa ctaacaccat cagcagggaa agccatgctt   3720
acgcccaaac cagcaggagg tgatgagaaa gacattaaag catttatggg aactccagtg   3780
cagaaactgg acctggcagg aactttacct ggcagcaaaa gacagctaca gactcctaag   3840
gaaaaggccc aggctctaga agacctggct ggctttaaag agctcttcca gactcctggt   3900
cacaccgagg aattagtggc tgctggtaaa accactaaaa taccctgcga ctctccacag   3960
tcagacccag tggacacccc aacaagcaca aagcaacgac ccaagagaag tatcaggaaa   4020
gcagatgtag agggagaact cttagcgtgc aggaatctaa tgccatcagc aggcaaagcc   4080
atgcacacgc ctaaaccatc agtaggtgaa gagaaagaca tcatcatatt tgtgggaact   4140
```

-continued

```
ccagtgcaga aactggacct gacagagaac ttaaccggca gcaagagacg gccacaaact   4200
cctaaggaag aggcccaggc tctggaagac ctgactggct ttaaagagct cttccagacc   4260
cctggtcata ctgaagaagc agtggctgct ggcaaaacta ctaaaatgcc ctgcgaatct   4320
tctccaccag aatcagcaga caccccaaca agcacaagaa ggcagcccaa gacacctttg   4380
gagaaaaggg acgtacagaa ggagctctca gccctgaaga agctcacaca gacatcaggg   4440
gaaaccacac acacagataa agtaccagga ggtgaggata aaagcatcaa cgcgtttagg   4500
gaaactgcaa aacagaaact ggacccagca gcaagtgtaa ctggtagcaa gaggcaccca   4560
aaaactaagg aaaaggccca acccctagaa gacctggctg gcttgaaaga gctcttccag   4620
acaccagtat gcactgacaa gcccacgact cacgagaaaa ctaccaaaat agcctgcaga   4680
tcacaaccag acccagtgga cacaccaaca agctccaagc cacagtccaa gagaagtctc   4740
aggaaagtgg acgtagaaga agaattcttc gcactcagga aacgaacacc atcagcaggc   4800
aaagccatgc acacacccaa accagcagta agtggtgaga aaaacatcta cgcatttatg   4860
ggaactccag tgcagaaact ggacctgaca gagaacttaa ctggcagcaa gagacggcta   4920
caaactccta aggaaaaggc ccaggctcta gaagacctgg ctggctttaa agagctcttc   4980
cagacacgag gtcacactga ggaatcaatg actaacgata aaactgccaa agtagcctgc   5040
aaatcttcac aaccagaccc agacaaaaac ccagcaagct ccaagcgacg gctcaagaca   5100
tccctgggga aagtgggcgt gaaagaagag ctcctagcag ttggcaagct cacacagaca   5160
tcaggagaga ctacacacac acacacagag ccaacaggag atggtaagag catgaaagca   5220
tttatggagt ctccaaagca gatcttagac tcagcagcaa gtctaactgg cagcaagagg   5280
cagctgagaa ctcctaaggg aaagtctgaa gtccctgaag acctggccgg cttcatcgag   5340
ctcttccaga caccaagtca cactaaggaa tcaatgacta acgaaaaaac taccaaagta   5400
tcctacagag cttcacagcc agacctagtg gacaccccaa caagctccaa gccacagccc   5460
aagagaagtc tcaggaaagc agacactgaa gaagaatttt tagcatttag gaaacaaacg   5520
ccatcagcag gcaaagccat gcacacaccc aaaccagcag taggtgaaga gaaagacatc   5580
aacacgtttt tgggaactcc agtgcagaaa ctggaccagc caggaaattt acctggcagc   5640
aatagacggc tacaaactcg taaggaaaag gcccaggctc tagaagaact gactggcttc   5700
agagagcttt tccagacacc atgcactgat aaccccacga ctgatgagaa aactaccaaa   5760
aaaatactct gcaaatctcc gcaatcagac ccagcggaca ccccaacaaa cacaaagcaa   5820
cggcccaaga gaagcctcaa gaaagcagac gtagaggaag aatttttagc attcaggaaa   5880
ctaacaccat cagcaggcaa agccatgcac acgcctaaag cagcagtagg tgaagagaaa   5940
gacatcaaca catttgtggg gactccagtg gagaaactgg acctgctagg aaatttacct   6000
ggcagcaaga gacggccaca aactcctaaa gaaaaggcca aggctctaga agatctggct   6060
ggcttcaaag agctcttcca gacaccaggt cacactgagg aatcaatgac cgatgacaaa   6120
atcacagaag tatcctgcaa atctccacaa ccagacccag tcaaaacccc aacaagctcc   6180
aagcaacgac tcaagatatc cttggggaaa gtaggtgtga aagaagaggt cctaccagtc   6240
ggcaagctca cacagacgtc agggaagacc acacagacac acagagagac agcaggagat   6300
ggaaagagca tcaaagcgtt taaggaatct gcaaagcaga tgctggaccc agcaaactat   6360
ggaactggga tggagaggtg gccaagaaca cctaaggaag aggcccaatc actagaagac   6420
ctggccggct tcaaagagct cttccagaca ccagaccaca ctgaggaatc aacaactgat   6480
```

-continued gacaaaacta ccaaaatagc ctgcaaatct ccaccaccag aatcaatgga cactccaaca 6540
agcacaagga ggcggcccaa aacacctttg gggaaaaggg atatagtgga agagctctca 6600
gccctgaagc agctcacaca gaccacacac acagacaaag taccaggaga tgaggataaa 6660
ggcatcaacg tgttcaggga aactgcaaaa cagaaactgg acccagcagc aagtgtaact 6720
ggtagcaaga ggcagccaag aactcctaag ggaaaagccc aacccctaga agacttggct 6780
ggcttgaaag agctcttcca gacaccaata tgcactgaca agcccacgac tcatgagaaa 6840
actaccaaaa tagcctgcag atctccacaa ccagacccag tgggtacccc aacaatcttc 6900
aagccacagt ccaagagaag tctcaggaaa gcagacgtag aggaagaatc cttagcactc 6960
aggaaacgaa caccatcagt agggaaagct atggacacac ccaaaccagc aggaggtgat 7020
gagaaagaca tgaaagcatt tatgggaact ccagtgcaga aattggacct gccaggaaat 7080
ttacctggca gcaaaagatg gccacaaact cctaaggaaa aggcccaggc tctagaagac 7140
ctggctggct tcaaagagct cttccagaca ccaggcactg acaagcccac gactgatgag 7200
aaaactacca aaatagcctg caaatctcca caaccagacc cagtggacac cccagcaagc 7260
acaaagcaac ggcccaagag aaacctcagg aaagcagacg tagaggaaga atttttagca 7320
ctcaggaaac gaacaccatc agcaggcaaa gccatggaca caccaaaacc agcagtaagt 7380
gatgagaaaa atatcaacac atttgtggaa actccagtgc agaaactgga cctgctagga 7440
aatttacctg gcagcaagag acagccacag actcctaagg aaaaggctga ggctctagag 7500
gacctggttg gcttcaaaga actcttccag acaccaggtc acactgagga atcaatgact 7560
gatgacaaaa tcacagaagt atcctgtaaa tctccacagc cagagtcatt caaaacctca 7620
agaagctcca agcaaaggct caagataccc ctggtgaaag tggacatgaa agaagagccc 7680
ctagcagtca gcaagctcac acggacatca ggggagacta cgcaaacaca cacagagcca 7740
acaggagata gtaagagcat caaagcgttt aaggagtctc caaagcagat cctggaccca 7800
gcagcaagtg taactggtag caggaggcag ctgagaactc gtaaggaaaa ggcccgtgct 7860
ctagaagacc tggttgactt caaagagctc ttctcagcac caggtcacac tgaagagtca 7920
atgactattg acaaaaacac aaaaattccc tgcaaatctc cccccaccaga actaacagac 7980
actgccacga gcacaaagag atgccccaag acacgtccca ggaaagaagt aaaagaggag 8040
ctctcagcag ttgagaggct cacgcaaaca tcagggcaaa gcacacacac acacaaagaa 8100
ccagcaagcg gtgatgaggg catcaaagta ttgaagcaac gtgcaaagaa gaaaccaaac 8160
ccagtagaag aggaacccag caggagaagg ccaagagcac ctaaggaaaa ggcccaaccc 8220
ctggaagacc tggccggctt cacagagctc tctgaaacat caggtcacac tcaggaatca 8280
ctgactgctg gcaaagccac taaaataccc tgcgaatctc ccccactaga agtggtagac 8340
accacagcaa gcacaaagag gcatctcagg acacgtgtgc agaaggtaca agtaaaagaa 8400
gagccttcag cagtcaagtt cacacaaaca tcaggggaaa ccacggatgc agacaaagaa 8460
ccagcaggtg aagataaagg catcaaagca ttgaaggaat ctgcaaaaca gacaccggct 8520
ccagcagcaa gtgtaactgg cagcaggaga cggccaagag cacccaggga aagtgcccaa 8580
gccatagaag acctagctgg cttcaaagac ccagcagcag gtcacactga agaatcaatg 8640
actgatgaca aaaccactaa aataccctgc aaatcatcac cagaactaga agacaccgca 8700
acaagctcaa agagacggcc caggacacgt gcccagaaag tagaagtgaa ggaggagctg 8760
ttagcagttg gcaagctcac acaaacctca ggggagacca cgcacaccga caaagagccg 8820
gtaggtgagg gcaaaggcac gaaagcattt aagcaacctg caaagcggaa gctggacgca 8880
gaagatgtaa ttggcagcag gagacagcca agagcaccta aggaaaaggc ccaacccctg 8940
gaagatctgg ccagcttcca agagctctct caaacaccag gccacactga ggaactggca 9000
aatggtgctg ctgatagctt tacaagcgct ccaaagcaaa cacctgacag tggaaaacct 9060
ctaaaaatat ccagaagagt tcttcgggcc cctaaagtag aacccgtggg agacgtggta 9120
agcaccagag accctgtaaa atcacaaagc aaaagcaaca cttccctgcc cccactgccc 9180
ttcaagaggg gaggtggcaa agatggaagc gtcacgggaa ccaagaggct gcgctgcatg 9240
ccagcaccag aggaaattgt ggaggagctg ccagccagca agaagcagag ggttgctccc 9300
agggcaagag gcaaatcatc cgaacccgtg gtcatcatga agagaagttt gaggacttct 9360
gcaaaaagaa ttgaacctgc ggaagagctg aacagcaacg acatgaaaac caacaaagag 9420
gaacacaaat tacaagactc ggtccctgaa aataagggaa tatccctgcg ctccagacgc 9480
caaaataaga ctgaggcaga acagcaaata actgaggtct ttgtattagc agaaagaata 9540
gaaataaaca gaaatgaaaa gaagcccatg aagacctccc cagagatgga cattcagaat 9600
ccagatgatg gagcccggaa acccatacct agagacaaag tcactgagaa caaaaggtgc 9660
ttgaggtctg ctagacagaa tgagagctcc cagcctaagg tggcagagga gagcggaggg 9720
cagaagagtg cgaaggttct catgcagaat cagaaaggga aaggagaagc aggaaattca 9780
gactccatgt gcctgagatc aagaaagaca aaaagccagc ctgcagcaag cactttggag 9840
agcaaatctg tgcagagagt aacgcggagt gtcaagaggt gtgcagaaaa tccaaagaag 9900
gctgaggaca atgtgtgtgt caagaaaata agaaccagaa gtcataggga cagtgaagat 9960
atttgacaga aaaatcgaac tgggaaaaat ataataaagt tagttttgtg ataagttcta 10020
gtgcagtttt tgtcataaat tacaagtgaa ttctgtaagt aaggctgtca gtctgcttaa 10080
gggaagaaaa ctttggattt gctgggtctg aatcggcttc ataaactcca ctgggagcac 10140
tgctgggctc ctggactgag aatagttgaa caccgggggc tttgtgaagg agtctgggcc 10200
aaggtttgcc ctcagctttg cagaatgaag ccttgaggtc tgtcaccacc cacagccacc 10260
ctacagcagc cttaactgtg acacttgcca cactgtgtcg tcgtttgttt gcctatgtcc 10320
tccagggcac ggtggcagga acaactatcc tcgtctgtcc caacactgag caggcactcg 10380
gtaaacacga atgaatggat gagcgcacgg atgaatggag cttacaagat ctgtctttcc 10440
aatggccggg ggcatttggt ccccaaatta aggctattgg acatctgcac aggacagtcc 10500
tatttttgat gtcctttcct ttctgaaaat aaagttttgt gctttggaga atgactcgtg 10560
agcacatctt tagggaccaa gagtgacttt ctgtaaggag tgactcgtgg cttgccttgg 10620
tctcttggga atacttttct aactagggtt gctctcacct gagacattct ccacccgcgg 10680
aatctcaggg tcccaggctg tgggccatca cgacctcaaa ctggctccta atctccagct 10740
ttcctgtcat tgaaagcttc ggaagtttac tggctctgct cccgcctgtt ttctttctga 10800
ctctatctgg cagcccgatg ccacccagta caggaagtga caccagtact ctgtaaagca 10860
tcatcatcct tggagagact gagcactcag caccttcagc cacgatttca ggatcgcttc 10920
cttgtgagcc gctgcctccg aaatctcctt tgaagcccag acatctttct ccagcttcag 10980
acttgtagat ataactcgtt catcttcatt tactttccac tttgcccct gtcctctctg 11040
tgttccccaa atcagagaat agcccgccat cccccaggtc acctgtctgg attcctcccc 11100
attcacccac cttgccaggt gcaggtgagg atggtgcacc agacagggta gctgtccccc 11160
aaaatgtgcc ctgtgcgggc agtgccctgt ctccacgttt gtttccccag tgtctggcgg 11220
ggagccaggt gacatcataa atacttgctg aatgaatgca gaaatcagcg gtactgactt 11280
gtactatatt ggctgccatg atagggttct cacagcgtca tccatgatcg taagggagaa 11340
tgacattctg cttgagggag ggaatagaaa ggggcaggga ggggacatct gagggcttca 11400
cagggctgca aagggtacag ggattgcacc agggcagaac aggggagggt gttcaaggaa 11460
gagtggctct tagcagaggc actttggaag gtgtgaggca taaatgcttc cttctacgta 11520
ggccaacctc aaaactttca gtaggaatgt tgctatgatc aagttgttct aacactttag 11580
acttagtagt aattatgaac ctcacataga aaaatttcat ccagccatat gcctgtggag 11640
tggaatattc tgtttagtag aaaaatcctt tagagttcag ctctaaccag aaatcttgct 11700
gaagtatgtc agcacctttt ctcaccctgg taagtacagt atttcaagag cacgctaagg 11760
gtggttttca ttttacaggg ctgttgatga tgggttaaaa atgttcattt aagggctacc 11820
cccgtgttta atagatgaac accacttcta cacaaccctc cttggtactg gggagggag 11880 agatctgaca aatactgccc attcccctag gctgactgga tttgagaaca aatacccacc 11940
catttccacc atggtatggt aacttctctg agcttcagtt tccaagtgaa tttccatgta 12000
ataggacatt cccattaaat acaagctgtt tttactttt cgcctcccag ggcctgtggg 12060
atctggtccc ccagcctctc ttgggctttc ttacactaac tctgtaccta ccatctcctg 12120
cctcccttag gcaggcacct ccaaccacca cacactccct gctgttttcc ctgcctggaa 12180
ctttccctcc tgccccacca agatcatttc atccagtcct gagctcagct taagggaggc 12240
ttcttgcctg tgggttccct cacccccatg cctgtcctcc aggctggggc aggttcttag 12300
tttgcctgga attgttctgt acctctttgt agcacgtagt gttgtggaaa ctaagccact 12360
aattgagttt ctggctcccc tcctggggtt gtaagttttg ttcattcatg agggccgact 12420
gcatttcctg gttactctat cccagtgacc agccacagga gatgtccaat aaagtatgtg 12480
atgaaatggt cttaaaaaaa aaaaaaa 12507

<210> SEQ ID NO 137
<211> LENGTH: 3771
<212> TYPE: DNA
<213> ORGANISM: Homo sapiens

<400> SEQUENCE: 137
gcgccgggac gtggccagtt gcccgcctgc cccggagagc caggcgctaa ccagccgctc 60
tgcgccccgc gccctgcttg cccccattat ccagccttgc cccggcgccc tgacctgacg 120
ccctggcctg acgccctgct tcgtcgcctc ctttctctcc caggtgctgg accagggact 180
gagcgtcccc cggagagggt ccggtgtgac cccgacaaga agcagaaatg gggaagaaac 240
tggatctttc caagctcact gatgaagagg cccagcatgt cttggaagtt gttcaacgag 300
attttgacct ccgaaggaaa gaagaggaac ggctagaggc gttgaagggc aagattaaga 360
aggaaagctc caagagggag ctgctttccg acactgccca tctgaacgag acccactgcg 420
cccgctgcct gcagccctac cagctgcttg tgaatagcaa aaggcagtgc ctggaatgtg 480
gcctcttcac ctgcaaaagc tgtggccgcg tccacccgga ggagcagggc tggatctgtg 540
acccctgcca tctggccaga gtcgtgaaga tcggctcact ggagtggtac tatgagcatg 600
tgaaagcccg cttcaagagg ttcggaagtg ccaaggtcat ccggtccctc cacgggcggc 660
tgcagggtgg agctgggcct gaactgatat ctgaagagag aagtggagac agcgaccaga 720
cagatgagga tggagaacct ggctcagagg cccaggccca ggcccagccc tttggcagca 780
aaaaaaagcg cctcctctcc gtccacgact tcgacttcga gggagactca gatgactcca 840

-continued

```
ctcagcctca aggtcactcc ctgcacctgt cctcagtccc tgaggccagg gacagcccac    900
agtccctcac agatgagtcc tgctcagaga aggcagcccc tcacaaggct gagggcctgg    960
aggaggctga tactggggcc tctgggtgcc actcccatcc ggaagagcag ccgaccagca   1020
tctcaccttc cagacacggc gccctggctg agctctgccc gcctggaggc tcccacagga   1080
tggccctggg gactgctgct gcactcgggt cgaatgtcat caggaatgag cagctgcccc   1140
tgcagtactt ggccgatgtg gacacctctg atgaggaaag catccgggct cacgtgatgg   1200
cctcccacca ttccaagcgg agaggccggg cgtcttctga gagtcagatc tttgagctga   1260
ataagcatat ttcagctgtg gaatgcctgc tgacctacct ggagaacaca gttgtgcctc   1320
ccttggccaa gggtctaggt gctggagtgc gcacggaggc cgatgtagag gaggaggccc   1380
tgaggaggaa gctggaggag ctgaccagca acgtcagtga ccaggagacc tcgtccgagg   1440
aggaggaagc caaggacgaa aaggcagagc ccaacaggga caaatcagtt gggcctctcc   1500
cccaggcgga cccggaggtg ggcacggctg cccatcaaac caacagacag gaaaaaagcc   1560
cccaggaccc tggggacccc gtccagtaca acaggaccac agatgaggag ctgtcagagc   1620
tggaggacag agtggcagtg acggcctcag aagtccagca ggcagagagc gaggtttcag   1680
acattgaatc caggattgca gccctgaggg ccgcagggct cacggtgaag ccctcgggaa   1740
agccccggag gaagtcaaac ctcccgatat ttctccctcg agtggctggg aaacttggca   1800
agagaccaga ggacccaaat gcagaccctt caagtgaggc caaggcaatg gctgtgccct   1860
atcttctgag aagaaagttc agtaattccc tgaaaagtca aggtaaagat gatgattctt   1920
ttgatcggaa atcagtgtac cgaggctcgc tgacacagag aaaccccaac gcgaggaaag   1980
gaatggccag ccacaccttc gcgaaacctg tggtggccca ccagtcctaa cgggacagga   2040
cagagagaca gagcagccct gcactgtttt ccctccacca cagccatcct gtccctcatt   2100
ggctctgtgc tttccactat acacagtcac cgtcccaatg agaaacaaga aggagcaccc   2160
tccacatgga ctcccacctg caagtggaca gcgacattca gtcctgcact gctcacctgg   2220
gtttactgat gactcctggc tgccccacca tcctctctga tctgtgagaa acagctaagc   2280
tgctgtgact tccctttagg acaatgttgt gtaaatcttt gaaggacaca ccgaagacct   2340
ttatactgtg atcttttacc cctttcactc ttggctttct tatgttgctt tcatgaatgg   2400
aatggaaaaa agatgactca gttaaggcac cagccatatg tgtattcttg atggtctata   2460
tcggggtgtg agcagatgtt tgcgtatttc ttgtgggtgt gactggatat tagacatccg   2520
gacaagtgac tgaactaatg atctgctgaa taatgaagga ggaatagaca ccccagtccc   2580
caccctacgt gcacccgctc tgcaagttcc catgtgatct gtagaccagg ggaaattaca   2640
ctgcggtcaa gggcagagcc tgcacatgac agcaagtgag catttgatag atgctcagat   2700
gctagtgcag agagcctgct gggagacgaa gagacagcag gcagagctcc agatgggcaa   2760
ggaagaggct tggttctagc ctggctctgc ccctcactgc agtggatcca gtggggcaga   2820
ggacagaggg tcacaaccaa tgagggatgt ctgccaagga tgggggtgca gaggccacag   2880
gagtcagctt gccactcgcc cattggttac atagatgatc tctcagacag gctgggactc   2940
agagttattt cctagtatcg gtgtgcccca tccagtttta agtggagccc tccaagactc   3000
tccagagctg cctttgaaca tcctaacagt aatcacatct caccctccct gaggttcact   3060
ttagacagga cccaatggct gcactgcctt tgtcagaggg ggtgctgaga ggagtggctt   3120
cttttagaat caaacagtag agacaagagt caagccttgt gtcttcaagc attgaccaag   3180
```

ttaagtgttt ccttccctct ctcaataaga cacttccagg agctttccaa tctctcactt 3240
aaaactaagg tttgaatctc aaagtgttgc tgggaggctg atactcctgc aacttcagga 3300
gacctgtgag cacacattag cagctgtttc tctgactcct tgtggcatca gataaaaacg 3360
tgggagtttt tccatataat tcccagcctt acttataaat tctattcttt gaaaaaatta 3420
ttcaggctag gtaaggtggc tcatacctat aatcccagcc ctttgagagg ccaaggtggg 3480
agaattgctt gaggccagga gtttgagacc tcctgggcaa catagtgaga tcccatctct 3540
acaaaaaaca aaacaaaaaa attacccaag catgatggta tatgcctgta gtcgtaccta 3600
cttacttagg aggctgaggc aggaggatca cttgagccct ggaggttggg gctgcagtga 3660
gccatgatcg catcactata ctcgagcctg ggcaacagag tgagaccttg tctcttaaaa 3720
aaattaataa taaataaatg aaaataattc ttcagaaaaa aaaaaaaaaa a 3771

<210> SEQ ID NO 138
<211> LENGTH: 2240
<212> TYPE: DNA
<213> ORGANISM: Homo sapiens

<400> SEQUENCE: 138
aagcccagca gccccggggc ggatggctcc ggccgcctgg ctccgcagcg cggccgcgcg 60
cgccctcctg cccccgatgc tgctgctgct gctccagccg ccgccgctgc tggcccgggc 120
tctgccgccg gacgcccacc acctccatgc cgagaggagg gggccacagc cctggcatgc 180
agccctgccc agtagcccgg cacctgcccc tgccacgcag gaagcccccc ggcctgccag 240
cagcctcagg cctccccgct gtggcgtgcc cgacccatct gatgggctga gtgcccgcaa 300
ccgacagaag aggttcgtgc tttctggcgg gcgctgggag aagacggacc tcacctacag 360
gatccttcgg ttcccatggc agttggtgca ggagcaggtg cggcagacga tggcagaggc 420
cctaaaggta tggagcgatg tgacgccact cacctttact gaggtgcacg agggccgtgc 480
tgacatcatg atcgacttcg ccaggtactg gcatggggac gacctgccgt ttgatgggcc 540
tgggggcatc ctggcccatg ccttcttccc caagactcac cgagaagggg atgtccactt 600
cgactatgat gagacctgga ctatcgggga tgaccagggc acagacctgc tgcaggtggc 660
agcccatgaa tttggccacg tgctggggct gcagcacaca acagcagcca aggccctgat 720
gtccgccttc tacacctttc gctacccact gagtctcagc ccagatgact gcaggggcgt 780
tcaacaccta tatggccagc cctggcccac tgtcacctcc aggaccccag ccctgggccc 840
ccaggctggg atagacacca atgagattgc accgctggag ccagacgccc cgccagatgc 900
ctgtgaggcc tcctttgacg cggtctccac catccgaggc gagctctttt tcttcaaagc 960
gggctttgtg tggcgcctcc gtgggggcca gctgcagccc ggctacccag cattggcctc 1020
tcgccactgg cagggactgc ccagccctgt ggacgctgcc ttcgaggatg cccagggcca 1080
catttggttc ttccaaggtg ctcagtactg ggtgtacgac ggtgaaaagc cagtcctggg 1140
ccccgcaccc ctcaccgagc tgggcctggt gaggttcccg gtccatgctg ccttggtctg 1200
gggtcccgag aagaacaaga tctacttctt ccgaggcagg gactactggc gtttccaccc 1260
cagcacccgg cgtgtagaca gtcccgtgcc ccgcagggcc actgactgga gaggggtgcc 1320
ctctgagatc gacgctgcct tccaggatgc tgatggctat gcctacttcc tgcgcggccg 1380
cctctactgg aagtttgacc ctgtgaaggt gaaggctctg gaaggcttcc ccgtctcgt 1440 gggtcctgac ttctttggct gtgccgagcc tgccaacact ttcctctgac catggcttgg 1500
atgccctcag gggtgctgac ccctgccagg ccacgaatat caggctagag acccatggcc 1560
atctttgtgg ctgtgggcac caggcatggg actgagccca tgtctcctca gggggatggg 1620
gtggggtaca accaccatga caactgccgg gagggccacg caggtcgtgg tcacctgcca 1680
gcgactgtct cagactgggc agggaggctt tggcatgact taagaggaag ggcagtcttg 1740
ggcccgctat gcaggtcctg gcaaacctgg ctgccctgtc tccatccctg tccctcaggg 1800
tagcaccatg gcaggactgg gggaactgga gtgtccttgc tgtatccctg ttgtgaggtt 1860
ccttccaggg gctggcactg aagcaagggt gctggggccc catggccttc agccctggct 1920
gagcaactgg gctgtagggc agggccactt cctgaggtca ggtcttggta ggtgcctgca 1980
tctgtctgcc ttctggctga caatcctgga aatctgttct ccagaatcca ggccaaaaag 2040
ttcacagtca aatggggagg ggtattcttc atgcaggaga ccccaggccc tggaggctgc 2100
aacatacctc aatcctgtcc caggccggat cctcctgaag ccctttcgc agcactgcta 2160 tcctccaaag ccattgtaaa tgtgtgtaca gtgtgtataa accttcttct tcttttttt 2220 tttttaaact gaggattgtc 2240

<210> SEQ ID NO 139
<211> LENGTH: 3167
<212> TYPE: DNA
<213> ORGANISM: Homo sapiens

<400> SEQUENCE: 139
tagcagcaca caagggttcg tgtttgtgga accaggtagc ttccttcaga gctgacattt 60
gcccacagcc agcctggccc agccccatac caccagccct ggcgctctgg ggcgtgaggt 120
gccttttctg ccccctgct ctagggcagg tggaaatcac ccatggtggg tctacatctg 180
atagaagcat cttatagttc tgcttctgga ccagaccatc ctgggttttt ctctgttctg 240
ctgaagggtt ccctccacgt gtccatcacc tcggtgaact cttgggagac ctgggaagat 300
gctggcctca cctctcgcct ctcctttccc tcattgtgct gccaccatcc ttctcacaca 360
ggctctccag ggagagctgg gcaggatggg atcttcctgg gttcccacct tgctccgtgc 420
cccctctcac tgttcctgaa gtgtggccac ggactgcctt gttttctgga aagtcccaag 480
tctggaccat gactgagcag cattctcggc tatctgccac ctgtctgggg ctcctggccc 540
ctcttagact cccctctccc ttctgtttcc cccgagcccc tgacttggac ctgcagggtg 600
gggagaggga tgggacgaga acctgtgctg gggccaaagg tcgcactggg ggaaggtgga 660
gccagggcag cagagtgcct ggcgtcggcc cctatcctgt cactagttcc cccgttctgg 720
cccctggcag gtttgtaacc ccagatcaga agtactccat ggacaacact ccccacacgc 780
caaccccgtt caagaacgcc ctggagaagt acggacccct gaagcccctg gtacgtggtg 840
tggtcactgc cgtggatctc tgcacagtgg gatcccttcg gttcatccaa ccatgttcag 900
tccacaggac ccttccctct gaggtctcat ttgattcttt ctcctgagaa gatgcagaga 960
tcctgataat ataaatgggg aagctgaggc tgctctttgt cacttcctcc gactgctcct 1020
gagcacctga gtttgcaagc acgcgccggc tggtgctaga gacatggtgg tatcccgtga 1080
cactcagcct caggatgggg gagactgatg tgaaatacaa ataacttaaa cactttcagg 1140
caaagataag cactgggcct agttcagaga agtggcaaat tgctactctg gcctgtctct 1200
gaccaactcc cagttctcta cagagcacgg gaaagcccct cggggacgtc tttcctgcag 1260
tgtgcaggct gcccttctcc cctgctcttc ccagttgatg ggatggttgt gttttctcta 1320
tgaaaaaagg agttggcacc ttgggctttc tgaaacacac aggtgtttta gaaatcagtg 1380

```
gagggtgaga gaaaggcatg gttgtggagg cactggactg tgaacaaggt ctgcagcggg   1440
tccccctgct gtctctctct actgcatgga gcctcctatg aagcccaagg tggctggggg   1500
ctgaggctcc cttgggcctg ccatggaact gattctgagt caagcagact ttccacggac   1560
catgctacat gagccgaggt gaggcactag ttagtgctcc tttcctgttg cagtggagat   1620
ttggctcctc tgtactaaaa tatctgcatg ctctccaaac aggtgtgagg gcaaatcaca   1680
tgaccttggc agctgtaatt aaagtttgtg ggggcttttc ggatgactta tgaggagtgg   1740
ctgtgattcg cacctttcac tcttagtagc actcgccctc ccctgttctc tgttgcctga   1800
agctggagag gtccttggaa ccccgaggcc tgagaaaggg aaatgggttt gagagccccc   1860
attagtgtgg aacaaagggt tgagtgagcc tgggctttga gctgtcgggg tcctaattca   1920
gcagctgtgt gactgtgtgc caggctgttg atctctgagc ttctgtttct acctgcttaa   1980
aatgacggtt actgcacagg gctgtgtgag ggttacagtg cgtctctggg ctgctcccag   2040
ccatggcagg cccctgggaa tcaaggtcat cagctgcttg tccaaggcag cagttagtgg   2100
ttgtgaatgg tgcgtgtgag atctgcatcc tggcgtcagg cctccttcct gccttaccca   2160
ggacagccca gttgcagctg ggttggtccc acagtcccac acacacacag cccgagtgtg   2220
gtgcctcacg tgggctgccc cgtgcctacc cacagccaca gaccccgcac ctggaggagg   2280
acttgaagga ggtgctgcgt tctgaggctg gcatcgaact catcatcgag gacgacatca   2340
ggcccgagaa gcagaagagg aagcctgggc tgcggcggag ccccatcaag aaagtccgga   2400
agtctctggc tcttgacatt gtggatgagg atgtgaagct gatgatgtcc acactgccca   2460
agtctctatc cttgccgaca actgcccctt caaactcttc cagcctcacc ctgtcaggta   2520
tcaaagaaga caacagcttg ctcaaccagg gcttcttgca ggccaagccc gagaaggcag   2580
cagtggccca gaagccccga agccacttca cgacacctgc ccctatgtcc agtgcctgga   2640
agacggtggc ctgcgggggg accagggacc agcttttcat gcaggagaaa gcccggcagc   2700
tcctgggccg cctgaagccc agccacacat ctcggaccct catcttgtcc tgaggtgttg   2760
agggtgtcac gagcccattc acatgtttac aggggttgtg gggcagaggg ggtctgtga    2820
atctgagagt cattcaggtg acctcctgca gggagccttc tgccaccagc ccctccccag   2880
actctcaggt ggaggcaaca gggccatgtg ctgccctgtt gccgagccca gctgtgggcg   2940
gctcctggtg ctaacaacaa agttccactt ccaggtctgc ctggttcccc ccccaaggcc   3000
acagggagct ccgtcagctt ctcccaagcc cacgtcaggc ctggcctcat ctcagaccct   3060
gcttaggatg ggggatgtgg ccaggggtgc tcctgtgctc accctctctt ggtgcatttt   3120
tttggaagaa taaaattgcc tctctctttg aaaaaaaaaa aaaaaaa                 3167
```

<210> SEQ ID NO 140
<211> LENGTH: 2379
<212> TYPE: DNA
<213> ORGANISM: Homo sapiens

<400> SEQUENCE: 140

```
gacccccgag ctgtgctgct cgcggccgcc accgccgggc cccggccgtc cctggctccc     60
ctcctgcctc gagaagggca gggcttctca gaggcttggc gggaaaaaga acggagggag    120
ggatcgcgct gagtataaaa gccggttttc ggggctttat ctaactcgct gtagtaattc    180
cagcgagagg cagagggagc gagcgggcgg ccggctaggg tggaagagcc gggcgagcag    240
agctgcgctg cgggcgtcct gggaagggag atccggagcg aatagggggc ttcgcctctg    300
gcccagccct cccgctgatc ccccagccag cggtccgcaa cccttgccgc atccacgaaa    360
```

-continued

```
ctttgcccat agcagcgggc gggcactttg cactggaact tacaacaccc gagcaaggac    420
gcgactctcc cgacgcgggg aggctattct gcccatttgg ggacacttcc ccgccgctgc    480
caggacccgc ttctctgaaa ggctctcctt gcagctgctt agacgctgga ttttttttcgg    540
gtagtggaaa accagcagcc tcccgcgacg atgcccctca acgttagctt caccaacagg    600
aactatgacc tcgactacga ctcggtgcag ccgtatttct actgcgacga ggaggagaac    660
ttctaccagc agcagcagca gagcgagctg cagcccccgg cgcccagcga ggatatctgg    720
aagaaattcg agctgctgcc caccccgccc ctgtccccta gccgccgctc cgggctctgc    780
tcgccctcct acgttgcggt cacacccttc tcccttcggg gagacaacga cggcggtggc    840
gggagcttct ccacggccga ccagctggag atggtgaccg agctgctggg aggagacatg    900
gtgaaccaga gtttcatctg cgacccggac gacgagacct tcatcaaaaa catcatcatc    960
caggactgta tgtggagcgg cttctcggcc gccgccaagc tcgtctcaga gaagctggcc   1020
tcctaccagg ctgcgcgcaa agacagcggc agcccgaacc ccgcccgcgg ccacagcgtc   1080
tgctccacct ccagcttgta cctgcaggat ctgagcgccg ccgcctcaga gtgcatcgac   1140
ccctcggtgg tcttccccta ccctctcaac gacagcagct cgcccaagtc ctgcgcctcg   1200
caagactcca gcgccttctc tccgtcctcg gattctctgc tctcctcgac ggagtcctcc   1260
ccgcagggca gccccgagcc cctggtgctc catgaggaga caccgcccac caccagcagc   1320
gactctgagg aggaacaaga agatgaggaa gaaatcgatg ttgtttctgt ggaaaagagg   1380
caggctcctg gcaaaaggtc agagtctgga tcaccttctg ctggaggcca cagcaaacct   1440
cctcacagcc cactggtcct caagaggtgc cacgtctcca cacatcagca caactacgca   1500
gcgcctccct ccactcggaa ggactatcct gctgccaaga gggtcaagtt ggacagtgtc   1560
agagtcctga gacagatcag caacaaccga aaatgcacca gccccaggtc ctcggacacc   1620
gaggagaatg tcaagaggcg aacacacaac gtcttggagc gccagaggag gaacgagcta   1680
aaacggagct tttttgccct gcgtgaccag atcccggagt tggaaaacaa tgaaaaggcc   1740
cccaaggtag ttatccttaa aaaagccaca gcatacatcc tgtccgtcca agcagaggag   1800
caaaagctca tttctgaaga ggacttgttg cggaaacgac gagaacagtt gaaacacaaa   1860
cttgaacagc tacggaactc ttgtgcgtaa ggaaaagtaa ggaaaacgat tccttctaac   1920
agaaatgtcc tgagcaatca cctatgaact tgtttcaaat gcatgatcaa atgcaacctc   1980
acaaccttgg ctgagtcttg agactgaaag atttagccat aatgtaaact gcctcaaatt   2040
ggactttggg cataaaagaa cttttttatg cttaccatct tttttttttc tttaacagat   2100
ttgtatttaa gaattgtttt taaaaaattt taagatttac acaatgtttc tctgtaaata   2160
ttgccattaa atgtaaataa ctttaataaa acgtttatag cagttacaca gaatttcaat   2220
cctagtatat agtacctagt attataggta ctataaaccc taattttttt tatttaagta   2280
cattttgctt tttaaagttg atttttttct attgttttta gaaaaaataa aataactggc   2340
aaatatatca ttgagccaaa tcttaaaaaa aaaaaaaaa                           2379
```

<210> SEQ ID NO 141
<211> LENGTH: 1799
<212> TYPE: DNA
<213> ORGANISM: Homo sapiens

<400> SEQUENCE: 141

```
gtgggaggat tgcattcagt ctagttcctg gttgccggct gaaataacct gctctccaaa     60
```

atgtccacaa aagtgactta agtcaggttc ccccaaacca gacaccaaga caagaatcca 120
tgtgtgtgtg actgaaggaa gtgctgggag agccccagct gcagcctgga tgtgaactgc 180
aactccaaag tgtgtccaga ctcaaggcaa gggcactagg ctttccagac ctcctactaa 240
gtcattgatc cagcactgcc ctgccaggac ataaatccct ggcacctctt gctctctgca 300
aaggagggca aagcagcttc aggagccctt gggagtcctc caaagagagt ctagggtaca 360
ggtccgaaag tagaagaaca cagaaggcag gccaggggca ctgtgagatg gtaaaagaga 420
tctgaaggga tccagaattc aagccaggaa gaagcagcaa tctgtcttct ggattaaaac 480
tgaagatcaa cctactttca acttactaag aaaggggatc atggacattg aagcatatct 540
tgaaagaatt ggctataaga agtctaggaa caaattggac ttggaaacat taactgatat 600
tcttcaacac cagatccgag ctgttccctt tgagaacctt aacatccatt gtggggatgc 660
catggactta ggcttagagg ccatttttga tcaagttgtg agaagaaatc ggggtggatg 720
gtgtctccag gtcaatcatc ttctgtactg ggctctgacc actattggtt ttgagaccac 780
gatgttggga gggtatgttt acagcactcc agccaaaaaa tacagcactg gcatgattca 840
ccttctcctg caggtgacca ttgatggcag gaactacatt gtcgatgctg ggtttggacg 900
ctcataccag atgtggcagc ctctggagtt aatttctggg aaggatcagc ctcaggtgcc 960
ttgtgtcttc cgtttgacgg aagagaatgg attctggtat ctagaccaaa tcagaaggga 1020
acagtacatt ccaaatgaag aatttcttca ttctgatctc ctagaagaca gcaaataccg 1080
aaaaatctac tcctttactc ttaagcctcg aacaattgaa gattttgagt ctatgaatac 1140
atacctgcag acatctccat catctgtgtt tactagtaaa tcattttgtt ccttgcagac 1200
cccagatggg gttcactgtt tggtgggctt caccctcacc cataggagat tcaattataa 1260
ggacaataca gatctaatag agttcaagac tctgagtgag gaagaaatag aaaaagtgct 1320
gaaaaatata tttaatattt ccttgcagag aaagcttgtg cccaaacatg gtgatagatt 1380
ttttactatt tagaataagg agtaaaacaa tcttgtctat ttgtcatcca gctcaccagt 1440
tatcaactga cgacctatca tgtatcttct gtacccttac cttattttga agaaaatcct 1500
agacatcaaa tcatttcacc tataaaaatg tcatcatata taattaaaca gctttttaaa 1560
gaaacataac cacaaacctt ttcaaataat aataataata ataataataa atgtctttta 1620
aagatggcct gtggttatct tggaaattgg tgatttatgc tagaaagctt ttaatgttgg 1680
tttattgttg aattcctaga aaagttttat gggtagatga gtaaataaaa tattgtaaaa 1740
aaacttattg tctataaagt atattaaaac attgttggct aatataaaaa aaaaaaaaa 1799

<210> SEQ ID NO 142
<211> LENGTH: 1644
<212> TYPE: DNA
<213> ORGANISM: Homo sapiens

<400> SEQUENCE: 142
gcgcgcgggt ttcgttgacc cgcggcgttc acgggaattg ttcgctttag tgccggcgcc 60
atggggtcgg agctgatcgg gcgcctagcc ccgcgcctgg gcctcgccga gcccgacatg 120
ctgaggaaag cagaggagta cttgcgcctg tcccgggtga agtgtgtcgg cctctccgca 180
cgcaccacgg agaccagcag tgcagtcatg tgcctggacc ttgcagcttc ctggatgaag 240
tgccccttgg acagggctta tttaattaaa ctttctggtt tgaacaagga gacatatcag 300
agctgtctta aatcttttga gtgtttactg ggcctgaatt caaatattgg aataagagac 360
ctagctgtac agtttagctg tatagaagca gtgaacatgg cttcaaagat actaaaaagc 420
tatgagtcca gtcttcccca gacacagcaa gtggatcttg acttatccag gccacttttc 480
acttctgctg cactgctttc agcatgcaag attctaaagc tgaaagtgga taaaaacaaa 540
atggtagcca catccggtgt aaaaaaagct atatttgatc gactgtgtaa acaactagag 600
aagattggac agcaggtcga cagagaacct ggagatgtag ctactccacc acggaagaga 660
aagaagatag tggttgaagc cccagcaaag gaaatggaga aggtagagga gatgccacat 720
aaaccacaga aagatgaaga tctgacacag gattatgaag aatggaaaag aaaaattttg 780
gaaaatgctg ccagtgctca aaaggctaca gcagagtgat ttcagcttcc aaactggtat 840
acattccaaa ctgatagtac attgccatct ccaggaagac ttgacggctt tgggattttg 900
tttaaacttt tataataagg atcctaagac tgttgccttt aaatagcaaa gcagcctacc 960
tggaggctaa gtctgggcag tgggctggcc cctggtgtga gcattagacc agccacagtg 1020
cctgattggt atagccttat gtgctttcct acaaaatgga attggaggcc gggcgcagtg 1080
gctcacgcct gtaatcccag cactttggga ggccaaggtg ggtggatcac ctgaggtcag 1140
gagctcgaga ccagcctggc caacatggtg aaaccccatc tctactaaaa atacaaaaat 1200
tagccaggtg tgatggtgca tgcctgtaat cccagctcct cagtaggctg agacaggagc 1260
atcacttgaa cgtgggaggc agaggttgca gtgagccgag attgcaccac cgcactccag 1320
cctgggtgac agagcgagac ttatctcata aataaataga tagatactcc agcctgggtg 1380
acagagcgag acttatagat agatagatag atagatggat agatagatag atagatagat 1440
agatagataa acggaattgg agccattttg ctttaagtga atggcagtcc cttgtcttat 1500
tcagaatata aaattcagtc tgaatggcat cttacagatt ttacttcaat ttttgtgtac 1560
ggtatttttt atttgactaa atcaatatat tgtacagcct aagttaataa atgttattta 1620
tatatgcaaa aaaaaaaaaa aaaa 1644

<210> SEQ ID NO 143
<211> LENGTH: 13037
<212> TYPE: DNA
<213> ORGANISM: Homo sapiens

<400> SEQUENCE: 143
agtccacagc tgtcactaat cggggtaagc cttgttgtat ttgtgcgtgt gggtggcatt 60
ctcaatgaga actagcttca cttgtcattt gagtgaaatc tacaacccga ggcggctagt 120
gctcccgcac tactgggatc tgagatcttc ggagatgact gtcgcccgca gtacggagcc 180
agcagaagtc cgacccttcc tgggaatggg ctgtaccgag aggtccgact agccccaggg 240
ttttagtgag ggggcagtgg aactcagcga gggactgaga gcttcacagc atgcacgagt 300
ttgatgccag agaaaaagtc gggagataaa ggagccgcgt gtcactaaat tgccgtcgca 360
gccgcagcca ctcaagtgcc ggacttgtga gtactctgcg tctccagtcc tcggacagaa 420
gttggagaac tctcttggag aactccccga gttaggagac gagatctcct aacaattact 480
actttttctt gcgctcccca cttgccgctc gctgggacaa acgacagcca cagttcccct 540
gacgacagga tggaggccaa gggcaggagc tgaccagcgc cgccctcccc cgccccccgac 600 ccaggaggtg gagatccctc cggtccagcc acattcaaca cccactttct cctccctctg 660
cccctatatt cccgaaaccc cctcctcctt cccttttccc tcctcctgga gacgggggag 720
gagaaaaggg gagtccagtc gtcatgactg agctgaaggc aaagggtccc cgggctcccc 780
acgtggcggg cggcccgccc tcccccgagg tcggatcccc actgctgtgt cgcccagccg 840

-continued caggtccgtt cccggggagc cagacctcgg acaccttgcc tgaagtttcg gccataccta 900
tctccctgga cgggctactc ttccctcggc cctgccaggg acaggacccc tccgacgaaa 960
agacgcagga ccagcagtcg ctgtcggacg tggagggcgc atattccaga gctgaagcta 1020
caaggggtgc tggaggcagc agttctagtc ccccagaaaa ggacagcgga ctgctggaca 1080
gtgtcttgga cactctgttg gcgccctcag gtcccgggca gagccaaccc agccctcccg 1140
cctgcgaggt caccagctct tggtgcctgt ttggccccga acttcccgaa gatccaccgg 1200
ctgcccccgc cacccagcgg gtgttgtccc cgctcatgag ccggtccggg tgcaaggttg 1260
gagacagctc cgggacggca gctgcccata aagtgctgcc ccggggcctg tcaccagccc 1320
ggcagctgct gctcccggcc tctgagagcc ctcactggtc cggggcccca gtgaagccgt 1380
ctccgcaggc cgctgcggtg gaggttgagg aggaggatgg ctctgagtcc gaggagtctg 1440
cgggtccgct tctgaagggc aaacctcggg ctctgggtgg cgcggcggct ggaggaggag 1500
ccgcggctgt cccgccgggg gcggcagcag gaggcgtcgc cctggtcccc aaggaagatt 1560
cccgcttctc agcgcccagg gtcgccctgg tggagcagga cgcgccgatg gcgcccgggc 1620
gctccccgct ggccaccacg gtgatggatt tcatccacgt gcctatcctg cctctcaatc 1680
acgccttatt ggcagcccgc actcggcagc tgctggaaga cgaaagttac gacggcgggg 1740
ccggggctgc cagcgccttt gccccgccgc ggagttcacc ctgtgcctcg tccaccccgg 1800
tcgctgtagg cgacttcccc gactgcgcgt acccgcccga cgccgagccc aaggacgacg 1860
cgtaccctct ctatagcgac ttccagccgc ccgctctaaa gataaaggag gaggaggaag 1920
gcgcggaggc ctccgcgcgc tccccgcgtt cctaccttgt ggccggtgcc aaccccgcag 1980
ccttcccgga tttcccgttg ggccaccgc ccccgctgcc gccgcgagcg accccatcca 2040
gacccgggga agcggcggtg acggccgcac ccgccagtgc ctcagtctcg tctgcgtcct 2100
cctcggggtc gaccctggag tgcatcctgt acaaagcgga gggcgcgccg ccccagcagg 2160
gcccgttcgc gccgccgccc tgcaaggcgc cgggcgcgag cggctgcctg ctcccgcggg 2220
acggcctgcc ctccacctcc gcctctgccg ccgccgccgg ggcggccccc gcgctctacc 2280
ctgcactcgg cctcaacggg ctcccgcagc tcggctacca ggccgccgtg ctcaaggagg 2340
gcctgccgca ggtctacccg ccctatctca actacctgag gccggattca gaagccagcc 2400
agagcccaca atacagcttc gagtcattac ctcagaagat ttgtttaatc tgtggggatg 2460
aagcatcagg ctgtcattat ggtgtcctta cctgtgggag ctgtaaggtc ttctttaaga 2520
gggcaatgga agggcagcac aactacttat gtgctggaag aaatgactgc atcgttgata 2580
aaatccgcag aaaaaactgc ccagcatgtc gccttagaaa gtgctgtcag gctggcatgg 2640
tccttggagg tcgaaaattt aaaaagttca ataaagtcag agttgtgaga gcactggatg 2700
ctgttgctct cccacagcca gtgggcgttc caaatgaaag ccaagcccta agccagagat 2760 tcacttttc accaggtcaa gacatacagt tgattccacc actgatcaac ctgttaatga 2820
gcattgaacc agatgtgatc tatgcaggac atgacaacac aaaacctgac acctccagtt 2880
ctttgctgac aagtcttaat caactaggcg agaggcaact tctttcagta gtcaagtggt 2940
ctaaatcatt gccaggtttt cgaaacttac atattgatga ccagataact ctcattcagt 3000
attcttggat gagcttaatg gtgtttggtc taggatggag atcctacaaa cacgtcagtg 3060
ggcagatgct gtattttgca cctgatctaa tactaaatga acagcggatg aaagaatcat 3120
cattctattc attatgcctt accatgtggc agatcccaca ggagtttgtc aagcttcaag 3180
ttagccaaga agagttcctc tgtatgaaag tattgttact tcttaataca attcctttgg 3240

-continued aagggctacg aagtcaaacc cagtttgagg agatgaggtc aagctacatt agagagctca 3300
tcaaggcaat tggtttgagg caaaaaggag ttgtgtcgag ctcacagcgt ttctatcaac 3360
ttacaaaact tcttgataac ttgcatgatc ttgtcaaaca acttcatctg tactgcttga 3420
atacatttat ccagtcccgg gcactgagtg ttgaatttcc agaaatgatg tctgaagtta 3480
ttgctgcaca attacccaag atattggcag ggatggtgaa accccttctc tttcataaaa 3540
agtgaatgtc atctttttct tttaaagaat taaattttgt ggtatgtctt tttgttttgg 3600
tcaggattat gaggtcttga gtttttataa tgttcttctg aaagccttac atttataaca 3660
tcatagtgtg taaatttaaa agaaaaattg tgaggttcta attattttct tttataaagt 3720
ataattagaa tgtttaactg ttttgtttac ccatattttc ttgaagaatt tacaagattg 3780
aaaaagtact aaaattgtta aagtaaacta tcttatccat attatttcat accatgtagg 3840
tgaggatttt taacttttgc atctaacaaa tcatcgactt aagagaaaaa atcttacatg 3900
taataacaca aagctattat atgttatttc taggtaactc cctttgtgtc aattatattt 3960
ccaaaaatga acctttaaaa tggtatgcaa aattttgtct atatatattt gtgtgaggag 4020
gaaattcata actttcctca gattttcaaa agtattttta atgcaaaaaa tgtagaaaga 4080
gtttaaaacc actaaaatag attgatgttc ttcaaactag gcaaaacaac tcatatgtta 4140
agaccatttt ccagattgga aacacaaatc tcttaggaag ttaataagta gattcatatc 4200
attatgcaaa tagtattgtg ggttttgtag gtttttaaaa taaccttttt tggggagaga 4260
attgtcctct aatgaggtat tgcgagtgga cataagaaat cagaagatta tggcctaact 4320
gtactcctta ccaactgtgg catgctgaaa gttagtcact cttactgatt ctcaattctc 4380
tcacctttga aagtagtaaa atatctttcc tgccaattgc tcctttgggt cagagcttat 4440
taacatcttt tcaaatcaaa ggaaagaaga aagggagagg aggaggaggg aggtatcaat 4500
tcacatacct ttctcctctt tatcctccac tatcatgaat tcatattatg tttcagccat 4560
gcaaatcttt ttaccatgaa atttcttcca gaattttccc cctttgacac aaattccatg 4620
catgtttcaa ccttcgagac tcagccaaat gtcatttctg taaaatcttc cctgagtctt 4680
ccaagcagta atttgccttc tcctagagtt tacctgccat tttgtgcaca tttgagttac 4740
agtagcatgt tattttacaa ttgtgactct cctgggagtc tgggagccat ataaagtggt 4800
caatagtgtt tgctgactga gagttgaatg acattttctc tctgtcttgg tattactgta 4860
gatttcgatc attctttggt tacatttctg catatttctg tacccatgac tttatcactt 4920
tcttctccca tgctttatct ccatcaatta tcttcattac ttttaaattt tccacctttg 4980
cttcctactt tgtgagatct ctccctttac tgactataac atagaagaat agaagtgtat 5040
tttatgtgtc ttaaggacaa tactttagat tccttgttct aagtttttaa actgaatgaa 5100
tggaatatta tttctctccc taagcaaaat tccacaaaac aattatttct tatgtttatg 5160
tagccttaaa ttgttttgta ctgtaaacct cagcataaaa actttcttca tttctaattt 5220
cattcaacaa atattgattg aatacctggt attagcacaa gaaaaatgtg ctaataagcc 5280
ttatgagaat ttggagctga agaaagacat ataactcagg aaagttacag tccagtagta 5340
ggtataaatt acagtgcctg ataaataggc attttaatat ttgtacactc aacgtatact 5400
aggtaggtgc aaaacattta catataattt tactgatacc catgcagcac aaaggtacta 5460
actttaaata ttaaataaca cctttatgtg tcagtaattc atttgcatta aatcttattg 5520
aaaaggcttt caatatattt tccccacaaa tgtcatccca agaaaaaagt atttttaaca 5580

-continued

```
tctcccaaat ataatagtta caggaaatct acctctgtga gagtgacacc tctcagaatg   5640
aactgtgtga cacaagaaaa tgaatgtagg tctatccaaa aaaaacccca agaaacaaaa   5700
acaatattat tagcccttta tgcttaagtg atggactcag ggaacagttg atgttgtgat   5760
cattttatta tctgattctt gttactttga attaaaccaa tattttgatg atataaatca   5820
tttccaccag catatattta atttccataa taactttaaa attttctaat ttcactcaac   5880
tatgagggaa tagaatgtgg tggccacagg tttggctttt gttaaaatgt ttgatatctt   5940
cgatgttgat ctctgtctgc aatgtagatg tctaaacact aggatttaat atttaaggct   6000
aagctttaaa aataaagtac ctttttaaaa agaatatggc ttcaccaaat ggaaaatacc   6060
taatttctaa atctttttct ctacaaagtc ctatctacta atgtctccat tactatttag   6120
tcatcataac cattatcttc attttacatg tcgtgttctt tctggtagct ctaaaatgac   6180
actaaatcat aagaagacag gttacatatc aggaaatact tgaaggttac tgaaatagat   6240
tcttgagtta atgaaaatat tttctgtaaa aaggtttgaa aagccatttg agtctaaagc   6300
attatacctc cattatcagt agttatgtga caattgtgtg tgtgtttaat gtttaaagat   6360
gtggcacttt ttaataaggc aatgctatgc tattttttcc catttaacat taagataatt   6420
tattgctata cagatgatat ggaaatatga tgaacaatat tttttttgcc aaaactatgc   6480
cttgtaagta gccatggaat gtcaacctgt aacttaaatt atccacagat agtcatgtgt   6540
ttgatgatgg gcactgtgga gataactgac ataggactgt gcccccccttc tctgccactt   6600
actagctgga tgagattaag caagtcattt aactgctctg attaaacctg cctttcccaa   6660
gtgctttgta atgaatagaa atggaaacca aaaaaaacgt atacaggcct tcagaaatag   6720
taattgctac tattttgttt tcattaagcc atagttctgg ctataatttt atcaaactca   6780
ccagctatat tctacagtga aagcaggatt ctagaaagtc tcactgtttt atttatgtca   6840
ccatgtgcta tgatatattt ggttgaattc atttgaaatt agggctggaa gtattcaagt   6900
aatttcttct gctgaaaaaa tacagtgttt tgagtttagg gcctgtttta tcaaagttct   6960
aaagagccta tcactcttcc attgtagaca ttttaaaata atgacactga ttttaacatt   7020
tttaagtgtc tttttagaac agagagcctg actagaacac agcccctcca aaaacccatg   7080
ctcaaattat ttttactatg gcagcaattc cacaaaaggg aacaatgggt ttagaaatta   7140
caatgaagtc atcaacccaa aaaacatccc tatccctaag aaggttatga tataaaatgc   7200
ccacaagaaa tctatgtctg ctttaatctg tcttttattg ctttggaagg atggctatta   7260
catttttagt ttttgctgtg aatacctgag cagtttctct catccatact tatccttcac   7320
acatcagaag tcaggataga atatgaatca ttttaaaaac ttttacaact ccagagccat   7380
gtgcataaga agcattcaaa acttgccaaa acatacattt tttttcaaat ttaaagatac   7440
tctatttttg tattcaatag ctcaacaact gtggtcccca ctgataaagt gaagtggaca   7500
aggagacaag taatggcata agtttgtttt tcccaaagta tgcctgttca atagccattg   7560
gatgtgggaa atttctacat ctcttaaaat tttacagaaa atacatagcc agatagtcta   7620
gcaaaagttc accaagtcct aaattgctta tccttacttc actaagtcat gaaatcattt   7680
taatgaaaag aacatcacct aggttttgtg gtttcttttt ttcttattca tggctgagtg   7740
aaaacaacaa tctctgtttc tccctagcat ctgtggacta tttaatgtac cattattcca   7800
cactctatgg tccttactaa atacaaaatt gaacaaaaag cagtaaaaca actgactctt   7860
cacccatatt ataaaatata atccaagcca gattagtcaa catccataag atgaatccaa   7920
gctgaactgg gcctagatta ttgagttcag gttggatcac atccctattt attaataaac   7980
```

ttaggaaaga aggccttaca gaccatcagt tagctggagc taatagaacc tacacttcta 8040
aagttcggcc tagaatcaat gtggccttaa aagctgaaaa gaagcaggaa agaacagttt 8100
tcttcaataa tttgtccacc ctgtcactgg agaaaattta agaatttggg ggtgttggta 8160
gtaagttaaa cacagcagct gttcatggca gaaattattc aatacatacc ttctctgaat 8220
atcctataac caaagcaaag aaaaacacca aggggtttgt tctcctcctt ggagttgacc 8280
tcattccaag gcagagctca ggtcacaggc acaggggctg cgcccaagct tgtccgcagc 8340
cttatgcagc tgtggagtct ggaagactgt tgcaggactg ctggcctagt cccagaatgt 8400
cagcctcatt ttcgatttac tggctcttgt tgctgtatgt catgctgacc ttattgttaa 8460
acacaggttt gtttgctttt tttccactca tggagacatg ggagaggcat tatttttaag 8520
ctggttgaaa gctttaaccg ataaagcatt tttagagaaa tgtgaatcag gcagctaaga 8580
aagcatactc tgtccattac ggtaaagaaa atgcacagat tattaactct gcagtgtggc 8640
attagtgtcc tggtcaatat tcggatagat atgaataaaa tatttaaatg gtattgtaaa 8700
tagttttcag gacatatgct atagcttatt tttattatct tttgaaattg ctcttaatac 8760
atcaaatcct gatgtattca atttatcaga tataaattat tctaaatgaa gcccagttaa 8820
atgtttttgt cttgtcagtt atatgttaag tttctgatct ctttgtctat gacgtttact 8880
aatctgcatt tttactgtta tgaattattt tagacagcag tggtttcaag ctttttgcca 8940
ctaaaaatac cttttatttt ctcctccccc agaaaagtct ataccttgaa gtatctatcc 9000
accaaactgt acttctatta agaaatagtt attgtgtttt cttaatgttt tgttattcaa 9060
agacatatca atgaaagctg ctgagcagca tgaataacaa ttatatccac acagatttga 9120
tatattttgt gcagccttaa cttgatagta taaaatgtca ttgcttttta aataatagtt 9180
agtcaatgga cttctatcat agctttccta aactaggtta agatccagag ctttggggtc 9240
ataatatatt acatacaatt aagttatctt tttctaaggg ctttaaaatt catgagaata 9300
accaaaaaag gtatgtggag agttaataca aacataccat attcttgttg aaacagagat 9360
gtggctctgc ttgttctcca taaggtagaa atactttcca gaatttgcct aaactagtaa 9420
gccctgaatt tgctatgatt agggatagga agagattttc acatggcaga ctttagaatt 9480
cttcacttta gccagtaaag tatctccttt tgatcttagt attctgtgta ttttaacttt 9540
tctgagttgt gcatgtttat aagaaaaatc agcacaaagg gtttaagtta aagccttttt 9600
actgaaattt gaaagaaaca gaagaaaata tcaaagttct ttgtattttg agaggattaa 9660
atatgattta caaaagttac atggagggct ctctaaaaca ttaaattaat tattttttgt 9720
tgaaaagtct tactttaggc atcattttat tcctcagcaa ctagctgtga agcctttact 9780
gtgctgtatg ccagtcactc tgctagattg tggagattac cagtgttccc gtcttctccg 9840
agcttagagt tggatgggga ataaagacag gtaaacagat agctacaata ttgtactgtg 9900
aatgcttatg ctggaggaag tacagggaac tattggagca cctaagagga gcacctacct 9960
tgaatttagg ggttagcaga ggcatcctga aaaaagtcaa agctaagcca caatctataa 10020
gcagtttagg aattagcaga acgtgcgtgg tgaggagatg ccaaaggcaa gaagagaaga 10080
gtattccaaa caggagggat tccaaagaga gaagagtatc ccaaacaaca tttgcacaaa 10140
cctgatgggg agagagaatg tggggtgggg atggatgatg agactgaaga agaaagccag 10200
gtctagataa tcagtggcct tgtacaccat gttaaagagt gtagacttga ttctgttgta 10260
aacaggaaag cagcacaatt catatgaata ttttagaaga ctcccactgg aatatggaga 10320

-continued ataaagttgg agatgactaa tcctggaagc agggagaaca tttttgagga agttgcacta 10380
ttttggtgaa aatgatgatc ataaacatga agaattgtag gtgatcatga cctcctctct 10440
aattttccag aagggttttg gaagatataa cataggaaca ttgacaggac tgacgaaagg 10500
agatgaaata caccatataa attgtcaaac acaaggccag atgtctaatt attttgctta 10560
tgtgttgaaa ttacaaattt ttcatcagga aaccaaaaac tacaaaactt agttttccca 10620
agtcccagaa ttctatctgt ccaaacaatc tgtaccactc cacctatatc cctacctttg 10680
catgtctgtc caacctcaaa gtccaggtct atacacacgg gtaagactag agcagttcaa 10740
gtttcagaaa atgagaaaga ggaactgagt tgtgctgaac ccatacaaaa taaacacatt 10800
ctttgtatag attcttggaa cctcgagagg aattcaccta actcataggt atttgatggt 10860
atgaatccat ggctgggctc ggcttttaaa aagccttatc tgggattcct tctatggaac 10920
caagttccat caaagcccat ttaaaagcct acattaaaaa caaaattctt gctgcattgt 10980
atacaaataa tgatgtcatg atcaaataat cagatgccat tatcaagtgg aattacaaaa 11040
tggtataccc actccaaaaa aaaaaaaaaa gctaaattct cagtagaaca ttgtgacttc 11100
atgagccctc cacagccttg gagctgagga gggagcactg gtgagcagta ggttgaagag 11160
aaaacttggc gcttaataat ctatccatgt tttttcatct aaaagagcct tctttttgga 11220
ttaccttatt caatttccat caaggaaatt gttagttcca ctaaccagac agcagctggg 11280
aaggcagaag cttactgtat gtacatggta gctgtgggaa ggaggtttct ttctccaggt 11340
cctcactggc catacaccag tcccttgtta gttatgcctg gtcatagacc cccgttgcta 11400
tcatctcata tttaagtctt tggcttgtga atttatctat tctttcagct tcagcactgc 11460
agagtgctgg gactttgcta acttccattt cttgctggct tagcacattc ctcataggcc 11520
cagctctttt ctcatctggc cctgctgtgg agtcaccttg ccccttcagg agagccatgg 11580
cttaccactg cctgctaagc ctccactcag ctgccaccac actaaatcca agcttctcta 11640
agatgttgca gactttacag gcaagcataa aaggcttgat cttcctggac ttccctttac 11700
ttgtctgaat ctcacctcct tcaactttca gtctcagaat gtaggcattt gtcctctttg 11760
ccctacatct tccttcttct gaatcatgaa agcctctcac ttcctcttgc tatgtgctgg 11820
aggcttctgt caggttttag aatgagttct catctagtcc tagtagcttt tgatgcttaa 11880
gtccaccttt taaggatacc tttgagattt agaccatgtt tttcgcttga gaaagcccta 11940
atctccagac ttgcctttct gtggatttca aagaccaact gaggaagtca aaagctgaat 12000
gttgactttc tttgaacatt tccgctataa caattccaat tctcctcaga gcaatatgcc 12060
tgcctccaac tgaccaggag aaaggtccag tgccaaagag aaaaacacaa agattaatta 12120
tttcagttga gcacatactt tcaaagtggt ttgggtattc atatgaggtt ttctgtcaag 12180
agggtgagac tcttcatcta tccatgtgtg cctgacagtt ctcctggcac tggctggtaa 12240
cagatgcaaa actgtaaaaa ttaagtgatc atgtatttta acgatatcat cacatactta 12300
ttttctatgt aatgttttaa atttccccta acatactttg actgttttgc acatggtaga 12360
tattcacatt tttttgtgtt gaagttgatg caatcttcaa agttatctac cccgttgctt 12420
attagtaaaa ctagtgttaa tacttggcaa gagatgcagg gaatctttct catgactcac 12480
gccctattta gttattaatg ctactaccct attttgagta agtagtaggt ccctaagtac 12540
attgtccaga gttatacttt taaagatatt tagccccata tacttcttga atctaaagtc 12600
atacaccttg ctcctcattt ctgagtggga aagacatttg agagtatgtt gacaattgtt 12660
ctgaaggttt ttgccaagaa ggtgaaactg tcctttcatc tgtgtatgcc tggggctggg 12720

```
tccctggcag tgatggggtg acaatgcaaa gctgtaaaaa ctaggtgcta gtgggcacct  12780

aatatcatca tcatatactt attttcaagc taatatgcaa aatcccatct ctgtttttaa  12840

actaagtgta gatttcagag aaaatatttt gtggttcaca taagaaaaca gtctactcag  12900

cttgacaagt gttttatgtt aaattggctg gtggtttgaa atgaatcatc ttcacataat  12960

gttttcttta aaaatattgt gaatttaact ctaattcttg ttattctgtg tgataataaa  13020

gaataaacta atttcta                                                 13037


<210> SEQ ID NO 144
<211> LENGTH: 3180
<212> TYPE: DNA
<213> ORGANISM: Homo sapiens

<400> SEQUENCE: 144

attctatgct gcagcctaag catcattcct cttctcttct tagtggagat aaaattaccc     60

actgctctcc ttacatttac tttgtccata tttgctccta tgctctaggc tcgtgcacaa    120

caaacacagt gtgggccctt accctagaag ccaacttctc atgacctttc tctatctcca    180

gaatccatgc agtgggaatg aaggtaaaag aaggttttca tgggatccag ctgagagctc    240

tacggggaaa atggatctga ggagccatgt gctccatctc ttttatttta caggtagaga    300

ctaggggtat agagtgaggt gaattaccgc agtgacccac acattgttgg cagacctagg    360

attagaactc tgtcttcctg gttcccagct tggtgctttt gaaagcatac ttgctgcttt    420

cttaccggcc tggtgtctgc cactttggga cagagtgtgg acttgctcac ctgccccatt    480

tcttagggat tctcattctg tgtttgagca agaatattct tattctggaa agaaccacat    540

accacaggat tctgggtgag cataaggaag attgtcttgg ggatctgact tagctcacgt    600

atagtggcta tgatgaattc agtgtcttat tttttgcata tgtatatttt tagtctaata    660

ttgcctgggt gtctgagcaa gtctagatga atttaattgc tctcattttt cccctgcccc    720

tcttcctttg gtctctcttt taggaaatgt ttttctttca acattcgttt cattcattat    780

ttactcattc ggccaaccaa catttattga gtgccttccc tgtatcaggg acaggggctt    840

acaaagtaga atttgatccc acctctgccc tcagtagctc agtgtctaat ggaggtagtg    900

atgttcatta agcgtcgcca gatactgtgc taggtgctgt gcctgttctc tctcgcttgt    960

tcctcacaca cttgagaagg ccgaagctga ttcatagctt ggaaggcagg ggccttggat   1020

ttgaacccag gcctgaccaa tggcagaacc tatcagatgt gtggacagat gacattgcct   1080

ttctttcttt ggatatatca aaatcagcca gcaggcagga actcccattt tgagcaagca   1140

atgtgcagga atgatagggt atacagagag gaacaggaga tggcccctga cttccagcat   1200

gtgtctgatg gacatccagg ctgcaggcat catggtgctg tctagagaga tgagccaggt   1260

gcccagagcc catgggccaa tgctgccctt tcttgagcat gccaaacaaa gcggttggtg   1320

tgttagaggc acagtctcct ccactctaag taaaaatcag catgagtcct agcccacatt   1380

tccctagtga gtacaccaaa gatatctatg aactggcagt catcagtgac ttcctaaggt   1440

tccggaaatg catctcttac tcaggagtaa gcaatgatgt gcctgcggct ttacgagttc   1500

tcacagaatg actttctgga cccaaatgtt ttttctgctt caggactgtg aaggccttat   1560

tgttcgctct gccaccaagg tgaccgctga tgtcatcaac gcagctgaga aactccaggt   1620

ggtgggcagg gctggcacag gtgtggacaa tgtggatctg gaggccgcaa caaggaaggg   1680

catcttggtt atgaacaccc ccaatgggaa cagcctcagt gccgcagaac tcacttgtgg   1740
```

aatgatcatg tgcctggcca ggcagattcc ccaggcgacg gcttcgatga aggacggcaa 1800
atgggagcgg aagaagttca tgggaacaga gctgaatgga aagaccctgg gaattcttgg 1860
cctgggcagg attgggagag aggtagctac ccggatgcag tcctttggga tgaagactat 1920
agggtatgac cccatcattt ccccagaggt ctcggcctcc tttggtgttc agcagctgcc 1980
cctggaggag atctggcctc tctgtgattt catcactgtg cacactcctc tcctgccctc 2040
cacgacaggc ttgctgaatg acaacacctt tgcccagtgc aagaaggggg tgcgtgtggt 2100
gaactgtgcc cgtggaggga tcgtggacga aggcgccctg ctccgggccc tgcagtctgg 2160
ccagtgtgcc ggggctgcac tggacgtgtt tacggaagag ccgccacggg accgggcctt 2220
ggtggaccat gagaatgtca tcagctgtcc ccacctgggt gccagcacca aggaggctca 2280
gagccgctgt ggggaggaaa ttgctgttca gttcgtggac atggtgaagg ggaaatctct 2340
cacgggggtt gtgaatgccc aggcccttac cagtgccttc tctccacaca ccaagccttg 2400
gattggtctg gcagaagctc tggggacact gatgcgagcc tgggctgggt cccccaaagg 2460
gaccatccag gtgataacac agggaacatc cctgaagaat gctgggaact gcctaagccc 2520
cgcagtcatt gtcggcctcc tgaaagaggc ttccaagcag gcggatgtga acttggtgaa 2580
cgctaagctg ctggtgaaag aggctggcct caatgtcacc acctcccaca gccctgctgc 2640
accagggggg caaggcttcg gggaatgcct cctggccgtg gccctggcag gcgcccctta 2700
ccaggctgtg ggcttggtcc aaggcactac acctgtactg caggggctca atggagctgt 2760
cttcaggcca gaagtgcctc tccgcaggga cctgcccctg ctcctattcc ggactcagac 2820
ctctgaccct gcaatgctgc ctaccatgat tggcctcctg gcagaggcag gcgtgcggct 2880
gctgtcctac cagacttcac tggtgtcaga tggggagacc tggcacgtca tgggcatctc 2940
ctccttgctg cccagcctgg aagcgtggaa gcagcatgtg actgaagcct tccagttcca 3000
cttctaacct tggagctcac tggtccctgc ctctggggct ttctgaaga aacccaccca 3060 ctgtgatcaa tagggagaga aaatccacat tcttgggctg aacgcgagcc tctgacactg 3120
cttacactgc actctgaccc tgtagtacag caataaccgt ctaataaaga gcctaccccc 3180

<210> SEQ ID NO 145
<211> LENGTH: 1301
<212> TYPE: DNA
<213> ORGANISM: Homo sapiens
<220> FEATURE:
<221> NAME/KEY: misc_feature
<222> LOCATION: (1301)..(1301)
<223> OTHER INFORMATION: n is a, c, g, or t

<400> SEQUENCE: 145
caaacaaaaa cagccaagct tttctgccaa aaagatgact gagaagactg ttaaagcaaa 60
aagctctgtt cctgcctcag atgatgccta tccagaaata gaaaaattct ttcccttcaa 120
tcctctagac tttgagagtt ttgacctgcc tgaagagcac cagattgcgc acctcccctt 180
gagtggagtg cctctcatga tccttgacga ggagagagag cttgaaaagc tgtttcagct 240
gggcccccct tcacctgtga agatgccctc tccaccatgg gaatccaatc tgttgcagtc 300
tccttcaagc attctgtcga ccctggatgt tgaattgcca cctgtttgct gtgacataga 360
tatttaaatt tcttagtgct tcagagtctg tgtgtatttg tattaataaa gcattcttta 420
acagaaaaaa aaaaaaaaaa aaaaaaaaaa aaaaaaaaaa aaaaaaaaaa aggggggga 480 gacacaaaaa gaattcccca agagggggcc acaagataat cagaggatat cacacaagat 540
ctctcggcgc accaacgacg gggccccaa ataagggaga gacccagaat cacaacagcc 600
aagacacggt ggacacgacg gaaacaaaca cacagcccag acacgggggc aaacacgcgc 660
gcacaccgcg gacaccatgg gacaaagcag acaccaccca caaaacaaca ccgcggaggg 720
ggaagaacaa caaaacaagt gcgcaaacag aacacaacca cagaaagaga aaaattaaaa 780
cggcccccaa gacggcgaca acacaacaaa acaaccacta cagagcgctc aacagccgag 840
taaaaacaca acaacggaca actaacacac aaaggaatga aacaaagcgg ggccacacac 900
cgacaccgga aatccggcga acaactcaca ccgagcgagg gtcccagaca acaaatacac 960
agacaacgaa accgagaaac aagaccagca agacgagcag gcaaaagaca aacaagacag 1020
aggagacgac gacgaacgca aaggacaaga ggacacaacg acgcgaggag cgagagcgag 1080
aggaagagac aacaaaaaga cacaaaagaa caacaagcaa gcagcgaaga acgacacaca 1140
accacacgag acagcaggag cagaggcgga gaaaacacaa cgagcaagcc aagaccaaga 1200
gaggagaaca aaataaaaaa atacgagagc aggcggacga gagcacgaga cgaacagaca 1260
aacgggaatc agaagcataa cgatccgcga cgcgaacaac n 1301

<210> SEQ ID NO 146
<211> LENGTH: 3203
<212> TYPE: DNA
<213> ORGANISM: Homo sapiens

<400> SEQUENCE: 146
gtgcaccctg tcccagccgt cctgtcctgg ctgctcgctc tgcttcgctg cgcctccact 60
atgctctccc tccgtgtccc gctcgcgccc atcacggacc cgcagcagct gcagctctcg 120
ccgctgaagg ggctcagctt ggtcgacaag gagaacacgc cgccggccct gagcgggacc 180
cgcgtcctgg ccagcaagac cgcgaggagg atcttccagg agaaaacccc cgccgctttg 240
tcatcttccc catcgagtac catgatatct ggcagatgta taagaaggca gaggcttcct 300
tttggaccgc cgaggaggtg gacctctcca aggacattca gcactgggaa tccctgaaac 360
ccgaggagag atattttata tcccatgttc tggctttctt tgcagcaagc gatggcatag 420
taaatgaaaa cttggtggag cgatttagcc aagaagttca gattacagaa gcccgctgtt 480
tctatggctt ccaaattgcc atggaaaaca tacattctga aatgtatagt cttcttattg 540
acacttacat aaaagatccc aaagaaaggg aatttctctt caatgccatt gaaacgatgc 600
cttgtgtcaa gaagaaggca gactgggcct tgcgctggat tggggacaaa gaggctacct 660
atggtgaacg tgttgtagcc tttgctgcag tggaaggcat tttcttttcc ggttcttttg 720
cgtcgatatt ctggctcaag aaacgaggac tgatgcctgg cctcacattt tctaatgaac 780
ttattagcag agatgagggt ttacactgtg attttgcttg cctgatgttc aaacacctgg 840
tacacaaacc atcggaggag agagtaagag aaataattat caatgctgtt cggatagaac 900
aggagttcct cactgaggcc ttgcctgtga agctcattgg gatgaattgc actctaatga 960
agcaatacat tgagtttgtg gcagacagac ttatgctgga actgggtttt agcaaggttt 1020
tcagagtaga gaacccattt gactttatgg agaatatttc actggaagga aagactaact 1080
tctttgagaa gagagtaggc gagtatcaga ggatgggagt gatgtcaagt ccaacagaga 1140
attcttttac cttggatgct gacttctaaa tgaactgaag atgtgccctt acttggctga 1200 ttttttttt tccatctcat aagaaaaatc agctgaagtg ttaccaacta gccacaccat 1260
gaattgtccg taatgttcat taacagcatc tttaaaactg tgtagctacc tcacaaccag 1320
tcctgtctgt ttatagtgct ggtagtatca ccttttgcca gaaggcctgg ctggctgtga 1380
cttaccatag cagtgacaat ggcagtcttg gctttaaagt gaggggtgac cctttagtga 1440
gcttagcaca gcgggattaa acagtccttt aaccagcaca gccagttaaa agatgcagcc 1500
tcactgcttc aacgcagatt ttaatgttta cttaaatata aacctggcac tttacaaaca 1560
aataaacatt gtttgtactc acaaggcgat aatagcttga tttatttggt ttctacacca 1620
aatacattct cctgaccact aatgggagcc aattcacaat tcactaagtg actaaagtaa 1680
gttaaacttg tgtagactaa gcatgtaatt tttaagtttt attttaatga attaaaatat 1740
ttgttaacca actttaaagt cagtcctgtg tatacctaga tattagtcag ttggtgccag 1800
atagaagaca ggttgtgttt ttatcctgtg gcttgtgtag tgtcctggga ttctctgccc 1860
cctctgagta gagtgttgtg ggataaagga atctctcagg gcaaggagct tcttaagtta 1920
aatcactaga aatttagggg tgatctgggc cttcatatgt gtgagaagcc gtttcatttt 1980
atttctcact gtattttcct caacgtctgg ttgatgagaa aaaattcttg aagagttttc 2040
atatgtggga gctaaggtag tattgtaaaa tttcaagtca tccttaaaca aaatgatcca 2100
cctaagatct tgcccctgtt aagtggtgaa atcaactaga ggtggttcct acaagttgtt 2160
cattctagtt ttgtttggtg taagtaggtt gtgtgagtta attcatttat atttactatg 2220
tctgttaaat cagaaatttt ttattatcta tgttcttcta gattttacct gtagttcata 2280
cttcagtcac ccagtgtctt attctggcat tgtctaaatc tgagcattgt ctagggggat 2340
cttaaacttt agtaggaaac catgagctgt taatacagtt tccattcaaa tattaatttc 2400
agaatgaaac ataatttttt tttttttttt ttgagatgga gtctcgctct gttgcccagg 2460
ctggagtgca gtggcgcgat tttggctcac tgtaacctcc atctcctggg ttcaagcaat 2520
tctcctgtct cagcctccct agtagctggg actgcaggta tgtgctacca cacctggcta 2580
atttttgtat ttttagtaga gatggagttt caccatattg gtcaggctgg tcttgaactc 2640
ctgacctcag gtgatccacc cacctcggcc tcccaaagtg ctgggattgc aggcgtgata 2700
aacaaatatt cttaataggg ctactttgaa ttaatctgcc tttatgtttg ggagaagaaa 2760
gctgagacat tgcatgaaag atgatgagag ataaatgttg atcttttggc cccatttgtt 2820
aattgtattc agtatttgaa cgtcgtcctg tttattgtta gttttcttca tcatttattg 2880
tatagacaat ttttaaatct ctgtaatatg atacattttc ctatctttta agttattgtt 2940
acctaaagtt aatccagatt atatggtcct tatatgtgta caacattaaa atgaaaggct 3000
ttgtcttgca ttgtgaggta caggcggaag ttggaatcag gttttaggat tctgtctctc 3060
attagctgaa taatgtgagg attaacttct gccagctcag accatttcct aatcagttga 3120
aagggaaaca agtatttcag tctcaaaatt gaataatgca caagtcttaa gtgattaaaa 3180
taaaactgtt cttatgtcag ttt 3203

<210> SEQ ID NO 147
<211> LENGTH: 4482
<212> TYPE: DNA
<213> ORGANISM: Homo sapiens

<400> SEQUENCE: 147
agcgggggca ctccagccct gcagcctccg gagtcagtgc cgcgcgcccg ccgccccgcg 60
ccttcctgct cgccgcacct ccgggagccg gggcgcaccc agcccgcagc gccgcctccc 120
cgcccgcgcc gcctccgacc gcaggccgag ggccgccact ggccgggggg accgggcagc 180
agcttgcggc cgcggagccg ggcaacgctg gggactgcgc cttttgtccc cggaggtccc 240
tggaagtttg cggcaggacg cgcgcgggga ggcggcggag gcagccccga cgtcgcggag 300

```
aacagggcgc agagccggca tgggcatcgg gcgcagcgag gggggccgcc gcggggcagc    360
cctgggcgtg ctgctggcgc tgggcgcggc gcttctggcc gtgggctcgg ccagcgagta    420
cgactacgtg agcttccagt cggacatcgg cccgtaccag agcgggcgct tctacaccaa    480
gccacctcag tgcgtggaca tccccgcgga cctgcggctg tgccacaacg tgggctacaa    540
gaagatggtg ctgcccaacc tgctggagca cgagaccatg gcggaggtga agcagcaggc    600
cagcagctgg gtgcccctgc tcaacaagaa ctgccacgcc ggcacccagg tcttcctctg    660
ctcgctcttc gcgcccgtct gcctggaccg gcccatctac ccgtgtcgct ggctctgcga    720
ggccgtgcgc gactcgtgcg agccggtcat gcagttcttc ggcttctact ggcccgagat    780
gcttaagtgt gacaagttcc ccgaggggga cgtctgcatc gccatgacgc cgcccaatgc    840
caccgaagcc tccaagcccc aaggcacaac ggtgtgtcct ccctgtgaca acgagttgaa    900
atctgaggcc atcattgaac atctctgtgc cagcgagttt gcactgagga tgaaaataaa    960
agaagtgaaa aaagaaaatg gcgacaagaa gattgtcccc aagaagaaga agcccctgaa   1020
gttggggccc atcaagaaga aggacctgaa gaagcttgtg ctgtacctga agaatggggc   1080
tgactgtccc tgccaccagc tggacaacct cagccaccac ttcctcatca tgggccgcaa   1140
ggtgaagagc cagtacttgc tgacggccat ccacaagtgg gacaagaaaa acaaggagtt   1200
caaaaacttc atgaagaaaa tgaaaaacca tgagtgcccc acctttcagt ccgtgtttaa   1260
gtgattctcc cgggggcagg gtggggaggg agcctcgggt ggggtgggag cggggggggac  1320
agtgccccgg gaacccggtg ggtcacacac acgcactgcg cctgtcagta gtggacattt   1380
aatccagtcg gcttgttctt gcagcattcc cgctcccttc cctccatagc cacgctccaa   1440
accccagggt agccatggcc gggtaaagca agggccattt agattaggaa ggtttttaag   1500
atccgcaatg tggagcagca gccactgcac aggaggaggt gacaaaccat ttccaacagc   1560
aacacagcca ctaaaacaca aaaaggggga ttgggcggaa agtgagagcc agcagcaaaa   1620
actacatttt gcaacttgtt ggtgtggatc tattggctga tctatgcctt tcaactagaa   1680
aattctaatg attggcaagt cacgttgttt tcaggtccag agtagtttct ttctgtctgc   1740
tttaaatgga aacagactca taccacactt acaattaagg tcaagcccag aaagtgataa   1800
gtgcagggag gaaaagtgca agtccattat gtaatagtga cagcaaaggg accaggggag   1860
aggcattgcc ttctctgccc acagtctttc cgtgtgattg tctttgaatc tgaatcagcc   1920
agtctcagat gccccaaagt ttcggttcct atgagcccgg ggcatgatct gatccccaag   1980
acatgtggag gggcagcctg tgcctgcctt tgtgtcagaa aaaggaaacc acagtgagcc   2040
tgagagagac ggcgattttc gggctgagaa ggcagtagtt ttcaaaacac atagttaaaa   2100
aagaaacaaa tgaaaaaaat tttagaacag tccagcaaat tgctagtcag ggtgaattgt   2160
gaaattgggt gaagagctta cgattctaat ctcatgtttt ttccttttca catttttaaa   2220
agaacaatga caaacaccca cttatttttc aaggttttaa aacagtctac attgagcatt   2280
tgaaaggtgt gctagaacaa ggtctcctga tccgtccgag gctgcttccc agaggagcag   2340
ctctccccag gcatttgcca agggaggcgg atttccctgg tagtgtagct gtgtggcttt   2400
ccttcctgaa gagtccgtgg ttgccctaga acctaacacc ccctagcaaa actcacagag   2460
ctttccgttt ttttctttcc tgtaaagaaa catttccttt gaacttgatt gcctatggat   2520
caaagaaatt cagaacagcc tgcctgtccc ccccgcacttt ttacatatat ttgtttcatt  2580
tctgcagatg gaaagttgac atgggtgggg tgtccccatc cagcgagaga gtttaaaaag   2640
```

-continued caaaacatct ctgcagtttt tcccaagtgc cctgagatac ttcccaaagc ccttatgttt 2700
aatcagcgat gtatataagc cagttcactt agacaacttt acccttcttg tccaatgtac 2760
aggaagtagt tctaaaaaaa atgcatatta atttcttccc ccaaagccgg attcttaatt 2820
ctctgcaaca ctttgaggac atttatgatt gtccctctgg gccaatgctt atacccagtg 2880
aggatgctgc agtgaggctg taaagtggcc ccctgcggcc ctagcctgac ccggaggaaa 2940
ggatggtaga ttctgttaac tcttgaagac tccagtatga aaatcagcat gcccgcctag 3000
ttacctaccg gagagttatc ctgataaatt aacctctcac agttagtgat cctgtccttt 3060
taacaccttt tttgtggggt tctctctgac ctttcatcgt aaagtgctgg ggaccttaag 3120
tgatttgcct gtaattttgg atgattaaaa aatgtgtata tatattagct aattagaaat 3180
attctacttc tctgttgtca aactgaaatt cagagcaagt tcctgagtgc gtggatctgg 3240
gtcttagttc tggttgattc actcaagagt tcagtgctca tacgtatctg ctcattttga 3300
caaagtgcct catgcaaccg ggccctctct ctgcggcaga gtccttagtg gaggggttta 3360
cctggaacat tagtagttac cacagaatac ggaagagcag gtgactgtgc tgtgcagctc 3420
tctaaatggg aattctcagg taggaagcaa cagcttcaga aagagctcaa aataaattgg 3480
aaatgtgaat cgcagctgtg ggttttacca ccgtctgtct cagagtccca ggaccttgag 3540
tgtcattagt tactttattg aaggttttag acccatagca gctttgtctc tgtcacatca 3600
gcaatttcag aaccaaaagg gaggctctct gtaggcacag agctgcacta tcacgagcct 3660
ttgtttttct ccacaaagta tctaacaaaa ccaatgtgca gactgattgg cctggtcatt 3720
ggtctccgag agaggaggtt tgcctgtgat ttcctaatta tcgctagggc caaggtggga 3780
tttgtaaagc tttacaataa tcattctgga tagagtcctg ggaggtcctt ggcagaactc 3840
agttaaatct ttgaagaata tttgtagtta tcttagaaga tagcatggga ggtgaggatt 3900
ccaaaaacat tttattttta aaatatcctg tgtaacactt ggctcttggt acctgtgggt 3960
tagcatcaag ttctccccag ggtagaattc aatcagagct ccagtttgca tttggatgtg 4020
taaattacag taatcccatt tcccaaacct aaaatctgtt tttctcatca gactctgagt 4080
aactggttgc tgtgtcataa cttcatagat gcaggaggct caggtgatct gtttgagcag 4140
agcaccctag gcagcctgca gggaataaca tactggccgt tctgacctgt tgccagcaga 4200
tacacaggac atggatgaaa ttcccgtttc ctctagtttc ttcctgtagt actcctcttt 4260
tagatcctaa gtctcttaca aaagctttga atactgtgaa aatgttttac attccatttc 4320
atttgtgttg ttttttttaac tgcattttac cagatgtttt gatgttatcg cttatgttaa 4380
tagtaattcc cgtacgtgtt cattttattt tcatgctttt tcagccatgt atcaatattc 4440
acttgactaa aatcactcaa ttaatcaaaa aaaaaaaaaa aa 4482

<210> SEQ ID NO 148
<211> LENGTH: 3637
<212> TYPE: DNA
<213> ORGANISM: Homo sapiens

<400> SEQUENCE: 148
agtcctgggc gaagggggcg gtggttcccc gcggcgctgc gcgcggcggt aattagtgat 60
tgtcttccag cttcgcgaag gctaggggcg cggctgccgg gtggctgcgc ggcgctgccc 120
ccggaccgag gggcagccaa cccaatgaaa ccaccgcgtg ttcgcgcctg gtagagattt 180
ctcgaagaca ccagtgggcc cgttccgagc cctctggacc gcccgtgtgg aaccaaacct 240
gcgcgcgtgg ccgggccgtg ggacaacgag gccgcggaga cgaaggcgca atggcgagga 300

-continued

```
agttatctgt aatcttgatc ctgacctttg ccctctctgt cacaaatccc cttcatgaac    360
taaaagcagc tgctttcccc cagaccactg agaaaattag tccgaattgg gaatctggca    420
ttaatgttga cttggcaatt tccacacggc aatatcatct acaacagctt ttctaccgct    480
atggagaaaa taattctttg tcagttgaag ggttcagaaa attacttcaa aatataggca    540
tagataagat taaaagaatc catatacacc atgaccacga ccatcactca gaccacgagc    600
atcactcaga ccatgagcgt cactcagacc atgagcatca ctcagaccac gagcatcact    660
ctgaccatga tcatcactct caccataatc atgctgcttc tggtaaaaat aagcgaaaag    720
ctctttgccc agaccatgac tcagatagtt caggtaaaga tcctagaaac agccagggga    780
aaggagctca ccgaccagaa catgccagtg gtagaaggaa tgtcaaggac agtgttagtg    840
ctagtgaagt gacctcaact gtgtacaaca ctgtctctga aggaactcac tttctagaga    900
caatagagac tccaagacct ggaaaactct tccccaaaga tgtaagcagc tccactccac    960
ccagtgtcac atcaaagagc cgggtgagcc ggctggctgg taggaaaaca aatgaatctg   1020
tgagtgagcc ccgaaaaggc tttatgtatt ccagaaacac aaatgaaaat cctcaggagt   1080
gtttcaatgc atcaaagcta ctgacatctc atggcatggg catccaggtt ccgctgaatg   1140
caacagagtt caactatctc tgtccagcca tcatcaacca aattgatgct agatcttgtc   1200
tgattcatac aagtgaaaag aaggctgaaa tccctccaaa gacctattca ttacaaatag   1260
cctgggttgg tggttttata gccatttcca tcatcagttt cctgtctctg ctgggggtta   1320
tcttagtgcc tctcatgaat cgggtgtttt tcaaatttct cctgagtttc cttgtggcac   1380
tggccgttgg gactttgagt ggtgatgctt ttttacacct tcttccacat tctcatgcaa   1440
gtcaccacca tagtcatagc catgaagaac cagcaatgga aatgaaaaga ggaccacttt   1500
tcagtcatct gtcttctcaa aacatagaag aaagtgccta ttttgattcc acgtggaagg   1560
gtctaacagc tctaggaggc ctgtatttca tgtttcttgt tgaacatgtc ctcacattga   1620
tcaaacaatt taaagataag aagaaaaaga atcagaagaa acctgaaaat gatgatgatg   1680
tggagattaa gaagcagttg tccaagtatg aatctcaact ttcaacaaat gaggagaaag   1740
tagatacaga tgatcgaact gaaggctatt tacgagcaga ctcacaagag ccctcccact   1800
ttgattctca gcagcctgca gtcttggaag aagaagaggt catgatagct catgctcatc   1860
cacaggaagt ctacaatgaa tatgtaccca gagggtgcaa gaataaatgc cattcacatt   1920
tccacgatac actcggccag tcagacgatc tcattcacca ccatcatgac taccatcata   1980
ttctccatca tcaccaccac caaaaccacc atcctcacag tcacagccag cgctactctc   2040
gggaggagct gaaagatgcc ggcgtcgcca ctctggcctg gatggtgata atgggtgatg   2100
gcctgcacaa tttcagcgat ggcctagcaa ttggtgctgc ttttactgaa ggcttatcaa   2160
gtggtttaag tacttctgtt gctgtgttct gtcatgagtt gcctcatgaa ttaggtgact   2220
ttgctgttct actaaaggct ggcatgaccg ttaagcaggc tgtcctttat aatgcattgt   2280
cagccatgct ggcgtatctt ggaatggcaa caggaatttt cattggtcat tatgctgaaa   2340
atgtttctat gtggatattt gcacttactg ctggcttatt catgtatgtt gctctggttg   2400
atatggtacc tgaaatgctg cacaatgatg ctagtgacca tggatgtagc cgctgggggt   2460
atttcttttt acagaatgct gggatgcttt tgggttttgg aattatgtta cttatttcca   2520
tatttgaaca taaaatcgtg tttcgtataa atttctagtt aaggtttaaa tgctagagta   2580
gcttaaaaag ttgtcatagt ttcagtaggt catagggaga tgagtttgta tgctgtacta   2640
```

tgcagcgttt aaagttagtg ggttttgtga tttttgtatt gaatattgct gtctgttaca 2700
aagtcagtta aaggtacgtt ttaatattta agttattcta tcttggagat aaaatctgta 2760
tgtgcaattc accggtatta ccagtttatt atgtaaacaa gagatttggc atgacatgtt 2820
ctgtatgttt cagggaaaaa tgtctttaat gctttttcaa gaactaacac agttattcct 2880
atactggatt ttaggtctct gaagaactgc tggtgtttag gaataagaat gtgcatgaag 2940
cctaaaatac caagaaagct tatactgaat ttaagcaaag aaataaagga gaaaagagaa 3000
gaatctgaga attggggagg catagattct tataaaaatc acaaaatttg ttgtaaatta 3060
gaggggagaa atttagaatt aagtataaaa aggcagaatt agtatagagt acattcatta 3120
aacatttttg tcaggattat ttcccgtaaa aacgtagtga gcacttttca tatactaatt 3180
tagttgtaca tttaactttg tataatacag aaatctaaat atatttaatg aattcaagca 3240
atatatcact tgaccaagaa attggaattt caaaatgttc gtgcgggtat ataccagatg 3300
agtacagtga gtagttttat gtatcaccag actgggttat tgccaagtta tatatcacca 3360
aaagctgtat gactggatgt tctggttacc tggtttacaa aattatcaga gtagtaaaac 3420
tttgatatat atgaggatat taaaactaca ctaagtatca tttgattcga ttcagaaagt 3480
actttgatat ctctcagtgc ttcagtgcta tcattgtgag caattgtctt ttatatacgg 3540
tactgtagcc atactaggcc tgtctgtggc attctctaga tgtttctttt ttacacaata 3600
aattccttat atcagcttga aaaaaaaaaa aaaaaaa 3637

<210> SEQ ID NO 149
<211> LENGTH: 2208
<212> TYPE: DNA
<213> ORGANISM: Homo sapiens

<400> SEQUENCE: 149
aacgcacttg gcgcgcggcg cgggctgcag acggctgcga ggcgctgggc acaggtgtcc 60
tgatggcaaa tttcaagggc cacgcgcttc cagggagttt cttcctgatc attgggctgt 120
gttggtcagt gaagtacccg ctgaagtact ttagccacac gcggaagaac agcccactac 180
attactatca gcgtctcgag atcgtcgaag ccgcaattag gactttgttt tccgtcactg 240
ggatcctggc agagcagttt gttccggatg ggccccacct gcacctctac catgagaacc 300
actggataaa gttaatgaat tggcagcaca gcaccatgta cctattcttt gcagtctcag 360
gaattgttga catgctcacc tatctggtca gccacgttcc cttgggggtg gacagactgg 420
ttatggctgt ggcagtattc atggaaggtt tcctcttcta ctaccacgtc cacaaccggc 480
ctccgctgga ccagcacatc cactcactcc tgctgtatgc tctgttcgga gggtgtgtta 540
gtatctccct agaggtgatc ttccgggacc acattgtgct ggaacttttc cgaaccagtc 600
tcatcattct tcagggaacc tggttctggc agattgggtt tgtgctgttc ccaccttttg 660
gaacacccga atgggaccag aaggatgatg ccaacctcat gttcatcacc atgtgcttct 720
gctggcacta cctggctgcc ctcagcattg tggccgtcaa ctattctctt gtttactgcc 780
ttttgactcg gatgaagaga cacggaaggg gagaaatcat tggaattcag aagctgaatt 840
cagatgacac ttaccagacc gccctcttga gtggctcaga tgaggaatga gccgagatgc 900
ggagggcgca gatgtcccac tgcacagctg gaatgaatgg agttcatccc ctccacctga 960
atgcctgctg tggtctgatc ttaagggtct atatatttgc acctcctcat tcaacacagg 1020
gctggaggtt ctacaacagg aaatcaggcc tacagcatcc tgtgtatctt gcagttggga 1080
tttttaaaca tactataaag tctgtgttgg tatagtaccc ttcataagga aaaatgaagt 1140

-continued

```
aatgcctata agtagcaggc ctttgtgcct cagtgtcaag agaaatcaag agatgctaaa   1200

agctttacaa tggaagtggc ctcatggatg aatccggggt atgagcccag gagaacgtgc   1260

tgcttttggt aacttatccc tttttctctt aagaaagcag gtactttctt attagaaata   1320

tgttagaatg tgtaagcaaa cgacagtgcc tttagaatta caattctaac ttacatattt   1380

tttgaaagta aaataattca caagctttgg tattttaaaa ttattgttaa acatatcata   1440

actaatcata ccagggtact gcaataccac tgtttataag tgacaaaatt aggccaaagg   1500

tgattttttt ttaaatcagg aagctggtta ctggctctac tgagagttgg agccctgatg   1560

ttctgattct tcaaagtcac cctaaaagaa gatctgacag gaaagctgta taatgagata   1620

gaaaaacgtc aggtatggaa ggctttcagt tttaatatgg ctgaaagcaa aggataacga   1680

attcagaatt agtaatgtaa aatcttgata ccctaatctt gcttctggat ctgttctttt   1740

tttaaaaaaa cttccttcac cgcgcctata atcctagcac tttgggaggc cgaggcaggc   1800

agatcacggg gtcaggagat caagaccatc ctggctaaca tggtgaaacc ccgtctctac   1860

tgaaaataca aaaaattagc cgggtgtggt ggcgggcgcc tgtagttcca gctactcggg   1920

aggctgaggc aagagaatgg catgaacccg gtaggggagc ttgcagtgag cccagatcat   1980

gccactgtac tccagcctag gtgacagagc aagactctgt ctcaaaaaca agcaaacaga   2040

cttccttcaa caaatattta ttaaatatcc actttgcaac agcactgaaa tggctgtaag   2100

gactcctgag atatgtgtcc agcaaggagt ttacagtcaa acaggagaga catgcctgta   2160

gttacatcca gtgtgatggg tgctgagagg caagtacaaa ccacgatg                2208
```

<210> SEQ ID NO 150
<211> LENGTH: 1678
<212> TYPE: DNA
<213> ORGANISM: Homo sapiens
<220> FEATURE:
<221> NAME/KEY: misc_feature
<222> LOCATION: (523)..(523)
<223> OTHER INFORMATION: n is a, c, g, or t
<220> FEATURE:
<221> NAME/KEY: misc_feature
<222> LOCATION: (569)..(569)
<223> OTHER INFORMATION: n is a, c, g, or t
<220> FEATURE:
<221> NAME/KEY: misc_feature
<222> LOCATION: (961)..(961)
<223> OTHER INFORMATION: n is a, c, g, or t
<220> FEATURE:
<221> NAME/KEY: misc_feature
<222> LOCATION: (1021)..(1021)
<223> OTHER INFORMATION: n is a, c, g, or t
<220> FEATURE:
<221> NAME/KEY: misc_feature
<222> LOCATION: (1066)..(1066)
<223> OTHER INFORMATION: n is a, c, g, or t
<220> FEATURE:
<221> NAME/KEY: misc_feature
<222> LOCATION: (1069)..(1069)
<223> OTHER INFORMATION: n is a, c, g, or t
<220> FEATURE:
<221> NAME/KEY: misc_feature
<222> LOCATION: (1194)..(1194)
<223> OTHER INFORMATION: n is a, c, g, or t
<220> FEATURE:
<221> NAME/KEY: misc_feature
<222> LOCATION: (1202)..(1202)
<223> OTHER INFORMATION: n is a, c, g, or t
<220> FEATURE:
<221> NAME/KEY: misc_feature
<222> LOCATION: (1287)..(1287)
<223> OTHER INFORMATION: n is a, c, g, or t
<220> FEATURE:

<221> NAME/KEY: misc_feature
<222> LOCATION: (1472)..(1472)
<223> OTHER INFORMATION: n is a, c, g, or t

<400> SEQUENCE: 150

```
tcccgccgcg ccacttcgcc tgcctccgtc ccccgcccgc cgcgccatgc ctgtggccgg     60
ctcggagctg ccgcgccggc ccttgccccc cgccgcacag gagcgggacg ccgagccgcg    120
tccgccgcac ggggagctgc agtacctggg gcagatccaa cacatcctcc gctgcggcgt    180
caggaaggac gcccgcccgg gcaccggtac cctgccggta ttcggcatgc aggcgcgcta    240
cagcctgaga gatgaattcc ctctgctgac aaccaaacgt gtgttctgga acggtgcttc    300
ggaggagctg ctgtggctta tcaagggatc cacaaacgct atagacctgt cttccccggc    360
agcgaaaatc tcgggatgcc actggatccc gacactctct ggacaccctg ggattctcca    420
ccagagaaga acgcgacttg ggcccagttt gtggctctca gcggaggcct cctgtggcag    480
aatacataca tttccaatca gatcacttcc cggacacgga ccntgaccag cctgccaaaa    540
agtggatttc cccccacccc agaacccanc ccctgacgca cagaaaccaa cccattcgtt    600
gttgccgcct tgcgaacccc aaccagaatc tctcccccct ggccggcgcg cctgccgctg    660
ccaatgcccc tatggcggcc tcttggcccg caccttccaa ttggtcgccc tgcgcaacca    720
gcgagaaaac actggcccgc ccgtctcccc cccgctccgc ctaccccact taatgcgcct    780
ccgtggcatg acgcacgcgt ttggtgtccg ccgccgtctc atgtccgcgc ggtgtggacc    840
ccctttctc tcgcggcaca tccccccctat tcccttgccc tttggggggc accccctcta    900
gacccgcgct tctcttctcg tccggtgggg gacattggtt tgcctgccgc ggcgggggcg    960
ntaaaaataa aaacagcctg ttagcccggc ccagtacccc cccccggccg gggccgcctt   1020
ncgtttgcat ttatacccca acccataaag ccgcgcccct ttagcnccnt aacttttgtg   1080
gtgtggcctc ccccctttt cccggggagc agcaacggac atctgtacac taatgctggc   1140
cccgaccttt cccaaaaacc ccccgcccgt gtcccgtata aatttggtgc caancctgac   1200
gngttctccc ccgccctcgc cccgttggcc gcccgtttaa agcccccccg gtggttgcgc   1260
cgcccaacga gtccacctat agttaantcc accaacaccc ccaccttttc ctccccgccg   1320
catcttcccc acgtaccccc ttttgtcgcg agatggccac tcccccccc ctgtttgttt   1380
aaaacaacga gaatggtgct gccaacgctg gtcttttccc cccccggacc gcgaccgcca   1440
gggggaatac gtaccataag cccccgcgcc cnccttttt cccccctccc cgccaatcaa   1500
gatccgccgt ccattagacg tattattttt cccgcgatac acgaaaaaac agggccgccc   1560
atttataact aaattcccgt cgccgccgcg cggatatgtt tcccaaaata ccacccccc   1620
ccccccattt tctttgcccc caactcctgc gcaccggtgt tcaccagcct cgcgccgc     1678
```

<210> SEQ ID NO 151
<211> LENGTH: 1611
<212> TYPE: DNA
<213> ORGANISM: Homo sapiens

<400> SEQUENCE: 151

```
ggacgcgtgg gtcgacccac gcgtccggac ccacgcgtcc ggtcgtgttc tccgagttcc     60
tgtctctctg ccaacgccgc ccggatggct tcccaaaacc gcgacccagc cgccactagc    120
gtcgccgccg cccgtaaagg agctgagccg agcgggggcg ccgcccgggg tccggtgggc    180
aaaaggctac agcaggagct gatgaccctc atggtgagtg attaagtgcc cagaacccca    240
gccttccatc caattttcag tagcctcctt ttttccgtca gctttttgc tagacatagg     300
```

-continued

```
ggtaatgtaa tttgctccct cctgggaaag aagttcatac accccaccta caccatttct    360
tccagcagtc cctcctccca attccatccc cccacacgaa gttatctcga acacttccct    420
gaagtcatac aagaccctcc ctatccagtg tgtccctact tcctagcccc aaccaagctt    480
tacccacacc caactccccg cccttcttgg tatttctagc ctatgaattt ggttgcttta    540
ttttggatca gagtgatgag attaagggga ggctgggcgc ggtagctcac accttataat    600
cccaaagtgc tgggattaca ggcgtgagcc accgcgcccg gccagcaact aatattctaa    660
ttgaactaaa gcacaggatg ccaatttaca atccttagac caaagagtca ctgatgtctc    720
caccagataa gaggaaagca tcaggctagg catagtggct cacacctgta atctcagcac    780
tttgggaggc tgaggcaggc agatcacatg agcccaggag tttgagactg gcctgggcaa    840
catggtgaaa ccctgtctct aaaataaaaa ctaaactaaa aaaacttttt aaaaaggcag    900
tggggagcat cagaaccagc tcaacagttt gtctactgtc cggtcccaga gaaactcaag    960
attctagcaa gccccttgtg tggggcttgg gttgggacat gaggctgctg ctggagctta   1020
ctctgcaact gtttctccaa atgccaggta tatgaagacc tgaggtataa gctctcgcta   1080
gagttcccca gtggctaccc ttacaatgcg cccacagtga agttcctcac gccctgctat   1140
caccccaacg tggacaccca gggtaacata tgcctggaca tcctgaagga aaagtggtct   1200
gccctgtatg atgtcaggac cattctgctc tccatccaga gccttctagg agaacccaac   1260
attgatagtc ccttgaacac acatgctgcc gagctctgga aaaaccccac agcttttaag   1320
aagtacctgc aagaaaccta ctcaaagcag gtcaccagcc aggagccctg acccaggctg   1380
cccagcctgt ccttgtgtcg tctttttaat ttttccttag atggtctgtc ctttttgtga   1440
tttctgtata ggactcttta tcttgagctg tggtattttt gttttgtttt tgtcttttaa   1500
attaagcctc ggttgagccc ttgtatatta aataaatgca tttttgtcct tttttaaaaa   1560
aaaaataaaa aaaaaaaaaa aaaaaaaaaa aaaaaaaaaa aaaaaaaaaa a            1611
```